(12) United States Patent
Anthony

(10) Patent No.: US 8,465,964 B2
(45) Date of Patent: Jun. 18, 2013

(54) INCREASED PRODUCTION OF ISOBUTANOL IN YEAST WITH REDUCED MITOCHONDRIAL AMINO ACID BIOSYNTHESIS

(75) Inventor: Larry Cameron Anthony, Aston, PA (US)

(73) Assignee: Butamax (TM) Advanced Biofules LLC, Wilmington, DE (US)

( * ) Notice: Subject to any disclaimer, the term of this patent is extended or adjusted under 35 U.S.C. 154(b) by 401 days.

(21) Appl. No.: 12/617,039

(22) Filed: Nov. 12, 2009

(65) Prior Publication Data

US 2010/0129887 A1    May 27, 2010

Related U.S. Application Data

(60) Provisional application No. 61/114,072, filed on Nov. 13, 2008.

(51) Int. Cl.
    *C12N 1/00* (2006.01)
(52) U.S. Cl.
    USPC ...................................................... 435/254.2
(58) Field of Classification Search
    USPC .......................................... 435/252.3, 254.2
    See application file for complete search history.

(56) References Cited

U.S. PATENT DOCUMENTS

| 4,683,202 A | 7/1987 | Mullis et al. |
| 2007/0031918 A1 | 2/2007 | Dunson et al. |
| 2007/0092957 A1 | 4/2007 | Donaldson et al. |
| 2008/0261230 A1 | 10/2008 | Liao et al. |
| 2009/0305363 A1 | 12/2009 | Anthony et al. |
| 2010/0081154 A1 | 4/2010 | Flint et al. |
| 2010/0129886 A1 | 5/2010 | Anthony et al. |

FOREIGN PATENT DOCUMENTS

| WO | 2007032522 | 3/2007 |

OTHER PUBLICATIONS

Altschul et al., J. Mol. Biol., 215:403 410 (1990).
Bianchi et al. Mol. Microbiol. (1996) 19(1):27-36.
Deshpande. Appl. Biochem. Biotechnol., 36:227, (1992).
Dickinson et al., J. Biol. Chem. 273(40):25752-25756 (1998).
Flikweert et al. Yeast (1996) 12:247-257.
Frohman et al., PNAS USA 85:8998 (1988).
Garcia et al., Process Biochemistry 29:303-309 (1994).
Guo et al., J. Membr. Sci. 245, 199-210 (2004).
Higgins and Sharp, CABIOS. 5:151-153 (1989).
Higgins et al., Comput. Appl. Biosci., 8:189-191 (1992).
Hohmann, Mol Gen Genet. (1993) 241:657-666.
Horton et al. (1989) Gene 77:61-68.
Loh et al., Science 243:217 (1989).
Mnaimneh et al. ((2004) Cell 118(1):31-44.
Ohara et al., PNAS USA 86:5673 (1989).
Sulter et al., Arch. Microbiol. 153:485 489 (1990).
Tabor, S. et al., Proc. Acad. Sci. USA 82:1074 (1985).
Van Ness et al., Nucl. Acids Res. 19:5143 5151 (1991).
Wach et al. (1994) Yeast 10:1793-1808.
Walker, et al., Proc. Natl. Acad. Sci. U.S.A., 89:392 (1992).
Bellion et al., Microb. Growth C1 Compd., [Int. Symp.], 7th (1993), 415 32, Editor(s): Murrell, J. Collin; Kelly, Don P. Publisher. Intercept, Andover, UK.
W. R. Pearson, Comput. Methods Genome Res., [Proc. Int. Symp.] (1994). Meeting Date 1992, 111 20. Editor(s): Suhai, Sandor. Plenum: New York, NY.
Rychlik, W., In Methods in Molecular Biology, White, B. A. Ed., (1993) vol. 15, pp. 31 39, PCR Protocols: Current Methods and Applications. Humania: Totowa, NJ.
Sambrook, J., Fritsch, E. F. and Maniatis, T. Molecular Cloning: A Laboratory Manual, 2nd ed., Cold Spring Harbor Laboratory: Cold Spring Harbor, NY (1989), particularly Chapter 11 and Table 11.1.
Thein and Wallace, "The use of oligonucleotides as specific hybridization probes in the diagnosis of genetic disorders", in Human Genetic Diseases: A Practical Approach, K. E. Davis Ed., (1986) pp. 33 50, IRL: Herndon, VA.
Hurt,et al., The amino-terminal region of an imported mitochondrial precursor polypeptide can direct cytoplasmic dihydrofolate reductase . . . , EMBO J. 3(13)3149-56, 1984.
Margeot, et al., In *Saccharomyces cerevisiae*, ATP2 mRNA sorting to vicinity of mitochondria is essential for respiratory function, EMBO J. 21:6893-904, 2002.

*Primary Examiner* — Maryam Monshipouri
(74) *Attorney, Agent, or Firm* — Christine M. Lhulier

(57) ABSTRACT

Yeast cells with reduced activity of certain enzymes involved in branched chain amino acid biosynthesis in yeast mitochondria are described. Target enzymes include threonine deaminase, isopropylmalate synthase, and optionally branched chain amino acid transaminase.

10 Claims, 1 Drawing Sheet

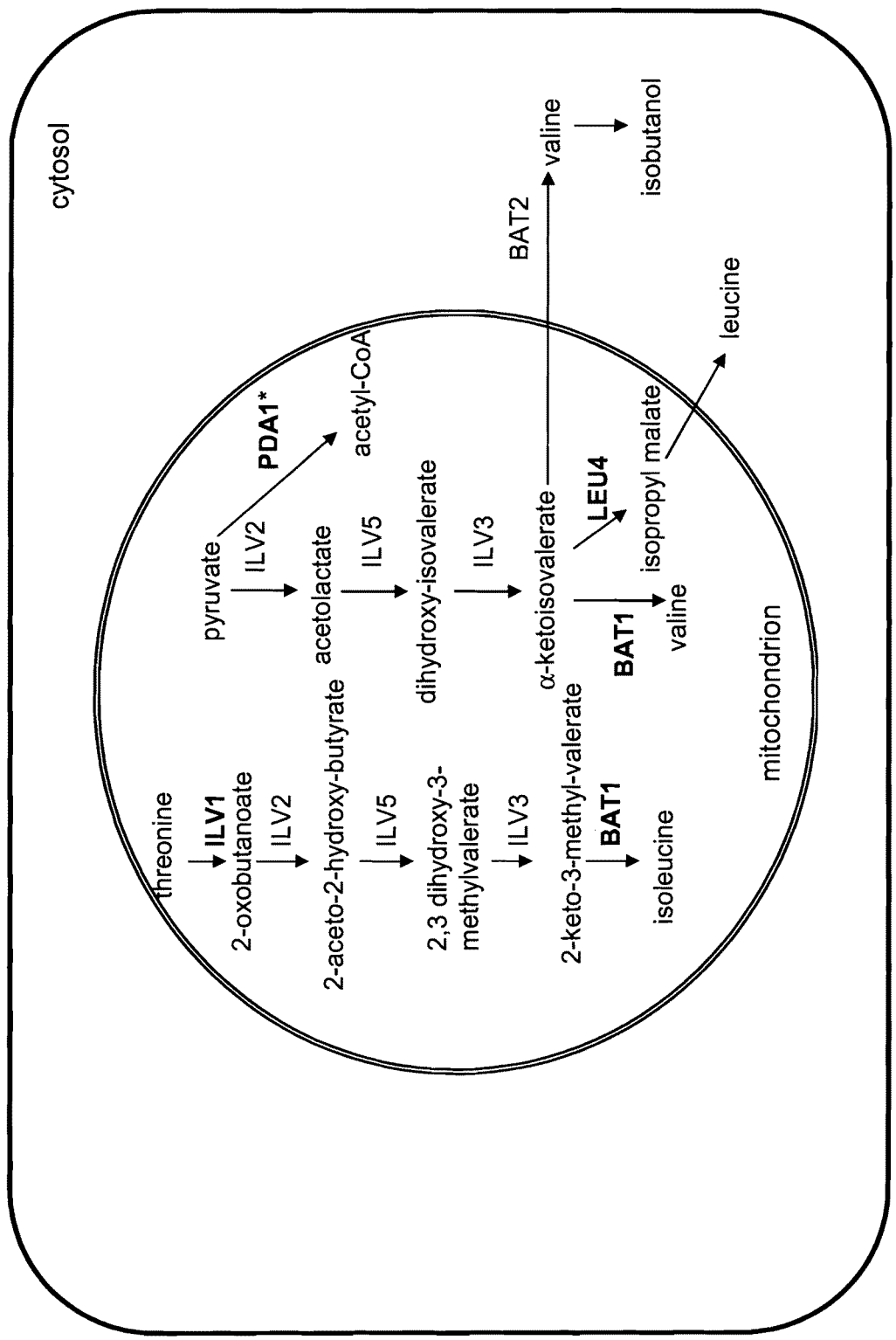

SEQUENCE LISTING

<160> NUMBER OF SEQ ID NOS: 128

<210> SEQ ID NO 1
<211> LENGTH: 1731
<212> TYPE: DNA
<213> ORGANISM: Saccharomyces cerevisiae

<400> SEQUENCE: 1

```
atgtcagcta ctctactaaa gcaaccatta tgtacggttg ttcggcaagg taaacagtcc      60
aaagtgtctg gattgaacct tttgagacta aaggctcatt tgcacagaca acacctgtca     120
ccttccttga taaaactaca ctctgaattg aaattggatg agctgcaaac tgataacacc     180
cctgattacg tccgtttagt tttaaggtcc tctgtatacg atgttattaa tgaatctcca     240
atctctcaag gtgtaggttt gtcttcccgt ctaaacacga atgtcatctt gaaaagagaa     300
gatctattgc ctgttttctc tttcaagctt cgtggtgcct ataacatgat tgccaagttg     360
gacgattctc aaagaaacca gggtgttatt gcctgttcag ctgggaatca tgcccaaggt     420
gtggcctttg ctgctaaaca cttgaaaata cctgctacta tcgttatgcc tgtttgtaca     480
ccatctatta agtatcaaaa tgtctcgaga ttagggtctc aagtcgtcct atatggtaac     540
gattttgacg aggctaaggc tgaatgtgcc aaattggctg aagagcgtgg cttgacgaac     600
attcctcctt tcgatcatcc ttatgtcatt gccggtcaag gtactgtagc tatggaaatc     660
ctaagacaag tacgtaccgc taataagatc ggtgctgtct ttgttcccgt cggcggtggt     720
ggtttaattg ctggtattgg tgcttatttg aaaagggttg ctcctcatat caaaatcatt     780
ggtgttgaaa cttacgatgc ggccacttta cataattcct tgcaacgcaa ccagagaact     840
cctttacctg tggtgggtac ttttgccgat ggtacgtctg tgcgtatgat tggtgaagaa     900
acatttagag tcgcccaaca agtggttgat gaagttgttc ttgttaacac tgacgaaatc     960
tgtgctgcag taaaggatat ttttgaagat actagaagta ttgtagaacc atctggtgcc    1020
ctttcagtag ccggtatgaa gaaatacatc tctaccgtac atccagaaat tgaccacact    1080
aaaaacacct atgttcccat cctttctggt gctaacatga actttgatag attaagattt    1140
```

```
gtttccgaac gtgctgttct tggtgaagga aaggaagtct tcatgttagt tactttaccc    1200
gacgtccctg gtgcgttcaa gaaaatgcaa aagatcatcc acccaagatc tgttactgaa    1260
ttctcttacc gttacaatga acatcgtcat gagtcctcta gtgaagtgcc caaggcttac    1320
atttacactt ctttcagcgt cgttgacaga gaaaaggaaa tcaagcaagt tatgcaacag    1380
ttgaatgctt taggttttga agctgtggat atctccgata acgaattggc taaatctcat    1440
ggtagatact tggttggtgg tgcttctaag gttcctaatg aaagaattat ttcatttgaa    1500
ttccctgaaa gaccaggtgc cttgactagg ttccttggag gcctaagcga ttcttggaat    1560
cttactttat tccattatag aaaccatggt gccgatatcg gtaaggtttt agctggtatt    1620
tccgttcctc aagggaaaa cttaaccttc caaaaattct tggaagattt aggctacact    1680
tatcatgatg aaactgataa cactgtttat caaaaattct tgaaatatta a             1731

<210> SEQ ID NO 2
<211> LENGTH: 576
<212> TYPE: PRT
<213> ORGANISM: Saccharomyces cerevisiae

<400> SEQUENCE: 2

Met Ser Ala Thr Leu Leu Lys Gln Pro Leu Cys Thr Val Val Arg Gln
1               5                   10                  15

Gly Lys Gln Ser Lys Val Ser Gly Leu Asn Leu Leu Arg Leu Lys Ala
            20                  25                  30

His Leu His Arg Gln His Leu Ser Pro Ser Leu Ile Lys Leu His Ser
        35                  40                  45

Glu Leu Lys Leu Asp Glu Leu Gln Thr Asp Asn Thr Pro Asp Tyr Val
    50                  55                  60

Arg Leu Val Leu Arg Ser Ser Val Tyr Asp Val Ile Asn Glu Ser Pro
65                  70                  75                  80

Ile Ser Gln Gly Val Gly Leu Ser Ser Arg Leu Asn Thr Asn Val Ile
                85                  90                  95

Leu Lys Arg Glu Asp Leu Leu Pro Val Phe Ser Phe Lys Leu Arg Gly
            100                 105                 110

Ala Tyr Asn Met Ile Ala Lys Leu Asp Asp Ser Gln Arg Asn Gln Gly
        115                 120                 125

Val Ile Ala Cys Ser Ala Gly Asn His Ala Gln Gly Val Ala Phe Ala
    130                 135                 140

Ala Lys His Leu Lys Ile Pro Ala Thr Ile Val Met Pro Val Cys Thr
145                 150                 155                 160

Pro Ser Ile Lys Tyr Gln Asn Val Ser Arg Leu Gly Ser Gln Val Val
                165                 170                 175

Leu Tyr Gly Asn Asp Phe Asp Glu Ala Lys Ala Glu Cys Ala Lys Leu
            180                 185                 190

Ala Glu Glu Arg Gly Leu Thr Asn Ile Pro Pro Phe Asp His Pro Tyr
        195                 200                 205

Val Ile Ala Gly Gln Gly Thr Val Ala Met Glu Ile Leu Arg Gln Val
    210                 215                 220

Arg Thr Ala Asn Lys Ile Gly Ala Val Phe Val Pro Val Gly Gly Gly
225                 230                 235                 240

Gly Leu Ile Ala Gly Ile Gly Ala Tyr Leu Lys Arg Val Ala Pro His
                245                 250                 255

Ile Lys Ile Ile Gly Val Glu Thr Tyr Asp Ala Ala Thr Leu His Asn
            260                 265                 270

Ser Leu Gln Arg Asn Gln Arg Thr Pro Leu Pro Val Val Gly Thr Phe
```

```
                275                 280                 285
Ala Asp Gly Thr Ser Val Arg Met Ile Gly Glu Glu Thr Phe Arg Val
290                 295                 300

Ala Gln Gln Val Val Asp Glu Val Leu Val Asn Thr Asp Glu Ile
305                 310                 315                 320

Cys Ala Ala Val Lys Asp Ile Phe Glu Asp Thr Arg Ser Ile Val Glu
                325                 330                 335

Pro Ser Gly Ala Leu Ser Val Ala Gly Met Lys Lys Tyr Ile Ser Thr
            340                 345                 350

Val His Pro Glu Ile Asp His Thr Lys Asn Thr Tyr Val Pro Ile Leu
        355                 360                 365

Ser Gly Ala Asn Met Asn Phe Asp Arg Leu Arg Phe Val Ser Glu Arg
    370                 375                 380

Ala Val Leu Gly Glu Gly Lys Glu Val Phe Met Leu Val Thr Leu Pro
385                 390                 395                 400

Asp Val Pro Gly Ala Phe Lys Lys Met Gln Lys Ile Ile His Pro Arg
                405                 410                 415

Ser Val Thr Glu Phe Ser Tyr Arg Tyr Asn Glu His Arg His Glu Ser
            420                 425                 430

Ser Ser Glu Val Pro Lys Ala Tyr Ile Tyr Thr Ser Phe Ser Val Val
        435                 440                 445

Asp Arg Glu Lys Glu Ile Lys Gln Val Met Gln Leu Asn Ala Leu
    450                 455                 460

Gly Phe Glu Ala Val Asp Ile Ser Asp Asn Gly Leu Ala Lys Ser His
465                 470                 475                 480

Gly Arg Tyr Leu Val Gly Gly Ala Ser Lys Val Pro Asn Glu Arg Ile
                485                 490                 495

Ile Ser Phe Glu Phe Pro Glu Arg Pro Gly Ala Leu Thr Arg Phe Leu
            500                 505                 510

Gly Gly Leu Ser Asp Ser Trp Asn Leu Thr Leu Phe His Tyr Arg Asn
        515                 520                 525

His Gly Ala Asp Ile Gly Lys Val Leu Ala Gly Ile Ser Val Pro Pro
    530                 535                 540

Arg Glu Asn Leu Thr Phe Gln Lys Phe Leu Glu Asp Leu Gly Tyr Thr
545                 550                 555                 560

Tyr His Asp Glu Thr Asp Asn Thr Val Tyr Gln Lys Phe Leu Lys Tyr
                565                 570                 575

<210> SEQ ID NO 3
<211> LENGTH: 1803
<212> TYPE: DNA
<213> ORGANISM: Schizosaccharomyces pombe

<400> SEQUENCE: 3
atgactggaa cgagttttta cacttcggta ctcagattgg gacgattggc tcaacagggc     60
ctaaaattcc aatctgtaaa acatattcgt ccatcatgtt tttcatcttt tggattacaa    120
gctaaacgtt ggaactctac tcaacaaaat gatagttcta ttgattgttt agaacctaag    180
ctgcaaggaa ttattgaaga caatatttct ccctcgacgg cacaaaaaga aatatcagac    240
atcaagttta atattccaaa ggaaatgctt cttccagatg aactcctga ttatttacgt     300 ttgactctca cgtctaacgt gtatgaagtt atcaaggaga ctcctcttac aaagggtgtt    360 gtcattctg aaagtaccgg tgttccagtc tacttaaaac gtgaagatct cactcctgtg    420
ttttcattta aaattcgagg ggctcataat aaaatggctt ctcttgataa gcagtcattg    480
```

-continued

```
aaaaatggag tcattgcttg ttccgctggc aatcacgccc agggtgttgc ttactccgct      540
aggactcttg gtgtaaaagc taccattgtt atgcctcaga atactcctga atcaaatgg       600 aggaacgtta agagattggg cgctaatgtt ctcttacatg gagctaattt tgacattgct      660
aaagcagaat gtgcacgttt ggctaaagag caaaatctcg aagttattca tcccttttga    720
gatccttatg taattgctgg acaaggaacc attggacttg aaattcttca tcaaatagat      780
cttcgcaagc tggatgctat ttactgcgct gttggcggtg gtggtttaat tgctggaata      840
gctacttacg ttaagcgtat tgctccccat gttaaggtca ttggtgtcga catttgac       900 gctgatgctt taaaaaagtc tttgaaggac aaaaagcggg taacccttaa ggaagttggc      960
ttattcgctg atggaactgc tgtgaaactt gttggagagg aaaccttccg tcttgtctcc     1020
aagaatattg cgatgtagt tcttgttgac aaagatgaga tttgtgcagc cattaaggat      1080 gttttttttgg ataccccgttc agtggtcgaa ccatcaggag ctatggctgt tgctggtatg    1140
aagcgttatg tcgctaaaca caagcctaaa atcccaatg ctgctcaggt ttgcatctta     1200
agtggtgcca atatggactt tgatcgcctt agatttattg ctgagcgtgc tgatcttggt     1260
ttgaacaagg aagtattctt gagtgtcact attcctgagc gccctggttc atttgaagcc     1320
ctacacaaca ttattactcc acgtagtatt accgaatttt cttatcgtta cgataatgat     1380
gactatgcta acatttacac atcgtttgtg gtaaaggacc gtgcaactga attgcctttg     1440
attcttcaac aaatctctga gcaaaatatg gttgcagaag atatcagcga taatgaactt     1500
gctaaaactc atgcccgtta tcttattgga ggaaaatcat ctgtttcaaa agagcgtttg     1560
taccgattgg atttccctga acgccctgga gctttatgta agtttttgag gagtataaag     1620
gaagtttgca gcatttcccct tttccattat cgtaattgtg gtggagatat agctagtgtg     1680
cttgctggcc ttagagtttt tgatggccaa gtggaaaaac ttcattcagt tttggaagag     1740
attggataca actgggtgga cgaaacaaat aatcccgttt acttgcgcta tcttcgtaaa     1800
tag                                                                   1803
```

<210> SEQ ID NO 4
<211> LENGTH: 600
<212> TYPE: PRT
<213> ORGANISM: Schizosaccharomyces pombe

<400> SEQUENCE: 4

```
Met Thr Gly Thr Ser Phe Tyr Thr Ser Val Leu Arg Leu Gly Arg Leu
1               5                   10                  15

Ala Gln Gln Gly Leu Lys Phe Gln Ser Val Lys His Ile Arg Pro Ser
            20                  25                  30

Cys Phe Ser Ser Phe Gly Leu Gln Ala Lys Arg Trp Asn Ser Thr Gln
        35                  40                  45

Gln Asn Asp Ser Ser Ile Asp Cys Leu Glu Pro Lys Leu Gln Gly Ile
    50                  55                  60

Ile Glu Asp Asn Ile Ser Pro Ser Thr Ala Gln Lys Glu Ile Ser Asp
65                  70                  75                  80

Ile Lys Phe Asn Ile Pro Lys Glu Met Leu Leu Pro Asp Gly Thr Pro
                85                  90                  95

Asp Tyr Leu Arg Leu Thr Leu Thr Ser Asn Val Tyr Glu Val Ile Lys
            100                 105                 110

Glu Thr Pro Leu Thr Lys Gly Val Val Ile Ser Glu Ser Thr Gly Val
        115                 120                 125

Pro Val Tyr Leu Lys Arg Glu Asp Leu Thr Pro Val Phe Ser Phe Lys
    130                 135                 140
```

```
Ile Arg Gly Ala His Asn Lys Met Ala Ser Leu Asp Lys Gln Ser Leu
145                 150                 155                 160

Lys Asn Gly Val Ile Ala Cys Ser Ala Gly Asn His Ala Gln Gly Val
            165                 170                 175

Ala Tyr Ser Ala Arg Thr Leu Gly Val Lys Ala Thr Ile Val Met Pro
        180                 185                 190

Gln Asn Thr Pro Glu Ile Lys Trp Arg Asn Val Lys Arg Leu Gly Ala
            195                 200                 205

Asn Val Leu Leu His Gly Ala Asn Phe Asp Ile Ala Lys Ala Glu Cys
        210                 215                 220

Ala Arg Leu Ala Lys Glu Gln Asn Leu Glu Val Ile His Pro Phe Asp
225                 230                 235                 240

Asp Pro Tyr Val Ile Ala Gly Gln Gly Thr Ile Gly Leu Glu Ile Leu
            245                 250                 255

His Gln Ile Asp Leu Arg Lys Leu Asp Ala Ile Tyr Cys Ala Val Gly
        260                 265                 270

Gly Gly Gly Leu Ile Ala Gly Ile Ala Thr Tyr Val Lys Arg Ile Ala
        275                 280                 285

Pro His Val Lys Val Ile Gly Val Glu Thr Phe Asp Ala Asp Ala Leu
        290                 295                 300

Lys Lys Ser Leu Lys Asp Lys Lys Arg Val Thr Leu Lys Glu Val Gly
305                 310                 315                 320

Leu Phe Ala Asp Gly Thr Ala Val Lys Leu Val Gly Glu Glu Thr Phe
            325                 330                 335

Arg Leu Val Ser Lys Asn Ile Asp Asp Val Val Leu Val Asp Lys Asp
            340                 345                 350

Glu Ile Cys Ala Ala Ile Lys Asp Val Phe Leu Asp Thr Arg Ser Val
        355                 360                 365

Val Glu Pro Ser Gly Ala Met Ala Val Ala Gly Met Lys Arg Tyr Val
        370                 375                 380

Ala Lys His Lys Pro Lys Asn Pro Asn Ala Ala Gln Val Cys Ile Leu
385                 390                 395                 400

Ser Gly Ala Asn Met Asp Phe Asp Arg Leu Arg Phe Ile Ala Glu Arg
            405                 410                 415

Ala Asp Leu Gly Leu Asn Lys Glu Val Phe Leu Ser Val Thr Ile Pro
        420                 425                 430

Glu Arg Pro Gly Ser Phe Glu Ala Leu His Asn Ile Ile Thr Pro Arg
        435                 440                 445

Ser Ile Thr Glu Phe Ser Tyr Arg Tyr Asp Asn Asp Tyr Ala Asn
450                 455                 460

Ile Tyr Thr Ser Phe Val Val Lys Asp Arg Ala Thr Glu Leu Pro Leu
465                 470                 475                 480

Ile Leu Gln Gln Ile Ser Glu Gln Asn Met Val Ala Glu Asp Ile Ser
            485                 490                 495

Asp Asn Glu Leu Ala Lys Thr His Ala Arg Tyr Leu Ile Gly Gly Lys
            500                 505                 510

Ser Ser Val Ser Lys Glu Arg Leu Tyr Arg Leu Asp Phe Pro Glu Arg
        515                 520                 525

Pro Gly Ala Leu Cys Lys Phe Leu Arg Ser Ile Lys Glu Val Cys Ser
        530                 535                 540

Ile Ser Leu Phe His Tyr Arg Asn Cys Gly Gly Asp Ile Ala Ser Val
545                 550                 555                 560

Leu Ala Gly Leu Arg Val Phe Asp Gly Gln Val Glu Lys Leu His Ser
```

```
                    565                 570                 575
    Val Leu Glu Glu Ile Gly Tyr Asn Trp Val Asp Glu Thr Asn Asn Pro
        580                 585                 590

Val Tyr Leu Arg Tyr Leu Arg Lys
        595                 600

<210> SEQ ID NO 5
<211> LENGTH: 1710
<212> TYPE: DNA
<213> ORGANISM: Candida albicans

<400> SEQUENCE: 5
atgtcaatca ctcgactttc aagtgctaag cttttattaa gtagcacgtc acgcaaacta      60
caggtattaa ggttaaatag tacaacgacc aaacccctta cccctagaca aaaatggccg     120
gaacttttgg actctgattt catagtgaat tctcaaggtg aaaaacaacc cgattatgtc     180
aaattgatat taacttcaag agtgtacgat gttgtggacg aagccggtac accattaacc     240
aatgctatca atttatctca tagatgtggt gccaatatct atcttaaaag agaggatttg     300
ttaccagttt tttcgttcaa gttgagaggt gcatataata tgattgccca tttgcattca     360
aattccccac aacctatatc aggggttatt gcttgttcgg caggaaacca tgcccaagga     420
gttgcatttt cttcgagtaa attaaatatc ccagccacaa ttgtcatgcc tactccaaca     480
ccttctatca agtacaccaa tgtttcaaga ttaggtgccc aagttgtatt gtatggagac     540
gattttgatt cagcaaaaca agagtgtgaa aggttgagca cagagcaaaa tttaatcaac     600
attccacctt ttaaccatcc ttacgttatt gctggtcagg gtacaattgc tttagagatt     660
gctagacaat tgagattaga taattgaat gccatatttg ttcctgtagg aggaggtggc     720
ttaattgcag gtgtggcagt gtatttgaag catattgccc ctcacgtcaa aatcatagga     780
gtagaaacgt atgatgccga tgcattgaac cagtctttaa agaatagtcg cctggttact     840
ttggaaaaag ttggtttgtt tgcagatggt actgccgtga agttcttgg agatgaaacc     900 tggagattag caaaagaata tgtagatgaa gttgtgcttg tcaacactga tgaattgtgt     960
gctgctatta aggatatttt tgaagacaca aggctgattg tcgaaccttc tggagcattg    1020
tctgttgctg gattgaaaaa gtacattgaa gaacacccag agattgacca cagagataag    1080
acatatgttc cagtttttgtc tggtgctaat atgaattttg atagattaag gtttgttagt    1140
gaaagagcag ttttgggtga aggaaaagaa gtctcattgg ctgttaccat tcctgagaaa    1200
cctggtgagt ttgccagatt gcaaaaagtt atcaatccac gtgctatcac tgaattttca    1260
tacaggtaca acggtgaaga aaacgccgat atatttgtgt cctttaatgt agtggacaag    1320
aaaaaagaaa gtcttcagt tatagcagca atggaaaatt gtggatttga agttgttgat    1380
atttcagaaa acgaattggc aaaatctcat ggacgttatt tagttggtgg taagtcacaa    1440
tctacaaaat cctcaaatga aaaatctat caatttgaat tccctgaaaa accaaatgct    1500
ttgtttaact ttttacaagc attaaggagc gactggaata tcagcttgtt taattataga    1560
aatcatggac atgatgtcgg aaaaatcttg tgtgcattta ctcttcctga aggatctgag    1620
gaagacttcc aagaattttt aagaatgtt ggttacactt tgttgatga atctgataac    1680 atcttttaca aaaattctt gagaagctaa                                      1710

<210> SEQ ID NO 6
<211> LENGTH: 569
<212> TYPE: PRT
<213> ORGANISM: Candida albicans
```

-continued

```
<400> SEQUENCE: 6

Met Ser Ile Thr Arg Leu Ser Ser Ala Lys Leu Leu Leu Ser Ser Thr
1               5                   10                  15

Ser Arg Lys Leu Gln Val Leu Arg Leu Asn Ser Thr Thr Thr Lys Pro
            20                  25                  30

Leu Thr Pro Arg Gln Lys Trp Pro Glu Leu Leu Asp Ser Asp Phe Ile
        35                  40                  45

Val Asn Ser Gln Gly Glu Lys Gln Pro Asp Tyr Val Lys Leu Ile Leu
    50                  55                  60

Thr Ser Arg Val Tyr Asp Val Asp Glu Ala Gly Thr Pro Leu Thr
65                  70                  75                  80

Asn Ala Ile Asn Leu Ser His Arg Cys Gly Ala Asn Ile Tyr Leu Lys
                85                  90                  95

Arg Glu Asp Leu Leu Pro Val Phe Ser Phe Lys Leu Arg Gly Ala Tyr
            100                 105                 110

Asn Met Ile Ala His Leu His Ser Asn Ser Pro Gln Pro Ile Ser Gly
        115                 120                 125

Val Ile Ala Cys Ser Ala Gly Asn His Ala Gln Gly Val Ala Phe Ser
    130                 135                 140

Ser Ser Lys Leu Asn Ile Pro Ala Thr Ile Val Met Pro Thr Pro Thr
145                 150                 155                 160

Pro Ser Ile Lys Tyr Thr Asn Val Ser Arg Leu Gly Ala Gln Val Val
                165                 170                 175

Leu Tyr Gly Asp Asp Phe Asp Ser Ala Lys Gln Glu Cys Glu Arg Leu
            180                 185                 190

Ser Thr Glu Gln Asn Leu Ile Asn Ile Pro Pro Phe Asn His Pro Tyr
        195                 200                 205

Val Ile Ala Gly Gln Gly Thr Ile Ala Leu Glu Ile Ala Arg Gln Leu
    210                 215                 220

Arg Leu Asp Lys Leu Asn Ala Ile Phe Val Pro Val Gly Gly Gly Gly
225                 230                 235                 240

Leu Ile Ala Gly Val Ala Val Tyr Leu Lys His Ile Ala Pro His Val
                245                 250                 255

Lys Ile Ile Gly Val Glu Thr Tyr Asp Ala Asp Ala Leu Asn Gln Ser
            260                 265                 270

Leu Lys Asn Ser Arg Ser Val Thr Leu Glu Lys Val Gly Leu Phe Ala
        275                 280                 285

Asp Gly Thr Ala Val Lys Val Leu Gly Asp Glu Thr Trp Arg Leu Ala
    290                 295                 300

Lys Glu Tyr Val Asp Glu Val Val Leu Val Asn Thr Asp Glu Leu Cys
305                 310                 315                 320

Ala Ala Ile Lys Asp Ile Phe Glu Asp Thr Arg Ser Ile Val Glu Pro
                325                 330                 335

Ser Gly Ala Leu Ser Val Ala Gly Leu Lys Lys Tyr Ile Glu Glu His
            340                 345                 350

Pro Glu Ile Asp His Arg Asp Lys Thr Tyr Val Pro Val Leu Ser Gly
        355                 360                 365

Ala Asn Met Asn Phe Asp Arg Leu Arg Phe Val Ser Glu Arg Ala Val
    370                 375                 380

Leu Gly Glu Gly Lys Glu Val Ser Leu Ala Val Thr Ile Pro Glu Lys
385                 390                 395                 400

Pro Gly Glu Phe Ala Arg Leu Gln Lys Val Ile Asn Pro Arg Ala Ile
                405                 410                 415
```

```
            Thr Glu Phe Ser Tyr Arg Tyr Asn Gly Glu Glu Asn Ala Asp Ile Phe
                        420                 425                 430

Val Ser Phe Asn Val Val Asp Lys Lys Glu Lys Ser Val Ile
                    435                 440                 445

Ala Ala Met Glu Asn Cys Gly Phe Glu Val Val Asp Ile Ser Glu Asn
                    450                 455                 460

Glu Leu Ala Lys Ser His Gly Arg Tyr Leu Val Gly Gly Lys Ser Gln
            465                 470                 475                 480

Ser Thr Lys Ser Ser Asn Glu Lys Ile Tyr Gln Phe Glu Phe Pro Glu
                            485                 490                 495

Lys Pro Asn Ala Leu Phe Asn Phe Leu Gln Ala Leu Arg Ser Asp Trp
                        500                 505                 510

Asn Ile Ser Leu Phe Asn Tyr Arg Asn His Gly His Asp Val Gly Lys
                    515                 520                 525

Ile Leu Cys Ala Phe Thr Leu Pro Glu Gly Ser Glu Glu Asp Phe Gln
            530                 535                 540

Glu Phe Leu Lys Asn Val Gly Tyr Thr Phe Val Asp Glu Ser Asp Asn
            545                 550                 555                 560

Ile Phe Tyr Lys Lys Phe Leu Arg Ser
                            565

<210> SEQ ID NO 7
<211> LENGTH: 1716
<212> TYPE: DNA
<213> ORGANISM: Candida glabrata

<400> SEQUENCE: 7
atgataccca agctgctgtg tggtaacaca ctgttgagtg catctgttac aacaagtagg      60
tctgtctatg gcttatctac cagatatttt actcaggatc tcgcaccttc attggttaaa     120
ctgcattccg agttaaagcc tgatgagctt cttactgata acacaccaga ctatgtgcgt     180
ttggtgctaa gatcatcggt ctatgatgtt ataaaggaat cgccaatctc acatggtgtt     240
ggtctatcgt ctagactaaa cacaaatgtc caactgaaaa gagaagattt actaccagtg     300
ttctctttca agctgcgtgg tgcatacaac atgatagcga agttagacga tactcagaga     360
aatcaaggtg tcatcgcatg ttccgcaggt aatcatgcac aaggtgtagc atatgccgct     420
agacatttgg atattccagc aactattgtc atgcctgtgt ctactccatc tataaaaat      480 caaaatgtgt cgagactggg ttcacaagtt gttctatatg gtaatgattt tgacgaagct     540
aaagctgaat gtactaaact ggcagaagag cgtggtttga ctaacatccc tccatttgat     600
catccatatg tcattgctgg tcaaggaaca gttgcgatgg aaatcttgag acaggtctat     660
aactcaaata agatcggtgc tgtctttgtt ccagttggtg gtggtgggtt gattgccggt     720
gttggtgcct atttgaagag agtcactcca cacatcaaga ttataggtgt ggaaacacat     780
gatgcagcaa cttacacac atctcttcaa agaaataaaa gaacaaatct agctagcgtt     840 ggtactttg ctgatggtac ttctgtgcgt attattggtg aagaaacctt tagagttgcc     900
agagaagttg tcgatgaaat tgtattggtc aatactgatg aaatttgtgc tgcggttaag     960
gatgtctttg aggataccag aagtattgtt gaaccatctg gtgctcttgc ggttgctggt    1020
atgaagaagt atattactca acttcatcca gaaatagatc actctaagca acatatgtc     1080 ccaattttgt caggtgctaa tatgaacttc gatagattaa gatttgtttc tgagcgtgct    1140
gtattaggtg aaggtaagga agttttttatg ctggttacca ttcctgacgt tccaggctct    1200
ttcaaaaaaa tgcagaaggt tattcatcca agagctgtta ctgagttctg ttaccgttat    1260
```

-continued

```
aatgaacatc gtcatgaatc ttctagtgag gttccaaagg cctatatcta tacatctttc    1320
agtgtggtag accgcgaaaa ggagattaaa caagtaatgc agcaactgaa caccctcggt    1380
tttgaagccg tcgatatttc tgacaatgaa ttagcaaaat cacatggtag atatttagtt    1440
ggtggtgcgt caaggtccc aaatgaaaga attatttcgt tcgaattccc agaaagacct    1500
ggggccttaa ccagattctt ggcaggttta agcgagtctt ggaatttgac attgttccat    1560
tacagaaacc atggtgctga tattggtaaa gtattggctg gtatttctgt gccacctaga    1620
gaaaatttaa ctttccaaaa attcttggaa gatttaggct ataagtacca agatgaaaca    1680
gaaaatatgg tatatcaaag actactgaaa tattaa                              1716
```

<210> SEQ ID NO 8
<211> LENGTH: 571
<212> TYPE: PRT
<213> ORGANISM: Candida glabrata

<400> SEQUENCE: 8

```
Met Ile Pro Lys Leu Leu Cys Gly Asn Thr Leu Leu Ser Ala Ser Val
1               5                   10                  15

Thr Thr Ser Arg Ser Val Tyr Gly Leu Ser Thr Arg Tyr Phe Thr Gln
            20                  25                  30

Asp Leu Ala Pro Ser Leu Val Lys Leu His Ser Glu Leu Lys Pro Asp
        35                  40                  45

Glu Leu Leu Thr Asp Asn Thr Pro Asp Tyr Val Arg Leu Val Leu Arg
    50                  55                  60

Ser Ser Val Tyr Asp Val Ile Lys Glu Ser Pro Ile Ser His Gly Val
65                  70                  75                  80

Gly Leu Ser Ser Arg Leu Asn Thr Asn Val Gln Leu Lys Arg Glu Asp
                85                  90                  95

Leu Leu Pro Val Phe Ser Phe Lys Leu Arg Gly Ala Tyr Asn Met Ile
            100                 105                 110

Ala Lys Leu Asp Asp Thr Gln Arg Asn Gln Gly Val Ile Ala Cys Ser
        115                 120                 125

Ala Gly Asn His Ala Gln Gly Val Ala Tyr Ala Ala Arg His Leu Asp
    130                 135                 140

Ile Pro Ala Thr Ile Val Met Pro Val Ser Thr Pro Ser Ile Lys Tyr
145                 150                 155                 160

Gln Asn Val Ser Arg Leu Gly Ser Gln Val Val Leu Tyr Gly Asn Asp
                165                 170                 175

Phe Asp Glu Ala Lys Ala Glu Cys Thr Lys Leu Ala Glu Glu Arg Gly
            180                 185                 190

Leu Thr Asn Ile Pro Pro Phe Asp His Pro Tyr Val Ile Ala Gly Gln
        195                 200                 205

Gly Thr Val Ala Met Glu Ile Leu Arg Gln Val Tyr Asn Ser Asn Lys
    210                 215                 220

Ile Gly Ala Val Phe Val Pro Val Gly Gly Gly Leu Ile Ala Gly
225                 230                 235                 240

Val Gly Ala Tyr Leu Lys Arg Val Thr Pro His Ile Lys Ile Ile Gly
                245                 250                 255

Val Glu Thr His Asp Ala Ala Thr Leu His Thr Ser Leu Gln Arg Asn
            260                 265                 270

Lys Arg Thr Asn Leu Ala Ser Val Gly Thr Phe Ala Asp Gly Thr Ser
        275                 280                 285

Val Arg Ile Ile Gly Glu Glu Thr Phe Arg Val Ala Arg Glu Val Val
    290                 295                 300
```

```
Asp Glu Ile Val Leu Val Asn Thr Asp Glu Ile Cys Ala Ala Val Lys
305                 310                 315                 320

Asp Val Phe Glu Asp Thr Arg Ser Ile Val Glu Pro Ser Gly Ala Leu
            325                 330                 335

Ala Val Ala Gly Met Lys Lys Tyr Ile Thr Gln Leu His Pro Glu Ile
            340                 345                 350

Asp His Ser Lys Gln Thr Tyr Val Pro Ile Leu Ser Gly Ala Asn Met
        355                 360                 365

Asn Phe Asp Arg Leu Arg Phe Val Ser Glu Arg Ala Val Leu Gly Glu
    370                 375                 380

Gly Lys Glu Val Phe Met Leu Val Thr Ile Pro Asp Val Pro Gly Ser
385                 390                 395                 400

Phe Lys Lys Met Gln Lys Val Ile His Pro Arg Ala Val Thr Glu Phe
            405                 410                 415

Cys Tyr Arg Tyr Asn Glu His Arg His Glu Ser Ser Ser Glu Val Pro
            420                 425                 430

Lys Ala Tyr Ile Tyr Thr Ser Phe Ser Val Val Asp Arg Glu Lys Glu
        435                 440                 445

Ile Lys Gln Val Met Gln Gln Leu Asn Thr Leu Gly Phe Glu Ala Val
    450                 455                 460

Asp Ile Ser Asp Asn Glu Leu Ala Lys Ser His Gly Arg Tyr Leu Val
465                 470                 475                 480

Gly Gly Ala Ser Lys Val Pro Asn Glu Arg Ile Ile Ser Phe Glu Phe
            485                 490                 495

Pro Glu Arg Pro Gly Ala Leu Thr Arg Phe Leu Ala Gly Leu Ser Glu
            500                 505                 510

Ser Trp Asn Leu Thr Leu Phe His Tyr Arg Asn His Gly Ala Asp Ile
        515                 520                 525

Gly Lys Val Leu Ala Gly Ile Ser Val Pro Pro Arg Glu Asn Leu Thr
    530                 535                 540

Phe Gln Lys Phe Leu Glu Asp Leu Gly Tyr Lys Tyr Gln Asp Glu Thr
545                 550                 555                 560

Glu Asn Met Val Tyr Gln Arg Leu Leu Lys Tyr
            565                 570

<210> SEQ ID NO 9
<211> LENGTH: 1704
<212> TYPE: DNA
<213> ORGANISM: Kluyveromyces lactis

<400> SEQUENCE: 9
atgctacaat ctatagtgag aactcctaga gttcttcgtg cttcaaatgc attaaaactt      60
tctgttcgct gtgttagcac ggaccagttc tctgataatt tgcagaggat gtactcccat     120
ttgaaggctg acgaacgatt ggaagatgga ctccagact acgtgcgttt aatttttaagg    180 tcttctgttt atgaagtcat tgaagagacc cccatttcac gtgcggtgtc attgtcctct     240
agactaaaca ctaacgttaa attgaaaaga gaggatttgt tgccagtgtt ttcccttcaag   300 ctgcgtggtg cttataacat gattgccaag ctagacgaaa cacagaagaa tgctggtgtt     360
attgcgtgct ctgctggtaa tcacgcacaa ggtgttgcct tttcaagtaa tcatatgaac     420
attccagcta ccattgtgat gcctgtttca acaccatcaa tcaaatatca aaacgtgtcg     480
agattaggtg cccaagtggt ctatacggt gacgacttcg atgaagccaa attggaatgt     540
gcgaggttag ctgaagaacg tggtatgaca gatattccac catttgatca tccttacgtt     600
```

-continued

```
atcgctggtc aaggtactat tgccatggag attctaagac aagtacaaaa tgggtctaac    660
atcggagcag tgttctgtgc cgtaggtggt ggtggtttga tttcaggtat tggttcatac    720
ttgaagagaa tcgcacctca tatcaaggtt attggtgtgg aaacttacga tgccgctacg    780
ttagatgttt cattaaagaa cggtaaacgt accccattgc caagtgttgg aacgttcgct    840
gatggtacct ctgtgaggtt aatcggtgaa gaaacattcc gtgtttgtca agacgtagtc    900
gatgaagtta tcttggtgaa caccgatgaa atctgtgctg ccgttaaaga tgtgtttgag    960
gacacaagat caattgtcga accaagtggt gctcttgctg ttgccggttt gaaaaaatat   1020
gtctctcaac tacaccctga aatagaccat tctaagaaga catacgttcc aattctttcc   1080
ggtgccaaca tgaatttcga ccgtttaaga ttcgtctcag aacgtgctgt attgggtgaa   1140
ggtaaagaag tgtttatgtt ggtcaccatt ccagatactc caggttcttt caagaagcta   1200
cagaatgtga tccatccaag agctgtcact gaattctcat accgttataa cgagcattgt   1260
cacgaaaatg actccgatgt accaaccgct tgtatctaca catcttttaa cgtcgttgac   1320
cgtgaaaagg aaatcaagca agtggttcaa caattgcatg ctttaggttt cgaagccgta   1380
gatatctctg acaacgaaat ggccaagtct cacggtagta tttggtcgg tggtgcttct   1440
aaaattgaaa atgagaaagt cattgcattc gaattcccag agagaccagg tgcactaact   1500
aaattcttat caggattgaa cgtttcctgg aacttgactt tattccatta cagaaaccat   1560
ggcgctgata ttgggaaaat tttggctggt atcagtgtgc ctccacaaga caacgaaatc   1620
ttccaaaagt tcttggacga tctaggatat aaatatcaag atgaaactga caatatggtt   1680
taccagaagt ttttgaagta ctag                                         1704
```

<210> SEQ ID NO 10
<211> LENGTH: 567
<212> TYPE: PRT
<213> ORGANISM: Kluyveromyces lactis

<400> SEQUENCE: 10

```
Met Leu Gln Ser Ile Val Arg Thr Pro Arg Val Leu Arg Ala Ser Asn
1               5                   10                  15

Ala Leu Lys Leu Ser Val Arg Cys Val Ser Thr Asp Gln Phe Ser Asp
                20                  25                  30

Asn Leu Gln Arg Met Tyr Ser His Leu Lys Ala Asp Glu Arg Leu Glu
            35                  40                  45

Asp Gly Ser Pro Asp Tyr Val Arg Leu Ile Leu Arg Ser Ser Val Tyr
        50                  55                  60

Glu Val Ile Glu Glu Thr Pro Ile Ser Arg Ala Val Ser Leu Ser Ser
65                  70                  75                  80

Arg Leu Asn Thr Asn Val Lys Leu Lys Arg Glu Asp Leu Leu Pro Val
                85                  90                  95

Phe Ser Phe Lys Leu Arg Gly Ala Tyr Asn Met Ile Ala Lys Leu Asp
                100                 105                 110

Glu Thr Gln Lys Asn Ala Gly Val Ile Ala Cys Ser Ala Gly Asn His
            115                 120                 125

Ala Gln Gly Val Ala Phe Ser Ser Asn His Met Asn Ile Pro Ala Thr
        130                 135                 140

Ile Val Met Pro Val Ser Thr Pro Ser Ile Lys Tyr Gln Asn Val Ser
145                 150                 155                 160

Arg Leu Gly Ala Gln Val Val Leu Tyr Gly Asp Asp Phe Asp Glu Ala
                165                 170                 175

Lys Leu Glu Cys Ala Arg Leu Ala Glu Glu Arg Gly Met Thr Asp Ile
```

```
                180              185                190
Pro Pro Phe Asp His Pro Tyr Val Ile Ala Gly Gln Gly Thr Ile Ala
            195                 200              205
Met Glu Ile Leu Arg Gln Val Gln Asn Gly Ser Asn Ile Gly Ala Val
210                 215                 220
Phe Cys Ala Val Gly Gly Gly Leu Ile Ser Gly Ile Gly Ser Tyr
225             230                 235                 240
Leu Lys Arg Ile Ala Pro His Ile Lys Val Ile Gly Val Glu Thr Tyr
                    245                 250                 255
Asp Ala Thr Leu Asp Val Ser Leu Lys Asn Gly Lys Arg Thr Pro
            260                 265                 270
Leu Pro Ser Val Gly Thr Phe Ala Asp Gly Thr Ser Val Arg Leu Ile
            275                 280                 285
Gly Glu Glu Thr Phe Arg Val Cys Gln Asp Val Val Asp Glu Val Ile
        290                 295                 300
Leu Val Asn Thr Asp Glu Ile Cys Ala Ala Val Lys Asp Val Phe Glu
305                 310                 315                 320
Asp Thr Arg Ser Ile Val Glu Pro Ser Gly Ala Leu Ala Val Ala Gly
                    325                 330                 335
Leu Lys Lys Tyr Val Ser Gln Leu His Pro Glu Ile Asp His Ser Lys
            340                 345                 350
Lys Thr Tyr Val Pro Ile Leu Ser Gly Ala Asn Met Asn Phe Asp Arg
            355                 360                 365
Leu Arg Phe Val Ser Glu Arg Ala Val Leu Gly Glu Gly Lys Glu Val
    370                 375                 380
Phe Met Leu Val Thr Ile Pro Asp Thr Pro Gly Ser Phe Lys Lys Leu
385                 390                 395                 400
Gln Asn Val Ile His Pro Arg Ala Val Thr Glu Phe Ser Tyr Arg Tyr
                    405                 410                 415
Asn Glu His Cys His Glu Asn Asp Ser Asp Val Pro Thr Ala Cys Ile
            420                 425                 430
Tyr Thr Ser Phe Asn Val Val Asp Arg Glu Lys Glu Ile Lys Gln Val
            435                 440                 445
Val Gln Gln Leu His Ala Leu Gly Phe Glu Ala Val Asp Ile Ser Asp
450                 455                 460
Asn Glu Met Ala Lys Ser His Gly Arg Tyr Leu Val Gly Gly Ala Ser
465                 470                 475                 480
Lys Ile Glu Asn Glu Lys Val Ile Ala Phe Glu Phe Pro Glu Arg Pro
                    485                 490                 495
Gly Ala Leu Thr Lys Phe Leu Ser Gly Leu Asn Val Ser Trp Asn Leu
            500                 505                 510
Thr Leu Phe His Tyr Arg Asn His Gly Ala Asp Ile Gly Lys Ile Leu
        515                 520                 525
Ala Gly Ile Ser Val Pro Pro Gln Asp Asn Glu Ile Phe Gln Lys Phe
            530                 535                 540
Leu Asp Asp Leu Gly Tyr Lys Tyr Gln Asp Glu Thr Asp Asn Met Val
545                 550                 555                 560
Tyr Gln Lys Phe Leu Lys Tyr
                565

<210> SEQ ID NO 11
<211> LENGTH: 1590
<212> TYPE: DNA
<213> ORGANISM: Yarrowia lipolytica
```

-continued

```
<400> SEQUENCE: 11
atgtccgaac cgactatct gaagctcatc ttgaagagcc gcgtctacga cgtgtgcaag      60
gaaacacctg tgacatctgc tcatggtctg agcgagaagc tgggctgcaa agtgctgctc    120
aagcggaag atcttcagcc ggttttctcg ttcaagctgc gaggagccta caacatgatt     180
tcgcagctga gtgacgagga aaagtggaag ggagtgattg cgtgtagcgc cggtaaccat    240
gcccaaggag tcgcctttc agccaactat ctcaacattc agcgactat tgtcatgccg      300
ttggccactc cttccatcaa gcacagtaat gtttctagac taggtggcaa ggtggttttg    360
cacggagacg attttgattc ggccaaggcc cactgcaagc agctgtgtga aaatatgga     420
ctcacagata tccctcccttt tgatcacccc cacgtgattg caggccaggg aactattggt    480
atggagattc ttcgtcaggc gtcggacaac ctgaaggccg tgtttatctg tgttggaggc    540
ggcggtctga ttgccggagt aggcgcttac atcaagcgga tccagcccga tgtcaaaatc    600
attgccgtgg agacctatga tgcatgtgct ctgaaacaga gtctcatcaa gggcgaacgg    660
gtgactctgc ctgaagtcgg tctgtttgcc gatggagctg ctgtcaagct gtgtggcgag    720
gagactttcc gactctgtcg caagtacgtt gatggagttg tgcttgtgaa cacggacgag    780
atctgcgccg ctatcaaaga tgtatttgag gccactagat cggtggtgga gcctgctggt    840
gctctgtcgg tggctggtct caagaagtac tgctccgacc cctcggccat ttggtggtca    900
cctgagtccg attccgcaaa ggccaatggt atccccacta acgttgccat ctcagaaacc    960
gacgagtatc tgtcaattct ctctggagcc aacatgaact ttgaccggct tcgattcgtg   1020
gccgaacgag ctatgcttgg agaaggaacc gaagtcttca tggtcgtcac catccccgat   1080
attcccggag cgtttgaaaa gctgcacgag atcattctcc ccagagctgt caccgagttc   1140
tcctacagaa agaagtccac tgctgagaac gaagacgcta acatttttgt gtcttttca    1200
gtcaaaaacc gacaagagga aattgcagac gtgctgaaaa agctgcaagc tgccggtatg   1260
agcggagtcg acgtttcaga caacgaactg caaagaccc acgctagata tctcgtggga   1320
ggccagccag acgtgcctaa tgagagactg ttccggttcg agttccctga acgacccaac   1380
gcgctcaaaa acttcctcgg aggtgtccag acaaagtgga atatcaccct gttccactac   1440
agaaacaacg gcagtgatat tggaaagatt ctgacagcct tggacgtgcc ggaaagcgac   1500
aatgaggcgc tcaaggagtt tcttgagaag ctcaagtacc cctttgtgga ggagacagac   1560
aatgtggtgt acaagcagtt tatgaagtaa                                    1590
```

```
<210> SEQ ID NO 12
<211> LENGTH: 529
<212> TYPE: PRT
<213> ORGANISM: Yarrowia lipolytica

<400> SEQUENCE: 12

Met Ser Glu Pro Asp Tyr Leu Lys Leu Ile Leu Lys Ser Arg Val Tyr
1               5                   10                  15

Asp Val Cys Lys Glu Thr Pro Val Thr Ser Ala His Gly Leu Ser Glu
            20                  25                  30

Lys Leu Gly Cys Lys Val Leu Leu Lys Arg Glu Asp Leu Gln Pro Val
        35                  40                  45

Phe Ser Phe Lys Leu Arg Gly Ala Tyr Asn Met Ile Ser Gln Leu Ser
    50                  55                  60

Asp Glu Glu Lys Trp Lys Gly Val Ile Ala Cys Ser Ala Gly Asn His
65                  70                  75                  80

Ala Gln Gly Val Ala Phe Ser Ala Asn Tyr Leu Asn Ile Pro Ala Thr
```

```
                    85                  90                  95
Ile Val Met Pro Leu Ala Thr Pro Ser Ile Lys His Ser Asn Val Ser
                100                 105                 110

Arg Leu Gly Gly Lys Val Val Leu His Gly Asp Asp Phe Asp Ser Ala
                115                 120                 125

Lys Ala His Cys Lys Gln Leu Cys Glu Lys Tyr Gly Leu Thr Asp Ile
                130                 135                 140

Pro Pro Phe Asp His Pro His Val Ile Ala Gly Gln Gly Thr Ile Gly
145                 150                 155                 160

Met Glu Ile Leu Arg Gln Ala Ser Asp Asn Leu Lys Ala Val Phe Ile
                165                 170                 175

Cys Val Gly Gly Gly Leu Ile Ala Gly Val Gly Ala Tyr Ile Lys
                180                 185                 190

Arg Ile Gln Pro Asp Val Lys Ile Ile Ala Val Glu Thr Tyr Asp Ala
                195                 200                 205

Cys Ala Leu Lys Gln Ser Leu Ile Lys Gly Glu Arg Val Thr Leu Pro
                210                 215                 220

Glu Val Gly Leu Phe Ala Asp Gly Ala Ala Val Lys Leu Cys Gly Glu
225                 230                 235                 240

Glu Thr Phe Arg Leu Cys Arg Lys Tyr Val Asp Gly Val Leu Val
                245                 250                 255

Asn Thr Asp Glu Ile Cys Ala Ala Ile Lys Asp Val Phe Glu Ala Thr
                260                 265                 270

Arg Ser Val Val Glu Pro Ala Gly Ala Leu Ser Val Ala Gly Leu Lys
                275                 280                 285

Lys Tyr Cys Ser Asp Pro Ser Ala Ile Trp Trp Ser Pro Glu Ser Asp
                290                 295                 300

Ser Ala Lys Ala Asn Gly Ile Pro Thr Asn Val Ala Ile Ser Glu Thr
305                 310                 315                 320

Asp Glu Tyr Leu Ser Ile Leu Ser Gly Ala Asn Met Asn Phe Asp Arg
                325                 330                 335

Leu Arg Phe Val Ala Glu Arg Ala Met Leu Gly Glu Gly Thr Glu Val
                340                 345                 350

Phe Met Val Val Thr Ile Pro Asp Ile Pro Gly Ala Phe Glu Lys Leu
                355                 360                 365

His Glu Ile Ile Leu Pro Arg Ala Val Thr Glu Phe Ser Tyr Arg Lys
                370                 375                 380

Lys Ser Thr Ala Glu Asn Glu Asp Ala Asn Ile Phe Val Ser Phe Ser
385                 390                 395                 400

Val Lys Asn Arg Gln Glu Glu Ile Ala Asp Val Leu Glu Lys Leu Gln
                405                 410                 415

Ala Ala Gly Met Ser Gly Val Asp Val Ser Asp Asn Glu Leu Ala Lys
                420                 425                 430

Thr His Ala Arg Tyr Leu Val Gly Gly Gln Pro Asp Val Pro Asn Glu
                435                 440                 445

Arg Leu Phe Arg Phe Glu Phe Pro Glu Arg Pro Asn Ala Leu Lys Asn
                450                 455                 460

Phe Leu Gly Gly Val Gln Thr Lys Trp Asn Ile Thr Leu Phe His Tyr
465                 470                 475                 480

Arg Asn Asn Gly Ser Asp Ile Gly Lys Ile Leu Thr Ala Leu Asp Val
                485                 490                 495

Pro Glu Ser Asp Asn Glu Ala Leu Lys Glu Phe Leu Glu Lys Leu Lys
                500                 505                 510
```

```
Tyr Pro Phe Val Glu Glu Thr Asp Asn Val Val Tyr Lys Gln Phe Met
        515                 520                 525

Lys

<210> SEQ ID NO 13
<211> LENGTH: 1620
<212> TYPE: DNA
<213> ORGANISM: Pichia stipitis

<400> SEQUENCE: 13 atgttttca gtagatctgg agaagttgaa aaatttccaa accttctcga cgccgatttc      60
aacgaagatg gtgatccaga ctacatcaaa ttgatcttga cttcacgagt gtatgatgtt     120
gtggaaaggg caggaacccc tctcacacat gccatcaatt tgtcccataa gtgcaattca     180
aacatctact tgaagagaga ggatttgctt cctgtattct ctttcaaatt gcgtggagca     240
tataatatga tttcacattt gcattctaac tcaaagatgc cactttcggg tgtaatagct     300
tgttctgctg gtaaccatgc tcaaggtgta gcttactctg ccaacagatt gaaaattcct     360
tccactatag ttatgcctac ggctacacct tctatcaagt ataccaatgt ttcgagactt     420
ggatcgcaag ttgttttgta tggtgacgac tttgactcgg ccaagcaaga atgtgcccgt     480
ttgagttcat tgaacaactt gacggatgtg cctcctttcg accatcccta tgtcatcgct     540
ggccagggta ccatagcatt ggagatcacg agacagttgc gcttggataa gttgaacgca     600
ttgtttgtcc ctgttggtgg tggtggtctt attgctggtg tcgctgtcta cttgaagaag     660
attgctcccc atgtgaagat cattggtgta gaaacaaacg atgctgatgc cttgtaccag     720
tcgctcaagg ctaaaaagct ggtggtactt gaccaagttg gtatgtttgc tgacggaact     780
gctgtcaagt cttaggtaa agaaacctgg agactctgtg aaaacttagt agacgaagtc     840
gttaaggttt ctactgatga gttgtgtgca gcaatcaagg atatctttga agacacaaga     900
ctgattactg aaccatccgg agccttgtct gtagccggct tgaagaagta cattgaacaa     960
aatccagaca ttgaccacag aaacaagttc tatgtgccca tcttgagtgg tgccaatatg    1020
aacttcgaca gattgagatt cgtcagcgag agagctgttc tcggtgaagg taaagaagtt    1080
tcgttggtgg ttactattcc tgaaaagcct ggtgaattcg ccaagttgca agtatcatc    1140 aatcctagag ccattacaga attctcgtac aggtgtaatg gtgctgatgc caacatcttt    1200
gtttccttca atgttattga caaaaagaag gaattaaccc caattattga agacatgaac    1260
aacaatgaac atggatacga agtagttgat atctctgaca tgaattagc caagacccat    1320 ggtcgttatt tggtcggcgg taagtcctct gaagaagttg ccaatgaaag attatacagt    1380
ttcgaatttc cagaaaagcc tggagcctta ttcaacttct acaagctttt gaaggctgat    1440
tggaacatta ctttgtttca ttacagaaat cacgggcacg acatcggcaa ggttttgtgt    1500
ggttttacgc ttcctgaagg aacagatgac gcagatttcc agtccttctt gaatgaactt    1560
ggatacaagt tcaatgttga aaatgacaac gttgtctata gaagttctt gagaagctga    1620

<210> SEQ ID NO 14
<211> LENGTH: 539
<212> TYPE: PRT
<213> ORGANISM: Pichia stipitis

<400> SEQUENCE: 14

Met Phe Phe Ser Arg Ser Gly Glu Val Glu Lys Phe Pro Asn Leu Leu
1               5                   10                  15

Asp Ala Asp Phe Asn Glu Asp Gly Asp Pro Asp Tyr Ile Lys Leu Ile
            20                  25                  30
```

Leu Thr Ser Arg Val Tyr Asp Val Val Glu Arg Ala Gly Thr Pro Leu
           35                  40                  45

Thr His Ala Ile Asn Leu Ser His Lys Cys Asn Ser Asn Ile Tyr Leu
 50                  55                  60

Lys Arg Glu Asp Leu Leu Pro Val Phe Ser Phe Lys Leu Arg Gly Ala
 65                  70                  75                  80

Tyr Asn Met Ile Ser His Leu His Ser Asn Ser Lys Met Pro Leu Ser
                 85                  90                  95

Gly Val Ile Ala Cys Ser Ala Gly Asn His Ala Gln Gly Val Ala Tyr
            100                 105                 110

Ser Ala Asn Arg Leu Lys Ile Pro Ser Thr Ile Val Met Pro Thr Ala
        115                 120                 125

Thr Pro Ser Ile Lys Tyr Thr Asn Val Ser Arg Leu Gly Ser Gln Val
        130                 135                 140

Val Leu Tyr Gly Asp Asp Phe Asp Ser Ala Lys Gln Glu Cys Ala Arg
145                 150                 155                 160

Leu Ser Ser Leu Asn Asn Leu Thr Asp Val Pro Pro Phe Asp His Pro
                165                 170                 175

Tyr Val Ile Ala Gly Gln Gly Thr Ile Ala Leu Glu Ile Thr Arg Gln
                180                 185                 190

Leu Arg Leu Asp Lys Leu Asn Ala Leu Phe Val Pro Val Gly Gly Gly
        195                 200                 205

Gly Leu Ile Ala Gly Val Ala Val Tyr Leu Lys Lys Ile Ala Pro His
        210                 215                 220

Val Lys Ile Ile Gly Val Glu Thr Asn Asp Ala Asp Ala Leu Tyr Gln
225                 230                 235                 240

Ser Leu Lys Ala Lys Lys Ser Val Val Leu Asp Gln Val Gly Met Phe
                245                 250                 255

Ala Asp Gly Thr Ala Val Lys Val Leu Gly Lys Glu Thr Trp Arg Leu
            260                 265                 270

Cys Glu Asn Leu Val Asp Glu Val Val Lys Val Ser Thr Asp Glu Leu
        275                 280                 285

Cys Ala Ala Ile Lys Asp Ile Phe Glu Asp Thr Arg Ser Ile Thr Glu
        290                 295                 300

Pro Ser Gly Ala Leu Ser Val Ala Gly Leu Lys Lys Tyr Ile Glu Gln
305                 310                 315                 320

Asn Pro Asp Ile Asp His Arg Asn Lys Phe Tyr Val Pro Ile Leu Ser
                325                 330                 335

Gly Ala Asn Met Asn Phe Asp Arg Leu Arg Phe Val Ser Glu Arg Ala
            340                 345                 350

Val Leu Gly Glu Gly Lys Glu Val Ser Leu Val Val Thr Ile Pro Glu
        355                 360                 365

Lys Pro Gly Glu Phe Ala Lys Leu Gln Ser Ile Ile Asn Pro Arg Ala
        370                 375                 380

Ile Thr Glu Phe Ser Tyr Arg Cys Asn Gly Ala Asp Ala Asn Ile Phe
385                 390                 395                 400

Val Ser Phe Asn Val Ile Asp Lys Lys Lys Glu Leu Thr Pro Ile Ile
                405                 410                 415

Glu Asp Met Asn Asn Glu His Gly Tyr Glu Val Val Asp Ile Ser
            420                 425                 430

Asp Asn Glu Leu Ala Lys Thr His Gly Arg Tyr Leu Val Gly Gly Lys
        435                 440                 445

Ser Ser Glu Glu Val Ala Asn Glu Arg Leu Tyr Ser Phe Glu Phe Pro

```
                450              455              460
Glu Lys Pro Gly Ala Leu Phe Asn Phe Leu Gln Ala Leu Lys Ala Asp
465                 470                 475                 480

Trp Asn Ile Thr Leu Phe His Tyr Arg Asn His Gly His Asp Ile Gly
                485                 490                 495

Lys Val Leu Cys Gly Phe Thr Leu Pro Glu Gly Thr Asp Asp Ala Asp
            500                 505                 510

Phe Gln Ser Phe Leu Asn Glu Leu Gly Tyr Lys Phe Asn Val Glu Asn
        515                 520                 525

Asp Asn Val Val Tyr Lys Lys Phe Leu Arg Ser
    530                 535
```

<210> SEQ ID NO 15
<211> LENGTH: 1182
<212> TYPE: DNA
<213> ORGANISM: Saccharomyces cerevisiae

<400> SEQUENCE: 15

```
atgttgcaga cattccttt gaagttgggg aaattctcca tcagaacact cgctactggt      60
gccccattag atgcatccaa actaaaaatt actagaaacc caaatccatc aagccaaga    120
ccaaatgaag aattagtgtt cggccagaca ttcaccgatc atatgttgac cattccttgg   180
tcagccaaag aagggtgggg cactccacac atcaagcctt acggtaatct ttctcttgac   240
ccatctgctt gtgtattcca ttatgcattt gaattatttg aaggtttgaa agcctacaga   300
actcctcaaa atactatcac catgttccgt ccggataaga catggcccg tatgaacaag   360
tctgccgcta gaatttgttt gccaactttc gaatctgaag aattgatcaa acttaccggg   420
aaattgatcg aacaagataa acacttggtt cctcaaggta atggttactc attatacatc   480
agaccaacaa tgattggtac atccaagggt ttaggtgttg cactccctc cgaggctctt   540
ctttatgtta ttacttctcc agtcggtcct tattataaga ctggtttcaa agccgtacgt   600
cttgaagcaa cagactatgc tacaagagct tggccaggtg tgttggcga caaaaaattg   660
ggtgctaact atgccccatg catcttacct caactacaag ctgccaaaag agggtaccaa   720
caaaatctat ggttgttcgg cccagaaaag aacatcactg aggttggtac tatgaacgtg   780
ttcttcgttt tcctcaacaa agtcactggc aagaaggaat tggttaccgc tccattagat   840
ggtaccattt tagaaggtgt taccagagac tctgttttaa cattggctcg tgacaaacta   900
gatcctcaag aatgggacat caacgagcgt tattacacta ttactgaagt cgccactaga   960
gcaaaacaag gtgaactatt agaagccttc ggttctggta ctgctgctgt cgtttcacct  1020
atcaaggaaa ttggctggaa caacgaagat attcatgttc cactattgcc tggtgaacaa  1080
tgtggtgcat tgaccaagca agttgctcaa tggattgctg atatccaata cggtagagtc  1140
aattatggta actggtcaaa aactgttgcc gacttgaact aa                      1182
```

<210> SEQ ID NO 16
<211> LENGTH: 393
<212> TYPE: PRT
<213> ORGANISM: Saccharomyces cerevisiae

<400> SEQUENCE: 16

```
Met Leu Gln Arg His Ser Leu Lys Leu Gly Lys Phe Ser Ile Arg Thr
1               5                   10                  15

Leu Ala Thr Gly Ala Pro Leu Asp Ala Ser Lys Leu Lys Ile Thr Arg
            20                  25                  30

Asn Pro Asn Pro Ser Lys Pro Arg Pro Asn Glu Glu Leu Val Phe Gly
```

```
                35                  40                  45
Gln Thr Phe Thr Asp His Met Leu Thr Ile Pro Trp Ser Ala Lys Glu
 50                  55                  60

Gly Trp Gly Thr Pro His Ile Lys Pro Tyr Gly Asn Leu Ser Leu Asp
 65                  70                  75                  80

Pro Ser Ala Cys Val Phe His Tyr Ala Phe Glu Leu Phe Glu Gly Leu
                 85                  90                  95

Lys Ala Tyr Arg Thr Pro Gln Asn Thr Ile Thr Met Phe Arg Pro Asp
            100                 105                 110

Lys Asn Met Ala Arg Met Asn Lys Ser Ala Ala Arg Ile Cys Leu Pro
            115                 120                 125

Thr Phe Glu Ser Glu Leu Ile Lys Leu Thr Gly Lys Leu Ile Glu
        130                 135                 140

Gln Asp Lys His Leu Val Pro Gln Gly Asn Gly Tyr Ser Leu Tyr Ile
145                 150                 155                 160

Arg Pro Thr Met Ile Gly Thr Ser Lys Gly Leu Gly Val Gly Thr Pro
                165                 170                 175

Ser Glu Ala Leu Leu Tyr Val Ile Thr Ser Pro Val Gly Pro Tyr Tyr
            180                 185                 190

Lys Thr Gly Phe Lys Ala Val Arg Leu Glu Ala Thr Asp Tyr Ala Thr
        195                 200                 205

Arg Ala Trp Pro Gly Gly Val Gly Asp Lys Lys Leu Gly Ala Asn Tyr
210                 215                 220

Ala Pro Cys Ile Leu Pro Gln Leu Gln Ala Ala Lys Arg Gly Tyr Gln
225                 230                 235                 240

Gln Asn Leu Trp Leu Phe Gly Pro Glu Lys Asn Ile Thr Glu Val Gly
                245                 250                 255

Thr Met Asn Val Phe Phe Val Phe Leu Asn Lys Val Thr Gly Lys Lys
            260                 265                 270

Glu Leu Val Thr Ala Pro Leu Asp Gly Thr Ile Leu Glu Gly Val Thr
        275                 280                 285

Arg Asp Ser Val Leu Thr Leu Ala Arg Asp Lys Leu Asp Pro Gln Glu
290                 295                 300

Trp Asp Ile Asn Glu Arg Tyr Tyr Thr Ile Thr Glu Val Ala Thr Arg
305                 310                 315                 320

Ala Lys Gln Gly Glu Leu Leu Glu Ala Phe Gly Ser Gly Thr Ala Ala
                325                 330                 335

Val Val Ser Pro Ile Lys Glu Ile Gly Trp Asn Asn Glu Asp Ile His
            340                 345                 350

Val Pro Leu Leu Pro Gly Glu Gln Cys Gly Ala Leu Thr Lys Gln Val
        355                 360                 365

Ala Gln Trp Ile Ala Asp Ile Gln Tyr Gly Arg Val Asn Tyr Gly Asn
370                 375                 380

Trp Ser Lys Thr Val Ala Asp Leu Asn
385                 390

<210> SEQ ID NO 17
<211> LENGTH: 1143
<212> TYPE: DNA
<213> ORGANISM: Schizosaccharomyces pombe

<400> SEQUENCE: 17
atggttcaaa ctgctgctct ccatggccca agcccatgg atagctccca tataaaagtt      60
actaatgtta aggagcttaa acctttgccc gaatggaaga gtttgaagtt tggtgagaat    120
```

```
tttactgatc atatgcttat tatgaaatgg aacagagaaa agggttggag tactcctgag    180
atcgttccat ttggtaaact ttgctttcac cctgcttcct ccgttttcca ttatggtttt    240
gagtgctttg aaggcatgaa agctttccgt gacgaaaagg gtgtcccacg tcttttccgt    300
cccatcaaga atgctgagcg tatgctttca actggtactc gtatatctct tccttccttc    360
gaccctgctg agcttgctga aattatcaga aagttcgtcg ctcacgaaaa ccgttgggtc    420
cctgatcagc gtggttactc tttgtacatt cgtcctactt tcattggtac tgatgaagcc    480
ttaggtgtcc accattgtga caacgctatg ctttatgtta ttgcctctcc cgttggcccc    540
tactacagct ctggtttcaa ggccgttaag ctttgttgct ccgaagaatc cgttcgtgct    600
tggcctggcg gtactggtca ctacaagctt ggtggtaact atgctcctag tgttttgcct    660
caaaaagagg ctgccaagaa ggggtatgct cagattctct ggctttatgg agacgaggac    720
tacattactg aggttggtac tatgaactgc tttactgttt ggattaacaa gaatggcgaa    780
aaagaaatca ttactgcccc tcttgacggt atgatcttac tggtgtcac tcgtgattct    840
attttggaaa tttgccgtga acgtctcgca cctaaaggct ggaagattac tgagggcaag    900
tattccatga agaggttgc tcaagcttct aaggaaggtc gccttttgga agtctttgga    960
gctggtactg ctgcccttgt ttcccccgtc aaggctatta actacaaggg tactgagtat   1020
gaaattccca tgcctgaggg tcaggaagct ggtcccatca cttctgaaat cagcaaatgg   1080
attttggata tccaatacgg caaggaacct aacaacccct ggagcgttcc tgctttgcct   1140
taa                                                                  1143
```

<210> SEQ ID NO 18
<211> LENGTH: 380
<212> TYPE: PRT
<213> ORGANISM: Schizosaccharomyces pombe

<400> SEQUENCE: 18

```
Met Val Gln Thr Ala Ala Leu His Gly Pro Lys Pro Met Asp Ser Ser
1               5                   10                  15

His Ile Lys Val Thr Asn Val Lys Glu Leu Lys Pro Leu Pro Glu Trp
            20                  25                  30

Lys Ser Leu Lys Phe Gly Glu Asn Phe Thr Asp His Met Leu Ile Met
        35                  40                  45

Lys Trp Asn Arg Glu Lys Gly Trp Ser Thr Pro Glu Ile Val Pro Phe
    50                  55                  60

Gly Lys Leu Cys Phe His Pro Ala Ser Ser Val Phe His Tyr Gly Phe
65                  70                  75                  80

Glu Cys Phe Glu Gly Met Lys Ala Phe Arg Asp Glu Lys Gly Val Pro
                85                  90                  95

Arg Leu Phe Arg Pro Ile Lys Asn Ala Glu Arg Met Leu Ser Thr Gly
            100                 105                 110

Thr Arg Ile Ser Leu Pro Ser Phe Asp Pro Ala Glu Leu Ala Glu Ile
        115                 120                 125

Ile Arg Lys Phe Val Ala His Glu Asn Arg Trp Val Pro Asp Gln Arg
    130                 135                 140

Gly Tyr Ser Leu Tyr Ile Arg Pro Thr Phe Ile Gly Thr Asp Glu Ala
145                 150                 155                 160

Leu Gly Val His His Cys Asp Asn Ala Met Leu Tyr Val Ile Ala Ser
                165                 170                 175

Pro Val Gly Pro Tyr Tyr Ser Ser Gly Phe Lys Ala Val Lys Leu Cys
            180                 185                 190
```

```
Cys Ser Glu Glu Ser Val Arg Ala Trp Pro Gly Gly Thr Gly His Tyr
            195                 200                 205
Lys Leu Gly Gly Asn Tyr Ala Pro Ser Val Leu Pro Gln Lys Glu Ala
        210                 215                 220
Ala Lys Lys Gly Tyr Ala Gln Ile Leu Trp Leu Tyr Gly Asp Glu Asp
225                 230                 235                 240
Tyr Ile Thr Glu Val Gly Thr Met Asn Cys Phe Thr Val Trp Ile Asn
                245                 250                 255
Lys Asn Gly Glu Lys Glu Ile Ile Thr Ala Pro Leu Asp Gly Met Ile
            260                 265                 270
Leu Pro Gly Val Thr Arg Asp Ser Ile Leu Gln Ile Cys Arg Glu Arg
        275                 280                 285
Leu Ala Pro Lys Gly Trp Lys Ile Thr Glu Gly Lys Tyr Ser Met Lys
290                 295                 300
Glu Val Ala Gln Ala Ser Lys Glu Gly Arg Leu Leu Glu Val Phe Gly
305                 310                 315                 320
Ala Gly Thr Ala Ala Leu Val Ser Pro Val Lys Ala Ile Asn Tyr Lys
                325                 330                 335
Gly Thr Glu Tyr Glu Ile Pro Met Pro Glu Gly Gln Ala Gly Pro
            340                 345                 350
Ile Thr Ser Glu Ile Ser Lys Trp Ile Leu Asp Ile Gln Tyr Gly Lys
        355                 360                 365
Glu Pro Asn Asn Pro Trp Ser Val Pro Ala Leu Pro
370                 375                 380

<210> SEQ ID NO 19
<211> LENGTH: 1110
<212> TYPE: DNA
<213> ORGANISM: Candida albicans

<400> SEQUENCE: 19
atgtcagctc cattagacgc cagtaaattg gaaatcacta aaactaccaa accaagtgaa      60
ccattaccaa agaagaatt ggttttcggt aaatcattca ctgaccatat cttgaagtt       120 gaatggactg ctgaaaaagg atggggtgtt ccaactatta accatacca caacttttcc      180 cttgatccag ccacctgtgt tttacattat tcttttgagt tatttgaagg tttaaaggca     240
taccgtgata gcaatggtaa aatcagaact tttagaccag acaaaaatat ggaaagaatg     300
aatagatcag ctaaaagagc tgcattacct acatttgatg gtgaagaatt tatcaaatta     360
gttgatcaat ttttgttgat tgaagaaaga tttgttccaa ctggttacgg atattcactt    420
tacttgagac aacttttaat tggtacttca attgggttag gtgtcagtgc accaactaaa    480
gcattattat atcttattgc ttcacctgtt ggtccatatt tcagtggtgg tttcaaacca    540
gtgtctttgg aagccacaga ttacgccgta agagcttggc caaaggtgt tggttcttat    600 aaattgggtg caaactatgt gtcttgtatt gaaccacaaa tggaagctgc aagagaggt    660 cattcccaaa atttgtggtt atttggtgaa gaaggttata ttactgaagt gggtgctatg    720 aatgttttt ttgcattcaa gaatgccgat ggcactaaag aattggtgac tccgccattg      780
gatggtatga tcttgccagg tgtcactcgt gattctactt tagaattggc taaaagcaaa    840
ttaccaagtg attggactgt caatgaaaga aaattgacta ttcatgaagt taaagaaaga    900
gctgctaaag gtgaattagt tgaagctttc ggtactggta ccgctgctat tgtttcacca    960
attgacaaca ttgaattcca aggcgaacaa attaaggttc cagtttctgc tggtagttcc   1020
ggagaaatag ctttgaagat caatgattgg ataaaggcta ttcaatatgg tgatgaaagt   1080
```
tttaaaaact ggtctagagt agcccaatag 1110

<210> SEQ ID NO 20
<211> LENGTH: 369
<212> TYPE: PRT
<213> ORGANISM: Candida albicans

<400> SEQUENCE: 20

Met Ser Ala Pro Leu Asp Ala Ser Lys Leu Glu Ile Thr Lys Thr Thr
1               5                   10                  15

Lys Pro Ser Glu Pro Leu Pro Lys Glu Glu Leu Val Phe Gly Lys Ser
            20                  25                  30

Phe Thr Asp His Ile Leu Glu Val Glu Trp Thr Ala Glu Lys Gly Trp
        35                  40                  45

Gly Val Pro Thr Ile Lys Pro Tyr His Asn Phe Ser Leu Asp Pro Ala
    50                  55                  60

Thr Cys Val Leu His Tyr Ser Phe Glu Leu Phe Glu Gly Leu Lys Ala
65                  70                  75                  80

Tyr Arg Asp Ser Asn Gly Lys Ile Arg Thr Phe Arg Pro Asp Lys Asn
                85                  90                  95

Met Glu Arg Met Asn Arg Ser Ala Lys Arg Ala Ala Leu Pro Thr Phe
            100                 105                 110

Asp Gly Glu Glu Phe Ile Lys Leu Val Asp Gln Phe Leu Leu Ile Glu
        115                 120                 125

Glu Arg Phe Val Pro Thr Gly Tyr Gly Tyr Ser Leu Tyr Leu Arg Pro
    130                 135                 140

Thr Leu Ile Gly Thr Ser Ile Gly Leu Gly Val Ser Ala Pro Thr Lys
145                 150                 155                 160

Ala Leu Leu Tyr Leu Ile Ala Ser Pro Val Gly Pro Tyr Phe Ser Gly
                165                 170                 175

Gly Phe Lys Pro Val Ser Leu Glu Ala Thr Asp Tyr Ala Val Arg Ala
            180                 185                 190

Trp Pro Lys Gly Val Gly Ser Tyr Lys Leu Gly Ala Asn Tyr Val Ser
        195                 200                 205

Cys Ile Glu Pro Gln Met Glu Ala Ala Lys Arg Gly His Ser Gln Asn
    210                 215                 220

Leu Trp Leu Phe Gly Glu Glu Gly Tyr Ile Thr Glu Val Gly Ala Met
225                 230                 235                 240

Asn Val Phe Phe Ala Phe Lys Asn Ala Asp Gly Thr Lys Glu Leu Val
                245                 250                 255

Thr Pro Pro Leu Asp Gly Met Ile Leu Pro Gly Val Thr Arg Asp Ser
            260                 265                 270

Thr Leu Glu Leu Ala Lys Ser Lys Leu Pro Ser Asp Trp Thr Val Asn
        275                 280                 285

Glu Arg Lys Leu Thr Ile His Glu Val Lys Glu Arg Ala Ala Lys Gly
    290                 295                 300

Glu Leu Val Glu Ala Phe Gly Thr Gly Thr Ala Ala Ile Val Ser Pro
305                 310                 315                 320

Ile Asp Asn Ile Glu Phe Gln Gly Glu Gln Ile Lys Val Pro Val Ser
                325                 330                 335

Ala Gly Ser Ser Gly Glu Ile Ala Leu Lys Ile Asn Asp Trp Ile Lys
            340                 345                 350

Ala Ile Gln Tyr Gly Asp Glu Ser Phe Lys Asn Trp Ser Arg Val Ala
        355                 360                 365

Gln

<210> SEQ ID NO 21
<211> LENGTH: 1224
<212> TYPE: DNA
<213> ORGANISM: Kluyveromyces lactis

<400> SEQUENCE: 21

```
atgaactaca ttggactacg gaattgtgca agagctgttt ccagcagagt ttccattcca      60
tcaagaggta ttaagagtca tattttaaca agttatagag ccatgtcctt agacgcatcc     120
aaggttaaaa tcaccaaggt cgaaacccca tcgaagccac gtccaaacga tgagttggtt     180
ttcggtcaaa cttttcactga ccatatgtta accatcgaat ggacagctga aaacggttgg     240
ggtgtcccag agattaaacc atacgggaac ttgtcgttag atccatcctc gtgtgtgttc     300
cactatgctt tcgaattgtt cgaaggtttg aaggcgtaca gaaccccaga caacaagatc     360
agcatgttcc gtgctgataa gaatatggaa cgtatgaaca agtcagcagc cagaatctgt     420
ttgccatctt ttaattcgga tgagttgatc aagttgatcg gtaagttgat cgaacaagac     480
aagcatttgg tgcctcaagg tcaaggttac tccttgtaca tcagacctac aatgattggt     540
actactaacg gattgggtgt tggtactcca gacagagctt tgttgtatgt gatcacatct     600
ccagtgggac catattacaa gactgggttc aaagccgtga gattggaagc tacggattat     660
gctactagag cttggccagg tggtgttggt gacaagaagc ttggtgccaa ctacgcacca     720
tgtatcttgc ctcaattgca agctgctgaa cgtggttacc aacaaaactt gtggttgttc     780
ggtccagaaa gaacatcac tgaagtcggt actatgaacg tcttcttcgt gttcaaggac     840
tccaagaccg gcaagaagga attggttact gctccattgg acggtaccat tttggaaggt     900
gtcactagag actctattct acaattggcc agagaaaaact tgaactctga cgagtggatc     960
gtctctgaac gttactacac tatcaccgaa gtggaagaaa gagctgccaa gggcgaattg    1020
gtcgaagcgt tcggttccgg taccgctgct gtcgtgtctc caatcaagga aatcggctgg    1080
aacggtcacg atatccaagt gccattgttg cctggtgaac aatgtggtcc attgaccaag    1140
caagtggctg aatggattgc cgatatccaa tatggcagaa aagaacacaa gggatggtcc    1200
cgtatcgttg ctgacttgaa ctaa                                           1224
```

<210> SEQ ID NO 22
<211> LENGTH: 407
<212> TYPE: PRT
<213> ORGANISM: Kluyveromyces lactis

<400> SEQUENCE: 22

Met Asn Tyr Ile Gly Leu Arg Asn Cys Ala Arg Ala Val Ser Ser Arg
1               5                   10                  15

Val Ser Ile Pro Ser Arg Gly Ile Lys Ser His Ile Leu Thr Ser Tyr
            20                  25                  30

Arg Ala Met Ser Leu Asp Ala Ser Lys Val Lys Ile Thr Lys Val Glu
        35                  40                  45

Thr Pro Ser Lys Pro Arg Pro Asn Asp Glu Leu Val Phe Gly Gln Thr
    50                  55                  60

Phe Thr Asp His Met Leu Thr Ile Glu Trp Thr Ala Glu Asn Gly Trp
65                  70                  75                  80

Gly Val Pro Glu Ile Lys Pro Tyr Gly Asn Leu Ser Leu Asp Pro Ser
                85                  90                  95

Ser Cys Val Phe His Tyr Ala Phe Glu Leu Phe Glu Gly Leu Lys Ala
            100                 105                 110

```
Tyr Arg Thr Pro Asp Asn Lys Ile Ser Met Phe Arg Ala Asp Lys Asn
            115                 120                 125

Met Glu Arg Met Asn Lys Ser Ala Ala Arg Ile Cys Leu Pro Ser Phe
    130                 135                 140

Asn Ser Asp Glu Leu Ile Lys Leu Ile Gly Lys Leu Ile Glu Gln Asp
145                 150                 155                 160

Lys His Leu Val Pro Gln Gly Gln Gly Tyr Ser Leu Tyr Ile Arg Pro
                165                 170                 175

Thr Met Ile Gly Thr Thr Asn Gly Leu Gly Val Gly Thr Pro Asp Arg
            180                 185                 190

Ala Leu Leu Tyr Val Ile Thr Ser Pro Val Gly Pro Tyr Tyr Lys Thr
            195                 200                 205

Gly Phe Lys Ala Val Arg Leu Glu Ala Thr Asp Tyr Ala Thr Arg Ala
    210                 215                 220

Trp Pro Gly Gly Val Gly Asp Lys Lys Leu Gly Ala Asn Tyr Ala Pro
225                 230                 235                 240

Cys Ile Leu Pro Gln Leu Gln Ala Ala Glu Arg Gly Tyr Gln Gln Asn
                245                 250                 255

Leu Trp Leu Phe Gly Pro Glu Lys Asn Ile Thr Glu Val Gly Thr Met
            260                 265                 270

Asn Val Phe Phe Val Phe Lys Asp Ser Lys Thr Gly Lys Lys Glu Leu
            275                 280                 285

Val Thr Ala Pro Leu Asp Gly Thr Ile Leu Glu Gly Val Thr Arg Asp
    290                 295                 300

Ser Ile Leu Gln Leu Ala Arg Glu Asn Leu Asn Ser Asp Glu Trp Ile
305                 310                 315                 320

Val Ser Glu Arg Tyr Tyr Thr Ile Thr Glu Val Glu Glu Arg Ala Ala
                325                 330                 335

Lys Gly Glu Leu Val Glu Ala Phe Gly Ser Gly Thr Ala Ala Val Val
            340                 345                 350

Ser Pro Ile Lys Glu Ile Gly Trp Asn Gly His Asp Ile Gln Val Pro
            355                 360                 365

Leu Leu Pro Gly Glu Gln Cys Gly Pro Leu Thr Lys Gln Val Ala Glu
    370                 375                 380

Trp Ile Ala Asp Ile Gln Tyr Gly Arg Lys Glu His Lys Gly Trp Ser
385                 390                 395                 400

Arg Ile Val Ala Asp Leu Asn
                405

<210> SEQ ID NO 23
<211> LENGTH: 1167
<212> TYPE: DNA
<213> ORGANISM: Yarrowia lipolytica

<400> SEQUENCE: 23
atgcttcgaa acaacttgag atcgctttcg cgggccttca gcacctcctc catgcgtctg      60
ggcgccggaa tggacgcctc caagctccag atcaccaaga ccaagtcccc caaggaaaag     120
caggccccca aggatctcat tttcggccat accttcaccg accacatgct gactgtcgag     180
tggactgcca aggacggctg ggctgctccc cagatcaccc cctacggtcc tcttgagctg     240
gatccctccg ccgtcgtcct gcactatgcc tttgagtgtt tcgagggcct caaggcttac     300
aaggacgagt ctggaaacgt gcgtctgttc cgagtcgaca agaacatgca ccgaatgaac     360
acatcggccg agcgaatctg cctgcccgag tttgatggcg ccgaggctgc caagctgatt     420
ggccaattgg ccaagcttga ttccgcttgg atccccgagg gacgaggcta ctccatgtac     480
```

-continued

```
ctccgacctt ctctgattgg aaccaccgcc gctctcggcg tcggaacccc cgataaggcg      540
ctcttttacg tcattgcatc ccccgtcggc ccctactacc ctaccggatt caaggccgtc      600
aagctggagg ctactgacta cgctgtccga gcctggcctg gaggagtcgg aaacaagaag      660
ctgggagcca actacgctcc ctgtatcaag cctcagcagc aggccgcttc tcgaggctac      720
cagcagaacc tgtggctgtt tggcgacgag ggcaacatca ccgaggtcgg taccatgaac      780
gccttctttg tgtttgagcg aaacggcaag aaggagcttg tcactgctcc tttggacggt      840
actattctcg agggtgtcac tcgagactcc attctggagc tggctcgaga acgattgcct      900
tctgctgact ggatcgtttc cgagcgatac tgcactatta agaggtcgc ggaggctgcc      960 gagaagggcg agcttgttga ggcctttgga gctggtactg ccgctgttgt ctcgcctatc      1020
aaggagattg gatggggaga aagactatt aacattcctc tccagcctgg caaggaggcc      1080
ggtaagctga ctgagactgt taatgagtgg attggagata ccagtacgg taaggatgaa      1140 tacaagggat ggtctaaggt ggtctaa                                          1167
```

<210> SEQ ID NO 24
<211> LENGTH: 388
<212> TYPE: PRT
<213> ORGANISM: Yarrowia lipolytica

<400> SEQUENCE: 24

```
Met Leu Arg Asn Asn Leu Arg Ser Leu Ser Arg Ala Phe Ser Thr Ser
1               5                   10                  15

Ser Met Arg Leu Gly Ala Gly Met Asp Ala Ser Lys Leu Gln Ile Thr
            20                  25                  30

Lys Thr Lys Ser Pro Lys Glu Lys Gln Ala Pro Lys Asp Leu Ile Phe
        35                  40                  45

Gly His Thr Phe Thr Asp His Met Leu Thr Val Glu Trp Thr Ala Lys
    50                  55                  60

Asp Gly Trp Ala Ala Pro Gln Ile Thr Pro Tyr Gly Pro Leu Glu Leu
65                  70                  75                  80

Asp Pro Ser Ala Val Val Leu His Tyr Ala Phe Glu Cys Phe Glu Gly
                85                  90                  95

Leu Lys Ala Tyr Lys Asp Glu Ser Gly Asn Val Arg Leu Phe Arg Val
            100                 105                 110

Asp Lys Asn Met His Arg Met Asn Thr Ser Ala Glu Arg Ile Cys Leu
        115                 120                 125

Pro Glu Phe Asp Gly Ala Glu Ala Ala Lys Leu Ile Gly Gln Leu Ala
    130                 135                 140

Lys Leu Asp Ser Ala Trp Ile Pro Glu Gly Arg Gly Tyr Ser Met Tyr
145                 150                 155                 160

Leu Arg Pro Ser Leu Ile Gly Thr Thr Ala Ala Leu Gly Val Gly Thr
                165                 170                 175

Pro Asp Lys Ala Leu Phe Tyr Val Ile Ala Ser Pro Val Gly Pro Tyr
            180                 185                 190

Tyr Pro Thr Gly Phe Lys Ala Val Lys Leu Glu Ala Thr Asp Tyr Ala
        195                 200                 205

Val Arg Ala Trp Pro Gly Gly Val Gly Asn Lys Lys Leu Gly Ala Asn
    210                 215                 220

Tyr Ala Pro Cys Ile Lys Pro Gln Gln Gln Ala Ala Ser Arg Gly Tyr
225                 230                 235                 240

Gln Gln Asn Leu Trp Leu Phe Gly Asp Glu Gly Asn Ile Thr Glu Val
                245                 250                 255
```

```
Gly Thr Met Asn Ala Phe Phe Val Phe Glu Arg Asn Gly Lys Lys Glu
            260                 265                 270
Leu Val Thr Ala Pro Leu Asp Gly Thr Ile Leu Glu Gly Val Thr Arg
        275                 280                 285
Asp Ser Ile Leu Glu Leu Ala Arg Glu Arg Leu Pro Ser Ala Asp Trp
    290                 295                 300
Ile Val Ser Glu Arg Tyr Cys Thr Ile Lys Glu Val Ala Glu Ala Ala
305                 310                 315                 320
Glu Lys Gly Glu Leu Val Glu Ala Phe Gly Ala Gly Thr Ala Ala Val
                325                 330                 335
Val Ser Pro Ile Lys Glu Ile Gly Trp Gly Glu Lys Thr Ile Asn Ile
            340                 345                 350
Pro Leu Gln Pro Gly Lys Glu Ala Gly Lys Leu Thr Glu Thr Val Asn
        355                 360                 365
Glu Trp Ile Gly Asp Ile Gln Tyr Gly Lys Asp Glu Tyr Lys Gly Trp
    370                 375                 380
Ser Lys Val Val
385

<210> SEQ ID NO 25
<211> LENGTH: 1113
<212> TYPE: DNA
<213> ORGANISM: Pichia stipitis

<400> SEQUENCE: 25
atgtctgctc cattagatgc ctccaagctt gtgatccaca agaccaccac ccccaaggaa      60
aagttgccca cgataagtt ggtcttcggc aagaccttca ccgaccacat gttggaaatc     120
gaatggactg ctcaagccgg ctggggcact cctaccattt ctccctacca caagttgtct     180
ttggatcctt ctactgtcgt attgcactac gcttttgagt tatttgaagg tatgaaagct     240
tacagagaca ctgataacaa catcagaacc ttcagaggtg acaagaacat ggacagaatg     300
aacaagtccg ctgacagaat cgccttacca acctttgatg gtgaagagtt gatgaagctc     360
attgatcagt tcttgctcgt agacgaaagc tttgttccac aaggtgctgg ctactcccct     420
tatttaagac caactatgat cggaaccacc gagtcattgg gtgtaggtac gccagataag     480
gcactcttgt atgttattgc atctcccgtt ggcccttact atggtactgg cttcaagcct     540
gtttccttag aagccactga ctatgctgtt agagcctggc caggtggtgt aggtaacaga     600
aagttgggtg ccaactatgc tccttgtgtc agacctcagt tagaggctgc taagagaggt     660
taccaacaaa acttgtggtt attcggagag gaaggctaca ttaccgaagt cggtaccatg     720
aacgctttct tgtattcaa gaacgctgac ggcaccaagg agttggccac tgctcctttg     780
gatggtacca tcttggaagg tgtcaccaga gactcgatct ggaactcac cagagaaaga     840 ttgccaaaga cgaatgggt agtgtccgaa cgtaagttca ccattggtga agttgaagaa     900
agagctgcca agggtgagtt gatcgaagca tttggtgctg gtactgctgc tgttgtttct     960
cctatcaagt ctattggctg gaagggcaag gaaatcgaag ttcctttggc tgctggcgat    1020
tccggcgaat tgaccgctca agttgctgag tggatcagaa agatccaata cggtgaagaa    1080
cagtacaaaa actggtccag agttgctcaa tag                                1113

<210> SEQ ID NO 26
<211> LENGTH: 370
<212> TYPE: PRT
<213> ORGANISM: Pichia stipitis
```

<400> SEQUENCE: 26

```
Met Ser Ala Pro Leu Asp Ala Ser Lys Leu Val Ile His Lys Thr Thr
1               5                   10                  15

Thr Pro Lys Glu Lys Leu Pro Asn Asp Lys Leu Val Phe Gly Lys Thr
            20                  25                  30

Phe Thr Asp His Met Leu Glu Ile Glu Trp Thr Ala Gln Ala Gly Trp
        35                  40                  45

Gly Thr Pro Thr Ile Ser Pro Tyr His Lys Leu Ser Leu Asp Pro Ser
    50                  55                  60

Thr Val Val Leu His Tyr Ala Phe Glu Leu Phe Glu Gly Met Lys Ala
65                  70                  75                  80

Tyr Arg Asp Thr Asp Asn Asn Ile Arg Thr Phe Arg Gly Asp Lys Asn
                85                  90                  95

Met Asp Arg Met Asn Lys Ser Ala Asp Arg Ile Ala Leu Pro Thr Phe
            100                 105                 110

Asp Gly Glu Glu Leu Met Lys Leu Ile Asp Gln Phe Leu Leu Val Asp
        115                 120                 125

Glu Ser Phe Val Pro Gln Gly Ala Gly Tyr Ser Leu Tyr Leu Arg Pro
130                 135                 140

Thr Met Ile Gly Thr Thr Glu Ser Leu Gly Val Gly Thr Pro Asp Lys
145                 150                 155                 160

Ala Leu Leu Tyr Val Ile Ala Ser Pro Val Gly Pro Tyr Tyr Gly Thr
                165                 170                 175

Gly Phe Lys Pro Val Ser Leu Glu Ala Thr Asp Tyr Ala Val Arg Ala
            180                 185                 190

Trp Pro Gly Gly Val Gly Asn Arg Lys Leu Gly Ala Asn Tyr Ala Pro
        195                 200                 205

Cys Val Arg Pro Gln Leu Glu Ala Ala Lys Arg Gly Tyr Gln Gln Asn
    210                 215                 220

Leu Trp Leu Phe Gly Glu Glu Gly Tyr Ile Thr Glu Val Gly Thr Met
225                 230                 235                 240

Asn Ala Phe Phe Val Phe Lys Asn Ala Asp Gly Thr Lys Glu Leu Ala
                245                 250                 255

Thr Ala Pro Leu Asp Gly Thr Ile Leu Glu Gly Val Thr Arg Asp Ser
            260                 265                 270

Ile Leu Glu Leu Thr Arg Glu Arg Leu Pro Lys Asn Glu Trp Val Val
        275                 280                 285

Ser Glu Arg Lys Phe Thr Ile Gly Glu Val Glu Arg Ala Ala Lys
290                 295                 300

Gly Glu Leu Ile Glu Ala Phe Gly Ala Gly Thr Ala Ala Val Val Ser
305                 310                 315                 320

Pro Ile Lys Ser Ile Gly Trp Lys Gly Lys Glu Ile Glu Val Pro Leu
                325                 330                 335

Ala Ala Gly Asp Ser Gly Glu Leu Thr Ala Gln Val Ala Glu Trp Ile
            340                 345                 350

Arg Lys Ile Gln Tyr Gly Glu Glu Gln Tyr Lys Asn Trp Ser Arg Val
        355                 360                 365

Ala Gln
    370

<210> SEQ ID NO 27
<211> LENGTH: 1860
<212> TYPE: DNA
<213> ORGANISM: Saccharomyces cerevisiae
```

```
<400> SEQUENCE: 27
atggttaaag agagtattat tgctcttgct gagcatgcgg cctccagagc ctcaagagtt      60
attcctccag tgaagctagc ctataaaaat atgcttaagg acccttcctc caagtacaag     120
ccatttaacg ctccaaagct atctaataga agtggccgg ataaccggat cacgagggct      180
cctcgttggt tatcaacaga tttgagagat ggtaaccaat ctctgccgga tcccatgtca     240
gtggaacaaa agaaagaata cttcacaag ctggtcaata ttgggttcaa agaaatcgag      300
gtttccttcc cctctgcatc tcaaacagat ttcgacttca ctagatatgc tgtagaaaac     360
gccccagacg atgttagtat tcaatgtctt gtccaatcta gagaacactt gattaagaga     420
acggtggaag cattaacagg tgctaaaaag gctactatac atacttactt ggcaacaagt     480
gatatgttcc gtgaaattgt ttttaatatg tctagagagg aagctatttc caaggcagta     540
gaggccacca aactagttag gaaactaact aaggatgacc cttcccaaca agccactcgt     600
tggtcctatg agttttcccc cgaatgtttc agtgatactc caggtgaatt tgctgtagaa     660
atttgcgaag ctgttaagaa ggcttgggaa cctaccgagg aaaatccaat cattttcaac     720
ttacctgcta ccgtagaagt tgcctctcca aatgtttatg ctgatcagat tgaatacttc     780
gctacccata ttactgagcg tgagaaggtt tgcatctcta cacattgtca caatgaccgt     840
ggttgcggtg tcgccgccac agagttaggt atgcttgcag tgccgaccg tgtagaagga      900
tgtctctttg gtaatggtga acgtacaggt aatgtggact tggttactgt tgctatgaat     960
atgtataccc aagtgtgttc tcctaatttg gatttctctg acttgacctc tgtcctagat    1020
gtggttgagc gttgtaataa gatcccagta tcgcaaagag caccatacgg cggtgacttg    1080
gtcgtttgtg cctttttccgg ttctcaccaa gacgccatta agaagggttt caacttacaa   1140
aacaagaagc gtgctcaagg tgaaactcaa tggagaatcc catacttgcc attggatcca    1200
aaggacattg gccgtgatta cgaagctgtc atcagagtca actctcagtc tggtaaaggt    1260
ggtgccgctt gggttatttt gagatctttg ggtttggatc taccaagaaa catgcaaatc    1320
gaattttcta cgccgttca agaccatgct gactccttgg gtagagaact aaaatcagat    1380
gagatttcca gttattcaa agaggcttac aactacaatg acgaacagta ccaagctatt    1440
agtttagtca attataatgt tgaaaaattc ggcactgaac gtagagtgtt cactggtcaa    1500
gtcaaagtag cgaccagat cgtcgatatt gaaggtacag gtaatggtcc aatctcttct    1560
ttggtcgacg ccctatcaaa cttgttgaac gtgagatttg ccgtagcaaa ctacacagag   1620
cattctctag gttctggttc ttctacgcaa gctgcttctt acatccatct atcgtatagg    1680
cgtaatgccg acaacgaaaa ggcctacaaa tggggtgtag gtgtctccga agatgtcggt    1740
gattcttcag tgagagccat ctttgccacc attaacaata ttatccattc tggtgatgtg   1800
tccattccat ctttggccga ggtcgaaggt aagaatgctg cggcatctgg ctctgcataa    1860
```

<210> SEQ ID NO 28
<211> LENGTH: 619
<212> TYPE: PRT
<213> ORGANISM: Saccharomyces cerevisiae

<400> SEQUENCE: 28

Met Val Lys Glu Ser Ile Ile Ala Leu Ala Glu His Ala Ala Ser Arg
1               5                   10                  15

Ala Ser Arg Val Ile Pro Pro Val Lys Leu Ala Tyr Lys Asn Met Leu
            20                  25                  30

Lys Asp Pro Ser Ser Lys Tyr Lys Pro Phe Asn Ala Pro Lys Leu Ser
        35                  40                  45

-continued

Asn Arg Lys Trp Pro Asp Asn Arg Ile Thr Arg Ala Pro Arg Trp Leu
         50                  55                  60

Ser Thr Asp Leu Arg Asp Gly Asn Gln Ser Leu Pro Asp Pro Met Ser
 65                  70                  75                  80

Val Glu Gln Lys Lys Glu Tyr Phe His Lys Leu Val Asn Ile Gly Phe
                 85                  90                  95

Lys Glu Ile Glu Val Ser Phe Pro Ser Ala Ser Gln Thr Asp Phe Asp
            100                 105                 110

Phe Thr Arg Tyr Ala Val Glu Asn Ala Pro Asp Asp Val Ser Ile Gln
            115                 120                 125

Cys Leu Val Gln Ser Arg Glu His Leu Ile Lys Arg Thr Val Glu Ala
130                 135                 140

Leu Thr Gly Ala Lys Lys Ala Thr Ile His Thr Tyr Leu Ala Thr Ser
145                 150                 155                 160

Asp Met Phe Arg Glu Ile Val Phe Asn Met Ser Arg Glu Glu Ala Ile
                165                 170                 175

Ser Lys Ala Val Glu Ala Thr Lys Leu Val Arg Lys Leu Thr Lys Asp
            180                 185                 190

Asp Pro Ser Gln Gln Ala Thr Arg Trp Ser Tyr Glu Phe Ser Pro Glu
            195                 200                 205

Cys Phe Ser Asp Thr Pro Gly Glu Phe Ala Val Glu Ile Cys Glu Ala
210                 215                 220

Val Lys Lys Ala Trp Glu Pro Thr Glu Glu Asn Pro Ile Ile Phe Asn
225                 230                 235                 240

Leu Pro Ala Thr Val Glu Val Ala Ser Pro Asn Val Tyr Ala Asp Gln
                245                 250                 255

Ile Glu Tyr Phe Ala Thr His Ile Thr Glu Arg Glu Lys Val Cys Ile
            260                 265                 270

Ser Thr His Cys His Asn Asp Arg Gly Cys Gly Val Ala Ala Thr Glu
            275                 280                 285

Leu Gly Met Leu Ala Gly Ala Asp Arg Val Glu Gly Cys Leu Phe Gly
290                 295                 300

Asn Gly Glu Arg Thr Gly Asn Val Asp Leu Val Thr Val Ala Met Asn
305                 310                 315                 320

Met Tyr Thr Gln Gly Val Ser Pro Asn Leu Asp Phe Ser Asp Leu Thr
                325                 330                 335

Ser Val Leu Asp Val Val Glu Arg Cys Asn Lys Ile Pro Val Ser Gln
            340                 345                 350

Arg Ala Pro Tyr Gly Gly Asp Leu Val Val Cys Ala Phe Ser Gly Ser
            355                 360                 365

His Gln Asp Ala Ile Lys Lys Gly Phe Asn Leu Gln Asn Lys Lys Arg
370                 375                 380

Ala Gln Gly Glu Thr Gln Trp Arg Ile Pro Tyr Leu Pro Leu Asp Pro
385                 390                 395                 400

Lys Asp Ile Gly Arg Asp Tyr Glu Ala Val Ile Arg Val Asn Ser Gln
                405                 410                 415

Ser Gly Lys Gly Gly Ala Ala Trp Val Ile Leu Arg Ser Leu Gly Leu
            420                 425                 430

Asp Leu Pro Arg Asn Met Gln Ile Glu Phe Ser Ser Ala Val Gln Asp
            435                 440                 445

His Ala Asp Ser Leu Gly Arg Glu Leu Lys Ser Asp Glu Ile Ser Lys
450                 455                 460

Leu Phe Lys Glu Ala Tyr Asn Tyr Asn Asp Glu Gln Tyr Gln Ala Ile

|     |     |     |     | 465 |     |     |     |     | 470 |     |     |     |     | 475 |     |     |     |     | 480 |
| --- | --- | --- | --- | --- | --- | --- | --- | --- | --- | --- | --- | --- | --- | --- | --- | --- | --- | --- | --- |

Ser Leu Val Asn Tyr Asn Val Glu Lys Phe Gly Thr Glu Arg Arg Val
                    485                    490                    495

Phe Thr Gly Gln Val Lys Val Gly Asp Gln Ile Val Asp Ile Glu Gly
          500                    505                    510

Thr Gly Asn Gly Pro Ile Ser Ser Leu Val Asp Ala Leu Ser Asn Leu
          515                    520                    525

Leu Asn Val Arg Phe Ala Val Ala Asn Tyr Thr Glu His Ser Leu Gly
          530                    535                    540

Ser Gly Ser Ser Thr Gln Ala Ala Ser Tyr Ile His Leu Ser Tyr Arg
545                    550                    555                    560

Arg Asn Ala Asp Asn Glu Lys Ala Tyr Lys Trp Gly Val Gly Val Ser
          565                    570                    575

Glu Asp Val Gly Asp Ser Ser Val Arg Ala Ile Phe Ala Thr Ile Asn
          580                    585                    590

Asn Ile Ile His Ser Gly Asp Val Ser Ile Pro Ser Leu Ala Glu Val
          595                    600                    605

Glu Gly Lys Asn Ala Ala Ala Ser Gly Ser Ala
          610                    615

<210> SEQ ID NO 29
<211> LENGTH: 1755
<212> TYPE: DNA
<213> ORGANISM: Schizosaccharomyces pombe

<400> SEQUENCE: 29

| | |
|---|---|
| atgaaatcta cttttgaggc tgctggccgc gttgccaaag ggatgctcaa ggatccctcc | 60 |
| aaaaagtata agccatttaa aggaattcaa ctacccaacc gtcaatggcc aaacaaggtt | 120 |
| ttgacgaaag ctccacgctg gctttctacg gacttgcgtg atggtaatca ggctttaccc | 180 |
| gatcctatga tgggcagga gaaattgaga tattttaaat tgctttgcag tattggcttc | 240 |
| aaagaaattg aggttggttt cccaagtgct tctcaaactg attttgcatt tgttcgtcat | 300 |
| ctgattgaaa cgccaggttt gattcctgac gatgttacta tttctgccct tactccttct | 360 |
| cgtgagcctt tgatcctacg tacgattgag gctcttcgag gcgctaagaa tgccactgtt | 420 |
| cacttgtata atgcctgttc tcctcttttc cgtgaagttg tcttccgcaa cagtaagcaa | 480 |
| gaaacattgg atttagccat caaaggctca aaaatcgtaa cagctgctac gaaaaatgct | 540 |
| cttgaatcga aggaaaccaa ctggggattt gaatattctc ctgaaacttt ttcagacacc | 600 |
| gaaccagact ttgctttgga agtttgtgaa gctgtcaagg gtatgtggaa accttctgct | 660 |
| gcccaaccta ttatcttcaa tcttcctgcc actgtcgaaa tgtctacgcc aacacatat | 720 |
| gctgacttaa ttgagtactt ttccactaac attagtgaac gtgaaaaagt ctgtgtttct | 780 |
| ctccatcccc ataacgaccg tggtactgct gtcgcagcag ctgaacttgg tcaacttgcc | 840 |
| ggaggtgacc gtattgaggg ctgtttgttt ggcaatggtg aacgtactgg taatgtagac | 900 |
| ttggttactt tggctttcaa cttgtatacc caaggtgttt ctcctaacct cgatttctcc | 960 |
| aagttggatg aaatcattcg tattactgaa gactgtaaca agataaacgt tcatcccgt | 1020 |
| catccttatg ctggcaatct tgtctttacc gccttttctg ttctcatca agatgccatt | 1080 |
| tctaagggtt gaaggcctta cgatgagcgt aaagctgtcg atcctgtttg gaaagtccct | 1140 |
| tacttgcctt tggatcccca tgatgtcaat tccgagtatg ctgctattat ccgcgttaac | 1200 |
| tctcaatctg gcaagggtgg tgtcgcatat ctgttgaaga ccaactgtgg tctcgattta | 1260 |
| cctcgtgctt tgcaagttga atttggtagt attgttaagg attatagcga cacaaaagga | 1320 |

```
aaggagctta gcattggtga gatcagcgac ctgttttata ccacatatta cctcgaattt   1380
cccggccgtt tctctgtaaa cgactacact ctttctagca acggacctca aagcaaatgt   1440
attaaatgcg ttgttgacat caagggtgaa agaaagata ctccttcgcg ggttgtgatc    1500
gagggtgttg gaaatggacc tttgtcggca ttggttgatg ctttacgccg tcagttcaat   1560
atttcatttg acattggtca atactctgaa catgctattg ttctggtaa cggcgtcaaa    1620 gctgcttctt atgttgagat cattttcaat aacacttctt tctggggtgt tggtattgat   1680
gctgacgtta cctctgccgg attaaaggct gtcatgtcag gcgttagtcg tgcctcccgc   1740
gcatttgcta agtaa                                                    1755

<210> SEQ ID NO 30
<211> LENGTH: 584
<212> TYPE: PRT
<213> ORGANISM: Schizosaccharomyces pombe

<400> SEQUENCE: 30

Met Lys Ser Thr Phe Glu Ala Ala Gly Arg Val Ala Lys Gly Met Leu
1               5                   10                  15

Lys Asp Pro Ser Lys Lys Tyr Lys Pro Phe Lys Gly Ile Gln Leu Pro
            20                  25                  30

Asn Arg Gln Trp Pro Asn Lys Val Leu Thr Lys Ala Pro Arg Trp Leu
        35                  40                  45

Ser Thr Asp Leu Arg Asp Gly Asn Gln Ala Leu Pro Asp Pro Met Asn
    50                  55                  60

Gly Gln Glu Lys Leu Arg Tyr Phe Lys Leu Leu Cys Ser Ile Gly Phe
65                  70                  75                  80

Lys Glu Ile Glu Val Gly Phe Pro Ser Ala Ser Gln Thr Asp Phe Ala
                85                  90                  95

Phe Val Arg His Leu Ile Glu Thr Pro Gly Leu Ile Pro Asp Asp Val
            100                 105                 110

Thr Ile Ser Ala Leu Thr Pro Ser Arg Glu Pro Leu Ile Leu Arg Thr
        115                 120                 125

Ile Glu Ala Leu Arg Gly Ala Lys Asn Ala Thr Val His Leu Tyr Asn
    130                 135                 140

Ala Cys Ser Pro Leu Phe Arg Glu Val Val Phe Arg Asn Ser Lys Gln
145                 150                 155                 160

Glu Thr Leu Asp Leu Ala Ile Lys Gly Ser Lys Ile Val Thr Ala Ala
                165                 170                 175

Thr Lys Asn Ala Leu Glu Ser Lys Glu Thr Asn Trp Gly Phe Glu Tyr
            180                 185                 190

Ser Pro Glu Thr Phe Ser Asp Thr Glu Pro Asp Phe Ala Leu Glu Val
        195                 200                 205

Cys Glu Ala Val Lys Gly Met Trp Lys Pro Ser Ala Ala Gln Pro Ile
    210                 215                 220

Ile Phe Asn Leu Pro Ala Thr Val Glu Met Ser Thr Pro Asn Thr Tyr
225                 230                 235                 240

Ala Asp Leu Ile Glu Tyr Phe Ser Thr Asn Ile Ser Glu Arg Glu Lys
                245                 250                 255

Val Cys Val Ser Leu His Pro His Asn Asp Arg Gly Thr Ala Val Ala
            260                 265                 270

Ala Ala Glu Leu Gly Gln Leu Ala Gly Gly Asp Arg Ile Glu Gly Cys
        275                 280                 285

Leu Phe Gly Asn Gly Glu Arg Thr Gly Asn Val Asp Leu Val Thr Leu
```

```
                290              295              300
Ala Phe Asn Leu Tyr Thr Gln Gly Val Ser Pro Asn Leu Asp Phe Ser
305              310                  315                  320

Lys Leu Asp Glu Ile Ile Arg Ile Thr Glu Asp Cys Asn Lys Ile Asn
                325                  330                  335

Val His Pro Arg His Pro Tyr Ala Gly Asn Leu Val Phe Thr Ala Phe
                340                  345                  350

Ser Gly Ser His Gln Asp Ala Ile Ser Lys Gly Leu Lys Ala Tyr Asp
                355                  360                  365

Glu Arg Lys Ala Val Asp Pro Val Trp Lys Val Pro Tyr Leu Pro Leu
            370                  375                  380

Asp Pro His Asp Val Asn Ser Glu Tyr Ala Ala Ile Ile Arg Val Asn
385                  390                  395                  400

Ser Gln Ser Gly Lys Gly Val Ala Tyr Leu Leu Lys Thr Asn Cys
                    405                  410                  415

Gly Leu Asp Leu Pro Arg Ala Leu Gln Val Glu Phe Gly Ser Ile Val
                420                  425                  430

Lys Asp Tyr Ser Asp Thr Lys Gly Lys Glu Leu Ser Ile Gly Glu Ile
                435                  440                  445

Ser Asp Leu Phe Tyr Thr Thr Tyr Tyr Leu Glu Phe Pro Gly Arg Phe
450                  455                  460

Ser Val Asn Asp Tyr Thr Leu Ser Ser Asn Gly Pro Gln Ser Lys Cys
465                  470                  475                  480

Ile Lys Cys Val Val Asp Ile Lys Gly Glu Lys Lys Asp Thr Pro Ser
                485                  490                  495

Arg Val Val Ile Glu Gly Val Gly Asn Gly Pro Leu Ser Ala Leu Val
                500                  505                  510

Asp Ala Leu Arg Arg Gln Phe Asn Ile Ser Phe Asp Ile Gly Gln Tyr
                515                  520                  525

Ser Glu His Ala Ile Gly Ser Gly Asn Gly Val Lys Ala Ala Ser Tyr
                530                  535                  540

Val Glu Ile Ile Phe Asn Asn Thr Ser Phe Trp Gly Val Gly Ile Asp
545                  550                  555                  560

Ala Asp Val Thr Ser Ala Gly Leu Lys Ala Val Met Ser Gly Val Ser
                565                  570                  575

Arg Ala Ser Arg Ala Phe Ala Lys
                580

<210> SEQ ID NO 31
<211> LENGTH: 1257
<212> TYPE: DNA
<213> ORGANISM: Schizosaccharomyces pombe

<400> SEQUENCE: 31
atgtctgtgt ccgaagctaa tggtactgag accatcaagc ctcctatgaa tggaaaccct     60
tatggtccca acccatctga ttttctttca cgtgtcaata acttttccat tattgagtct    120
actcttcgtg aaggtgagca attcgcaaac gcttttttcg acaccgagaa gaaaattcaa    180
attgctaagg cattggacaa ctttggtgtc gattacattg aattgacttc tcccgtggct    240
tctgagcagt cccgccaaga ttgcgaagct atttgcaaat gggcttaaa  gtgtaaaatt    300 ttaactcata ttcgctgtca tatggatgac gctcgtgtcg ctgttgagac tggagttgat    360
ggtgttgatg ttgttatcgg aacttctcaa tatcttcgca atattcccca tggaaaggac    420
atgacttaca ttattgacag cgctaccgaa gttatcaact ttgtcaagag caagggtatt    480
```

```
gaagtccgct tttcatctga ggattctttc cgttctgatc ttgtcgatct cctttctctc    540
tacaaggctg tagacaagat tggcgtcaac cgtgttggta ttgctgacac cgttggttgc    600
gctactcctc gccaagtcta cgatcttatt cgtaccttac gtggtgttgt ctcttgtgat    660
attgaatgtc attttcacaa tgacactggt atggctattg ctaatgccta ttgcgcattg    720
gaagctggtg ctacccatat cgatacttcc attcttggta ttggtgagcg taatggtatt    780
actcctcttg gtgccttgtt ggctcgtatg tatgtcaccg ataggaata cattacccac    840 aaatacaagc ttaaccagtt acgtgagctt gaaaaccttg tcgctgatgc cgttgaagtt    900
caaattcctt tcaacaatta cattaccgga atgtgtgctt ttacccataa ggctggtatc    960
catgctaaag ctattctcgc taaccctct acatatgaaa ttcttaagcc cgaggacttt   1020
ggcatgagtc gttatgttca tgttggctct cgtttgactg gttggaatgc catcaaatct   1080
cgtgctgagc agcttaacct tcatcttact gatgcccaag ccaaggaact taccgttcgc   1140
atcaagaaat tggctgatgt ccgtacttta gccatggatg atgttgatcg tgttctacgt   1200
gaataccatg ctgacttgag tgatgctgat agaatcacca agaagcgtc tgcttaa      1257
```

<210> SEQ ID NO 32
<211> LENGTH: 418
<212> TYPE: PRT
<213> ORGANISM: Schizosaccharomyces pombe

<400> SEQUENCE: 32

```
Met Ser Val Ser Glu Ala Asn Gly Thr Glu Thr Ile Lys Pro Pro Met
1               5                  10                  15

Asn Gly Asn Pro Tyr Gly Pro Asn Pro Ser Asp Phe Leu Ser Arg Val
            20                  25                  30

Asn Asn Phe Ser Ile Ile Glu Ser Thr Leu Arg Glu Gly Glu Gln Phe
        35                  40                  45

Ala Asn Ala Phe Phe Asp Thr Glu Lys Lys Ile Gln Ile Ala Lys Ala
    50                  55                  60

Leu Asp Asn Phe Gly Val Asp Tyr Ile Glu Leu Thr Ser Pro Val Ala
65                  70                  75                  80

Ser Glu Gln Ser Arg Gln Asp Cys Glu Ala Ile Cys Lys Leu Gly Leu
                85                  90                  95

Lys Cys Lys Ile Leu Thr His Ile Arg Cys His Met Asp Asp Ala Arg
            100                 105                 110

Val Ala Val Glu Thr Gly Val Asp Gly Val Asp Val Ile Gly Thr
        115                 120                 125

Ser Gln Tyr Leu Arg Lys Tyr Ser His Gly Lys Asp Met Thr Tyr Ile
    130                 135                 140

Ile Asp Ser Ala Thr Glu Val Ile Asn Phe Val Lys Ser Lys Gly Ile
145                 150                 155                 160

Glu Val Arg Phe Ser Ser Glu Asp Ser Phe Arg Ser Asp Leu Val Asp
                165                 170                 175

Leu Leu Ser Leu Tyr Lys Ala Val Asp Lys Ile Gly Val Asn Arg Val
            180                 185                 190

Gly Ile Ala Asp Thr Val Gly Cys Ala Thr Pro Arg Gln Val Tyr Asp
        195                 200                 205

Leu Ile Arg Thr Leu Arg Gly Val Val Ser Cys Asp Ile Glu Cys His
    210                 215                 220

Phe His Asn Asp Thr Gly Met Ala Ile Ala Asn Ala Tyr Cys Ala Leu
225                 230                 235                 240

Glu Ala Gly Ala Thr His Ile Asp Thr Ser Ile Leu Gly Ile Gly Glu
```

```
                   245                 250                 255
Arg Asn Gly Ile Thr Pro Leu Gly Ala Leu Leu Ala Arg Met Tyr Val
            260                 265                 270

Thr Asp Arg Glu Tyr Ile Thr His Lys Tyr Lys Leu Asn Gln Leu Arg
            275                 280                 285

Glu Leu Glu Asn Leu Val Ala Asp Ala Val Glu Val Gln Ile Pro Phe
            290                 295                 300

Asn Asn Tyr Ile Thr Gly Met Cys Ala Phe Thr His Lys Ala Gly Ile
305                 310                 315                 320

His Ala Lys Ala Ile Leu Ala Asn Pro Ser Thr Tyr Glu Ile Leu Lys
                325                 330                 335

Pro Glu Asp Phe Gly Met Ser Arg Tyr Val His Val Gly Ser Arg Leu
            340                 345                 350

Thr Gly Trp Asn Ala Ile Lys Ser Arg Ala Glu Gln Leu Asn Leu His
            355                 360                 365

Leu Thr Asp Ala Gln Ala Lys Glu Leu Thr Val Arg Ile Lys Lys Leu
            370                 375                 380

Ala Asp Val Arg Thr Leu Ala Met Asp Val Asp Arg Val Leu Arg
385                 390                 395                 400

Glu Tyr His Ala Asp Leu Ser Asp Ala Asp Arg Ile Thr Lys Glu Ala
                405                 410                 415

Ser Ala

<210> SEQ ID NO 33
<211> LENGTH: 1740
<212> TYPE: DNA
<213> ORGANISM: Candida albicans

<400> SEQUENCE: 33
atgcaaaagg ttttccaaag atgggtatct agaataccc cagttaagct ccaatataag        60
aatatgctta gagacccttc caaaaaatac tctccaccaa acagatcaa cttgcccaat       120
agaacttggc ccaccaaagt aatcactaaa gctccccgct ggctttccac tgatttaaga       180
gacggtaacc agtccttgcc agatccaatg tcggttccag aaaaaaaga atacttccat       240
aaattaattg atattgggtt taaagaaatc gaagtttcgt tcccctctgc ttcgcaaact       300
gattttgatt tcacccgata cgccgttgaa atgcgccag atgatgtaac tattcaagtc       360
ttgacccaat ctcgtgaacc attgatcaga agaacagtgg aatcggtaaa agggccaag       420
cgtgctacca tcatacata tttggcaacc tctgatgtat ccgtgaagt tgttttcggt       480
atgagcaaac aagacgctat agacaaggcc attgaaacta caaaattagt gagatcatta       540
actaaagatg accctaacat gcaagacact gaatggaatt tggagttttc tccagagtgt       600
ttctcagata cgccagttga atttgccgtt gagatttgtg aagccgttaa aaaagcttgg       660
gaaccaacag tggaaaaccc aatgatcttc aatttgcctg ccacagttga agttgctggt       720
cctaatgttt atgctgatca gattgaatac ttttgtcaaa acataactga acgtgaaaag       780
attattgtct ccaccatac tcataatgac cgtggctgtg gtgtcgctgc taccgaattg       840
ggtatgttgg ctggtgccga tagagtggaa ggttgtgtgt ttggaaacgg tgaaagaacc       900
ggtaatgttg acttggtcac ggtggcattg aacttgtaca cccaaggtat tgcgccaaat       960
ttggactttt ccgatatcga gagcattatt gaggttagtg aacgttgtaa taaaatcccg      1020
gtgcccgcaa gatcacctta cggtggctca cttgtggtgt gtgccttcag tggatctcat      1080
caagacgcca ttaaaagggg ttttgctaaa caaaagggag acaaatgggc tatcccatac      1140
```

```
ttgccattag atccaaaaga tatttggcaga acttacgaag ccgtgattag agtcaactcc    1200
caatcaggta aaggtggtgc tgcctgggtc atccttagat ctttgggatt ggacttgcca    1260
agacacttac aagttgcctt ttcaggattg gtgcaaaaca ctgctgacct gttgggtaga    1320
gaattgaagg ttgatgaaat tgtcaacttg ttcaacgaac aatacttggt gagtgcccct    1380
ttaagcattc aggattttga aatcaccaag aataaaaacg atgaaagaga aattgttgct    1440
caattaaatg atggcatcac cattaaaggt caaggtaatg gtcctatctc tgcttttatt    1500
gatgcaattt ctaacaagtt cggtgttttg tttgaagttg taaactatca agaacattct    1560
ttgggaggtg gttctagtag taaggcagca acttatatcg aattatcata tgttaatgcc    1620
aatggtgaaa aagttactag atgggggttgt ggtatcaatc acgatgtgtc acaagcctca    1680
atcgaagcca ttcttagtgt tgtaaactct ttgattaaaa agaatgaatt aactgtatag    1740
```

<210> SEQ ID NO 34
<211> LENGTH: 579
<212> TYPE: PRT
<213> ORGANISM: Candida albicans

<400> SEQUENCE: 34

```
Met Gln Lys Val Phe Gln Arg Trp Val Ser Arg Ile Pro Pro Val Lys
1               5                   10                  15

Leu Gln Tyr Lys Asn Met Leu Arg Asp Pro Ser Lys Lys Tyr Ser Pro
            20                  25                  30

Pro Lys Gln Ile Asn Leu Pro Asn Arg Thr Trp Pro Thr Lys Val Ile
        35                  40                  45

Thr Lys Ala Pro Arg Trp Leu Ser Thr Asp Leu Arg Asp Gly Asn Gln
    50                  55                  60

Ser Leu Pro Asp Pro Met Ser Val Pro Glu Lys Lys Glu Tyr Phe His
65                  70                  75                  80

Lys Leu Ile Asp Ile Gly Phe Lys Glu Ile Glu Val Ser Phe Pro Ser
                85                  90                  95

Ala Ser Gln Thr Asp Phe Asp Phe Thr Arg Tyr Ala Val Glu Asn Ala
            100                 105                 110

Pro Asp Asp Val Thr Ile Gln Val Leu Thr Gln Ser Arg Glu Pro Leu
        115                 120                 125

Ile Arg Arg Thr Val Glu Ser Val Lys Gly Ala Lys Arg Ala Thr Ile
    130                 135                 140

His Thr Tyr Leu Ala Thr Ser Asp Val Phe Arg Glu Val Val Phe Gly
145                 150                 155                 160

Met Ser Lys Gln Asp Ala Ile Asp Lys Ala Ile Glu Thr Thr Lys Leu
                165                 170                 175

Val Arg Ser Leu Thr Lys Asp Asp Pro Asn Met Gln Asp Thr Glu Trp
            180                 185                 190

Asn Leu Glu Phe Ser Pro Glu Cys Phe Ser Asp Thr Pro Val Glu Phe
        195                 200                 205

Ala Val Glu Ile Cys Glu Ala Val Lys Lys Ala Trp Glu Pro Thr Val
    210                 215                 220

Glu Asn Pro Met Ile Phe Asn Leu Pro Ala Thr Val Glu Val Ala Gly
225                 230                 235                 240

Pro Asn Val Tyr Ala Asp Gln Ile Glu Tyr Phe Cys Gln Asn Ile Thr
                245                 250                 255

Glu Arg Glu Lys Ile Ile Val Ser Thr His Thr His Asn Asp Arg Gly
            260                 265                 270

Cys Gly Val Ala Ala Thr Glu Leu Gly Met Leu Ala Gly Ala Asp Arg
```

|     |     |     |     |     | 275 |     |     |     | 280 |     |     |     |     | 285 |
| --- | --- | --- | --- | --- | --- | --- | --- | --- | --- | --- | --- | --- | --- | --- |

Val Glu Gly Cys Val Phe Gly Asn Gly Glu Arg Thr Gly Asn Val Asp
                290                 295                 300

Leu Val Thr Val Ala Leu Asn Leu Tyr Thr Gln Gly Ile Ala Pro Asn
305                 310                 315                 320

Leu Asp Phe Ser Asp Ile Glu Ser Ile Ile Glu Val Ser Glu Arg Cys
                325                 330                 335

Asn Lys Ile Pro Val Pro Ala Arg Ser Pro Tyr Gly Gly Ser Leu Val
                340                 345                 350

Val Cys Ala Phe Ser Gly Ser His Gln Asp Ala Ile Lys Lys Gly Phe
                355                 360                 365

Ala Lys Gln Lys Gly Asp Lys Trp Ala Ile Pro Tyr Leu Pro Leu Asp
                370                 375                 380

Pro Lys Asp Ile Gly Arg Thr Tyr Glu Ala Val Ile Arg Val Asn Ser
385                 390                 395                 400

Gln Ser Gly Lys Gly Gly Ala Ala Trp Val Ile Leu Arg Ser Leu Gly
                405                 410                 415

Leu Asp Leu Pro Arg His Leu Gln Val Ala Phe Ser Gly Leu Val Gln
                420                 425                 430

Asn Thr Ala Asp Ser Leu Gly Arg Glu Leu Lys Val Asp Glu Ile Val
                435                 440                 445

Asn Leu Phe Asn Glu Gln Tyr Leu Val Ser Ala Pro Leu Ser Ile Gln
                450                 455                 460

Asp Phe Glu Ile Thr Lys Asn Lys Asn Asp Glu Arg Glu Ile Val Ala
465                 470                 475                 480

Gln Leu Asn Asp Gly Ile Thr Ile Lys Gly Gln Gly Asn Gly Pro Ile
                485                 490                 495

Ser Ala Phe Ile Asp Ala Ile Ser Asn Lys Phe Gly Val Leu Phe Glu
                500                 505                 510

Val Val Asn Tyr Gln Glu His Ser Leu Gly Gly Gly Ser Ser Ser Lys
                515                 520                 525

Ala Ala Thr Tyr Ile Glu Leu Ser Tyr Val Asn Ala Asn Gly Glu Lys
                530                 535                 540

Val Thr Arg Trp Gly Cys Gly Ile Asn His Asp Val Ser Gln Ala Ser
545                 550                 555                 560

Ile Glu Ala Ile Leu Ser Val Val Asn Ser Leu Ile Lys Lys Asn Glu
                565                 570                 575

Leu Thr Val

<210> SEQ ID NO 35
<211> LENGTH: 1722
<212> TYPE: DNA
<213> ORGANISM: Candida albicans

<400> SEQUENCE: 35
atgcctatgt taaaagatcc ctcagtgaaa tataagaagt ttccaaatgt caatttgcca      60
aaccgtcaat ggccatcaag aagcttggat aaaccaccaa gatggttatc tactgatttg     120
agagatggta accaatcatt acctgatcca atgtcgatct ctgaaaagaa agaatatttc     180
aagaaattgg ttgatatagg attcaaagaa atcgaagttg ccttcccctc agcctctcaa     240
attgatttcg atttcactag atttgccgtt gaaactgccc ctgaagatgt ttcgattcaa     300 gttcttctc catgtcgtcc cgaattgatt ggtagaactg ttgaatcttt gaaaggtgct     360
aaaagagcaa ctgtccacat atatcttgcc acttctgatt gttttagaaa tgttgtgttt     420

```
ggactttcca aagaagaatc aaaggcctta gctgtgaaat gtaccaaatt ggtgagacaa      480
ttaactaaag atgatccttc aactgccggt acagattggg attttgaatt ttctccagaa      540
acttttcctg acacagattt ggattatgct gttgaagtat gtgaagcagt caaagaagcc      600
tgggggccaa cagaagataa accaattata tttaatttgc cagcaactgt tgaaatggcc      660
actcctaaca tatatgctga tcaaattgaa tattttgcca ctcatattac tgaccgtgaa      720
acagtttgta tttcattgca tcctcacaat gatagaggt gtagtgttgc tgctgccgaa       780
ttaggtcaat tagctggtgc tgacagagtt gaaggttgtc ttttcggtaa tggtgaaaga      840
accggtaatg ttgatttagt cactttagca ttgaacttgt atacccaggg ggtatcacca      900
aaattggact tttctgattt gaattcggtc attgatatag ttgaaaaatg caacaaaatt      960
cctgttcatg ctagagctcc atacggaggg tctcttgttg tttgtgcctt tagtggatct     1020
catcaagatg ccatcaaaaa ggggttcctg gctcacgaaa agaaaaaaga aaagcgggga     1080
ggcaaagaag ttcattggca attaccttat ttaccattgg atccagaaga tattggaaga     1140
acatacgagg ctattattag agtgaattct caatctggta aaggtggttc tgcttgggtg     1200
atcttgagaa atttggaatt agatttacct cgtggtttac aaattgcctt ctctaaagtg     1260
gttcaagcac gtgctgaagt taaaggtcaa gaattaacta cgaagaatt atgtgagtta      1320 ttcaagcaag aatatttcat tgattatgat gatgaagccc cagaacaata ctttaaatta     1380
gtagattact cgatatcgac accaagcaaa ggaatcaagg aaatccaagc tgatattgaa     1440
gtcgatggta aagtcatttc tatcaaaggt gaaggtaatg gtcaattatc tgcctttaat     1500
aatgccattg ctaaatattt gaatattgat attgacgtga acattatca cgaacattcc      1560 cttggtgaag attcaaaagc ccgtgccgcc acttatattg aagtcttggt cgataaaaaa     1620
gttgcaagat ggggtgtggg tattcatact gatgtttctc aagcttcatt cttatctttg     1680
atatctattt tgaatggttt gcataaaaat aaaaacattt aa                        1722
```

<210> SEQ ID NO 36
<211> LENGTH: 573
<212> TYPE: PRT
<213> ORGANISM: Candida albicans

<400> SEQUENCE: 36

```
Met Pro Met Leu Lys Asp Pro Ser Val Lys Tyr Lys Lys Phe Pro Asn
1               5                   10                  15

Val Asn Leu Pro Asn Arg Gln Trp Pro Ser Arg Ser Leu Asp Lys Pro
            20                  25                  30

Pro Arg Trp Leu Ser Thr Asp Leu Arg Asp Gly Asn Gln Ser Leu Pro
        35                  40                  45

Asp Pro Met Ser Ile Ser Glu Lys Lys Glu Tyr Phe Lys Lys Leu Val
    50                  55                  60

Asp Ile Gly Phe Lys Glu Ile Glu Val Ala Phe Pro Ser Ala Ser Gln
65                  70                  75                  80

Ile Asp Phe Asp Phe Thr Arg Phe Ala Val Glu Thr Ala Pro Glu Asp
                85                  90                  95

Val Ser Ile Gln Val Leu Ser Pro Cys Arg Pro Glu Leu Ile Gly Arg
            100                 105                 110

Thr Val Glu Ser Leu Lys Gly Ala Lys Arg Ala Thr Val His Ile Tyr
        115                 120                 125

Leu Ala Thr Ser Asp Cys Phe Arg Asn Val Val Phe Gly Leu Ser Lys
    130                 135                 140

Glu Glu Ser Lys Ala Leu Ala Val Lys Cys Thr Lys Leu Val Arg Gln
```

-continued

```
            145                 150                 155                 160
        Leu Thr Lys Asp Asp Pro Ser Thr Ala Gly Thr Asp Trp Asp Phe Glu
                            165                 170                 175

Phe Ser Pro Glu Thr Phe Ser Asp Thr Asp Leu Asp Tyr Ala Val Glu
                        180                 185                 190

Val Cys Glu Ala Val Lys Glu Ala Trp Gly Pro Thr Glu Asp Lys Pro
                    195                 200                 205

Ile Ile Phe Asn Leu Pro Ala Thr Val Glu Met Ala Thr Pro Asn Ile
                210                 215                 220

Tyr Ala Asp Gln Ile Glu Tyr Phe Ala Thr His Ile Thr Asp Arg Glu
        225                 230                 235                 240

Thr Val Cys Ile Ser Leu His Pro His Asn Asp Arg Gly Cys Ser Val
                            245                 250                 255

Ala Ala Ala Glu Leu Gly Gln Leu Ala Gly Ala Asp Arg Val Glu Gly
                        260                 265                 270

Cys Leu Phe Gly Asn Gly Glu Arg Thr Gly Asn Val Asp Leu Val Thr
                    275                 280                 285

Leu Ala Leu Asn Leu Tyr Thr Gln Gly Val Ser Pro Lys Leu Asp Phe
                290                 295                 300

Ser Asp Leu Asn Ser Val Ile Asp Ile Val Glu Lys Cys Asn Lys Ile
        305                 310                 315                 320

Pro Val His Ala Arg Ala Pro Tyr Gly Gly Ser Leu Val Val Cys Ala
                            325                 330                 335

Phe Ser Gly Ser His Gln Asp Ala Ile Lys Lys Gly Phe Ser Ala His
                        340                 345                 350

Glu Lys Lys Lys Glu Lys Ala Gly Gly Lys Glu Val His Trp Gln Leu
                    355                 360                 365

Pro Tyr Leu Pro Leu Asp Pro Glu Asp Ile Gly Arg Thr Tyr Glu Ala
                370                 375                 380

Ile Ile Arg Val Asn Ser Gln Ser Gly Lys Gly Ser Ala Trp Val
        385                 390                 395                 400

Ile Leu Arg Asn Leu Glu Leu Asp Leu Pro Arg Gly Leu Gln Ile Ala
                            405                 410                 415

Phe Ser Lys Val Val Gln Ala Arg Ala Glu Val Lys Gly Gln Glu Leu
                        420                 425                 430

Thr Asn Glu Glu Leu Cys Glu Leu Phe Lys Gln Glu Tyr Phe Ile Asp
                    435                 440                 445

Tyr Asp Asp Glu Ala Pro Glu Gln Tyr Phe Lys Leu Val Asp Tyr Ser
                450                 455                 460

Ile Ser Thr Pro Ser Lys Gly Ile Lys Glu Ile Gln Ala Asp Ile Glu
        465                 470                 475                 480

Val Asp Gly Lys Val Ile Ser Ile Lys Gly Glu Gly Asn Gly Gln Leu
                            485                 490                 495

Ser Ala Phe Asn Asn Ala Ile Ala Lys Tyr Leu Asn Ile Asp Ile Asp
                        500                 505                 510

Val Lys His Tyr His Glu His Ser Leu Gly Glu Asp Ser Lys Ala Arg
                    515                 520                 525

Ala Ala Thr Tyr Ile Glu Val Leu Val Asp Lys Lys Val Ala Arg Trp
                530                 535                 540

Gly Val Gly Ile His Thr Asp Val Ser Gln Ala Ser Phe Leu Ser Leu
        545                 550                 555                 560

Ile Ser Ile Leu Asn Gly Leu His Lys Asn Lys Asn Ile
                            565                 570
```

<210> SEQ ID NO 37
<211> LENGTH: 1254
<212> TYPE: DNA
<213> ORGANISM: Candida albicans

<400> SEQUENCE: 37

```
atgtctgttg cttctaatcc atatggtcca aatccatctg atttcttatc taatgtgaat        60
aaatttgaag tcattgaatc aactttaaga gaaggtgaac aatttgccaa tgccttttc       120
accactgaaa aaaaaattga aattgctaaa gctttagatg attttggggt tgattatatt       180
gaattgactt caccagtggc atctgaacaa tcaagaagag attgtgaagc catttgtaaa       240
ttgggtttaa agccaaaat attgacacat attagatgtc atatggatga tgcccgtgtt       300
gccgttgaaa ctggggttga tggggttgat gtggttattg gaacttcaca attttttaaga      360
caatattctc atggtaaaga tatgaattat attgctcaaa gtgctattga agtcattgaa       420
tttgttaaat ctaaaggtat tgaaattcgt tttagttctg aagattcttt tagatcagat       480
attgttgatt tattaaacat ttatcgtact gttgataaaa tcggagtgaa tagagttggt       540
attgccgata ctgttggttg tgctaaccca agacaagttt atgaattggt taaaactttg       600
aaatcggtgg tttcttgtga tattgaatgt catttccata acgatactgg ttgtgccatt       660
gctaatgctt atactgcctt ggaagccggt gctaaattga ttgatgtttc tgtgttgggt       720
attggtgaaa ggaatggtat tactccattg ggggcattaa tggcaagaat gattactgct       780
gatcgtgatt atgtgttatc taaatataaa ttacacaaat tgagagattt agaaaatttg       840
gttgctgatg ccgtacaaat taatattcca ttcaataatc caattactgg attctgtgct       900
tttactcata aagctggtat tcatgctaaa gccatcttgg ccaatccatc aacatatgaa       960
atcttgaatc aaatgatttt cggtttaacc agatatattc actttgctaa tagattgact      1020
ggttggaatg ccattaaatc aagagttgat caattgaatt tacatttgac tgatgatcaa      1080
gttaaagaag ttacaaataa aattaaaaaa ttgggtgatg ttagacaatt gaacattgat      1140
gatgtcgatt caattattaa agatttccat gctgaacaaa gcactaccaa tactcctctt      1200
ttaaaaccag tagaggatga tgaaggtcca gaaattaaaa acaaaaagt atag           1254
```

<210> SEQ ID NO 38
<211> LENGTH: 417
<212> TYPE: PRT
<213> ORGANISM: Candida albicans

<400> SEQUENCE: 38

Met Ser Val Ala Ser Asn Pro Tyr Gly Pro Asn Pro Ser Asp Phe Leu
1               5                   10                  15

Ser Asn Val Asn Lys Phe Glu Val Ile Glu Ser Thr Leu Arg Glu Gly
            20                  25                  30

Glu Gln Phe Ala Asn Ala Phe Phe Thr Thr Glu Lys Lys Ile Glu Ile
        35                  40                  45

Ala Lys Ala Leu Asp Asp Phe Gly Val Asp Tyr Ile Glu Leu Thr Ser
    50                  55                  60

Pro Val Ala Ser Glu Gln Ser Arg Arg Asp Cys Glu Ala Ile Cys Lys
65                  70                  75                  80

Leu Gly Leu Lys Ala Lys Ile Leu Thr His Ile Arg Cys His Met Asp
                85                  90                  95

Asp Ala Arg Val Ala Val Glu Thr Gly Val Asp Gly Val Asp Val Val
            100                 105                 110

Ile Gly Thr Ser Gln Phe Leu Arg Gln Tyr Ser His Gly Lys Asp Met

```
                115                 120                 125
Asn Tyr Ile Ala Gln Ser Ala Ile Glu Val Ile Glu Phe Val Lys Ser
    130                 135                 140

Lys Gly Ile Glu Ile Arg Phe Ser Ser Glu Asp Ser Phe Arg Ser Asp
145                 150                 155                 160

Ile Val Asp Leu Leu Asn Ile Tyr Arg Thr Val Asp Lys Ile Gly Val
                165                 170                 175

Asn Arg Val Gly Ile Ala Asp Thr Val Gly Cys Ala Asn Pro Arg Gln
            180                 185                 190

Val Tyr Glu Leu Val Lys Thr Leu Lys Ser Val Ser Cys Asp Ile
        195                 200                 205

Glu Cys His Phe His Asn Asp Thr Gly Cys Ala Ile Ala Asn Ala Tyr
    210                 215                 220

Thr Ala Leu Glu Ala Gly Ala Lys Leu Ile Asp Val Ser Val Leu Gly
225                 230                 235                 240

Ile Gly Glu Arg Asn Gly Ile Thr Pro Leu Gly Ala Leu Met Ala Arg
                245                 250                 255

Met Ile Thr Ala Asp Arg Asp Tyr Val Leu Ser Lys Tyr Lys Leu His
            260                 265                 270

Lys Leu Arg Asp Leu Glu Asn Leu Val Ala Asp Ala Val Gln Ile Asn
        275                 280                 285

Ile Pro Phe Asn Asn Pro Ile Thr Gly Phe Cys Ala Phe Thr His Lys
    290                 295                 300

Ala Gly Ile His Ala Lys Ala Ile Leu Ala Asn Pro Ser Thr Tyr Glu
305                 310                 315                 320

Ile Leu Asn Pro Asn Asp Phe Gly Leu Thr Arg Tyr Ile His Phe Ala
                325                 330                 335

Asn Arg Leu Thr Gly Trp Asn Ala Ile Lys Ser Arg Val Asp Gln Leu
            340                 345                 350

Asn Leu His Leu Thr Asp Asp Gln Val Lys Glu Val Thr Asn Lys Ile
        355                 360                 365

Lys Lys Leu Gly Asp Val Arg Gln Leu Asn Ile Asp Asp Val Asp Ser
    370                 375                 380

Ile Ile Lys Asp Phe His Ala Glu Gln Ser Thr Thr Asn Thr Pro Leu
385                 390                 395                 400

Leu Lys Pro Val Glu Asp Asp Glu Gly Pro Glu Ile Lys Lys Gln Lys
                405                 410                 415

Val

<210> SEQ ID NO 39
<211> LENGTH: 1287
<212> TYPE: DNA
<213> ORGANISM: Candida albicans

<400> SEQUENCE: 39
atggttgacg gatataaaga agtatcagaa tcatttgatc gttccaaaat ccaacataac      60
ccttatggtc ctaatccagg tgattttctt tcgaatgttg caattttca  attgattgaa     120 tcaactttga gagaaggtga acagtttgcc aatgcatttt tcagcaccga aaccaaaatt    180
gaaattgcta agcccttaga tgattttggg gttgattata ttgaattgac ttcaccagtg    240
gcatctgaac aatcaagaaa agattgtgaa gccatttgta aattaggttt aaaagccaaa    300
atattgactc acattagatg tcatatggat gatgccagag ttgctgttga aactggggtc    360
gatggagttg atgtggttat tggaacttcc caattttta  acaatactc  tcatggtaag    420
```

-continued

```
gatatgaatt atattgcaca aagtgctatt gaagtcattg aatttgtcaa atctaaaggt    480
attgaaatcc gtttcagttc tgaagattct tttagatcag atttggttga tttattaaac    540
atttaccgta ctgttgataa aattggggtt aacagagttg gtattgctga tactgttggt    600
tgtgctaatc caagacaagt ttatgaattg gtgagaacat tgaaatcagt agtcaagtgt    660
gacattgaat gtcatttcca taatgatact ggctgtgcca ttgccaatgc atacacagct    720
ttggaaggtg gggccagatt gattgatgtt tccgtattgg gtattggtga agaaatggt     780 attactccat tgggtgggtt aatggcgaga atgattgctg ctgatcgtga atatgttttg    840
tcaaaatata aagttcataa attgagagat attgaaaatt tggttgctga ggcggttcaa    900
gttaacattc cattcaataa tccgatcact gggttctgtg ctttcactca taaagctggt    960
atccatgcta aagctatctt ggccaatcca tctacttatg aaattttgag tccaagtgat   1020
ttcggtttaa ccagatatat tcactttgct aatagattga ctggttggaa tgccatcaaa   1080
tcaagagttg atcagttgaa cttgcattta actgatgaac agtgtaaaga agtcactaac   1140
aagattaaga aattgggtga tgtcagacaa ttgaatatcg atgatgtgga ttcaatcatc   1200
aaagatttcc atgctgatat gtcaacacca cttttgaaat caaatggagc ggaagaagaa   1260
ccagatgtaa aaaacaaaa agtttaa                                        1287
```

<210> SEQ ID NO 40
<211> LENGTH: 428
<212> TYPE: PRT
<213> ORGANISM: Candida albicans

<400> SEQUENCE: 40

```
Met Val Asp Gly Tyr Lys Glu Val Ser Glu Ser Phe Asp Arg Ser Lys
1               5                   10                  15

Ile Gln His Asn Pro Tyr Gly Pro Asn Pro Gly Asp Phe Leu Ser Asn
            20                  25                  30

Val Gly Asn Phe Gln Leu Ile Glu Ser Thr Leu Arg Glu Gly Glu Gln
        35                  40                  45

Phe Ala Asn Ala Phe Phe Ser Thr Glu Thr Lys Ile Glu Ile Ala Lys
    50                  55                  60

Ala Leu Asp Asp Phe Gly Val Asp Tyr Ile Glu Leu Thr Ser Pro Val
65                  70                  75                  80

Ala Ser Glu Gln Ser Arg Lys Asp Cys Glu Ala Ile Cys Lys Leu Gly
                85                  90                  95

Leu Lys Ala Lys Ile Leu Thr His Ile Arg Cys His Met Asp Asp Ala
            100                 105                 110

Arg Val Ala Val Glu Thr Gly Val Asp Gly Val Asp Val Ile Gly
        115                 120                 125

Thr Ser Gln Phe Leu Arg Gln Tyr Ser His Gly Lys Asp Met Asn Tyr
    130                 135                 140

Ile Ala Gln Ser Ala Ile Glu Val Ile Glu Phe Val Lys Ser Lys Gly
145                 150                 155                 160

Ile Glu Ile Arg Phe Ser Ser Glu Asp Ser Phe Arg Ser Asp Leu Val
                165                 170                 175

Asp Leu Leu Asn Ile Tyr Arg Thr Val Asp Lys Ile Gly Val Asn Arg
            180                 185                 190

Val Gly Ile Ala Asp Thr Val Gly Cys Ala Asn Pro Arg Gln Val Tyr
        195                 200                 205

Glu Leu Val Arg Thr Leu Lys Ser Val Val Lys Cys Asp Ile Glu Cys
    210                 215                 220
```

```
His Phe His Asn Asp Thr Gly Cys Ala Ile Ala Asn Ala Tyr Thr Ala
225                 230                 235                 240

Leu Glu Gly Gly Ala Arg Leu Ile Asp Val Ser Val Leu Gly Ile Gly
            245                 250                 255

Glu Arg Asn Gly Ile Thr Pro Leu Gly Gly Leu Met Ala Arg Met Ile
        260                 265                 270

Ala Ala Asp Arg Glu Tyr Val Leu Ser Lys Tyr Lys Val His Lys Leu
    275                 280                 285

Arg Asp Ile Glu Asn Leu Val Ala Glu Ala Val Gln Val Asn Ile Pro
290                 295                 300

Phe Asn Asn Pro Ile Thr Gly Phe Cys Ala Phe Thr His Lys Ala Gly
305                 310                 315                 320

Ile His Ala Lys Ala Ile Leu Ala Asn Pro Ser Thr Tyr Glu Ile Leu
            325                 330                 335

Ser Pro Ser Asp Phe Gly Leu Thr Arg Tyr Ile His Phe Ala Asn Arg
        340                 345                 350

Leu Thr Gly Trp Asn Ala Ile Lys Ser Arg Val Asp Gln Leu Asn Leu
    355                 360                 365

His Leu Thr Asp Glu Gln Cys Lys Glu Val Thr Asn Lys Ile Lys Lys
370                 375                 380

Leu Gly Asp Val Arg Gln Leu Asn Ile Asp Asp Val Asp Ser Ile Ile
385                 390                 395                 400

Lys Asp Phe His Ala Asp Met Ser Thr Pro Leu Leu Lys Ser Asn Gly
            405                 410                 415

Ala Glu Glu Glu Pro Asp Val Lys Lys Gln Lys Val
        420                 425

<210> SEQ ID NO 41
<211> LENGTH: 1827
<212> TYPE: DNA
<213> ORGANISM: Candida glabrata

<400> SEQUENCE: 41
atgagagcta ccgttatcag actctcgagg gctgcgaagt caattccgcc cgtgaaattg      60
gcgtataaga acatgttgaa agacccttcc atcaaataca aaccattctc cattgctcca     120
aagcttactg acaggaaatg gccagacaat accattacca aggcaccaag gtggttgtct     180
acagacttga gagacggtaa ccagtctctc ccggacccga tgtccattga gcagaagaaa     240
gagtacttcc acaagctggt ggagattggc ttcaaagaga tagaagtcag ttttccatct     300
gcctcgcaga ccgacttcga tttcacaagg tacgctgtgg agaatgctcc agatgatgtt     360
accatacagt gtcttgtgca atccagagaa cacttgatca agagaactgt ggagtcgttg     420
actggtgcca agcgtgccac tatacatact tacttggcca ccagcgacat gttcagagag     480
atagtcttca acatgtctaa ggaagacgct atcgccaaag ccgtcgaagc cactaaactg     540
gtcagaagct tgaccaagga cgaccttcct cagcaggcta cccgttggtc ctatgagttc     600
tctccagaat gtttcagtga taccccagtc gaatttgccg ttgaaatctg tgaagcagta     660
aaagctgcct gggaaccaac cgaggacaac cctatcatat ttaacctacc tgccacagtc     720
gaggtcgcct ctccaaacat ctacgctgac caaatcgaat atttctgcac acacatcacc     780
gaaagagaga aggtgtgtgt ctctacgcat acccacaacg accgtggctg cggtgttgcc     840
gctaccgaac ttggtataat ggcaggcgct gatcgtgttg aaggttgtgt cttcggaaat     900
ggtgaacgta ctggtaacgt tgacttggta accgtggcat tgaacatgta cacgcaaggt     960
gtctctccta acttggactt ctccgacata aggtctgtaa tcgaggttgt tgaacgttgt    1020
```

```
aacaaattgc ctgtcccagc cagagcacca tacggtggtg acttggtcgt atgtgcattc  1080
tctggttctc accaggacgc catcaagaag ggtttctcgg ttcaacaaaa gaagcgtgac  1140
caaggcgaca ttcaatggag aatcccatat ttgccattgg atccaaagga tatcggccgt  1200
gactacgaag ctgtcatcag agtcaactct caatctggta agggtggtgc tgcttgggtt  1260
gtcctaagag ccttgggcct agacatgcca agaaccatgc aaattgagtt ctccaccagt  1320
gtacaagaac acgctgactc tctaggtaga gaactaaagg ccgaagagat tgtcaacttg  1380
tttaaggaat cttacaacta caacaacgaa atcttccaac atatctcttt ggttgattac  1440
aacgttgaga aattcggtgc tgagcgcaga attctaaatg gtcaagttga atcaatggt  1500 gaagttgtcg acatcaaggg taccggtaac ggtccaatct cttctttggt cgatgctttg  1560
tccaacttat tgaacatcaa acttggtgtc agcaactata gtgaacactc tttgggttca  1620
ggttcatcca ctcaagccgc ttctttcatc aacttaactt acagacgtga tgaagataat  1680
gaaaaggctt accaatgggg tgtaggtgtg tctgaggatt ttggtgatgc ttctgtcaag  1740
gcaatctttg ccactttgaa ttctgtaatt caaaaggtg acattagtat cccaaagtct  1800
aagaaggctg cctctggttc tgcttaa                                      1827
```

<210> SEQ ID NO 42
<211> LENGTH: 608
<212> TYPE: PRT
<213> ORGANISM: Candida glabrata

<400> SEQUENCE: 42

```
Met Arg Ala Thr Val Ile Arg Leu Ser Arg Ala Ala Lys Ser Ile Pro
1               5                   10                  15

Pro Val Lys Leu Ala Tyr Lys Asn Met Leu Lys Asp Pro Ser Ile Lys
            20                  25                  30

Tyr Lys Pro Phe Ser Ile Ala Pro Lys Leu Thr Asp Arg Lys Trp Pro
        35                  40                  45

Asp Asn Thr Ile Thr Lys Ala Pro Arg Trp Leu Ser Thr Asp Leu Arg
    50                  55                  60

Asp Gly Asn Gln Ser Leu Pro Asp Pro Met Ser Ile Glu Gln Lys Lys
65                  70                  75                  80

Glu Tyr Phe His Lys Leu Val Glu Ile Gly Phe Lys Glu Ile Glu Val
                85                  90                  95

Ser Phe Pro Ser Ala Ser Gln Thr Asp Phe Asp Phe Thr Arg Tyr Ala
            100                 105                 110

Val Glu Asn Ala Pro Asp Asp Val Thr Ile Gln Cys Leu Val Gln Ser
        115                 120                 125

Arg Glu His Leu Ile Arg Arg Thr Val Glu Ser Leu Thr Gly Ala Lys
    130                 135                 140

Arg Ala Thr Ile His Thr Tyr Leu Ala Thr Ser Asp Met Phe Arg Glu
145                 150                 155                 160

Ile Val Phe Asn Met Ser Lys Glu Asp Ala Ile Ala Lys Ala Val Glu
                165                 170                 175

Ala Thr Lys Leu Val Arg Ser Leu Thr Lys Asp Asp Pro Ser Gln Gln
            180                 185                 190

Ala Thr Arg Trp Ser Tyr Glu Phe Ser Pro Glu Cys Phe Ser Asp Thr
        195                 200                 205

Pro Val Glu Phe Ala Val Glu Ile Cys Glu Ala Val Lys Ala Ala Trp
    210                 215                 220

Glu Pro Thr Glu Asp Asn Pro Ile Ile Phe Asn Leu Pro Ala Thr Val
```

```
            225                 230                 235                 240
Glu Val Ala Ser Pro Asn Ile Tyr Ala Asp Gln Ile Glu Tyr Phe Cys
                    245                 250                 255

Thr His Ile Thr Glu Arg Glu Lys Val Cys Val Ser Thr His Thr His
                260                 265                 270

Asn Asp Arg Gly Cys Gly Val Ala Ala Thr Glu Leu Gly Ile Met Ala
            275                 280                 285

Gly Ala Asp Arg Val Glu Gly Cys Val Phe Gly Asn Gly Glu Arg Thr
        290                 295                 300

Gly Asn Val Asp Leu Val Thr Val Ala Leu Asn Met Tyr Thr Gln Gly
305                 310                 315                 320

Val Ser Pro Asn Leu Asp Phe Ser Asp Ile Arg Ser Val Ile Glu Val
                325                 330                 335

Val Glu Arg Cys Asn Lys Leu Pro Val Pro Ala Arg Ala Pro Tyr Gly
                340                 345                 350

Gly Asp Leu Val Val Cys Ala Phe Ser Gly Ser His Gln Asp Ala Ile
            355                 360                 365

Lys Lys Gly Phe Ser Val Gln Gln Lys Lys Arg Asp Gln Gly Asp Ile
        370                 375                 380

Gln Trp Arg Ile Pro Tyr Leu Pro Leu Asp Pro Lys Asp Ile Gly Arg
385                 390                 395                 400

Asp Tyr Glu Ala Val Ile Arg Val Asn Ser Gln Ser Gly Lys Gly Gly
                405                 410                 415

Ala Ala Trp Val Val Leu Arg Ala Leu Gly Leu Asp Met Pro Arg Thr
                420                 425                 430

Met Gln Ile Glu Phe Ser Thr Ser Val Gln Glu His Ala Asp Ser Leu
            435                 440                 445

Gly Arg Glu Leu Lys Ala Glu Glu Ile Val Asn Leu Phe Lys Glu Ser
        450                 455                 460

Tyr Asn Tyr Asn Asn Glu Ile Phe Gln His Ile Ser Leu Val Asp Tyr
465                 470                 475                 480

Asn Val Glu Lys Phe Gly Ala Glu Arg Arg Ile Leu Asn Gly Gln Val
                485                 490                 495

Glu Ile Asn Gly Glu Val Val Asp Ile Lys Gly Thr Gly Asn Gly Pro
            500                 505                 510

Ile Ser Ser Leu Val Asp Ala Leu Ser Asn Leu Leu Asn Ile Lys Leu
        515                 520                 525

Gly Val Ser Asn Tyr Ser Glu His Ser Leu Gly Ser Gly Ser Ser Thr
        530                 535                 540

Gln Ala Ala Ser Phe Ile Asn Leu Thr Tyr Arg Arg Asp Glu Asp Asn
545                 550                 555                 560

Glu Lys Ala Tyr Gln Trp Gly Val Gly Val Ser Glu Asp Val Gly Asp
                565                 570                 575

Ala Ser Val Lys Ala Ile Phe Ala Thr Leu Asn Ser Val Ile Gln Lys
            580                 585                 590

Gly Asp Ile Ser Ile Pro Lys Ser Lys Lys Ala Ala Ser Gly Ser Ala
        595                 600                 605

<210> SEQ ID NO 43
<211> LENGTH: 1818
<212> TYPE: DNA
<213> ORGANISM: Candida glabrata

<400> SEQUENCE: 43
atgagacaaa caattccaaa ttttgcagag catgtctctc gtgcagccaa gacaattgct      60
```

```
ccagtcaaat tgggtttcaa gaatatgctt gctaatccaa gtgtcaaata tagaccattt    120
caaggcccaa aattgacaaa tagacaatgg cctaacaaga caattaagag agctccaaga    180
tggctttcta ccgatttgag agatggtaac caatctctcc cggaccctat gtcagtagag    240
caaaagaaag aatactttca caaacttgtt gaaatcgggt ttaaagagat agaagtcagt    300
tttccgtcag catcgcaaac cgatttcgat tcacaagat acgctgtaga aaacgcacca     360
gacgatgttt ctatccagtg tcttgtccaa tctagggagc atctgatcaa gaggacagtt    420
gaagcattga ccggtgctaa gcgtgctacc atacatacat acttggccac aagtgatatg    480
ttccgtgaga ttgttttcaa tatgtctcaa gaagaagcca ttgccaaagc tgtagaagca    540
accaagctag tacggaaatt gaccaaggat gatccatctc aaaaagcaac taggtggtct    600
tacgaatttt ctccagaatg ttttagtgat acaccagtag aatttgccgt tgaaatctgt    660
gaggctgtga agctgcatg ggaaccaacg gttgataatc ctattatctt taacttacct     720
gcaaccgttg aagtagcaac tccaaatgta tacgctgatc agatcgaata cttctctact    780
catattagcg aacgtgaaaa ggtttgtatc tccacccatg ctcacaatga ccgtggctgt    840
ggcgttgctg ctacagagtt gggtatcttg gctggtgctg atcgagttga aggctgtata    900
ttcgggaatg gtgaacgtac aggtaatgtc gacctggtaa ccgtcgcctt aaacatgtat    960
acccagggtg tttctcccgg tcttgacttt tcagacatga aagtgttat cgagatcgtt    1020 gaacgttgta caagattcc agtaccagct agagctccat atggtggtga ccttgttgtt    1080
tgcgcctttt caggctctca ccaagatgct attaaaaaag gatttgcttt acaacaaaag    1140
aagcgtgctc aaggtgaaac tttatggagg attccatatt tgccattaga tccaaaggac    1200 atcgccgtg actatgaagc ggttatcagg gtcaactcac aatctggtaa gggtggtgct    1260
gcttgggtta ttttaaggtc tttgggtcta gacaccccaa gaaacatgca aatgcaattc    1320
tctaccattg tgcaaaatga agctgacaca agaggcaagg aattatctgc agaggagatt    1380
actgcattat tcaagtctac ctataattac aacaacgaaa cccatcaata cgtatctttg    1440
ctcgactatg atgtgaagaa gattgacaac gaccgtagaa tcctaacagg gcaagttgaa    1500
attaacgaca agatcattcc aattaagggt attggtaacg gtcctatttc ttctttagta    1560
gatgccctat caaacttatt caacgtcaaa tttggtgttg aaaactatac agaacatgct    1620
ttaggttccg gttccaaaac ccaagccgcc tctttcattc acatctctta cagagatgct    1680
gctaccaatg aaaaggagta cagttggggt gtcggtgtct ctgaagatgt tggtgaagca    1740
tctgttaggg ccatttctc aaccattaac agcattatcc attcaggtga agtcactctt    1800
cctactgaaa acaattag                                                  1818
```

<210> SEQ ID NO 44  
<211> LENGTH: 605  
<212> TYPE: PRT  
<213> ORGANISM: Candida glabrata

<400> SEQUENCE: 44

Met Arg Gln Thr Ile Pro Asn Phe Ala Glu His Val Ser Arg Ala Ala
1               5                   10                  15

Lys Thr Ile Ala Pro Val Lys Leu Gly Phe Lys Asn Met Leu Ala Asn
            20                  25                  30

Pro Ser Val Lys Tyr Arg Pro Phe Gln Gly Pro Lys Leu Thr Asn Arg
        35                  40                  45

Gln Trp Pro Asn Lys Thr Ile Lys Arg Ala Pro Arg Trp Leu Ser Thr
    50                  55                  60

```
Asp Leu Arg Asp Gly Asn Gln Ser Leu Pro Asp Pro Met Ser Val Glu
 65                  70                  75                  80

Gln Lys Lys Glu Tyr Phe His Lys Leu Val Glu Ile Gly Phe Lys Glu
                 85                  90                  95

Ile Glu Val Ser Phe Pro Ser Ala Ser Gln Thr Asp Phe Asp Phe Thr
            100                 105                 110

Arg Tyr Ala Val Glu Asn Ala Pro Asp Val Ser Ile Gln Cys Leu
            115                 120                 125

Val Gln Ser Arg Glu His Leu Ile Lys Arg Thr Val Glu Ala Leu Thr
        130                 135                 140

Gly Ala Lys Arg Ala Thr Ile His Thr Tyr Leu Ala Thr Ser Asp Met
145                 150                 155                 160

Phe Arg Glu Ile Val Phe Asn Met Ser Gln Glu Glu Ala Ile Ala Lys
                165                 170                 175

Ala Val Glu Ala Thr Lys Leu Val Arg Lys Leu Thr Lys Asp Asp Pro
            180                 185                 190

Ser Gln Lys Ala Thr Arg Trp Ser Tyr Glu Phe Ser Pro Glu Cys Phe
        195                 200                 205

Ser Asp Thr Pro Val Glu Phe Ala Val Glu Ile Cys Glu Ala Val Lys
210                 215                 220

Ala Ala Trp Glu Pro Thr Val Asp Asn Pro Ile Ile Phe Asn Leu Pro
225                 230                 235                 240

Ala Thr Val Glu Val Ala Thr Pro Asn Val Tyr Ala Asp Gln Ile Glu
                245                 250                 255

Tyr Phe Ser Thr His Ile Ser Glu Arg Glu Lys Val Cys Ile Ser Thr
            260                 265                 270

His Ala His Asn Asp Arg Gly Cys Gly Val Ala Ala Thr Glu Leu Gly
        275                 280                 285

Ile Leu Ala Gly Ala Asp Arg Val Glu Gly Cys Ile Phe Gly Asn Gly
        290                 295                 300

Glu Arg Thr Gly Asn Val Asp Leu Val Thr Val Ala Leu Asn Met Tyr
305                 310                 315                 320

Thr Gln Gly Val Ser Pro Gly Leu Asp Phe Ser Asp Met Arg Ser Val
                325                 330                 335

Ile Glu Ile Val Glu Arg Cys Asn Lys Ile Pro Val Pro Ala Arg Ala
            340                 345                 350

Pro Tyr Gly Gly Asp Leu Val Val Cys Ala Phe Ser Gly Ser His Gln
        355                 360                 365

Asp Ala Ile Lys Lys Gly Phe Ala Leu Gln Gln Lys Lys Arg Ala Gln
370                 375                 380

Gly Glu Thr Leu Trp Arg Ile Pro Tyr Leu Pro Leu Asp Pro Lys Asp
385                 390                 395                 400

Ile Gly Arg Asp Tyr Glu Ala Val Ile Arg Val Asn Ser Gln Ser Gly
                405                 410                 415

Lys Gly Gly Ala Ala Trp Val Ile Leu Arg Ser Leu Gly Leu Asp Thr
            420                 425                 430

Pro Arg Asn Met Gln Met Gln Phe Ser Thr Ile Val Gln Asn Glu Ala
        435                 440                 445

Asp Thr Arg Gly Lys Glu Leu Ser Ala Glu Ile Thr Ala Leu Phe
450                 455                 460

Lys Ser Thr Tyr Asn Tyr Asn Asn Glu Thr His Gln Tyr Val Ser Leu
465                 470                 475                 480

Leu Asp Tyr Asp Val Lys Lys Ile Asp Asn Asp Arg Arg Ile Leu Thr
```

```
                     485                 490                 495
Gly Gln Val Glu Ile Asn Asp Lys Ile Pro Ile Lys Gly Ile Gly
            500                 505                 510

Asn Gly Pro Ile Ser Ser Leu Val Asp Ala Leu Ser Asn Leu Phe Asn
        515                 520                 525

Val Lys Phe Gly Val Glu Asn Tyr Thr Glu His Ala Leu Gly Ser Gly
    530                 535                 540

Ser Lys Thr Gln Ala Ala Ser Phe Ile His Ile Ser Tyr Arg Asp Ala
545                 550                 555                 560

Ala Thr Asn Glu Lys Glu Tyr Ser Trp Gly Val Gly Val Ser Glu Asp
                565                 570                 575

Val Gly Glu Ala Ser Val Arg Ala Ile Phe Ser Thr Ile Asn Ser Ile
            580                 585                 590

Ile His Ser Gly Glu Val Thr Leu Pro Thr Glu Asn Asn
        595                 600                 605

<210> SEQ ID NO 45
<211> LENGTH: 1752
<212> TYPE: DNA
<213> ORGANISM: Kluyveromyces lactis

<400> SEQUENCE: 45
atgccattct acaaagatcc ttcagtgaag tataaaccat tcgttagcaa cgtcaaatta      60
caggacagga atggcctag taaaaccctt aataaggctc aagatggtt agctaccgat       120
ttaagagatg ggaatcagtc tttacctgac ccgatgaatt tggaagagaa gaaactgatg     180
ctcgataagt tatgcgaatt gggtttcaaa gagattgaag ttgctttccc tagtgcttct     240
aatatcgatt ccaattcac tcaatatgca gtgaaaaacg taccagaaga cgtttccatt     300
caagttcttt ctccatgtcg tgaacccttg atcgaacgta ccgttgaatc tttggtcggt     360
gccaagagag ccattgtaca tatctatctc gcgacatcac catgtttcag agaaatcgtt     420
ttcaacaata tgtctcatga agaaagtatt gaaaaggctg tgaaatgtgc caaacttgtt     480
aggtccttga caaaagacca tccggataga caagataccc attggtcatt tgagttttct     540
ccagaaacgt tcagcgatag tgaaccggat ttcgttctag agatttgtga agctgttaag     600
gctgcttggg gacccactga agataatcca atcattttca atttgccagc taccgtcgag     660
atggctacac caaacgtgta cgctgaccaa atcgaatatt tcgctcaaag tatctccgaa     720
cgtgagaaag tatgtatctc tctccatcca cataacgatc gtgggtgtgc cgtggcagct     780
gcagaattag ctcaaatggc tggtgcagat cgtgtcgagg gatgtctctt cggtaacggt     840
gaacgtaccg gtaacgttga tttggttacc ttggcattaa acctctacac acagggtgta     900
tctccaaacc tcgatttctc cgatatggct tctattattg aagtcgttga gaaatgtaat     960
aagattcccg tgcatgctag agcaccctac ggaggacaac ttgtcgtttg tgcattcagt    1020
ggttctcatc aagatgccat caaaaagggt ttcgaaaaat acgacaacaa ggttaaggct    1080
ttacaagaaa aagagggtcc agatgcagtg gtaccttgga aatgccata tctccccttg    1140
gatcctcagg atattggaag aacgtatgag gctatcatca gagtcaactc gcaatcaggt    1200
aaaggtggtt cttcttgggt tatcctaaag aacttggagc tagatttacc aagagatcta    1260
caaattgcat actctaagat cgttcaaaat gaaactgaga tagtcggtag agagttgaag    1320
agcgatgaac taatctcttt attcgagaaa tcgtatttcg ttggatctca ttcaactact    1380
ggtaaattca gtttatcga ctataaatat gacaaatctc cggagaattt cactctttcg    1440
gtgcagctat cagatggaac tactcaatgg gatttggaag gtactggtaa cggtccaatc    1500
```

-continued

```
tcttctttca tcgatgctgt gaataaaaac ttcaaaacta atcttgatgt gaaaaactat    1560
catgagcatt ccttgggtaa gagttccgat tcgagagctg ctactatat ctctgtctct     1620 catgaaggat tgttcaatg gggtgttggt attcatgagg atactactct ggcttcattc     1680
ttggcgttgt tatcttgtat aaacggtctt gatagggcaa agaacttcac tgtcaattca    1740
gctgccaatt ga                                                         1752
```

<210> SEQ ID NO 46
<211> LENGTH: 583
<212> TYPE: PRT
<213> ORGANISM: Kluyveromyces lactis

<400> SEQUENCE: 46

```
Met Pro Phe Tyr Lys Asp Pro Ser Val Lys Tyr Lys Pro Phe Val Ser
1               5                  10                  15

Asn Val Lys Leu Gln Asp Arg Lys Trp Pro Ser Lys Thr Leu Asn Lys
            20                  25                  30

Ala Pro Arg Trp Leu Ala Thr Asp Leu Arg Asp Gly Asn Gln Ser Leu
        35                  40                  45

Pro Asp Pro Met Asn Leu Glu Glu Lys Lys Leu Met Leu Asp Lys Leu
    50                  55                  60

Cys Glu Leu Gly Phe Lys Glu Ile Glu Val Ala Phe Pro Ser Ala Ser
65                  70                  75                  80

Asn Ile Asp Phe Gln Phe Thr Gln Tyr Ala Val Lys Asn Val Pro Glu
                85                  90                  95

Asp Val Ser Ile Gln Val Leu Ser Pro Cys Arg Glu Pro Leu Ile Glu
            100                 105                 110

Arg Thr Val Glu Ser Leu Val Gly Ala Lys Arg Ala Ile Val His Ile
        115                 120                 125

Tyr Leu Ala Thr Ser Pro Cys Phe Arg Glu Ile Val Phe Asn Asn Met
    130                 135                 140

Ser His Glu Glu Ser Ile Glu Lys Ala Val Lys Cys Ala Lys Leu Val
145                 150                 155                 160

Arg Ser Leu Thr Lys Asp His Pro Asp Arg Gln Asp Thr His Trp Ser
                165                 170                 175

Phe Glu Phe Ser Pro Glu Thr Phe Ser Asp Ser Glu Pro Asp Phe Val
            180                 185                 190

Leu Glu Ile Cys Glu Ala Val Lys Ala Ala Trp Gly Pro Thr Glu Asp
        195                 200                 205

Asn Pro Ile Ile Phe Asn Leu Pro Ala Thr Val Glu Met Ala Thr Pro
    210                 215                 220

Asn Val Tyr Ala Asp Gln Ile Glu Tyr Phe Ala Gln Ser Ile Ser Glu
225                 230                 235                 240

Arg Glu Lys Val Cys Ile Ser Leu His Pro His Asn Asp Arg Gly Cys
                245                 250                 255

Ala Val Ala Ala Ala Glu Leu Ala Gln Met Ala Gly Ala Asp Arg Val
            260                 265                 270

Glu Gly Cys Leu Phe Gly Asn Gly Glu Arg Thr Gly Asn Val Asp Leu
        275                 280                 285

Val Thr Leu Ala Leu Asn Leu Tyr Thr Gln Gly Val Ser Pro Asn Leu
    290                 295                 300

Asp Phe Ser Asp Met Ala Ser Ile Ile Glu Val Val Glu Lys Cys Asn
305                 310                 315                 320

Lys Ile Pro Val His Ala Arg Ala Pro Tyr Gly Gly Gln Leu Val Val
```

```
                        325                 330                 335
Cys Ala Phe Ser Gly Ser His Gln Asp Ala Ile Lys Lys Gly Phe Glu
                    340                 345                 350
Lys Tyr Asp Asn Lys Val Lys Ala Leu Gln Glu Lys Glu Gly Pro Asp
                355                 360                 365
Ala Val Val Pro Trp Lys Met Pro Tyr Leu Pro Leu Asp Pro Gln Asp
            370                 375                 380
Ile Gly Arg Thr Tyr Glu Ala Ile Ile Arg Val Asn Ser Gln Ser Gly
385                 390                 395                 400
Lys Gly Gly Ser Ser Trp Val Ile Leu Lys Asn Leu Glu Leu Asp Leu
                405                 410                 415
Pro Arg Asp Leu Gln Ile Ala Tyr Ser Lys Ile Val Gln Asn Glu Thr
            420                 425                 430
Glu Ile Val Gly Arg Glu Leu Lys Ser Asp Glu Leu Ile Ser Leu Phe
        435                 440                 445
Glu Lys Ser Tyr Phe Val Gly Ser His Ser Thr Thr Gly Lys Phe Lys
    450                 455                 460
Phe Ile Asp Tyr Lys Tyr Asp Lys Ser Pro Glu Asn Phe Thr Leu Ser
465                 470                 475                 480
Val Gln Leu Ser Asp Gly Thr Thr Gln Trp Asp Leu Glu Gly Thr Gly
                485                 490                 495
Asn Gly Pro Ile Ser Ser Phe Ile Asp Ala Val Asn Lys Asn Phe Lys
            500                 505                 510
Thr Asn Leu Asp Val Lys Asn Tyr His Glu His Ser Leu Gly Lys Ser
        515                 520                 525
Ser Asp Ser Arg Ala Ala Thr Tyr Ile Ser Val Ser His Glu Gly Phe
    530                 535                 540
Val Gln Trp Gly Val Gly Ile His Glu Asp Thr Thr Leu Ala Ser Phe
545                 550                 555                 560
Leu Ala Leu Leu Ser Cys Ile Asn Gly Leu Asp Arg Ala Lys Asn Phe
                565                 570                 575
Thr Val Asn Ser Ala Ala Asn
            580

<210> SEQ ID NO 47
<211> LENGTH: 1830
<212> TYPE: DNA
<213> ORGANISM: Kluyveromyces lactis

<400> SEQUENCE: 47
atgatattca ggaacaccgt tgtgcgttta gcacaggctg ggaaaaaagc tattcctcca      60
gtgaaactag cgtacaagaa tatgctaaaa gatccatcga cgaaatatag accataccca     120
cagatcaact tggaaaatag acaatggcct tcgaagacca tcaccaaggc tcctaggtgg     180
ctttctaccg atctaagaga cgggaatcaa tctttaccag atcctatgtc tgtcgagcag     240
aagaaggaat atttccataa gttgattgag attggtttca agaaattgaa ggtctcattc     300
ccatctgcgt cgcaaacaga tttcgacttc acaagatacg ctgttgaaaa cgccccagaa     360 gatgttttcca ttcaatgtct tgttcaatcg agagaacatt tgattagaag aacagttgaa     420
gctttgcatg gtgctaagaa agccaccatc catacgtatt tggccacctc cgacatgttc     480
cgtgacattg tgttcaacat gtcccaagaa gaagctattg ctaaagctgt ggaagccacc     540
aagttagtta ggaaattgac caaggatgat ccttcgcaaa gtgctacaca atggacttac     600
cagttctctc cagaatgttt cagtgataca cctgtagaat ttgctgttga gatctgtgaa     660
```

-continued

```
gccgtaaagg ctgcttggga accaactgag gaaaacccaa tcattttcaa cctacctgct    720
accgtcgaag tcgctactcc aaacatttac gctgatcaaa ttgaatactt ttcaactcac    780
atatctgaac gtgaaaaggt ctgtatctcc acacatgcgc acaacgaccg tggctgtggt    840
gttgctgctt ctgaactagg tattttggct ggtgctgacc gtgtcgaagg ttgtttattc    900
ggtaatggtg aacgtactgg taacgttgac ttggttactg tcgcattgaa catgtacact    960
caaggtgttt ctccagaatt agacttatct gatattaact cagtcattga agtagtggaa   1020
agatgtaaca agattgcagt ttcaccaaga gccccatatg gtggtgactt ggtcgtttgt   1080
gctttcagtg ttctcatca agatgctatc aaaaagggtt tcaatcttca agaaaagaga   1140
cgtagtcaag gtgatactct atggaaaatt ccatacttgc cattggatcc aaaggatatc   1200
ggtagagact acgaagctgt catccgtgtc aactctcaat ctggtaaggg gggtgccgct   1260
tgggttgtct tgagatcttt gggcctagat ttgccaagaa acttgcaaat tgaatttttcc   1320 actcaagtgc aagaaaaggc tgatgctcta ggtaaggaac taaaggcaaa cgaaattgtc   1380
agcaccttca agtcgttata caacctcgat ggaagcgcct ccaacatttc tttgttagaa   1440
tacaatgttt ctaaagtaca gggtgatcag aagagttttg ttggtcaagt ccagatcgac   1500
aacgaagtcg tcggcattga aggtctcgga aacggtccaa tttcctctct aatcgatgcg   1560
ttgtcaaatt tgctcggtgt taaacttggt gttgccaact acaccgaaca ttccttagga   1620
tctggttctt caacaaaggc tgcttcttac gtgcatattg cttacagaag agaaattgac   1680
aacgaaaagg cctaccaatg gggtattggt atgtctgaag atgttggaga ggcttctgcc   1740
aaagccatcc tttctgctgt taataacttg atcaaaaagg gcgaactaac aataccagct   1800
catcgtgact cagcctcagc atctgcatag                                   1830
```

<210> SEQ ID NO 48
<211> LENGTH: 609
<212> TYPE: PRT
<213> ORGANISM: Kluyveromyces lactis

<400> SEQUENCE: 48

```
Met Ile Phe Arg Asn Thr Val Val Arg Leu Ala Gln Ala Gly Lys Lys
1               5                   10                  15

Ala Ile Pro Pro Val Lys Leu Ala Tyr Lys Asn Met Leu Lys Asp Pro
            20                  25                  30

Ser Thr Lys Tyr Arg Pro Tyr Pro Gln Ile Asn Leu Glu Asn Arg Gln
        35                  40                  45

Trp Pro Ser Lys Thr Ile Thr Lys Ala Pro Arg Trp Leu Ser Thr Asp
    50                  55                  60

Leu Arg Asp Gly Asn Gln Ser Leu Pro Asp Pro Met Ser Val Glu Gln
65                  70                  75                  80

Lys Lys Glu Tyr Phe His Lys Leu Ile Glu Ile Gly Phe Lys Glu Ile
                85                  90                  95

Glu Val Ser Phe Pro Ser Ala Ser Gln Thr Asp Phe Asp Phe Thr Arg
            100                 105                 110

Tyr Ala Val Glu Asn Ala Pro Glu Asp Val Ser Ile Gln Cys Leu Val
        115                 120                 125

Gln Ser Arg Glu His Leu Ile Arg Arg Thr Val Glu Ala Leu His Gly
    130                 135                 140

Ala Lys Lys Ala Thr Ile His Thr Tyr Leu Ala Thr Ser Asp Met Phe
145                 150                 155                 160

Arg Asp Ile Val Phe Asn Met Ser Gln Glu Glu Ala Ile Ala Lys Ala
                165                 170                 175
```

```
Val Glu Ala Thr Lys Leu Val Arg Lys Leu Thr Lys Asp Asp Pro Ser
            180                 185                 190
Gln Ser Ala Thr Gln Trp Thr Tyr Gln Phe Ser Pro Glu Cys Phe Ser
            195                 200                 205
Asp Thr Pro Val Glu Phe Ala Val Glu Ile Cys Glu Ala Val Lys Ala
            210                 215                 220
Ala Trp Glu Pro Thr Glu Glu Asn Pro Ile Ile Phe Asn Leu Pro Ala
225                 230                 235                 240
Thr Val Glu Val Ala Thr Pro Asn Ile Tyr Ala Asp Gln Ile Glu Tyr
            245                 250                 255
Phe Ser Thr His Ile Ser Glu Arg Glu Lys Val Cys Ile Ser Thr His
            260                 265                 270
Ala His Asn Asp Arg Gly Cys Gly Val Ala Ala Ser Glu Leu Gly Ile
            275                 280                 285
Leu Ala Gly Ala Asp Arg Val Glu Gly Cys Leu Phe Gly Asn Gly Glu
            290                 295                 300
Arg Thr Gly Asn Val Asp Leu Val Thr Val Ala Leu Asn Met Tyr Thr
305                 310                 315                 320
Gln Gly Val Ser Pro Glu Leu Asp Leu Ser Asp Ile Asn Ser Val Ile
            325                 330                 335
Glu Val Val Glu Arg Cys Asn Lys Ile Ala Val Ser Pro Arg Ala Pro
            340                 345                 350
Tyr Gly Gly Asp Leu Val Val Cys Ala Phe Ser Gly Ser His Gln Asp
            355                 360                 365
Ala Ile Lys Lys Gly Phe Asn Leu Gln Glu Lys Arg Arg Ser Gln Gly
            370                 375                 380
Asp Thr Leu Trp Lys Ile Pro Tyr Leu Pro Leu Asp Pro Lys Asp Ile
385                 390                 395                 400
Gly Arg Asp Tyr Glu Ala Val Ile Arg Val Asn Ser Gln Ser Gly Lys
            405                 410                 415
Gly Gly Ala Ala Trp Val Val Leu Arg Ser Leu Gly Leu Asp Leu Pro
            420                 425                 430
Arg Asn Leu Gln Ile Glu Phe Ser Thr Gln Val Gln Glu Lys Ala Asp
            435                 440                 445
Ala Leu Gly Lys Glu Leu Lys Ala Asn Glu Ile Val Ser Thr Phe Lys
            450                 455                 460
Ser Leu Tyr Asn Leu Asp Gly Ser Ala Ser Asn Ile Ser Leu Leu Glu
465                 470                 475                 480
Tyr Asn Val Ser Lys Val Gln Asp Gln Lys Ser Phe Val Gly Gln
            485                 490                 495
Val Gln Ile Asp Asn Glu Val Val Gly Ile Glu Gly Leu Gly Asn Gly
            500                 505                 510
Pro Ile Ser Ser Leu Ile Asp Ala Leu Ser Asn Leu Leu Gly Val Lys
            515                 520                 525
Leu Gly Val Ala Asn Tyr Thr Glu His Ser Leu Gly Ser Gly Ser Ser
            530                 535                 540
Thr Lys Ala Ala Ser Tyr Val His Ile Ala Tyr Arg Arg Glu Ile Asp
545                 550                 555                 560
Asn Glu Lys Ala Tyr Gln Trp Gly Ile Gly Met Ser Glu Asp Val Gly
            565                 570                 575
Glu Ala Ser Ala Lys Ala Ile Leu Ser Ala Val Asn Asn Leu Ile Lys
            580                 585                 590
Lys Gly Glu Leu Thr Ile Pro Ala His Arg Asp Ser Ala Ser Ala Ser
```

595                 600                 605
Ala

<210> SEQ ID NO 49
<211> LENGTH: 1341
<212> TYPE: DNA
<213> ORGANISM: Yarrowia lipolytica

<400> SEQUENCE: 49
atgtgcgcaa cagataacgc ccccgccgct aacgctgctc ctgagaagcc ctccaacgtt      60
ggagtcgagg tcggtcacac cggcgagcag actaatcctt acggagccaa ccccgccgat     120
ttccttttcta acgtgtccaa gttccagctc atcgagtcca ctctgcgaga gggagagcag     180
tttgcctctg ccttctttga caccgagacc aagatcgaga ttgccaaggc tctggacgac     240
tttggtgtcg actacatcga gctgacctcc cccgcagcat cggagcagtc gcggtccgat     300
tgcgaggcca tctgcaagct cggtcttaag gccaagattc tcactcacat ccgatgccac     360
atggacgacg caagactcgc tgtctccacc ggtgtcgatg tgtcgatgt cgtcattggt     420
acctcccagt cctgcgaca gtactcccac ggcaaggaca tgaactacat tgcacagtcc     480
gctgtcgagg tcattgagtt tgtcaagagc cacggcattg agatccgatt ctcctccgag     540
gattctttcc gatccgacct ggtcgatctc ctcaacatct accgaactgt cgacaagatt     600
ggtgtcaacc gagtcggtat tgctgacact gttggatgcg ccaaccccg acaggtctac     660
gagcttgtcc gaaccctcaa gtccgttgtc tcgtgcgaca ttgagtgcca tttccacaac     720
gacaccggct gtgccattgc caacgcctac accgccctcg aggctggtgc caacctcatc     780
gatgtctccg ttctcggtat cggtgagcga aacggtatca cctctctcgg tggtctgatg     840
gctcgaatga ttgctgctga ccgagactac gttctctcca agtacaagct gcacaagctg     900
cgagacctcg agaacctcgt cgccgacgcc gtccaggtca catcccctt caacaacccc     960
atcaccggtt tctgcgcctt cacccacaag gccggtatcc acgccaaggc cattctcgcc    1020
aaccccctcca cttacgagat tctcaacccc gccgatttcg gtctgacccg atacatccac    1080
tttgccaacc gtcttaccgg ctggaacgcc atcaagtcgc gagttgacca gctcaacctg    1140
cacctgaccg acgcccagtg caaggatgtc actgccaaga tcaagaagct tggtgacgtt    1200
cgatctctca cattgacga tgttgactcc atcatccgag agttccacgc cgatgtcacc    1260
agcactccca ccgttgctgc caccgaggga cctgccgttg aggacgagcc cgccgccaag    1320
aaggccaaga ctgaagagta a                                               1341

<210> SEQ ID NO 50
<211> LENGTH: 446
<212> TYPE: PRT
<213> ORGANISM: Yarrowia lipolytica

<400> SEQUENCE: 50

Met Cys Ala Thr Asp Asn Ala Pro Ala Ala Asn Ala Ala Pro Glu Lys
1               5                   10                  15

Pro Ser Asn Val Gly Val Glu Val Gly His Thr Gly Glu Gln Thr Asn
            20                  25                  30

Pro Tyr Gly Ala Asn Pro Ala Asp Phe Leu Ser Asn Val Ser Lys Phe
        35                  40                  45

Gln Leu Ile Glu Ser Thr Leu Arg Glu Gly Glu Gln Phe Ala Ser Ala
    50                  55                  60

Phe Phe Asp Thr Glu Thr Lys Ile Glu Ile Ala Lys Ala Leu Asp Asp
65                  70                  75                  80

Phe Gly Val Asp Tyr Ile Glu Leu Thr Ser Pro Ala Ala Ser Glu Gln
                85                  90                  95

Ser Arg Ser Asp Cys Glu Ala Ile Cys Lys Leu Gly Leu Lys Ala Lys
            100                 105                 110

Ile Leu Thr His Ile Arg Cys His Met Asp Asp Ala Arg Leu Ala Val
            115                 120                 125

Ser Thr Gly Val Asp Gly Val Asp Val Val Ile Gly Thr Ser Gln Phe
130                 135                 140

Leu Arg Gln Tyr Ser His Gly Lys Asp Met Asn Tyr Ile Ala Gln Ser
145                 150                 155                 160

Ala Val Glu Val Ile Glu Phe Val Lys Ser His Gly Ile Glu Ile Arg
                165                 170                 175

Phe Ser Ser Glu Asp Ser Phe Arg Ser Asp Leu Val Asp Leu Leu Asn
            180                 185                 190

Ile Tyr Arg Thr Val Asp Lys Ile Gly Val Asn Arg Val Gly Ile Ala
            195                 200                 205

Asp Thr Val Gly Cys Ala Asn Pro Arg Gln Val Tyr Glu Leu Val Arg
210                 215                 220

Thr Leu Lys Ser Val Val Ser Cys Asp Ile Glu Cys His Phe His Asn
225                 230                 235                 240

Asp Thr Gly Cys Ala Ile Ala Asn Ala Tyr Thr Ala Leu Glu Ala Gly
                245                 250                 255

Ala Asn Leu Ile Asp Val Ser Val Leu Gly Ile Gly Glu Arg Asn Gly
            260                 265                 270

Ile Thr Ser Leu Gly Gly Leu Met Ala Arg Met Ile Ala Ala Asp Arg
            275                 280                 285

Asp Tyr Val Leu Ser Lys Tyr Lys Leu His Lys Leu Arg Asp Leu Glu
290                 295                 300

Asn Leu Val Ala Asp Ala Val Gln Val Asn Ile Pro Phe Asn Asn Pro
305                 310                 315                 320

Ile Thr Gly Phe Cys Ala Phe Thr His Lys Ala Gly Ile His Ala Lys
                325                 330                 335

Ala Ile Leu Ala Asn Pro Ser Thr Tyr Glu Ile Leu Asn Pro Ala Asp
            340                 345                 350

Phe Gly Leu Thr Arg Tyr Ile His Phe Ala Asn Arg Leu Thr Gly Trp
            355                 360                 365

Asn Ala Ile Lys Ser Arg Val Asp Gln Leu Asn Leu His Leu Thr Asp
370                 375                 380

Ala Gln Cys Lys Asp Val Thr Ala Lys Ile Lys Lys Leu Gly Asp Val
385                 390                 395                 400

Arg Ser Leu Asn Ile Asp Asp Val Asp Ser Ile Ile Arg Glu Phe His
                405                 410                 415

Ala Asp Val Thr Ser Thr Pro Thr Val Ala Ala Thr Glu Gly Pro Ala
            420                 425                 430

Val Glu Asp Glu Pro Ala Ala Lys Lys Ala Lys Thr Glu Glu
            435                 440                 445

<210> SEQ ID NO 51
<211> LENGTH: 1728
<212> TYPE: DNA
<213> ORGANISM: Yarrowia lipolytica

<400> SEQUENCE: 51
atgccctacc tggccgatcc ctccaccaaa tacaagccgt tccccccgat caatctgccc      60

```
aaccggcagt ggccgtcgaa aacgctgcag aagcccccgc ggtggctgtc gacggacctg      120
cgggacggca accagtcgct gccggatccc atgaccatgg cggagaagaa ggagtacttc      180
cagaagattg tcgacattgg ctacaaggag atcgaggtgg cgttcccgtc cgcctcgcag      240
gtggactttg acttcacccg ctttgcctgc gacaccgccc cgaagacgt gtggatccag       300 gtgctggctc cgtgccgaga ggatctcatc acccgaaccg tcgagtccgt caagggcgcc      360
aacaaggcca tcatccacat ctacctcgcc acctccaagt gcttccggga cattgtcttc      420
aaccattcgc gagaagaggc cctggccaag gccgtggcat cgccaagca cgtgcgagcc       480 ctgaccaagg actcggacga ccccgagtgc aaaaagacca cctggggttt tgagttctcc      540
cccgagacct tctccgacac cgacgtggac tacgccattg aggtctgtga ggccgtgaag      600
gccgcctggg gcccctccga ggagaacccc atcattttca acctccccgc caccgtcgaa      660
atggccaccc ccaacatcta cgccgaccag attgagtact ttgccaccaa catttccgag      720
cgggagaaga tttgcatttc tctgcacccc cacaacgacc gaggttgtgc cgtggctgct      780
gccgagctgg ccagatggc cggagccgac cgagtcgagg gctgtctgtt tggcaacggc       840
gagcgaaccg gaaacgtcga cctcgtcact ctgggtctga atttgtacac ccagggcgtg      900
catcccaaga ttgacttctc cgacatcacc tcgatcatcg acattgtgga gcgatgcaac      960
aagatccccg tgcaccccg agctccctac ggcggccagc tggtggtgtg tgccttctcc      1020
ggctctcacc aggacgccat caagaagggc tttgctcgaa tcgaagacgt caaggatgag      1080
gtggccgagg caagcgaca gtggcagatc ccctacctgc ctcttgaccc caaggacatt      1140
ggccgaacct acgaggcagt cattcgagtc aattcgcagt ccggcaaggg aggagccgcc      1200
tggatcattc tgcgatctct ggagctcgat ctgccccgag gcctgcaggt tgccttctcc      1260
aaggtggtcc agaaggaggc cgaggtggtt ggacaggagc tgtctgccca gcagttggtg      1320
gatctctttg agcgagagta cggcgtgttt gaggagcagc agggcaagta ccagctggac      1380
gactttgagg tgaccaacaa gtccaaggag gagcgagagc tgaccggagc tctgaccgtc      1440
gagggcaagc gagtcgagct caagggtacc ggtaacggtc ccatttcgtc cttcctggat      1500
gccatcaaga acgcctttgg ctacaacctc gaggttctca actaccacga gcactccatt      1560
ggtaagggtt ccaagaccaa ggctgctact tacattgagc tggcctatga ggaggacggc      1620
aagacttcca gcgatggggg tgttggtatt gacgaggatg tttcccaggc ttctattcat      1680
gctattctgt ctgccatgaa cgccattagc gagtcctaca agaaataa                  1728
```

<210> SEQ ID NO 52
<211> LENGTH: 575
<212> TYPE: PRT
<213> ORGANISM: Yarrowia lipolytica

<400> SEQUENCE: 52

```
Met Pro Tyr Leu Ala Asp Pro Ser Thr Lys Tyr Lys Pro Phe Pro Pro
1               5                   10                  15

Ile Asn Leu Pro Asn Arg Gln Trp Pro Ser Lys Thr Leu Gln Lys Pro
            20                  25                  30

Pro Arg Trp Leu Ser Thr Asp Leu Arg Asp Gly Asn Gln Ser Leu Pro
        35                  40                  45

Asp Pro Met Thr Met Ala Glu Lys Lys Glu Tyr Phe Gln Lys Ile Val
    50                  55                  60

Asp Ile Gly Tyr Lys Glu Ile Glu Val Ala Phe Pro Ser Ala Ser Gln
65                  70                  75                  80

Val Asp Phe Asp Phe Thr Arg Phe Ala Cys Asp Thr Ala Pro Glu Asp
```

```
                    85                  90                  95
Val Trp Ile Gln Val Leu Ala Pro Cys Arg Glu Asp Leu Ile Thr Arg
                100                 105                 110

Thr Val Glu Ser Val Lys Gly Ala Asn Lys Ala Ile Ile His Ile Tyr
                115                 120                 125

Leu Ala Thr Ser Lys Cys Phe Arg Asp Ile Val Phe Asn His Ser Arg
                130                 135                 140

Glu Glu Ala Leu Ala Lys Ala Val Ala Cys Ala Lys His Val Arg Ala
145                 150                 155                 160

Leu Thr Lys Asp Ser Asp Pro Glu Cys Lys Lys Thr Thr Trp Gly
                165                 170                 175

Phe Glu Phe Ser Pro Glu Thr Phe Ser Asp Thr Asp Val Asp Tyr Ala
                180                 185                 190

Ile Glu Val Cys Glu Ala Val Lys Ala Ala Trp Gly Pro Ser Glu Glu
                195                 200                 205

Asn Pro Ile Ile Phe Asn Leu Pro Ala Thr Val Glu Met Ala Thr Pro
                210                 215                 220

Asn Ile Tyr Ala Asp Gln Ile Glu Tyr Phe Ala Thr Asn Ile Ser Glu
225                 230                 235                 240

Arg Glu Lys Ile Cys Ile Ser Leu His Pro His Asn Asp Arg Gly Cys
                245                 250                 255

Ala Val Ala Ala Ala Glu Leu Gly Gln Met Ala Gly Ala Asp Arg Val
                260                 265                 270

Glu Gly Cys Leu Phe Gly Asn Gly Glu Arg Thr Gly Asn Val Asp Leu
                275                 280                 285

Val Thr Leu Gly Leu Asn Leu Tyr Thr Gln Gly Val His Pro Lys Ile
                290                 295                 300

Asp Phe Ser Asp Ile Thr Ser Ile Ile Asp Ile Val Glu Arg Cys Asn
305                 310                 315                 320

Lys Ile Pro Val His Pro Arg Ala Pro Tyr Gly Gly Gln Leu Val Val
                325                 330                 335

Cys Ala Phe Ser Gly Ser His Gln Asp Ala Ile Lys Lys Gly Phe Ala
                340                 345                 350

Arg Ile Glu Asp Val Lys Asp Glu Val Ala Glu Gly Lys Arg Gln Trp
                355                 360                 365

Gln Ile Pro Tyr Leu Pro Leu Asp Pro Lys Asp Ile Gly Arg Thr Tyr
                370                 375                 380

Glu Ala Val Ile Arg Val Asn Ser Gln Ser Gly Lys Gly Gly Ala Ala
385                 390                 395                 400

Trp Ile Ile Leu Arg Ser Leu Glu Leu Asp Leu Pro Arg Gly Leu Gln
                405                 410                 415

Val Ala Phe Ser Lys Val Val Gln Lys Glu Ala Glu Val Val Gly Gln
                420                 425                 430

Glu Leu Ser Ala Gln Leu Val Asp Leu Phe Glu Arg Glu Tyr Gly
                435                 440                 445

Val Phe Glu Glu Gln Gly Lys Tyr Gln Leu Asp Asp Phe Glu Val
                450                 455                 460

Thr Asn Lys Ser Lys Glu Glu Arg Glu Leu Thr Gly Ala Leu Thr Val
465                 470                 475                 480

Glu Gly Lys Arg Val Glu Leu Lys Gly Thr Gly Asn Gly Pro Ile Ser
                485                 490                 495

Ser Phe Leu Asp Ala Ile Lys Asn Ala Phe Gly Tyr Asn Leu Glu Val
                500                 505                 510
```

| Leu | Asn | Tyr | His | Glu | His | Ser | Ile | Gly | Lys | Gly | Ser | Lys | Thr | Lys | Ala |
|---|---|---|---|---|---|---|---|---|---|---|---|---|---|---|---|
| | | | | 515 | | | | 520 | | | | | 525 | | |

| Ala | Thr | Tyr | Ile | Glu | Leu | Ala | Tyr | Glu | Glu | Asp | Gly | Lys | Thr | Ser | Lys |
|---|---|---|---|---|---|---|---|---|---|---|---|---|---|---|---|
| | 530 | | | | | 535 | | | | | 540 | | | | |

| Arg | Trp | Gly | Val | Gly | Ile | Asp | Glu | Asp | Val | Ser | Gln | Ala | Ser | Ile | His |
|---|---|---|---|---|---|---|---|---|---|---|---|---|---|---|---|
| 545 | | | | | 550 | | | | | 555 | | | | | 560 |

| Ala | Ile | Leu | Ser | Ala | Met | Asn | Ala | Ile | Ser | Glu | Ser | Tyr | Lys | Lys |
|---|---|---|---|---|---|---|---|---|---|---|---|---|---|---|
| | | | | 565 | | | | | 570 | | | | 575 | |

<210> SEQ ID NO 53
<211> LENGTH: 1716
<212> TYPE: DNA
<213> ORGANISM: Pichia stipitis

<400> SEQUENCE: 53

```
atgttaaagg atccttccac caaatatgct gcctttaaag gagtcaagtt ggacaagaga      60
acctggccct caaagtctat caccaaggct cctaggtggt tatctactga tttaagagat     120
ggtaaccaag cgttgcctga tcccatgtct gtcgaagaga agaaggagta ttttcacaag     180
ctcttggaga tcggattcaa agaaatcgag gtatctttcc cttctgcatc tcaaacagat     240
tttgacttca ccagatatgc tgtggagaac gcaccagatg atgtttcgat ccaagttttg     300
actcagtcta gagaaccttt gatcagaaga actgttgaat ccgtaaaggg tgctaagaag     360
gctaccatac atacatactt ggctacttct gacgttttcc gtgatgttgt tttcaacatg     420
tcacaagaag atgcaattgc caaagccatt gaaactacca agttggtcaa gtctttgaca     480
aaggacgatc cagaaatgca ggaaaccgag tggaccttgg aattctctcc tgaatgcttc     540
tcagatactc ctaccgaatt tgctgtgcaa atttgtgaag cagtcaagaa cgtctgggag     600
ccaactgtag agaatcctat cattttcaac ttgccagcta ccgttgaagt tgcttctcca     660
aacgtctacg ctgaccagat cgaatacttt gctacccaca tttccgaacg tgaaaaggtg     720
tgtatttctc ttcatgctca caatgaccgt ggctgcggtg ttgctgcctc ggaattaggt     780
ttattggctg gcggagacag agtcgaaggt tgtttgtttg gaaacggtga agaaccggt     840
aacgtagact tgatcactgt tgctctcaac atgtacacca atggagttgc accggagttg     900
gacttttcag aaatcgaaaa gctcatcgag gtcagtgaaa gatgtaacaa atcccagtt     960
cacccaagag ctccatactc tggatccttg gtcgtttgtg ccttctctgg ttctcaccaa    1020
gatgctatca agaagggatt ctccaaggct gaagccagag ctgctagggg tgacaccaaa    1080
tgggccattc atacttgcc attagaccct aaggatatcg gtagaaacta cgaggccgtt    1140
atcagagtca actctcaatc tggtaaggga ggtgctgcct gggtcatctt gagatctctc    1200
ggcttggact tgccaagaca cttgcaagtt gtcttttctg gtattgttca ggaaagagct    1260
gactctttgg gtagagaatt gaagtctgaa gagattgccg cttttgttcaa cgagcagtac    1320
tgctctactt ccaacttgtc tgtcaaggac ttcagataa ctaagagaaa gaatgctcca    1380
gagaacaagg accgtgagat ctttgctgtc ttgcaggctg atccaagac cgttgacgtc    1440
agtggacaag gtaacggacc tatttcggcc tttgtggatg ccatatccaa gaaatacggt    1500
gtttcctttg aagtcgtcaa ctacagtgaa cacagtttag gcagtggtac ccagagtaag    1560
gctgctactt acattgagtt agcctacaac aactctaaca acgagcatgt tacaaagtgg    1620
ggatgcggca ttaacacaga tgtgtcgcag gcttcgatgg aggccattct ttctgttgtg    1680
aactcattga ttgatagcaa ggaaattaat ttgtag                              1716
```

<210> SEQ ID NO 54

```
<211> LENGTH: 571
<212> TYPE: PRT
<213> ORGANISM: Pichia stipitis

<400> SEQUENCE: 54

Met Leu Lys Asp Pro Ser Thr Lys Tyr Ala Ala Phe Lys Gly Val Lys
1               5                   10                  15

Leu Asp Lys Arg Thr Trp Pro Ser Lys Ser Ile Thr Lys Ala Pro Arg
            20                  25                  30

Trp Leu Ser Thr Asp Leu Arg Asp Gly Asn Gln Ala Leu Pro Asp Pro
        35                  40                  45

Met Ser Val Glu Glu Lys Lys Glu Tyr Phe His Lys Leu Leu Glu Ile
    50                  55                  60

Gly Phe Lys Glu Ile Glu Val Ser Phe Pro Ser Ala Ser Gln Thr Asp
65                  70                  75                  80

Phe Asp Phe Thr Arg Tyr Ala Val Glu Asn Ala Pro Asp Asp Val Ser
                85                  90                  95

Ile Gln Val Leu Thr Gln Ser Arg Glu Pro Leu Ile Arg Arg Thr Val
            100                 105                 110

Glu Ser Val Lys Gly Ala Lys Lys Ala Thr Ile His Thr Tyr Leu Ala
        115                 120                 125

Thr Ser Asp Val Phe Arg Asp Val Val Phe Asn Met Ser Gln Glu Asp
    130                 135                 140

Ala Ile Ala Lys Ala Ile Glu Thr Thr Lys Leu Val Lys Ser Leu Thr
145                 150                 155                 160

Lys Asp Asp Pro Glu Met Gln Glu Thr Glu Trp Thr Leu Glu Phe Ser
                165                 170                 175

Pro Glu Cys Phe Ser Asp Thr Pro Thr Glu Phe Ala Val Gln Ile Cys
            180                 185                 190

Glu Ala Val Lys Asn Val Trp Glu Pro Thr Val Glu Asn Pro Ile Ile
        195                 200                 205

Phe Asn Leu Pro Ala Thr Val Glu Val Ala Ser Pro Asn Val Tyr Ala
    210                 215                 220

Asp Gln Ile Glu Tyr Phe Ala Thr His Ile Ser Glu Arg Glu Lys Val
225                 230                 235                 240

Cys Ile Ser Leu His Ala His Asn Asp Arg Gly Cys Gly Val Ala Ala
                245                 250                 255

Ser Glu Leu Gly Leu Leu Ala Gly Gly Asp Arg Val Glu Gly Cys Leu
            260                 265                 270

Phe Gly Asn Gly Glu Arg Thr Gly Asn Val Asp Leu Ile Thr Val Ala
        275                 280                 285

Leu Asn Met Tyr Thr Asn Gly Val Ala Pro Glu Leu Asp Phe Ser Glu
    290                 295                 300

Ile Glu Lys Leu Ile Glu Val Ser Glu Arg Cys Asn Lys Ile Pro Val
305                 310                 315                 320

His Pro Arg Ala Pro Tyr Ser Gly Ser Leu Val Val Cys Ala Phe Ser
                325                 330                 335

Gly Ser His Gln Asp Ala Ile Lys Lys Gly Phe Ser Lys Ala Glu Ala
            340                 345                 350

Arg Ala Ala Arg Gly Asp Thr Lys Trp Ala Ile Pro Tyr Leu Pro Leu
        355                 360                 365

Asp Pro Lys Asp Ile Gly Arg Asn Tyr Glu Ala Val Ile Arg Val Asn
    370                 375                 380

Ser Gln Ser Gly Lys Gly Gly Ala Ala Trp Val Ile Leu Arg Ser Leu
385                 390                 395                 400
```

| | | | |
|---|---|---|---|
|Gly Leu Asp Leu Pro Arg His Leu Gln Val Val Phe Ser Gly Ile Val| | | |
| |405| |410| |415| | |

Gly Leu Asp Leu Pro Arg His Leu Gln Val Val Phe Ser Gly Ile Val
                  405                    410                    415

Gln Glu Arg Ala Asp Ser Leu Gly Arg Glu Leu Lys Ser Glu Glu Ile
                  420                    425                    430

Ala Ala Leu Phe Asn Glu Gln Tyr Cys Ser Thr Ser Asn Leu Ser Val
                  435                    440                    445

Lys Asp Phe Glu Ile Thr Lys Arg Lys Asn Ala Pro Glu Asn Lys Asp
                  450                    455                    460

Arg Glu Ile Phe Ala Val Leu Gln Ala Gly Ser Lys Thr Val Asp Val
465                  470                    475                    480

Ser Gly Gln Gly Asn Gly Pro Ile Ser Ala Phe Val Asp Ala Ile Ser
                  485                    490                    495

Lys Lys Tyr Gly Val Ser Phe Glu Val Val Asn Tyr Ser Glu His Ser
                  500                    505                    510

Leu Gly Ser Gly Thr Gln Ser Lys Ala Ala Thr Tyr Ile Glu Leu Ala
                  515                    520                    525

Tyr Asn Asn Ser Asn Asn Glu His Val Thr Lys Trp Gly Cys Gly Ile
                  530                    535                    540

Asn Thr Asp Val Ser Gln Ala Ser Met Glu Ala Ile Leu Ser Val Val
545                  550                    555                    560

Asn Ser Leu Ile Asp Ser Lys Glu Ile Asn Leu
                  565                    570

<210> SEQ ID NO 55
<211> LENGTH: 1728
<212> TYPE: DNA
<213> ORGANISM: Pichia stipitis

<400> SEQUENCE: 55

```
atgcctatgt tagctgatcc atcccaaaag tacaagcctt tccctcctgt acatttaccc       60
aatcgtcaat ggccatctcg tacgcttgaa aaaccaccta gatggctttc caccgacttg      120
agagatggaa accagtcctt accagatccc atgtcaattg ctgaaaagaa ggagtacttc      180
aagaagttgg tagatattgg tttcaaggaa atcgaagtgg cctttccttc ggcatcgcag      240
atcgactttg acttcaccag attcgctgtg aaacagctc cagcagacgt tgctgtccag       300
gtcttgtctc cctgtagaga ggacttgatc aagcgtactg tagagtcgtt gaccggagcc      360
aaaaaggcta ttgtgcacat atacttggct acgtcggact gcttccgtaa cgtagtcttt      420
ggattaacca aggaagagtc gaaggctctt gccgtaaaat cgccaagtt ggtcagatct       480 ttgactaaag atgaccccaa gcaacaagca actgagtggg actttgagtt ctcgccagaa      540
accttttcag acaccgatat ggactacgct gtagaggtct cgaagccgt caaggaggcc       600 tggggcccta ctgaagacag acctatcatc ttcaacttgc cagctaccgt ggaaatggct      660
actccaaaca tatatgccga ccagatcgag tactttgcta ctcacatctc ggaaagagaa      720
aagatcgcaa tttcgttaca tccccacaac gacagaggat gttctgttgc tgccgctgag      780
ctcggccagt tagctggtgc tgacagagtt gagggatgct atttggaaa tggagaaaga     840 acaggtaacg ttgacttggt caccttggct ctcaacttgt atactcaggg tgtttcacct      900
aagcttgact ctccgatat caactctgtt atcgacgtag tagaaaagtg taacaagatt       960
cctgttcatg caagagctcc ttatggaggt gcccttgtcg tttgtgcctt cagtggatcg     1020
caccaagacg ccatcaagaa aggtttcaat gtgcacgaga agaaggtcga agctgctgca     1080
ggaaaacatg tccactggca gttaccctac ttgccattgg accctcagga tattggcaga     1140
```

```
acttacgagg ccatcatcag agtcaactcg cagtctggta agggtggttc cgcttgggtc    1200
atcttgagaa acttggagct cgacttgccc agaggattgc aagtggcttt ctccaaggtg    1260
gttcaacagc gtgctgaagt caagggtcag gagttgacca acgaagaatt gtgtgacttg    1320
ttcaagcaag aatactacat tgactacgag ggtgacaact caacgacca gacctacaag    1380 ttgatcgact actccatcct gactcctgcc aagggccaga aggaaattga agccgaaatc    1440
cagatcgatg acaagatcgt caagatcaag ggccagggta acggtcagct ttcggctttc    1500
aatgctgccc tctccaaaca cctcaacatc gacttaaacg tcaagcacta ccacgaacac    1560
tcattgggtg tagactcgaa ttctcgtgca gccacctaca tcgaagtctc actcaaaaac    1620
gacaacgtca ccagatgggg tgtgggtatc catgaagatg tctcgcaagc ttctttctta    1680
tctctcatct ccatcttgaa cggcttgcac agaaacaagg atatttag             1728
```

```
<210> SEQ ID NO 56
<211> LENGTH: 575
<212> TYPE: PRT
<213> ORGANISM: Pichia stipitis

<400> SEQUENCE: 56

Met Pro Met Leu Ala Asp Pro Ser Gln Lys Tyr Lys Pro Phe Pro Pro
1               5                   10                  15

Val His Leu Pro Asn Arg Gln Trp Pro Ser Arg Thr Leu Glu Lys Pro
            20                  25                  30

Pro Arg Trp Leu Ser Thr Asp Leu Arg Asp Gly Asn Gln Ser Leu Pro
        35                  40                  45

Asp Pro Met Ser Ile Ala Glu Lys Lys Glu Tyr Phe Lys Lys Leu Val
    50                  55                  60

Asp Ile Gly Phe Lys Glu Ile Glu Val Ala Phe Pro Ser Ala Ser Gln
65                  70                  75                  80

Ile Asp Phe Asp Phe Thr Arg Phe Ala Val Glu Thr Ala Pro Ala Asp
                85                  90                  95

Val Ala Val Gln Val Leu Ser Pro Cys Arg Glu Asp Leu Ile Lys Arg
            100                 105                 110

Thr Val Glu Ser Leu Thr Gly Ala Lys Lys Ala Ile Val His Ile Tyr
        115                 120                 125

Leu Ala Thr Ser Asp Cys Phe Arg Asn Val Val Phe Gly Leu Thr Lys
    130                 135                 140

Glu Glu Ser Lys Ala Leu Ala Val Lys Cys Ala Lys Leu Val Arg Ser
145                 150                 155                 160

Leu Thr Lys Asp Asp Pro Lys Gln Gln Ala Thr Glu Trp Asp Phe Glu
                165                 170                 175

Phe Ser Pro Glu Thr Phe Ser Asp Thr Asp Met Asp Tyr Ala Val Glu
            180                 185                 190

Val Cys Glu Ala Val Lys Glu Ala Trp Gly Pro Thr Glu Asp Arg Pro
        195                 200                 205

Ile Ile Phe Asn Leu Pro Ala Thr Val Glu Met Ala Thr Pro Asn Ile
    210                 215                 220

Tyr Ala Asp Gln Ile Glu Tyr Phe Ala Thr His Ile Ser Glu Arg Glu
225                 230                 235                 240

Lys Ile Ala Ile Ser Leu His Pro His Asn Asp Arg Gly Cys Ser Val
                245                 250                 255

Ala Ala Ala Glu Leu Gly Gln Leu Ala Gly Ala Asp Arg Val Glu Gly
            260                 265                 270

Cys Leu Phe Gly Asn Gly Glu Arg Thr Gly Asn Val Asp Leu Val Thr
```

|   |   |   |   | 275 |   |   |   |   | 280 |   |   |   |   | 285 |   |   |   |
|---|---|---|---|-----|---|---|---|---|-----|---|---|---|---|-----|---|---|---|
| Leu | Ala | Leu | Asn | Leu | Tyr | Thr | Gln | Gly | Val | Ser | Pro | Lys | Leu | Asp | Phe |
|   |   |   |   | 290 |   |   |   |   | 295 |   |   |   |   | 300 |   |   |   |
| Ser | Asp | Ile | Asn | Ser | Val | Ile | Asp | Val | Val | Glu | Lys | Cys | Asn | Lys | Ile |
| 305 |   |   |   |   | 310 |   |   |   |   | 315 |   |   |   |   | 320 |
| Pro | Val | His | Ala | Arg | Ala | Pro | Tyr | Gly | Gly | Ala | Leu | Val | Val | Cys | Ala |
|   |   |   |   | 325 |   |   |   |   | 330 |   |   |   |   | 335 |   |   |   |
| Phe | Ser | Gly | Ser | His | Gln | Asp | Ala | Ile | Lys | Lys | Gly | Phe | Asn | Val | His |
|   |   |   |   | 340 |   |   |   |   | 345 |   |   |   |   | 350 |   |   |   |
| Glu | Lys | Lys | Val | Glu | Ala | Ala | Gly | Lys | His | Val | His | Trp | Gln | Leu |   |
|   |   |   |   | 355 |   |   |   |   | 360 |   |   |   |   | 365 |   |   |   |
| Pro | Tyr | Leu | Pro | Leu | Asp | Pro | Gln | Asp | Ile | Gly | Arg | Thr | Tyr | Glu | Ala |
|   |   |   |   | 370 |   |   |   |   | 375 |   |   |   |   | 380 |   |   |   |
| Ile | Ile | Arg | Val | Asn | Ser | Gln | Ser | Gly | Lys | Gly | Gly | Ser | Ala | Trp | Val |
| 385 |   |   |   |   | 390 |   |   |   |   | 395 |   |   |   |   | 400 |
| Ile | Leu | Arg | Asn | Leu | Glu | Leu | Asp | Leu | Pro | Arg | Gly | Leu | Gln | Val | Ala |
|   |   |   |   | 405 |   |   |   |   | 410 |   |   |   |   | 415 |   |   |   |
| Phe | Ser | Lys | Val | Val | Gln | Gln | Arg | Ala | Glu | Val | Lys | Gly | Gln | Glu | Leu |
|   |   |   |   | 420 |   |   |   |   | 425 |   |   |   |   | 430 |   |   |   |
| Thr | Asn | Glu | Glu | Leu | Cys | Asp | Leu | Phe | Lys | Gln | Glu | Tyr | Tyr | Ile | Asp |
|   |   |   |   | 435 |   |   |   |   | 440 |   |   |   |   | 445 |   |   |   |
| Tyr | Glu | Gly | Asp | Asn | Phe | Asn | Asp | Gln | Thr | Tyr | Lys | Leu | Ile | Asp | Tyr |
|   |   |   |   | 450 |   |   |   |   | 455 |   |   |   |   | 460 |   |   |   |
| Ser | Ile | Ser | Thr | Pro | Ala | Lys | Gly | Gln | Lys | Glu | Ile | Glu | Ala | Glu | Ile |
| 465 |   |   |   |   | 470 |   |   |   |   | 475 |   |   |   |   | 480 |
| Gln | Ile | Asp | Asp | Lys | Ile | Val | Lys | Ile | Lys | Gly | Gln | Gly | Asn | Gly | Gln |
|   |   |   |   | 485 |   |   |   |   | 490 |   |   |   |   | 495 |   |   |   |
| Leu | Ser | Ala | Phe | Asn | Ala | Ala | Leu | Ser | Lys | His | Leu | Asn | Ile | Asp | Leu |
|   |   |   |   | 500 |   |   |   |   | 505 |   |   |   |   | 510 |   |   |   |
| Asn | Val | Lys | His | Tyr | His | Glu | His | Ser | Leu | Gly | Val | Asp | Ser | Asn | Ser |
|   |   |   |   | 515 |   |   |   |   | 520 |   |   |   |   | 525 |   |   |   |
| Arg | Ala | Ala | Thr | Tyr | Ile | Glu | Val | Ser | Leu | Lys | Asn | Asp | Asn | Val | Thr |
|   |   |   |   | 530 |   |   |   |   | 535 |   |   |   |   | 540 |   |   |   |
| Arg | Trp | Gly | Val | Gly | Ile | His | Glu | Asp | Val | Ser | Gln | Ala | Ser | Phe | Leu |
| 545 |   |   |   |   | 550 |   |   |   |   | 555 |   |   |   |   | 560 |
| Ser | Leu | Ile | Ser | Ile | Leu | Asn | Gly | Leu | His | Arg | Asn | Lys | Asp | Ile |   |
|   |   |   |   | 565 |   |   |   |   | 570 |   |   |   |   | 575 |   |   |   |

<210> SEQ ID NO 57
<211> LENGTH: 1101
<212> TYPE: DNA
<213> ORGANISM: Saccharomyces cerevisiae

<400> SEQUENCE: 57

```
atgttttcca gactgccaac atcattggcc agaaatgttg cacgtcgtgc cccaacttct    60
tttgtaagac cctctgcagc agcagcagca ttgagattct catcaacaaa gacgatgacc   120
gtcagagagg ccttgaatag tgccatggcg gaagaattgg accgtgatga tgatgtcttc   180
cttattggtg aagaagttgc acaatataac ggggcttata aggtgtcaaa gggtttattg   240
gacaggttcg gtaacgtcg tgtggttgac acacctatta ccgaatacgg gttcacaggt   300
ttggccgttg gtgccgcttt gaagggtttg aagccaattg tagagtttat gtcgttcaat   360
ttctctatgc aagctatcga tcatgttgtc aattccgctg caaagactca ctacatgtct   420
ggtggtactc aaaaatgtca aatggtcttc agaggtccta atggtgctgc agtgggtgtt   480
```

-continued

```
ggtgctcaac attcacagga cttttctcct tggtacggtt ccattccagg gttaaaggtc    540
cttgtcccrt attctgctga agatgctagg ggtttgttaa aggccgccat cagagatcca    600
aaccctgttg tatttttaga gaacgaattg ttgtacggtg aatcttttga aatctcagaa    660
gaagctttat cccctgagtt caccttgcca tacaaggcta agatcgaaag agaaggtacc    720
gatatttcca ttgttacgta cacaagaaac gttcagtttt ctttggaagc cgctgaaatt    780
ctacaaaaga aatatggtgt ctctgcagaa gttatcaact tgcgttctat tagaccttta    840
gatactgaag ctatcatcaa aactgtcaag aagacaaacc acttgattac tgttaatcc     900 actttcccat catttggtgt tggtgctgaa attgtcgccc aagttatgga gtctgaagcc    960
tttgattact tggatgctcc aatccaaaga gttactggtg ccgatgttcc aacaccttac   1020
gctaaagaat tagaagattt cgctttccct gatactccaa ccatcgttaa agctgtcaaa   1080
gaagtcttgt caattgaata a                                             1101
```

<210> SEQ ID NO 58
<211> LENGTH: 366
<212> TYPE: PRT
<213> ORGANISM: Saccharomyces cerevisiae

<400> SEQUENCE: 58

```
Met Phe Ser Arg Leu Pro Thr Ser Leu Ala Arg Asn Val Ala Arg Arg
1               5                   10                  15

Ala Pro Thr Ser Phe Val Arg Pro Ser Ala Ala Ala Ala Ala Leu Arg
            20                  25                  30

Phe Ser Ser Thr Lys Thr Met Thr Val Arg Glu Ala Leu Asn Ser Ala
        35                  40                  45

Met Ala Glu Glu Leu Asp Arg Asp Asp Asp Val Phe Leu Ile Gly Glu
    50                  55                  60

Glu Val Ala Gln Tyr Asn Gly Ala Tyr Lys Val Ser Lys Gly Leu Leu
65                  70                  75                  80

Asp Arg Phe Gly Glu Arg Arg Val Val Asp Thr Pro Ile Thr Glu Tyr
                85                  90                  95

Gly Phe Thr Gly Leu Ala Val Gly Ala Ala Leu Lys Gly Leu Lys Pro
            100                 105                 110

Ile Val Glu Phe Met Ser Phe Asn Phe Ser Met Gln Ala Ile Asp His
        115                 120                 125

Val Val Asn Ser Ala Ala Lys Thr His Tyr Met Ser Gly Gly Thr Gln
    130                 135                 140

Lys Cys Gln Met Val Phe Arg Gly Pro Asn Gly Ala Ala Val Gly Val
145                 150                 155                 160

Gly Ala Gln His Ser Gln Asp Phe Ser Pro Trp Tyr Gly Ser Ile Pro
                165                 170                 175

Gly Leu Lys Val Leu Val Pro Tyr Ser Ala Glu Asp Ala Arg Gly Leu
            180                 185                 190

Leu Lys Ala Ala Ile Arg Asp Pro Asn Pro Val Val Phe Leu Glu Asn
        195                 200                 205

Glu Leu Leu Tyr Gly Glu Ser Phe Glu Ile Ser Glu Glu Ala Leu Ser
    210                 215                 220

Pro Glu Phe Thr Leu Pro Tyr Lys Ala Lys Ile Glu Arg Glu Gly Thr
225                 230                 235                 240

Asp Ile Ser Ile Val Thr Tyr Thr Arg Asn Val Gln Phe Ser Leu Glu
                245                 250                 255

Ala Ala Glu Ile Leu Gln Lys Lys Tyr Gly Val Ser Ala Glu Val Ile
            260                 265                 270
```

```
Asn Leu Arg Ser Ile Arg Pro Leu Asp Thr Glu Ala Ile Ile Lys Thr
            275                 280                 285

Val Lys Lys Thr Asn His Leu Ile Thr Val Glu Ser Thr Phe Pro Ser
        290                 295                 300

Phe Gly Val Gly Ala Glu Ile Val Ala Gln Val Met Glu Ser Glu Ala
305                 310                 315                 320

Phe Asp Tyr Leu Asp Ala Pro Ile Gln Arg Val Thr Gly Ala Asp Val
            325                 330                 335

Pro Thr Pro Tyr Ala Lys Glu Leu Glu Asp Phe Ala Phe Pro Asp Thr
        340                 345                 350

Pro Thr Ile Val Lys Ala Val Lys Glu Val Leu Ser Ile Glu
        355                 360                 365

<210> SEQ ID NO 59
<211> LENGTH: 1101
<212> TYPE: DNA
<213> ORGANISM: Schizosaccharomyces pombe

<400> SEQUENCE: 59
```

| | | | | | |
|---|---|---|---|---|---|
| atgattcgtc | ttcaaaagtt | tggtgaaatt | gttgggacca | gtcgttcttg | gaaacttctt | 60 |
| agttcaacca | tcgcaaagcg | ctattcttct | tcttccaatg | gagtgaagga | aatgaccgtt | 120 |
| cgtgatgctt | tgaacagtgc | aatggaagaa | gaaatgaaac | gtgacgatcg | tgtcttcttg | 180 |
| attggcgaag | aggttgcgca | atacaatggt | gcttataaga | tatctagagg | tttattagac | 240 |
| aagtttggtc | ctaaacgtgt | tatcgacact | cccattactg | aaatgggttt | tactggtttg | 300 |
| gcaacaggtg | ctgcttttgc | tggtttacgt | cctatttgtg | agtttatgac | tttcaatttt | 360 |
| tccatgcagg | ctatcgatca | tatcgttaac | tcggccgcca | gaaccctgta | catgtctggt | 420 |
| ggtattcagg | cttgtcctat | tgtcttccgt | ggacctaatg | ggcctgccgc | tgcagttgct | 480 |
| gctcagcatt | ctcaacactt | tgctccatgg | tatggtagta | tccctggtct | taaagtagtt | 540 |
| tctccttact | cagcagaaga | tgctcgtggt | ttgttgaagg | ctgctattcg | tgatcctaat | 600 |
| cccgttgttg | tacttgaaaa | cgaaattctt | tatggtaaaa | cctttccaat | ttcgaaagaa | 660 |
| gcgttgagcg | aggactttgt | gcttcccttt | ggccttgcta | aggtggagcg | ccccggtaaa | 720 |
| gatatcacca | tcgttggtga | gtctatttct | gttgttactg | ctttagaagc | agctgacaag | 780 |
| ctcaaggctg | actatggtgt | tgaagctgaa | gttataaact | tgcgtagtat | tcgtcccttta | 840 |
| gacatcaata | ctatcgcggc | cagtgttaag | aagacaaatc | gtattgtgac | tgttgaccag | 900 |
| gcatatagtc | aacatggtat | tggtagtgaa | attgctgctc | aaattatgga | gtctgacgca | 960 |
| tttgattatc | ttgatgctcc | tgttgaacgt | gtaagtatgg | cagatgttcc | catgccttat | 1020 |
| agtcatcctg | ttgaggctgc | ttctgtccca | aatgccgatg | ttgttgttgc | tgctgctaaa | 1080 |
| aaatgcttgt | atattaaata | a | | | | 1101 |

```
<210> SEQ ID NO 60
<211> LENGTH: 366
<212> TYPE: PRT
<213> ORGANISM: Schizosaccharomyces pombe

<400> SEQUENCE: 60

Met Ile Arg Leu Gln Lys Phe Gly Glu Ile Val Gly Thr Ser Arg Ser
1               5                   10                  15

Trp Lys Leu Leu Ser Ser Thr Ile Ala Lys Arg Tyr Ser Ser Ser
            20                  25                  30

Asn Gly Val Lys Glu Met Thr Val Arg Asp Ala Leu Asn Ser Ala Met
```

```
                35                  40                  45
Glu Glu Glu Met Lys Arg Asp Asp Arg Val Phe Leu Ile Gly Glu Glu
 50                  55                  60

Val Ala Gln Tyr Asn Gly Ala Tyr Lys Ile Ser Arg Gly Leu Leu Asp
 65                  70                  75                  80

Lys Phe Gly Pro Lys Arg Val Ile Asp Thr Pro Ile Thr Glu Met Gly
                 85                  90                  95

Phe Thr Gly Leu Ala Thr Gly Ala Ala Phe Ala Gly Leu Arg Pro Ile
                100                 105                 110

Cys Glu Phe Met Thr Phe Asn Phe Ser Met Gln Ala Ile Asp His Ile
                115                 120                 125

Val Asn Ser Ala Ala Arg Thr Leu Tyr Met Ser Gly Gly Ile Gln Ala
130                 135                 140

Cys Pro Ile Val Phe Arg Gly Pro Asn Gly Pro Ala Ala Val Ala
145                 150                 155                 160

Ala Gln His Ser Gln His Phe Ala Pro Trp Tyr Gly Ser Ile Pro Gly
                165                 170                 175

Leu Lys Val Val Ser Pro Tyr Ser Ala Glu Asp Ala Arg Gly Leu Leu
                180                 185                 190

Lys Ala Ala Ile Arg Asp Pro Asn Pro Val Val Leu Glu Asn Glu
                195                 200                 205

Ile Leu Tyr Gly Lys Thr Phe Pro Ile Ser Lys Glu Ala Leu Ser Glu
210                 215                 220

Asp Phe Val Leu Pro Phe Gly Leu Ala Lys Val Glu Arg Pro Gly Lys
225                 230                 235                 240

Asp Ile Thr Ile Val Gly Glu Ser Ile Ser Val Val Thr Ala Leu Glu
                245                 250                 255

Ala Ala Asp Lys Leu Lys Ala Asp Tyr Gly Val Glu Ala Glu Val Ile
                260                 265                 270

Asn Leu Arg Ser Ile Arg Pro Leu Asp Ile Asn Thr Ile Ala Ala Ser
                275                 280                 285

Val Lys Lys Thr Asn Arg Ile Val Thr Val Asp Gln Ala Tyr Ser Gln
290                 295                 300

His Gly Ile Gly Ser Glu Ile Ala Ala Gln Ile Met Glu Ser Asp Ala
305                 310                 315                 320

Phe Asp Tyr Leu Asp Ala Pro Val Glu Arg Val Ser Met Ala Asp Val
                325                 330                 335

Pro Met Pro Tyr Ser His Pro Val Glu Ala Ala Ser Val Pro Asn Ala
                340                 345                 350

Asp Val Val Ala Ala Ala Lys Lys Cys Leu Tyr Ile Lys
                355                 360                 365

<210> SEQ ID NO 61
<211> LENGTH: 1140
<212> TYPE: DNA
<213> ORGANISM: Candida albicans

<400> SEQUENCE: 61
atgtcatcat tatcatcagt caccaggagt gctaaattag ccactcaatc tttgaaatac      60
aacactagac catcattatc taaaattggt caatttcaaa catcaaaaat cacttatcgt     120
gccaattcca cacaatcaac tcctgtcaaa gaaattactg tcagagatgc tcttaaccaa     180
gctttatctg aagaattaga cagagatgaa gatgttttcc ttatgggtga agaagttgcc     240
caatacaatg gtgcctataa agtcagtaga ggattattgg acaaatttgg tgaaaagaga     300
```

-continued

```
gttattgaca ctccaattac tgaaatgggg ttcactggat tagctgttgg tgctgcttta    360
catggtctta aaccagtttt ggaatttatg acttggaatt ttgctatgca aggtattgat    420
catattttaa attctgctgc taaaactctt tatatgtctg gtggtaaaca accatgtaat    480
ataactttcc gtggtcctaa tggtgctgct gctggtgttg ctgctcaaca ttctcagtgt    540
tatgctgctt ggtatggttc aattcctggt ttaaaagttt tatctcctta ttctgctgaa    600
gattataagg gttacttaa agctgccatt agagatccta acccagttgt tttcttggaa     660
aatgaaattg cttatggtga aactttaaa gtttctgaag aattttcatc tccagatttc     720
attttaccaa ttggtaaagc caaaattgaa aagaaggta ctgatttaac cattgttggt     780
catagtcgtg cccttaaatt tgccgttgaa gccgctgaaa ttttggaaaa agatttcgga    840
attaaagctg aagtgctcaa tttaagatca attaaaccat ggatgttcc agctattgtt     900
gattcagtta aaaagactaa tcatttggtt actgttgaaa atggattccc aggttttggt    960
gttggttcag aaatttgtgc tcaaattatg gaaagtgaag cctttgatta tttggatgct   1020
ccagttgaaa gagttactgg ttgtgaagtt ccaactccat atgctaaaga attggaagat   1080
tttgctttcc cagacactga agttatcttg agagcttgta aaaaagtatt aagtttgtaa   1140
```

<210> SEQ ID NO 62
<211> LENGTH: 379
<212> TYPE: PRT
<213> ORGANISM: Candida albicans

<400> SEQUENCE: 62

```
Met Ser Ser Leu Ser Ser Val Thr Arg Ser Ala Lys Leu Ala Thr Gln
 1               5                  10                  15
Ser Leu Lys Tyr Asn Thr Arg Pro Ser Leu Ser Lys Ile Gly Gln Phe
             20                  25                  30
Gln Thr Ser Lys Ile Thr Tyr Arg Ala Asn Ser Thr Gln Ser Thr Pro
         35                  40                  45
Val Lys Glu Ile Thr Val Arg Asp Ala Leu Asn Gln Ala Leu Ser Glu
     50                  55                  60
Glu Leu Asp Arg Asp Glu Asp Val Phe Leu Met Gly Glu Glu Val Ala
 65                  70                  75                  80
Gln Tyr Asn Gly Ala Tyr Lys Val Ser Arg Gly Leu Leu Asp Lys Phe
                 85                  90                  95
Gly Glu Lys Arg Val Ile Asp Thr Pro Ile Thr Glu Met Gly Phe Thr
            100                 105                 110
Gly Leu Ala Val Gly Ala Ala Leu His Gly Leu Lys Pro Val Leu Glu
        115                 120                 125
Phe Met Thr Trp Asn Phe Ala Met Gln Gly Ile Asp His Ile Leu Asn
    130                 135                 140
Ser Ala Ala Lys Thr Leu Tyr Met Ser Gly Gly Lys Gln Pro Cys Asn
145                 150                 155                 160
Ile Thr Phe Arg Gly Pro Asn Gly Ala Ala Ala Gly Val Ala Ala Gln
                165                 170                 175
His Ser Gln Cys Tyr Ala Ala Trp Tyr Gly Ser Ile Pro Gly Leu Lys
            180                 185                 190
Val Leu Ser Pro Tyr Ser Ala Glu Asp Tyr Lys Gly Leu Leu Lys Ala
        195                 200                 205
Ala Ile Arg Asp Pro Asn Pro Val Val Phe Leu Glu Asn Glu Ile Ala
    210                 215                 220
Tyr Gly Glu Thr Phe Lys Val Ser Glu Glu Phe Ser Ser Pro Asp Phe
225                 230                 235                 240
```

Ile Leu Pro Ile Gly Lys Ala Lys Ile Glu Lys Glu Gly Thr Asp Leu
             245                 250                 255

Thr Ile Val Gly His Ser Arg Ala Leu Lys Phe Ala Val Glu Ala Ala
                 260                 265                 270

Glu Ile Leu Glu Lys Asp Phe Gly Ile Lys Ala Glu Val Leu Asn Leu
             275                 280                 285

Arg Ser Ile Lys Pro Leu Asp Val Pro Ala Ile Val Asp Ser Val Lys
290                 295                 300

Lys Thr Asn His Leu Val Thr Val Glu Asn Gly Phe Pro Gly Phe Gly
305                 310                 315                 320

Val Gly Ser Glu Ile Cys Ala Gln Ile Met Glu Ser Glu Ala Phe Asp
                 325                 330                 335

Tyr Leu Asp Ala Pro Val Glu Arg Val Thr Gly Cys Glu Val Pro Thr
             340                 345                 350

Pro Tyr Ala Lys Glu Leu Glu Asp Phe Ala Phe Pro Asp Thr Glu Val
             355                 360                 365

Ile Leu Arg Ala Cys Lys Lys Val Leu Ser Leu
             370                 375

<210> SEQ ID NO 63
<211> LENGTH: 1065
<212> TYPE: DNA
<213> ORGANISM: Kluyveromyces lactis

<400> SEQUENCE: 63
atgatgatgc tttctaacac ttttaagagg gctgttcctt ctgtggttca atccatgaga      60
tttgcttcta ccaagaccat gaccgtcaga gaagctttga attctgccat ggccgaagaa     120
atggaccgtg atgatgatgt tttcatcatt ggtgaagaag ttgctcaata taatggtgct     180
tacaaggtta ccaagggttt attggaccgt tcggtgaaaa gaagagttgt tgacactcca     240
attaccgaaa tgggtttcac tggtttggct gttggtgccg ctttgaaggg tttaaagcca     300
attgttgaat tcatgtcttt caacttctcc atgcaagcta tggatcaagt cattaactcc     360
gctgctaaga cttactatat gtccggtggt actcagaaat gtcaaatcgt tttcagaggt     420
ccaaacggtt ctgctgtcgg tgttgctgct caacattccc aagattattc tgcttggtac     480
ggttctgttc aggtatgaa ggttttggtt ccatactctg ctgaagatgc tagaggtttg     540
ttgaaggctg ccattcgtga tccaaaccca gttgttttct ggaaaacga attgttatac     600 ggtcaatctt tcgaagtctc tgaagaatct ctgtctactg atttcacttt gccatacaaa     660
gcaaaggttg aaagagaagg ttctgatatc tctatcatca gttacaccag aaatgttcaa     720
ttctctttgg aagctgctga aattttgtct aagcaatacg tgtttctgc tgaagttatc     780 aatttgagag ccattagacc tttggatgtt gaagctatca tcaacactgt caagaagacc     840
aaccacttga ttactgttga atctactttc ccagctttcg gtgttggtgc tgaaattatc     900
gctcaaatta tggaatctga agccttcgat tatttggatg ctccaattca agagttact     960 ggtgctgaag tcccaactcc ttatgctaag gaattagaag attttgcttt cccagaccct    1020
gacaccattg tcagagctgc taaaagtgtt ttgtctattg aatga                    1065

<210> SEQ ID NO 64
<211> LENGTH: 354
<212> TYPE: PRT
<213> ORGANISM: Kluyveromyces lactis

<400> SEQUENCE: 64

-continued

```
Met Met Met Leu Ser Asn Thr Phe Lys Arg Ala Val Pro Ser Val
1               5                  10                 15

Gln Ser Met Arg Phe Ala Ser Thr Lys Thr Met Thr Val Arg Glu Ala
            20                  25                  30

Leu Asn Ser Ala Met Ala Glu Glu Met Asp Arg Asp Asp Asp Val Phe
            35              40                  45

Ile Ile Gly Glu Glu Val Ala Gln Tyr Asn Gly Ala Tyr Lys Val Thr
50                      55                  60

Lys Gly Leu Leu Asp Arg Phe Gly Glu Arg Arg Val Val Asp Thr Pro
65                  70                  75                  80

Ile Thr Glu Met Gly Phe Thr Gly Leu Ala Val Gly Ala Ala Leu Lys
                85                  90                  95

Gly Leu Lys Pro Ile Val Glu Phe Met Ser Phe Asn Phe Ser Met Gln
            100                 105                 110

Ala Met Asp Gln Val Ile Asn Ser Ala Ala Lys Thr Tyr Tyr Met Ser
            115                 120                 125

Gly Gly Thr Gln Lys Cys Gln Ile Val Phe Arg Gly Pro Asn Gly Ser
        130                 135                 140

Ala Val Gly Val Ala Ala Gln His Ser Gln Asp Tyr Ser Ala Trp Tyr
145                 150                 155                 160

Gly Ser Val Pro Gly Met Lys Val Leu Val Pro Tyr Ser Ala Glu Asp
                165                 170                 175

Ala Arg Gly Leu Leu Lys Ala Ala Ile Arg Asp Pro Asn Pro Val Val
            180                 185                 190

Phe Leu Glu Asn Glu Leu Leu Tyr Gly Gln Ser Phe Glu Val Ser Glu
            195                 200                 205

Glu Ser Leu Ser Thr Asp Phe Thr Leu Pro Tyr Lys Ala Lys Val Glu
210                 215                 220

Arg Glu Gly Ser Asp Ile Ser Ile Ser Tyr Thr Arg Asn Val Gln
225                 230                 235                 240

Phe Ser Leu Glu Ala Ala Glu Ile Leu Ser Lys Gln Tyr Gly Val Ser
                245                 250                 255

Ala Glu Val Ile Asn Leu Arg Ala Ile Arg Pro Leu Asp Val Glu Ala
            260                 265                 270

Ile Ile Asn Thr Val Lys Lys Thr Asn His Leu Ile Thr Val Glu Ser
            275                 280                 285

Thr Phe Pro Ala Phe Gly Val Gly Ala Glu Ile Ile Ala Gln Ile Met
            290                 295                 300

Glu Ser Glu Ala Phe Asp Tyr Leu Asp Ala Pro Ile Gln Arg Val Thr
305                 310                 315                 320

Gly Ala Glu Val Pro Thr Pro Tyr Ala Lys Glu Leu Glu Asp Phe Ala
                325                 330                 335

Phe Pro Asp Pro Asp Thr Ile Val Arg Ala Ala Lys Ser Val Leu Ser
            340                 345                 350

Ile Glu
```

<210> SEQ ID NO 65
<211> LENGTH: 993
<212> TYPE: DNA
<213> ORGANISM: Yarrowia lipolytica

<400> SEQUENCE: 65
atgactgtca gagacgccct caacaccgca ctgcgagagg agatggaccg aaacgataat    60
gttttcatca tgggtgagga ggtcggccag tacaacggtg cctacaaggt caccaagggc   120

-continued

```
cttctcgaca agttcggcga gaagcgagtg gttgacaccc ctatcaccga gatgggtttc    180
gccggtgttt gtgtcggtgc cgccctggcc ggtctcaccc ccgtctgcga gttcatgacc    240
tggaacttcg ccatgcaggc cattgatcag atcatcaatt ccggtgccaa gacctactac    300
atgtccggag gtacccagca gtgcaatgtc accttccgag gtcctaacgg tgccgccgct    360
ggtgttgctg cccaacactc tcaggatttc accgggtggt acggccagat tcccggtctc    420
aaggtcgtct ctccctacag ctctgaggat gccaagggtc tgctcaaggc cgccatccga    480
gaccccaacg tgactgtttt cctcgagaac gagatcatgt acggagagtc tttccccatg    540
tctgaggagg ccatgtcccc cgacttcgtt ctgccccttg gaaaggccaa gattgagcga    600
gagggtaagg atatcactct tgtcggtcac tcccgaaacg tcgagaccgc cctcaaggcc    660
gccgacctcc tcaagaagca ccacaacgtc gatgccgagg tcattaacct gcgaactgtc    720
aagcctctcg acactgagac cattttcaac tccatcaaga agactaaccg acttgtctct    780
gtcgaggctg gcttccccgc ctttggcatg ggctccgagc tctgtggtgt cgtcaacgac    840
tcctgggcct gggattacct tgatgccccc atccagcgag ttaccggagc tgaggttccc    900
actccttacg ccattgagct tgagaacttc gccttcccca cacccgagat tgttgtcaag    960
gctgccaagg acgccctcta cattgaggag tag                                 993
```

<210> SEQ ID NO 66
<211> LENGTH: 330
<212> TYPE: PRT
<213> ORGANISM: Yarrowia lipolytica

<400> SEQUENCE: 66

```
Met Thr Val Arg Asp Ala Leu Asn Thr Ala Leu Arg Glu Glu Met Asp
1               5                   10                  15

Arg Asn Asp Asn Val Phe Ile Met Gly Glu Glu Val Gly Gln Tyr Asn
            20                  25                  30

Gly Ala Tyr Lys Val Thr Lys Gly Leu Leu Asp Lys Phe Gly Glu Lys
        35                  40                  45

Arg Val Val Asp Thr Pro Ile Thr Glu Met Gly Phe Ala Gly Val Cys
    50                  55                  60

Val Gly Ala Ala Leu Ala Gly Leu Thr Pro Val Cys Glu Phe Met Thr
65                  70                  75                  80

Trp Asn Phe Ala Met Gln Ala Ile Asp Gln Ile Ile Asn Ser Gly Ala
                85                  90                  95

Lys Thr Tyr Tyr Met Ser Gly Gly Thr Gln Gln Cys Asn Val Thr Phe
            100                 105                 110

Arg Gly Pro Asn Gly Ala Ala Ala Gly Val Ala Ala Gln His Ser Gln
        115                 120                 125

Asp Phe Thr Gly Trp Tyr Gly Gln Ile Pro Gly Leu Lys Val Val Ser
    130                 135                 140

Pro Tyr Ser Ser Glu Asp Ala Lys Gly Leu Leu Lys Ala Ala Ile Arg
145                 150                 155                 160

Asp Pro Asn Val Thr Val Phe Leu Glu Asn Glu Ile Met Tyr Gly Glu
                165                 170                 175

Ser Phe Pro Met Ser Glu Glu Ala Met Ser Pro Asp Phe Val Leu Pro
            180                 185                 190

Leu Gly Lys Ala Lys Ile Glu Arg Glu Gly Lys Asp Ile Thr Leu Val
        195                 200                 205

Gly His Ser Arg Asn Val Glu Thr Ala Leu Lys Ala Ala Asp Leu Leu
    210                 215                 220
```

```
Lys Lys His His Asn Val Asp Ala Glu Val Ile Asn Leu Arg Thr Val
225                 230                 235                 240

Lys Pro Leu Asp Thr Glu Thr Ile Phe Asn Ser Ile Lys Lys Thr Asn
            245                 250                 255

Arg Leu Val Ser Val Glu Ala Gly Phe Pro Ala Phe Gly Met Gly Ser
        260                 265                 270

Glu Leu Cys Gly Val Val Asn Asp Ser Trp Ala Trp Asp Tyr Leu Asp
        275                 280                 285

Ala Pro Ile Gln Arg Val Thr Gly Ala Glu Val Pro Thr Pro Tyr Ala
        290                 295                 300

Ile Glu Leu Glu Asn Phe Ala Phe Pro Thr Pro Glu Ile Val Val Lys
305                 310                 315                 320

Ala Ala Lys Asp Ala Leu Tyr Ile Glu Glu
            325                 330
```

<210> SEQ ID NO 67
<211> LENGTH: 1170
<212> TYPE: DNA
<213> ORGANISM: Pichia stipitis

<400> SEQUENCE: 67

```
atggctccca agttatccca gatcgcccag acggcccgct tggccgcttc ggccactaga      60
gcccacaaca tcgccaatgt gactggaaac actaccagat ccgtagccca agctggccag     120
taccaggcat tgagaatgat ggattcgcgt gccgcttcgt cgtcggctgt aggctcaaag     180
accatcaccg tcagagacgc ccttaatgcc gggcttgccg aggagttgga caaggacgac     240
gatgtcttcc tcatgggtga agaagtggcc aatacaacg gtgcctacaa ggtgtcacgt     300
ggtttgttgg atcgttttgg tgaaagacgt gtgattgata cccctatcac tgaaatgggt     360
ttcactggtt tggctgttgg agctgccctt catggtttga gcctgtgtt ggagttcatg     420
accttcaact cgctatgca agctatcgat caaatcgtta actctgccgc taagacctat     480
tacatgtccg gaggtaaaca accgtgtaac atcaccttcc gtggtcccaa tggtgctgct     540
gccggtgtcg gtgctcaaca ttcgcaatgt tacgctgcat ggtatggatc tattcctggt     600
ttgaaggttg tttcgcccta ctctgccgag gactacaagg gtttgatcaa ggctgccatc     660
agagacccta acccagttgt gttttttggaa aacgaaatcg cctacggtga aaccttcgat     720
atctccgagg aagctctctc cacagacttt gttttgccta tcggcaaggc caatgtcgaa     780
agagaaggaa ctgacttgac atttgtatcg cattccagat ctgtcaagtt ctgtatggaa     840
gccgctgaaa ccttggagaa ggaatacggc gtcaaggccg aagtcatcaa cttgagatcc     900
atcaagcctt tggatgttcc taccattgtt gagtcagtca agaagactaa ccacttggtc     960
actgttgaag ccggattccc agcctttggt gttggttctg aaatctgtgc ccagatcatg    1020
gaatccgagg ctttttgatta cttggatgct ccagtcgaaa gagtcactgg ttgcgaagtt    1080
ccaactccat atgctaagga attggaagac tttgctttcc cagacgaacc taccgtaatc    1140
agagccgcca aaaaggtgtt atctttgtaa                                      1170
```

<210> SEQ ID NO 68
<211> LENGTH: 389
<212> TYPE: PRT
<213> ORGANISM: Pichia stipitis

<400> SEQUENCE: 68

```
Met Ala Pro Lys Leu Ser Gln Ile Ala Gln Thr Ala Arg Leu Ala Ala
1               5                   10                  15
```

Ser Ala Thr Arg Ala His Asn Ile Ala Asn Val Thr Gly Asn Thr Thr
             20                  25                  30

Arg Ser Val Ala Gln Ala Gly Gln Tyr Gln Ala Leu Arg Met Met Asp
         35                  40                  45

Ser Arg Ala Ala Ser Ser Ala Val Gly Ser Lys Thr Ile Thr Val
 50                  55                  60

Arg Asp Ala Leu Asn Ala Gly Leu Ala Glu Glu Leu Asp Lys Asp Asp
 65                  70                  75                  80

Asp Val Phe Leu Met Gly Glu Val Ala Gln Tyr Asn Gly Ala Tyr
                 85                  90                  95

Lys Val Ser Arg Gly Leu Leu Asp Arg Phe Gly Glu Arg Val Ile
            100                 105                 110

Asp Thr Pro Ile Thr Glu Met Gly Phe Thr Gly Leu Ala Val Gly Ala
            115                 120                 125

Ala Leu His Gly Leu Lys Pro Val Leu Glu Phe Met Thr Phe Asn Phe
    130                 135                 140

Ala Met Gln Ala Ile Asp Gln Ile Val Asn Ser Ala Ala Lys Thr Tyr
145                 150                 155                 160

Tyr Met Ser Gly Gly Lys Gln Pro Cys Asn Ile Thr Phe Arg Gly Pro
                165                 170                 175

Asn Gly Ala Ala Ala Gly Val Gly Ala Gln His Ser Gln Cys Tyr Ala
            180                 185                 190

Ala Trp Tyr Gly Ser Ile Pro Gly Leu Lys Val Val Ser Pro Tyr Ser
            195                 200                 205

Ala Glu Asp Tyr Lys Gly Leu Ile Lys Ala Ala Ile Arg Asp Pro Asn
210                 215                 220

Pro Val Val Phe Leu Glu Asn Glu Ile Ala Tyr Gly Glu Thr Phe Asp
225                 230                 235                 240

Ile Ser Glu Glu Ala Leu Ser Thr Asp Phe Val Leu Pro Ile Gly Lys
                245                 250                 255

Ala Asn Val Glu Arg Glu Gly Thr Asp Leu Thr Phe Val Ser His Ser
            260                 265                 270

Arg Ser Val Lys Phe Cys Met Glu Ala Ala Glu Thr Leu Glu Lys Glu
            275                 280                 285

Tyr Gly Val Lys Ala Glu Val Ile Asn Leu Arg Ser Ile Lys Pro Leu
290                 295                 300

Asp Val Pro Thr Ile Val Glu Ser Val Lys Lys Thr Asn His Leu Val
305                 310                 315                 320

Thr Val Glu Ala Gly Phe Pro Ala Phe Gly Val Gly Ser Glu Ile Cys
                325                 330                 335

Ala Gln Ile Met Glu Ser Glu Ala Phe Asp Tyr Leu Asp Ala Pro Val
            340                 345                 350

Glu Arg Val Thr Gly Cys Glu Val Pro Thr Pro Tyr Ala Lys Glu Leu
            355                 360                 365

Glu Asp Phe Ala Phe Pro Asp Glu Pro Thr Val Ile Arg Ala Ala Lys
370                 375                 380

Lys Val Leu Ser Leu
385

<210> SEQ ID NO 69
<211> LENGTH: 1263
<212> TYPE: DNA
<213> ORGANISM: Saccharomyces cerevisiae

<400> SEQUENCE: 69

-continued

```
atgcttgctg cttcattcaa acgccaacca tcacaattgg tccgcgggtt aggagctgtt    60
cttcgcactc ccaccaggat aggtcatgtt cgtaccatgg caactttaaa aacaactgat   120
aagaaggccc ctgaggacat cgagggctcg gacacagtgc aaattgagtt gcctgaatct   180
tccttcgagt cgtatatgct agagcctcca gacttgtctt atgagacttc gaaagccacc   240
ttgttacaga tgtataaaga tatggtcatc atcagaagaa tggagatggc ttgtgacgcc   300
ttgtacaagg ccaagaaaat cagaggtttt tgccatctat ctgttggtca ggaggccatt   360
gctgtcggta tcgagaatgc catcacaaaa ttggattcca tcatcacatc ttacagatgt   420
cacggtttca cttttatgag aggtgcctca gtgaaagccg ttctggctga attgatgggt   480
agaagagccg gtgtctctta tggtaagggt ggttccatgc acctttacgc tccaggcttc   540
tatggtggta atggtatcgt gggtgcccag gttcctttag gtgcaggttt agcttttgct   600
caccaataca agaacgagga cgcctgctct ttcactttgt atggtgatgg tgcctctaat   660
caaggtcaag ttttgaatc tttcaacatg gccaaattat ggaatttgcc cgtcgtgttt   720
tgctgtgaga acaacaagta cggtatgggt accgccgctt caagatcctc cgcgatgact   780
gaatatttca gcgtggtca atatattcca ggtttaaaag ttaacggtat ggatattcta   840
gctgtctacc aagcatccaa gtttgctaag gactggtgtc tatccggcaa aggtcctctc   900
gttctagaat atgaaaccta taggtacggt ggccattcta tgtctgatcc cggtactacc   960
tacagaacta gagacgagat tcagcatatg agatccaaga cgatccaat tgctggtctt  1020
aagatgcatt tgattgatct aggtattgcc actgaagctg aagtcaaagc ttacgacaag  1080
tccgctagaa aatacgttga cgaacaagtt gaattagctg atgctgctcc tcctccagaa  1140
gccaaattat ccatcttgtt tgaagacgtc tacgtgaaag gtacagaaac tccaacccta  1200
agaggtagga tccctgaaga tacttgggac ttcaaaaagc aaggttttgc ctctagggat  1260
taa                                                                 1263
```

<210> SEQ ID NO 70
<211> LENGTH: 420
<212> TYPE: PRT
<213> ORGANISM: Saccharomyces cerevisiae

<400> SEQUENCE: 70

```
Met Leu Ala Ala Ser Phe Lys Arg Gln Pro Ser Gln Leu Val Arg Gly
1               5                   10                  15
Leu Gly Ala Val Leu Arg Thr Pro Thr Arg Ile Gly His Val Arg Thr
            20                  25                  30
Met Ala Thr Leu Lys Thr Thr Asp Lys Lys Ala Pro Glu Asp Ile Glu
        35                  40                  45
Gly Ser Asp Thr Val Gln Ile Glu Leu Pro Glu Ser Ser Phe Glu Ser
    50                  55                  60
Tyr Met Leu Glu Pro Pro Asp Leu Ser Tyr Glu Thr Ser Lys Ala Thr
65                  70                  75                  80
Leu Leu Gln Met Tyr Lys Asp Met Val Ile Ile Arg Arg Met Glu Met
                85                  90                  95
Ala Cys Asp Ala Leu Tyr Lys Ala Lys Lys Ile Arg Gly Phe Cys His
            100                 105                 110
Leu Ser Val Gly Gln Glu Ala Ile Ala Val Gly Ile Glu Asn Ala Ile
        115                 120                 125
Thr Lys Leu Asp Ser Ile Ile Thr Ser Tyr Arg Cys His Gly Phe Thr
    130                 135                 140
Phe Met Arg Gly Ala Ser Val Lys Ala Val Leu Ala Glu Leu Met Gly
```

```
                145                 150                 155                 160
Arg Arg Ala Gly Val Ser Tyr Gly Lys Gly Gly Ser Met His Leu Tyr
                    165                 170                 175
Ala Pro Gly Phe Tyr Gly Gly Asn Gly Ile Val Gly Ala Gln Val Pro
                    180                 185                 190
Leu Gly Ala Gly Leu Ala Phe Ala His Gln Tyr Lys Asn Glu Asp Ala
                    195                 200                 205
Cys Ser Phe Thr Leu Tyr Gly Asp Gly Ala Ser Asn Gln Gly Gln Val
        210                 215                 220
Phe Glu Ser Phe Asn Met Ala Lys Leu Trp Asn Leu Pro Val Val Phe
225                 230                 235                 240
Cys Cys Glu Asn Asn Lys Tyr Gly Met Gly Thr Ala Ala Ser Arg Ser
                    245                 250                 255
Ser Ala Met Thr Glu Tyr Phe Lys Arg Gly Gln Tyr Ile Pro Gly Leu
                260                 265                 270
Lys Val Asn Gly Met Asp Ile Leu Ala Val Tyr Gln Ala Ser Lys Phe
                275                 280                 285
Ala Lys Asp Trp Cys Leu Ser Gly Lys Gly Pro Leu Val Leu Glu Tyr
        290                 295                 300
Glu Thr Tyr Arg Tyr Gly Gly His Ser Met Ser Asp Pro Gly Thr Thr
305                 310                 315                 320
Tyr Arg Thr Arg Asp Glu Ile Gln His Met Arg Ser Lys Asn Asp Pro
                    325                 330                 335
Ile Ala Gly Leu Lys Met His Leu Ile Asp Leu Gly Ile Ala Thr Glu
                340                 345                 350
Ala Glu Val Lys Ala Tyr Asp Lys Ser Ala Arg Lys Tyr Val Asp Glu
                355                 360                 365
Gln Val Glu Leu Ala Asp Ala Ala Pro Pro Glu Ala Lys Leu Ser
        370                 375                 380
Ile Leu Phe Glu Asp Val Tyr Val Lys Gly Thr Glu Thr Pro Thr Leu
385                 390                 395                 400
Arg Gly Arg Ile Pro Glu Asp Thr Trp Asp Phe Lys Lys Gln Gly Phe
                    405                 410                 415
Ala Ser Arg Asp
        420

<210> SEQ ID NO 71
<211> LENGTH: 1230
<212> TYPE: DNA
<213> ORGANISM: Schizosaccharomyces pombe

<400> SEQUENCE: 71
atgtttcgaa cttgtacgaa gattggaaca gttcccaagg ttcttgtgaa ccaaaagggc     60
ttgatcgatg gccttcgtcg ggtcaccaca gacgcaacca cttctcgtgc caatccggct    120
catgtgcctg aggaacatga caagccattt cctgttaaat tagatgatag tgtattcgaa    180
ggatacaaga tcgatgtccc ttctactgaa atcgaagtta caagggagag gttattgggt    240
ttgtacgaga agatggtgac tattcgtcgt ctagaacttg catgcgatgc cttgtataag    300
gctaagagaa ttcgtggatt ctgtcatctt agcattggcc aagaagctgt agctgcagga    360
attgaaggtg ctattacact tgacgacagt attatcacat cttatagatg ccacggtttt    420 gcttatacccc gtggttttgtc aattcgaagc attattggtg agctcatggg acgtcaatgt    480
ggtgcttcca agggcaaggg tggttctatg cacattttcg ccaaaaactt ctatggtggt    540
aatggtattg ttggtgctca aattcctttg ggtgctggta ttggtttcgc acagaagtat    600
```

-continued

```
cttgaaaaac ccactactac ttttgctcta tatggtgatg gtgcatctaa ccaaggtcaa      660
gctttcgagg ccttcaacat ggccaaatta tggggtcttc ccgttatttt tgcttgtgaa      720
aacaacaaat acggtatggg tactagtgct gaacgctctt ctgccatgac tgagttctac      780
aaacgtggac agtacattcc cggtcttttg gttaacggta tggatgtttt ggctgttttg      840
caggcttcaa agtttgctaa gaagtacact gttgaaaact ctcaacctct gcttatggaa      900
tttgtgactt atcgttatgg tggtcactcc atgtccgatc ccggtactac ttatcgtagc      960
cgtgaagaag tgcaaaaagt acgtgctgct agagatccta ttgagggttt gaagaagcac     1020
atcatggagt ggggcgtcgc taatgccaat gagcttaaaa acattgagaa agagaatccgt     1080 ggtatggttg atgaggaggt tcgtatcgct gaagaaagcc ctttccccga tcctattgag     1140
gagagtttgt tttcagatgt ttacgttgca ggaactgaac ccgcttacgc ccgtggtaga     1200
aattccctgg aatatcatca atataagtaa                                      1230
```

<210> SEQ ID NO 72
<211> LENGTH: 409
<212> TYPE: PRT
<213> ORGANISM: Schizosaccharomyces pombe

<400> SEQUENCE: 72

```
Met Phe Arg Thr Cys Thr Lys Ile Gly Thr Val Pro Lys Val Leu Val
  1               5                  10                  15

Asn Gln Lys Gly Leu Ile Asp Gly Leu Arg Arg Val Thr Thr Asp Ala
             20                  25                  30

Thr Thr Ser Arg Ala Asn Pro Ala His Val Pro Glu Glu His Asp Lys
         35                  40                  45

Pro Phe Pro Val Lys Leu Asp Asp Ser Val Phe Glu Gly Tyr Lys Ile
     50                  55                  60

Asp Val Pro Ser Thr Glu Ile Glu Val Thr Lys Gly Glu Leu Leu Gly
 65                  70                  75                  80

Leu Tyr Glu Lys Met Val Thr Ile Arg Arg Leu Glu Leu Ala Cys Asp
                 85                  90                  95

Ala Leu Tyr Lys Ala Lys Lys Ile Arg Gly Phe Cys His Leu Ser Ile
            100                 105                 110

Gly Gln Glu Ala Val Ala Ala Gly Ile Glu Gly Ala Ile Thr Leu Asp
        115                 120                 125

Asp Ser Ile Ile Thr Ser Tyr Arg Cys His Gly Phe Ala Tyr Thr Arg
    130                 135                 140

Gly Leu Ser Ile Arg Ser Ile Ile Gly Glu Leu Met Gly Arg Gln Cys
145                 150                 155                 160

Gly Ala Ser Lys Gly Lys Gly Ser Met His Ile Phe Ala Lys Asn
                165                 170                 175

Phe Tyr Gly Gly Asn Gly Ile Val Gly Ala Gln Ile Pro Leu Gly Ala
            180                 185                 190

Gly Ile Gly Phe Ala Gln Lys Tyr Leu Glu Lys Pro Thr Thr Thr Phe
        195                 200                 205

Ala Leu Tyr Gly Asp Gly Ala Ser Asn Gln Gly Gln Ala Phe Glu Ala
    210                 215                 220

Phe Asn Met Ala Lys Leu Trp Gly Leu Pro Val Ile Phe Ala Cys Glu
225                 230                 235                 240

Asn Asn Lys Tyr Gly Met Gly Thr Ser Ala Glu Arg Ser Ser Ala Met
                245                 250                 255

Thr Glu Phe Tyr Lys Arg Gly Gln Tyr Ile Pro Gly Leu Leu Val Asn
```

|  |  |  | 260 |  |  |  | 265 |  |  |  | 270 |  |
|---|---|---|---|---|---|---|---|---|---|---|---|---|
| Gly | Met | Asp | Val | Leu | Ala | Val | Leu | Gln | Ala | Ser | Lys | Phe | Ala | Lys | Lys |
|  |  |  | 275 |  |  |  | 280 |  |  |  | 285 |  |

Tyr Thr Val Glu Asn Ser Gln Pro Leu Leu Met Glu Phe Val Thr Tyr
              290                 295                 300

Arg Tyr Gly Gly His Ser Met Ser Asp Pro Gly Thr Thr Tyr Arg Ser
305                 310                 315                 320

Arg Glu Glu Val Gln Lys Val Arg Ala Ala Arg Asp Pro Ile Glu Gly
                325                 330                 335

Leu Lys Lys His Ile Met Glu Trp Gly Val Ala Asn Ala Asn Glu Leu
                340                 345                 350

Lys Asn Ile Glu Lys Arg Ile Arg Gly Met Val Asp Glu Glu Val Arg
                355                 360                 365

Ile Ala Glu Glu Ser Pro Phe Pro Asp Pro Ile Glu Glu Ser Leu Phe
                370                 375                 380

Ser Asp Val Tyr Val Ala Gly Thr Glu Pro Ala Tyr Ala Arg Gly Arg
385                 390                 395                 400

Asn Ser Leu Glu Tyr His Gln Tyr Lys
                405

<210> SEQ ID NO 73
<211> LENGTH: 1206
<212> TYPE: DNA
<213> ORGANISM: Candida albicans

<400> SEQUENCE: 73

```
atgtaccgtg caacagctac tagtcgccaa ttggtcggta ctaccgccaa tatacttgtc      60
gccaaaagat caatggccaa agccgcctca gatttggtca ctatcgaatt accagccagc     120
tcctacgaag gatacaattt ggaagttcca gctttgagtt ttgaaaccga aaagaaacc      180
ttattgaaaa tgtacaaaga tatgattatc atcagaagaa tggaaatggc agccgatgct     240
ttatacaaga gtaaaaaaat tagaggtttc tgtcacttgt ctgtcggtca agaagccatt     300
gctgttggta ttgaaaatgc cattacacca actgacactg tcattacctc ttatagatgt     360
cacggttttg cattcatgag aggtgcttct gtcaaatctg ttttggccga gttaatgggt     420
agaagatctg gtattgccaa cggtaagggt ggatcaatgc atatgttcac taacggattc     480
tacggtggta acggtattgt tggtgcccaa gttccattgg gtgctggatt ggctttctcc     540
cacaagtaca agaacgacaa agctgtcact tttgatttgt atggtgatgg tgcgtctaac     600
caaggacaag ttttcgaagc ttacaacatg gccaaattgt ggaacttacc agttattttc     660
gcctgtgaaa acaacaagta tggtatgggt acctctgctg ccagatcatc agctatgacc     720
gaatactaca agagaggtca atatatccca ggtttgaaaa tcaacggtat ggatgtgttg     780
gccacctacc aagcctccaa attcgccaaa gactgggctt ctcaaggcaa tggacctctt     840
gttttagaat acgaaactta cagatatggt ggtcactcca tgtctgatcc aggtaccact     900
tacagaacca gagaagaagt ccaacatatg agatctagaa acgatccaat tgctggattg     960
aaagctgttt tgttagaaaa agagattgct tctgaagacg aaatcaaatc ttacgacaaa    1020
gccgctagaa aatacgttga tgaacaagtt gctgctgctg aagctgatgc tccaccagaa    1080
gctaaaatgg atatttttatt cgaagacgtt tatgttccag gtagtgagat tcctgttttg    1140
agaggtagaa tctccgacga tagttgggat ttcaaaaaca agactttttt gaacaaggtc    1200
tattaa                                                               1206
```

-continued

```
<210> SEQ ID NO 74
<211> LENGTH: 401
<212> TYPE: PRT
<213> ORGANISM: Candida albicans

<400> SEQUENCE: 74

Met Tyr Arg Ala Thr Ala Thr Ser Arg Gln Leu Val Gly Thr Thr Ala
1               5                   10                  15

Asn Ile Leu Val Ala Lys Arg Ser Met Ala Lys Ala Ala Ser Asp Leu
            20                  25                  30

Val Thr Ile Glu Leu Pro Ala Ser Ser Tyr Glu Gly Tyr Asn Leu Glu
        35                  40                  45

Val Pro Ala Leu Ser Phe Glu Thr Glu Lys Glu Thr Leu Leu Lys Met
    50                  55                  60

Tyr Lys Asp Met Ile Ile Arg Arg Met Glu Met Ala Ala Asp Ala
65                  70                  75                  80

Leu Tyr Lys Ser Lys Lys Ile Arg Gly Phe Cys His Leu Ser Val Gly
                85                  90                  95

Gln Glu Ala Ile Ala Val Gly Ile Glu Asn Ala Ile Thr Pro Thr Asp
            100                 105                 110

Thr Val Ile Thr Ser Tyr Arg Cys His Gly Phe Ala Phe Met Arg Gly
        115                 120                 125

Ala Ser Val Lys Ser Val Leu Ala Glu Leu Met Gly Arg Arg Ser Gly
    130                 135                 140

Ile Ala Asn Gly Lys Gly Gly Ser Met His Met Phe Thr Asn Gly Phe
145                 150                 155                 160

Tyr Gly Gly Asn Gly Ile Val Gly Ala Gln Val Pro Leu Gly Ala Gly
                165                 170                 175

Leu Ala Phe Ser His Lys Tyr Lys Asn Asp Lys Ala Val Thr Phe Asp
            180                 185                 190

Leu Tyr Gly Asp Gly Ala Ser Asn Gln Gly Gln Val Phe Glu Ala Tyr
        195                 200                 205

Asn Met Ala Lys Leu Trp Asn Leu Pro Val Ile Phe Ala Cys Glu Asn
    210                 215                 220

Asn Lys Tyr Gly Met Gly Thr Ser Ala Ala Arg Ser Ser Ala Met Thr
225                 230                 235                 240

Glu Tyr Tyr Lys Arg Gly Gln Tyr Ile Pro Gly Leu Lys Ile Asn Gly
                245                 250                 255

Met Asp Val Leu Ala Thr Tyr Gln Ala Ser Lys Phe Ala Lys Asp Trp
            260                 265                 270

Ala Ser Gln Gly Asn Gly Pro Leu Val Leu Glu Tyr Glu Thr Tyr Arg
        275                 280                 285

Tyr Gly Gly His Ser Met Ser Asp Pro Gly Thr Thr Tyr Arg Thr Arg
    290                 295                 300

Glu Glu Val Gln His Met Arg Ser Arg Asn Asp Pro Ile Ala Gly Leu
305                 310                 315                 320

Lys Ala Val Leu Leu Glu Lys Glu Ile Ala Ser Glu Asp Glu Ile Lys
                325                 330                 335

Ser Tyr Asp Lys Ala Ala Arg Lys Tyr Val Asp Glu Gln Val Ala Ala
            340                 345                 350

Ala Glu Ala Asp Ala Pro Pro Glu Ala Lys Met Asp Ile Leu Phe Glu
        355                 360                 365

Asp Val Tyr Val Pro Gly Ser Glu Ile Pro Val Leu Arg Gly Arg Ile
    370                 375                 380

Ser Asp Asp Ser Trp Asp Phe Lys Asn Lys Thr Phe Leu Asn Lys Val
```

385         390         395         400
Tyr

<210> SEQ ID NO 75
<211> LENGTH: 1227
<212> TYPE: DNA
<213> ORGANISM: Kluyveromyces lactis

<400> SEQUENCE: 75

```
atgctatctt tgaaagctca atcctctgtg gttgggaagt ccagctcttt gagattggtt      60
agaaactttt ctaaaaacgt ccgtgctttg tcccaggttg ctgatgaaac taagccaggt     120
gatgatgacc tagttcaaat tgatttgcca gaaacctctt ttgaaggtta tcttttggat     180
gttcctgaat taagttatca aaccaccaag tccaatttgc tacaaatgta caaggatatg     240
attatcgtta aagaatgga atggcctgt gacgctttgt acaaggctaa gaaaattaga       300
ggtttctgtc actcctctgt cggtcaagaa gccattgccg ttggtattga aaacgctatc     360
actaagcgtg ataccgtcat cacctcttac agatgtcatg gtttcaccta catgagaggt     420
gctgctgttc aagctgtgtt ggctgaattg atgggtagaa gaactggtgt gtccttcggt     480
aagggtggtt ccatgcactt gtacgcccct ggtttctacg gtggtaatgg tatcgttggt     540
gcccaagtcc cattgggtgc tggtttggcc ttcgctcatc aatacaaaca cgaagatgct     600
tgttcttttg ccttgtacgg tgatggtgcc tctaaccaag gtcaagtttt cgaatccttc     660
aacatggcca gttatggaa cttaccagcc gtcttctgtt gtgaaaacaa caagtacggt     720
atgggtaccg ctgccgcaag atcttcagcc atgactgaat acttcaagcg tggtcaatac     780
attcctggtt tgaaggttaa cggtatggat atcttggctg ttaccaagct taaggactgg     840
actgtctccg gtaacggtcc aatcgttctt gaatacgaaa cttacagata tggtggtcac     900
tctatgtctg atccaggtac tacttacaga accagagatg aaatccaaca catgagatct     960
aagaacgatc caattgcagg tttaaagatg cacttattgg aattgggtat cgccacggaa    1020
gatgaaatta aggcttacga caaggctgct agaaagtacg tcgatgagca agtcgaatta    1080
gctgatgctc cccagctcc agaagctaag atgtccatct tgttcgagga tgtctacgtt    1140
ccaggttctg aaactccaac cctaagaggt agattgcaag aagatacttg ggattttgct    1200
aagaagagct ttgctttcag agattag                                        1227
```

<210> SEQ ID NO 76
<211> LENGTH: 408
<212> TYPE: PRT
<213> ORGANISM: Kluyveromyces lactis

<400> SEQUENCE: 76

```
Met Leu Ser Leu Lys Ala Gln Ser Ser Val Val Gly Lys Ser Ser
1               5                   10                  15

Leu Arg Leu Val Arg Asn Phe Ser Lys Asn Val Arg Ala Leu Ser Gln
            20                  25                  30

Val Ala Asp Glu Thr Lys Pro Gly Asp Asp Leu Val Gln Ile Asp
        35                  40                  45

Leu Pro Glu Thr Ser Phe Glu Gly Tyr Leu Leu Asp Val Pro Glu Leu
    50                  55                  60

Ser Tyr Gln Thr Thr Lys Ser Asn Leu Leu Gln Met Tyr Lys Asp Met
65                  70                  75                  80

Ile Ile Val Arg Arg Met Glu Met Ala Cys Asp Ala Leu Tyr Lys Ala
                85                  90                  95
```

```
Lys Lys Ile Arg Gly Phe Cys His Ser Ser Val Gly Gln Glu Ala Ile
                100                 105                 110
Ala Val Gly Ile Glu Asn Ala Ile Thr Lys Arg Asp Thr Val Ile Thr
            115                 120                 125
Ser Tyr Arg Cys His Gly Phe Thr Tyr Met Arg Gly Ala Ala Val Gln
130                 135                 140
Ala Val Leu Ala Glu Leu Met Gly Arg Arg Thr Gly Val Ser Phe Gly
145                 150                 155                 160
Lys Gly Gly Ser Met His Leu Tyr Ala Pro Gly Phe Tyr Gly Gly Asn
                165                 170                 175
Gly Ile Val Gly Ala Gln Val Pro Leu Gly Ala Gly Leu Ala Phe Ala
            180                 185                 190
His Gln Tyr Lys His Glu Asp Ala Cys Ser Phe Ala Leu Tyr Gly Asp
        195                 200                 205
Gly Ala Ser Asn Gln Gly Gln Val Phe Glu Ser Phe Asn Met Ala Lys
210                 215                 220
Leu Trp Asn Leu Pro Ala Val Phe Cys Cys Glu Asn Asn Lys Tyr Gly
225                 230                 235                 240
Met Gly Thr Ala Ala Arg Ser Ser Ala Met Thr Glu Tyr Phe Lys
                245                 250                 255
Arg Gly Gln Tyr Ile Pro Gly Leu Lys Val Asn Gly Met Asp Ile Leu
                260                 265                 270
Ala Val Thr Lys Leu Lys Asp Trp Thr Val Ser Gly Asn Gly Pro Ile
            275                 280                 285
Val Leu Glu Tyr Glu Thr Tyr Arg Tyr Gly Gly His Ser Met Ser Asp
        290                 295                 300
Pro Gly Thr Thr Tyr Arg Thr Arg Asp Glu Ile Gln His Met Arg Ser
305                 310                 315                 320
Lys Asn Asp Pro Ile Ala Gly Leu Lys Met His Leu Leu Glu Leu Gly
                325                 330                 335
Ile Ala Thr Glu Asp Glu Ile Lys Ala Tyr Asp Lys Ala Ala Arg Lys
                340                 345                 350
Tyr Val Asp Glu Gln Val Glu Leu Ala Asp Ala Ala Pro Ala Pro Glu
            355                 360                 365
Ala Lys Met Ser Ile Leu Phe Glu Asp Val Tyr Val Pro Gly Ser Glu
        370                 375                 380
Thr Pro Thr Leu Arg Gly Arg Leu Gln Glu Asp Thr Trp Asp Phe Ala
385                 390                 395                 400
Lys Lys Ser Phe Ala Phe Arg Asp
                405

<210> SEQ ID NO 77
<211> LENGTH: 1185
<212> TYPE: DNA
<213> ORGANISM: Yarrowia lipolytica

<400> SEQUENCE: 77
atgctcactg ccgctcgacg atctacacgg ctcaccagcc gactcggcca ccaggtccga      60
gcatactcca tcgctgacga tgccgacaag aaatgcacaa tcacgctcaa ggaggattct     120
tacaccacct acatgcttga ttctccccct cctctcgagt tcgagatgac caagggtgag     180
cttctgcaaa tgtacaagga catggtgacc gtccgacgac tcgagatggc tgctgatgcc     240
ctctacaagg ccaagaagat ccgaggtttc tgccatctgt ctactggtca ggaggctgtt     300
gccgtcggta tcgagaaggc catcgaccac gacgattctg tcatcaccgc ctaccgatgc     360
```

```
cacggtttcg cctacatgcg aggtgcctct gtccgagcaa tcatcgccga gctgctcgga    420
aagcgaaccg tgtctcccta cggtaagggt ggatccatgc acatgttcac cgagggtttc    480
tacggaggaa acggtattgt cggagcccag gtccccgtcg agctggtctc gccttcgcc     540 cacaagtacc tcgagcagac cggaaaggcc acctttgccc tgtacggtga cggtgcttcc    600
aaccagggtc agatcttcga ggcctacaac atggccaagc tctgggacct cccctgcatc    660
tttgcatgcg agaacaacaa gtacggaatg ggtaccgctg ctgctcgatc tctgccctg     720 acgcagtact acaagcgagg tcagtacatt cccggtctca aggttaacgg aatggacatt    780
ctgtccgtct accagggagc caagttcgcc aaggagtgga ccacacacgg caagggtccc    840
ctcgtcatgg agttcgagac ctaccgatac ggtggtcact ccatgtccga tcccggaacc    900
acctaccgaa cccgagagga gatccagtac atgcgatccc acaacgatcc tatttctggt    960
ctcaaggccc acatcctgga gcttaatttc gccactgagg acgagcttaa gtctgtggac   1020
aaggctgctc gagctatggt tgacaaggag gttgcccttg ctgagtccga ccctgctcct   1080
gaggctactg ccaaggttct gtttgaggat atctacgttc ccggcaccga gcctcctgtg   1140
atccgaggcc gaatcccttc cgaggactac tactttaaga actaa                   1185
```

<210> SEQ ID NO 78
<211> LENGTH: 394
<212> TYPE: PRT
<213> ORGANISM: Yarrowia lipolytica

<400> SEQUENCE: 78

```
Met Leu Thr Ala Ala Arg Arg Ser Thr Arg Leu Thr Ser Arg Leu Gly
1               5                   10                  15

His Gln Val Arg Ala Tyr Ser Ile Ala Asp Asp Ala Asp Lys Lys Cys
            20                  25                  30

Thr Ile Thr Leu Lys Glu Asp Ser Tyr Thr Thr Tyr Met Leu Asp Ser
        35                  40                  45

Pro Pro Pro Leu Glu Phe Glu Met Thr Lys Gly Glu Leu Leu Gln Met
    50                  55                  60

Tyr Lys Asp Met Val Thr Val Arg Arg Leu Glu Met Ala Ala Asp Ala
65                  70                  75                  80

Leu Tyr Lys Ala Lys Lys Ile Arg Gly Phe Cys His Leu Ser Thr Gly
                85                  90                  95

Gln Glu Ala Val Ala Val Gly Ile Glu Lys Ala Ile Asp His Asp Asp
            100                 105                 110

Ser Val Ile Thr Ala Tyr Arg Cys His Gly Phe Ala Tyr Met Arg Gly
        115                 120                 125

Ala Ser Val Arg Ala Ile Ile Ala Glu Leu Leu Gly Lys Arg Thr Gly
    130                 135                 140

Val Ser Tyr Gly Lys Gly Gly Ser Met His Met Phe Thr Glu Gly Phe
145                 150                 155                 160

Tyr Gly Gly Asn Gly Ile Val Gly Ala Gln Val Pro Val Gly Ala Gly
                165                 170                 175

Leu Ala Phe Ala His Lys Tyr Leu Glu Gln Thr Gly Lys Ala Thr Phe
            180                 185                 190

Ala Leu Tyr Gly Asp Gly Ala Ser Asn Gln Gly Gln Ile Phe Glu Ala
        195                 200                 205

Tyr Asn Met Ala Lys Leu Trp Asp Leu Pro Cys Ile Phe Ala Cys Glu
    210                 215                 220

Asn Asn Lys Tyr Gly Met Gly Thr Ala Ala Ala Arg Ser Ser Ala Leu
225                 230                 235                 240
```

```
Thr Gln Tyr Tyr Lys Arg Gly Gln Tyr Ile Pro Gly Leu Lys Val Asn
            245                 250                 255
Gly Met Asp Ile Leu Ser Val Tyr Gln Gly Ala Lys Phe Ala Lys Glu
        260                 265                 270
Trp Thr Thr His Gly Lys Gly Pro Leu Val Met Glu Phe Glu Thr Tyr
            275                 280                 285
Arg Tyr Gly Gly His Ser Met Ser Asp Pro Gly Thr Thr Tyr Arg Thr
    290                 295                 300
Arg Glu Glu Ile Gln Tyr Met Arg Ser His Asn Asp Pro Ile Ser Gly
305                 310                 315                 320
Leu Lys Ala His Ile Leu Glu Leu Asn Phe Ala Thr Glu Asp Glu Leu
                325                 330                 335
Lys Ser Val Asp Lys Ala Ala Arg Ala Met Val Asp Lys Glu Val Ala
            340                 345                 350
Leu Ala Glu Ser Asp Pro Ala Pro Glu Ala Thr Ala Lys Val Leu Phe
        355                 360                 365
Glu Asp Ile Tyr Val Pro Gly Thr Glu Pro Pro Val Ile Arg Gly Arg
    370                 375                 380
Ile Pro Ser Glu Asp Tyr Tyr Phe Lys Asn
385                 390
```

<210> SEQ ID NO 79
<211> LENGTH: 1191
<212> TYPE: DNA
<213> ORGANISM: Pichia stipitis

<400> SEQUENCE: 79

```
atgttacgta ctgctgctgt tcgtcctctt aagggcggtg ttgtcatcgc cagaagagcc     60
atggcctcgt ccagcgactt ggtcagcatc gaattgcctg aatcgtcgtt tgaaggctac    120
aacttggaga tccccgagtt gactttcgaa accgaaaagg aaaccttgtt gaagatgtac    180
aaggatatga tcatcatcag aagaatggaa atggcttcag acgccttgta caaggccaag    240
aagatcagag ggttctgcca cttgtctgtt ggtcaagaag ccattgccgt tggaattgag    300
aacgccatta ctcctgaaga tactgtcatc acctcttaca gatgtcacgg ttttgctttc    360
atgagaggtg cttctgtcaa ggaagttctc ggagaattga tgggtaagag atctggtgtt    420
tcttatggta aggtggttc tatgcacatg tttgccccag cttttacgg aggaaacggt     480
atcgttggag ctcaagttcc attgggtgct ggtttagctt ctcccacaa gtacaggga     540
cagaaggctg ctgccttcac tttgtacggt gacggtgcct ccaaccaggg acaagttttc    600
gaagcctaca catggccaa gttgtggaac ttgccttgta tctttgcctg tgaaaacaac    660
aagtacggta tgggtactgc tgctgccaga tcctctgcta ttactgagta ctacaagaga    720
ggtcaataca ttcctggttt gaagatcaac ggtatggacg ttttggctac ctaccaggct    780
tccaagtttg ccaaggactg gctgctcaa ggcaacggac cattggtttt ggaatacgaa     840
acctacagat acggtggtca ctccatgtct gacccaggta ccacctacag aacaagagaa    900
gaagtgcaac acatgagatc cagaaacgat cctattgccg gcttaaaggc tactttgttg    960
gacaagggca ttgctaccga agaagaaatc aagtcctatg acaaggctgc cagaaagtac   1020
gtcgacgaac aagtcgctgc tgctgaagct gacgctcctc ctgaagccaa gatggacatc   1080
ttattcgaag atgtatatgt cccaggatct gaaatcccag tgttgagagg cagaatctcg   1140
gacgactcgt gggacttcaa gaacaaaact ttcttgaaca aggtctacta g            1191
```

```
<210> SEQ ID NO 80
<211> LENGTH: 396
<212> TYPE: PRT
<213> ORGANISM: Pichia stipitis

<400> SEQUENCE: 80

Met Leu Arg Thr Ala Ala Val Arg Pro Leu Lys Gly Gly Val Val Ile
1               5                   10                  15

Ala Arg Arg Ala Met Ala Ser Ser Asp Leu Val Ser Ile Glu Leu
            20                  25                  30

Pro Glu Ser Ser Phe Glu Gly Tyr Asn Leu Glu Ile Pro Glu Leu Thr
            35                  40                  45

Phe Glu Thr Glu Lys Glu Thr Leu Leu Lys Met Tyr Lys Asp Met Ile
50                  55                  60

Ile Ile Arg Arg Met Glu Met Ala Ser Asp Ala Leu Tyr Lys Ala Lys
65                  70                  75                  80

Lys Ile Arg Gly Phe Cys His Leu Ser Val Gly Gln Glu Ala Ile Ala
                85                  90                  95

Val Gly Ile Glu Asn Ala Ile Thr Pro Glu Asp Thr Val Ile Thr Ser
            100                 105                 110

Tyr Arg Cys His Gly Phe Ala Phe Met Arg Gly Ala Ser Val Lys Glu
        115                 120                 125

Val Leu Gly Glu Leu Met Gly Lys Arg Ser Gly Val Ser Tyr Gly Lys
    130                 135                 140

Gly Gly Ser Met His Met Phe Ala Pro Gly Phe Tyr Gly Gly Asn Gly
145                 150                 155                 160

Ile Val Gly Ala Gln Val Pro Leu Gly Ala Gly Leu Ala Phe Ser His
                165                 170                 175

Lys Tyr Arg Gly Gln Lys Ala Ala Phe Thr Leu Tyr Gly Asp Gly
            180                 185                 190

Ala Ser Asn Gln Gly Gln Val Phe Glu Ala Tyr Asn Met Ala Lys Leu
        195                 200                 205

Trp Asn Leu Pro Cys Ile Phe Ala Cys Glu Asn Asn Lys Tyr Gly Met
    210                 215                 220

Gly Thr Ala Ala Ala Arg Ser Ser Ala Ile Thr Glu Tyr Tyr Lys Arg
225                 230                 235                 240

Gly Gln Tyr Ile Pro Gly Leu Lys Ile Asn Gly Met Asp Val Leu Ala
                245                 250                 255

Thr Tyr Gln Ala Ser Lys Phe Ala Lys Asp Trp Ala Ala Gln Gly Asn
            260                 265                 270

Gly Pro Leu Val Leu Glu Tyr Glu Thr Tyr Arg Tyr Gly Gly His Ser
        275                 280                 285

Met Ser Asp Pro Gly Thr Thr Tyr Arg Thr Arg Glu Glu Val Gln His
    290                 295                 300

Met Arg Ser Arg Asn Asp Pro Ile Ala Gly Leu Lys Ala Thr Leu Leu
305                 310                 315                 320

Asp Lys Gly Ile Ala Thr Glu Glu Ile Lys Ser Tyr Asp Lys Ala
                325                 330                 335

Ala Arg Lys Tyr Val Asp Glu Gln Val Ala Ala Glu Ala Asp Ala
            340                 345                 350

Pro Pro Glu Ala Lys Met Asp Ile Leu Phe Glu Asp Val Tyr Val Pro
        355                 360                 365

Gly Ser Glu Ile Pro Val Leu Arg Gly Arg Ile Ser Asp Ser Trp
    370                 375                 380

Asp Phe Lys Asn Lys Thr Phe Leu Asn Lys Val Tyr
```

385            390            395

<210> SEQ ID NO 81
<211> LENGTH: 76
<212> TYPE: DNA
<213> ORGANISM: artificial sequence
<220> FEATURE:
<223> OTHER INFORMATION: primer

<400> SEQUENCE: 81
gtgagtgcta caagccacat ttaaactaag tcaattacac aaagttagtg ggtcgcctga    60
cgcatatacc tttttc                                                    76

<210> SEQ ID NO 82
<211> LENGTH: 76
<212> TYPE: DNA
<213> ORGANISM: artificial sequence
<220> FEATURE:
<223> OTHER INFORMATION: primer

<400> SEQUENCE: 82
attttaccta acaagttgtt gcgtaaattt ataaagtaaa ttgtcggttt ttttgtgtgg    60
tgccctcctc cttgtc                                                    76

<210> SEQ ID NO 83
<211> LENGTH: 33
<212> TYPE: DNA
<213> ORGANISM: artificial sequence
<220> FEATURE:
<223> OTHER INFORMATION: primer

<400> SEQUENCE: 83
gagtcatctc aaacatatgt ctgcagatac ttc                                 33

<210> SEQ ID NO 84
<211> LENGTH: 31
<212> TYPE: DNA
<213> ORGANISM: artificial sequence
<220> FEATURE:
<223> OTHER INFORMATION: primer

<400> SEQUENCE: 84
gaaatagctt taagaacctt aatggcttcg g                                   31

<210> SEQ ID NO 85
<211> LENGTH: 4280
<212> TYPE: DNA
<213> ORGANISM: artificial sequence
<220> FEATURE:
<223> OTHER INFORMATION: vector

<400> SEQUENCE: 85
ggggatcctc tagagtcgac ctgcaggcat gcaagcttgg cgtaatcatg gtcatagctg    60
tttcctgtgt gaaattgtta tccgctcaca attccacaca acatacgagc cggaagcata   120
aagtgtaaag cctggggtgc ctaatgagtg agctaactca cattaattgc gttgcgctca   180
ctgcccgctt tccagtcggg aaacctgtcg tgccagctgc attaatgaat cggccaacgc   240
gcggggagag gcggtttgcg tattgggcgc tcttccgctt cctcgctcac tgactcgctg   300
cgctcggtcg ttcggctgcg gcgagcggta tcagctcact caaaggcggt aatacggtta   360
tccacagaat caggggataa cgcaggaaag aacatgtgag caaaaggcca gcaaaaggcc   420
aggaaccgta aaaaggccgc gttgctggcg tttttccata ggctccgccc ccctgacgag   480

-continued

```
catcacaaaa atcgacgctc aagtcagagg tggcgaaacc cgacaggact ataaagatac    540
caggcgtttc ccctggaag ctccctcgtg cgctctcctg ttccgaccct gccgcttacc     600
ggatacctgt ccgcctttct cccttcggga agcgtggcgc tttctcatag ctcacgctgt    660
aggtatctca gttcggtgta ggtcgttcgc tccaagctgg gctgtgtgca cgaaccccc     720 gttcagcccg accgctgcgc cttatccggt aactatcgtc ttgagtccaa cccggtaaga    780
cacgacttat cgccactggc agcagccact ggtaacagga ttagcagagc gaggtatgta    840
ggcggtgcta cagagttctt gaagtggtgg cctaactacg gctacactag aaggacagta    900
tttggtatct gcgctctgct gaagccagtt accttcggaa aaagagttgg tagctcttga    960
tccggcaaac aaaccaccgc tggtagcggt ggtttttttg tttgcaagca gcagattacg   1020
cgcagaaaaa aaggatctca agaagatcct ttgatctttt ctacgggtc tgacgctcag    1080 tggaacgaaa actcacgtta agggattttg gtcatgagat tatcaaaaag gatcttcacc   1140
tagatccttt taaattaaaa atgaagtttt aaatcaatct aaagtatata tgagtaaact   1200
tggtctgaca gttaccaatg cttaatcagt gaggcaccta tctcagcgat ctgtctattt   1260
cgttcatcca tagttgcctg actccccgtc gtgtagataa ctacgatacg ggagggctta   1320
ccatctggcc ccagtgctgc aatgataccg cgagacccac gctcaccggc tccagattta   1380
tcagcaataa accagccagc cggaagggcc gagcgcagaa gtggtcctgc aactttatcc   1440
gcctccatcc agtctattaa ttgttgccgg gaagctagag taagtagttc gccagttaat   1500
agtttgcgca acgttgttgc cattgctaca ggcatcgtgg tgtcacgctc gtcgtttggt   1560
atggcttcat tcagctccgg ttcccaacga tcaaggcgag ttacatgatc ccccatgttg   1620
tgcaaaaaag cggttagctc cttcggtcct ccgatcgttg tcagaagtaa gttggccgca   1680
gtgttatcac tcatggttat ggcagcactg cataattctc ttactgtcat gccatccgta   1740
agatgctttt ctgtgactgg tgagtactca accaagtcat tctgagaata gtgtatgcgg   1800
cgaccgagtt gctcttgccc ggcgtcaata cgggataata ccgcgccaca tagcagaact   1860
ttaaaagtgc tcatcattgg aaaacgttct cggggcgaa aactctcaag gatcttaccg    1920
ctgttgagat ccagttcgat gtaacccact cgtgcaccca actgatcttc agcatctttt   1980
actttcacca gcgtttctgg gtgagcaaaa acaggaaggc aaaatgccgc aaaaaaggga   2040
ataagggcga cacggaaatg ttgaatactc atactcttcc ttttcaata ttattgaagc    2100 atttatcagg gttattgtct catgagcgga tacatatttg aatgtattta gaaaaataaa   2160
caaatagggg ttccgcgcac atttccccga aaagtgccac ctgacgtcta agaaaccatt   2220
attatcatga cattaaccta taaaaatagg cgtatcacga ggccctttcg tctcgcgcgt   2280
ttcggtgatg acggtgaaaa cctctgacac atgcagctcc ggagacggt cacagcttgt    2340 ctgtaagcgg atgccgggag cagacaagcc cgtcagggcg cgtcagcggg tgttggcggg   2400
tgtcggggct ggcttaacta tgcggcatca gagcagattg tactgagagt gcaccatatg   2460
cggtgtgaaa taccgcacag atgcgtaagg agaaaatacc gcatcaggcg ccattcgcca   2520
ttcaggctgc gcaactgttg ggaagggcga tcggtgcggg cctcttcgct attacgccag   2580
ctggcgaaag ggggatgtgc tgcaaggcga ttaagttggg taacgccagg gttttcccag   2640
tcacgacgtt gtaaaacgac ggccagtgaa ttcgagctcg gtaccccgg ctctgagaca    2700 gtagtaggtt agtcatcgct ctaccgacgc gcaggaaaag aaagaagcat tgcggattac   2760
gtattctaat gttcagcccg cggaacgcca gcaaatcacc acccatgcgc atgatactga   2820
gtcttgtaca cgctgggctt ccagtgtact gagagtgcac cataccacag ctttttcaatt  2880
```

-continued

| | |
|---|---|
| caattcatca ttttttttttt attctttttt ttgatttcgg tttctttgaa attttttga | 2940 |
| ttcggtaatc tccgaacaga aggaagaacg aaggaaggag cacagactta gattggtata | 3000 |
| tatacgcata tgtagtgttg aagaaacatg aaattgccca gtattcttaa cccaactgca | 3060 |
| cagaacaaaa acctgcagga aacgaagata atcatgtcg aaagctacat ataaggaacg | 3120 |
| tgctgctact catcctagtc ctgttgctgc caagctattt aatatcatgc acgaaaagca | 3180 |
| aacaaacttg tgtgcttcat tggatgttcg taccaccaag gaattactgg agttagttga | 3240 |
| agcattaggt cccaaaattt gtttactaaa acacatgtg gatatcttga ctgattttc | 3300 |
| catggagggc acagttaagc cgctaaaggc attatccgcc aagtacaatt ttttactctt | 3360 |
| cgaagacaga aaatttgctg acattggtaa tacagtcaaa ttgcagtact ctgcgggtgt | 3420 |
| atacagaata gcagaatggg cagacattac gaatgcacac ggtgtggtgg gcccaggtat | 3480 |
| tgttagcggt ttgaagcagg cggcagaaga agtaacaaag gaacctagag gccttttgat | 3540 |
| gttagcagaa ttgtcatgca agggctccct atctactgga gaatatacta agggtactgt | 3600 |
| tgacattgcg aagagcgaca aagattttgt tatcggcttt attgctcaaa gagacatggg | 3660 |
| tggaagagat gaaggttacg attggttgat tatgacaccc ggtgtgggtt tagatgacaa | 3720 |
| gggagacgca ttgggtcaac agtatagaac cgtggatgat gtggtctcta caggatctga | 3780 |
| cattattatt gttggaagag gactatttgc aaagggaagg gatgctaagg tagagggtga | 3840 |
| acgttacaga aaagcaggct gggaagcata tttgagaaga tgcggccagc aaaactaaaa | 3900 |
| aactgtatta taagtaaatg catgtatact aaactcacaa attagagctt caatttaatt | 3960 |
| atatcagtta ttaccctatg cggtgtgaaa taccgcacag atgcgtaagg agaaaatacc | 4020 |
| gcatcaggaa attgtaaacg ttaatatttt gttaaaattc gcgttaaatt tttgttaaat | 4080 |
| cagctcattt tttaaccaat aggccgaaat cggcaaaatc ttcagcccgc ggaacgccag | 4140 |
| caaatcacca cccatgcgca tgatactgag tcttgtacac gctgggcttc cagtgatgat | 4200 |
| acaacgagtt agccaaggtg agcacggatg tctaaattag aattacgttt taatatcttt | 4260 |
| ttttccatat ctagggctag | 4280 |

<210> SEQ ID NO 86
<211> LENGTH: 85
<212> TYPE: DNA
<213> ORGANISM: artificial sequence
<220> FEATURE:
<223> OTHER INFORMATION: primer

<400> SEQUENCE: 86

| | |
|---|---|
| ccggctctga gacagtagta ggttagtcat cgctctaccg acgcgcagga aaagaaagaa | 60 |
| gcattgcgga ttacgtattc taatg | 85 |

<210> SEQ ID NO 87
<211> LENGTH: 86
<212> TYPE: DNA
<213> ORGANISM: artificial sequence
<220> FEATURE:
<223> OTHER INFORMATION: primer

<400> SEQUENCE: 87

| | |
|---|---|
| ctagccctag atatggaaaa aaagatatta aaacgtaatt ctaatttaga catccgtgct | 60 |
| caccttggct aactcgttgt atcatc | 86 |

<210> SEQ ID NO 88
<211> LENGTH: 22
<212> TYPE: DNA

<210> SEQ ID NO 88
<211> LENGTH: 22
<212> TYPE: DNA
<213> ORGANISM: artificial sequence
<220> FEATURE:
<223> OTHER INFORMATION: primer

<400> SEQUENCE: 88
gagaagatgc ggccagcaaa ac    22

<210> SEQ ID NO 89
<211> LENGTH: 30
<212> TYPE: DNA
<213> ORGANISM: artificial sequence
<220> FEATURE:
<223> OTHER INFORMATION: primer

<400> SEQUENCE: 89
cgccaaacaa gtttcgggtc accccacacg    30

<210> SEQ ID NO 90
<211> LENGTH: 29
<212> TYPE: DNA
<213> ORGANISM: artificial sequence
<220> FEATURE:
<223> OTHER INFORMATION: primer

<400> SEQUENCE: 90
ctcaaaattc tattgtgttt gccggtacc    29

<210> SEQ ID NO 91
<211> LENGTH: 85
<212> TYPE: DNA
<213> ORGANISM: artificial sequence
<220> FEATURE:
<223> OTHER INFORMATION: primer

<400> SEQUENCE: 91
cattagaata cgtaatccgc aatgcttctt tcttttcctg cgcgtcggta gagcgatcgg    60
tgaatgtctg gccgaacact aattc    85

<210> SEQ ID NO 92
<211> LENGTH: 87
<212> TYPE: DNA
<213> ORGANISM: artificial sequence
<220> FEATURE:
<223> OTHER INFORMATION: primer

<400> SEQUENCE: 92
gatgatacaa cgagttagcc aaggtgagca cggatgtcta aattagaatt acgtttgtta    60
ccgctccatt agatggtacc atttag    87

<210> SEQ ID NO 93
<211> LENGTH: 30
<212> TYPE: DNA
<213> ORGANISM: artificial sequence
<220> FEATURE:
<223> OTHER INFORMATION: primer

<400> SEQUENCE: 93
atagatcgtg gaaactttc actacaaagc    30

<210> SEQ ID NO 94
<211> LENGTH: 61
<212> TYPE: DNA
<213> ORGANISM: artificial sequence
<220> FEATURE:
<223> OTHER INFORMATION: primer

```
<400> SEQUENCE: 94
gaattagtgt tcggccagac attcaccgat cgctctaccg acgcgcagga aaagaaagaa    60
g                                                                    61

<210> SEQ ID NO 95
<211> LENGTH: 60
<212> TYPE: DNA
<213> ORGANISM: artificial sequence
<220> FEATURE:
<223> OTHER INFORMATION: primer

<400> SEQUENCE: 95
ctaaaatggt accatctaat ggagcggtaa caaacgtaat tctaatttag acatccgtgc    60

<210> SEQ ID NO 96
<211> LENGTH: 20
<212> TYPE: DNA
<213> ORGANISM: artificial sequence
<220> FEATURE:
<223> OTHER INFORMATION: primer

<400> SEQUENCE: 96
cccttggggc cgctaattag                                                20

<210> SEQ ID NO 97
<211> LENGTH: 30
<212> TYPE: DNA
<213> ORGANISM: artificial sequence
<220> FEATURE:
<223> OTHER INFORMATION: primer

<400> SEQUENCE: 97
gcattgcgga ttacgtattc taatgttcag                                     30

<210> SEQ ID NO 98
<211> LENGTH: 64
<212> TYPE: DNA
<213> ORGANISM: artificial sequence
<220> FEATURE:
<223> OTHER INFORMATION: primer

<400> SEQUENCE: 98
cgtcggaggg ctgtcgcccg ctcggcggct tctaatcacc ttggctaact cgttgtatca    60
tcac                                                                 64

<210> SEQ ID NO 99
<211> LENGTH: 8459
<212> TYPE: DNA
<213> ORGANISM: artificial sequence
<220> FEATURE:
<223> OTHER INFORMATION: vector

<400> SEQUENCE: 99
ggtggagctc cagcttttgt tccctttagt gagggttaat tgcgcgcttg gcgtaatcat    60
ggtcatagct gtttcctgtg tgaaattgtt atccgctcac aattccacac aacataggag   120
ccggaagcat aaagtgtaaa gcctggggtg cctaatgagt gaggtaactc acattaattg   180
cgttgcgctc actgcccgct ttccagtcgg gaaacctgtc gtgccagctg cattaatgaa   240
tcggccaacg cgcggggaga ggcggtttgc gtattgggcg ctcttccgct tcctcgctca   300
ctgactcgct gcgctcggtc gttcggctgc ggcgagcggt atcagctcac tcaaaggcgg   360
taatacggtt atccacagaa tcaggggata acgcaggaaa gaacatgtga gcaaaaggcc   420
```

```
agcaaaaggc caggaaccgt aaaaaggccg cgttgctggc gttttTccat aggctccgcc    480
cccctgacga gcatcacaaa aatcgacgct caagtcagag gtggcgaaac cgacaggac    540 tataaagata ccaggcgttt ccccctggaa gctccctcgt gcgctctcct gttccgaccc    600
tgccgcttac cggatacctg tccgcctttc tcccttcggg aagcgtggcg ctttctcata    660
gctcacgctg taggtatctc agttcggtgt aggtcgttcg ctccaagctg gctgtgtgc    720 acgaaccccc cgttcagccc gaccgctgcg ccttatccgg taactatcgt cttgagtcca    780
acccggtaag acacgactta tcgccactgg cagcagccac tggtaacagg attagcagag    840
cgaggtatgt aggcggtgct acagagttct gaagtggtg gcctaactac ggctacacta    900
gaaggacagt atttggtatc tgcgctctgc tgaagccagt taccttcgga aaagagttg    960 gtagctcttg atccggcaaa caaccaccg ctggtagcgg tggttttttt gtttgcaagc    1020
agcagattac gcgcagaaaa aaaggatctc aagaagatcc tttgatcttt tctacggggt    1080
ctgacgctca gtggaacgaa aactcacgtt aagggatttt ggtcatgaga ttatcaaaaa    1140
ggatcttcac ctagatcctt ttaaattaaa aatgaagttt aaatcaatc taaagtatat    1200 atgagtaaac ttggtctgac agttaccaat gcttaatcag tgaggcacct atctcagcga    1260
tctgtctatt tcgttcatcc atagttgcct gactccccgt cgtgtagata actacgatac    1320
gggagggctt accatctggc cccagtgctg caatgatacc gcgagaccca cgctcaccgg    1380
ctccagattt atcagcaata aaccagccag ccggaagggc cgagcgcaga gtggtcctg    1440 caactttatc cgcctccatc cagtctatta attgttgccg gaagctaga gtaagtagtt    1500 cgccagttaa tagtttgcgc aacgttgttg ccattgctac aggcatcgtg gtgtcacgct    1560
cgtcgtttgg tatggcttca ttcagctccg gttcccaacg atcaaggcga gttacatgat    1620
cccccatgtt gtgcaaaaaa gcggttagct ccttcggtcc tccgatcgtt gtcagaagta    1680
agttggccgc agtgttatca ctcatggtta tggcagcact gcataattct cttactgtca    1740
tgccatccgt aagatgcttt tctgtgactg gtgagtactc aaccaagtca ttctgagaat    1800
agtgtatgcg gcgaccgagt tgctcttgcc cggcgtcaat acgggataat accgcgccac    1860
atagcagaac tttaaaagtg ctcatcattg gaaaacgttc ttcggggcga aaactctcaa    1920
ggatcttacc gctgttgaga tccagttcga tgtaacccac tcgtgcaccc aactgatctt    1980
cagcatcttt tactttcacc agcgtttctg ggtgagcaaa acaggaagg caaaatgccg    2040 caaaaaggg aataagggcg acacggaaat gttgaatact catactcttc cttttTcaat    2100
attattgaag catttatcag ggttattgtc tcatgagcgg atacatattt gaatgtattt    2160
agaaaaataa acaaataggg gttccgcgca catttccccg aaaagtgcca cctgaacgaa    2220
gcatctgtgc ttcattttgt agaacaaaaa tgcaacgcga gagcgctaat ttttcaaaca    2280
aagaatctga gctgcatttt tacagaacag aaatgcaacg cgaaagcgct attttaccaa    2340
cgaagaatct gtgcttcatt tttgtaaaac aaaaatgcaa cgcgagagcg ctaatttttc    2400
aaacaaagaa tctgagctgc atttttacag aacagaaatg caacgcgaga gcgctatttt    2460
accaacaaag aatctatact tcttttttgt tctacaaaaa tgcatcccga gagcgctatt    2520
tttctaacaa agcatcttag attactttt ttctcctttg tgcgctctat aatgcagtct    2580
cttgataact ttttgcactg taggtccgtt aaggttagaa gaaggctact ttggtgtcta    2640
ttttctcttc cataaaaaaa gcctgactcc acttcccgcg tttactgatt actagcgaag    2700
ctgcgggtgc atttttTcaa gataaaggca tccccgatta tattctatac cgatgtggat    2760
tgcgcatact ttgtgaacag aaagtgatag cgttgatgat tcttcattgg tcagaaaatt    2820
```

```
atgaacggtt tcttctattt tgtctctata tactacgtat aggaaatgtt tacattttcg    2880
tattgttttc gattcactct atgaatagtt cttactacaa ttttttttgtc taaagagtaa   2940 tactagagat aaacataaaa aatgtagagg tcgagtttag atgcaagttc aaggagcgaa    3000
aggtggatgg gtaggttata tagggatata gcacagagat atatagcaaa agagatacttt  3060 tgagcaatgt ttgtggaagc ggtattcgca atattttagt agctcgttac agtccggtgc   3120 gttttttggtt ttttgaaagt gcgtcttcag agcgcttttg gttttcaaaa gcgctctgaa  3180
gttcctatac tttctagaga ataggaactt cggaatagga acttcaaagc gtttccgaaa   3240
acgagcgctt ccgaaaatgc aacgcgagct gcgcacatac agctcactgt tcacgtcgca   3300
cctatatctg cgtgttgcct gtatatatat atacatgaga agaacggcat agtgcgtgtt   3360
tatgcttaaa tgcgtactta tatgcgtcta tttatgtagg atgaaaggta gtctagtacc   3420
tcctgtgata ttatcccatt ccatgcgggg tatcgtatgc ttccttcagc actaccctt    3480 agctgttcta tatgctgcca ctcctcaatt ggattagtct catccttcaa tgctatcatt   3540 tccttttgata ttggatcata ctaagaaacc attattatca tgacattaac ctataaaaat  3600
aggcgtatca cgaggccctt tcgtctcgcg cgtttcggtg atgacggtga aaacctctga   3660
cacatgcagc tcccggagac ggtcacagct tgtctgtaag cggatgccgg gagcagacaa   3720
gcccgtcagg gcgcgtcagc gggtgttggc gggtgtcggg gctggcttaa ctatgcggca   3780
tcagagcaga ttgtactgag agtgcaccat accacagctt tcaattcaa ttcatcattt    3840 tttttttatt cttttttttg atttcggttt ctttgaaatt ttttgattc ggtaatctcc    3900 gaacagaagg aagaacgaag gaaggagcac agacttagat tggtatatat acgcatatgt  3960
agtgttgaag aaacatgaaa ttgcccagta ttcttaaccc aactgcacag aacaaaaacc   4020
tgcaggaaac gaagataaat catgtcgaaa gctacatata aggaacgtgc tgctactcat   4080
cctagtcctg ttgctgccaa gctatttaat atcatgcacg aaaagcaaac aaacttgtgt   4140
gcttcattgg atgttcgtac caccaaggaa ttactggagt tagttgaagc attaggtccc   4200
aaaatttgtt tactaaaaac acatgtggat atcttgactg atttttccat ggagggcaca   4260
gttaagccgc taaaggcatt atccgccaag tacaattttt tactcttcga agacagaaaa   4320
tttgctgaca ttggtaatac agtcaaattg cagtactctg cgggtgtata cagaatagca   4380
gaatgggcag acattacgaa tgcacacggt gtggtgggcc caggtattgt tagcggtttg   4440
aagcaggcgg cagaagaagt aacaaaggaa cctagaggcc ttttgatgtt agcagaattg   4500
tcatgcaagg gctccctatc tactggagaa tatactaagg gtactgttga cattgcgaag   4560
agcgacaaag attttgttat cggctttatt gctcaaagag acatgggtgg aagagatgaa   4620
ggttacgatt ggttgattat gacacccggt gtgggtttag atgacaaggg agacgcattg   4680
ggtcaacagt atagaaccgt ggatgatgtg gtctctacag gatctgacat tattattgtt   4740
ggaagaggac tatttgcaaa gggaagggat gctaaggtag agggtgaacg ttacagaaaa   4800
gcaggctggg aagcatattt gagaagatgc ggccagcaaa actaaaaaac tgtattataa   4860
gtaaatgcat gtatactaaa ctcacaaatt agagcttcaa tttaattata tcagttatta   4920
ccctatgcgg tgtgaaatac cgcacagatg cgtaaggaga aaataccgca tcaggaaatt   4980
gtaaacgtta atattttgtt aaaattcgcg ttaaattttt gttaaatcag ctcattttt    5040 aaccaatagg ccgaaatcgg caaaatccct tataaatcaa agaatagac cgagataggg   5100 ttgagtgttg ttccagtttg gaacaagagt ccactattaa agaacgtgga ctccaacgtc   5160
aaagggcgaa aaaccgtcta tcagggcgat ggcccactac gtgaaccatc accctaatca   5220
```

```
agtttttttgg ggtcgaggtg ccgtaaagca ctaaatcgga accctaaagg gagcccccga   5280
tttagagctt gacggggaaa gccggcgaac gtggcgagaa aggaagggaa gaaagcgaaa   5340
ggagcgggcg ctagggcgct ggcaagtgta gcggtcacgc tgcgcgtaac caccacaccc   5400
gccgcgctta atgcgccgct acagggcgcg tcgcgccatt cgccattcag gctgcgcaac   5460
tgttgggaag ggcgatcggt gcgggcctct tcgctattac gccagctggc gaaaggggga   5520
tgtgctgcaa ggcgattaag ttgggtaacg ccagggtttt cccagtcacg acgttgtaaa   5580
acgacggcca gtgagcgcgc gtaatacgac tcactatagg gcgaattggg taccgggccc   5640
cccctcgagg tcgacggtat cgataagctt gatatcgaat tcctgcagcc cggggggatcc   5700 gcatgcttgc atttagtcgt gcaatgtatg actttaagat ttgtgagcag gaagaaaagg   5760
gagaatcttc taacgataaa cccttgaaaa actgggtaga ctacgctatg ttgagttgct   5820
acgcaggctg cacaattaca cgagaatgct cccgcctagg atttaaggct aagggacgtg   5880
caatgcagac gacagatcta aatgaccgtg tcggtgaagt gttcgccaaa cttttcggtt   5940
aacacatgca gtgatgcacg cgcgatggtg ctaagttaca tatatatata tatatatata   6000
tatagccata gtgatgtcta agtaaccttt atggtatatt tcttaatgtg aaagatact    6060 agcgcgcgca cccacacaca agcttcgtct tttcttgaag aaaagaggaa gctcgctaaa   6120
tgggattcca ctttccgttc cctgccagct gatggaaaaa ggttagtgga acgatgaaga   6180 ataaaagag agatccactg aggtgaaatt tcagctgaca gcgagtttca tgatcgtgat    6240
gaacaatggt aacgagttgt ggctgttgcc agggagggtg gttctcaact tttaatgtat   6300
ggccaaatcg ctacttgggt ttgttatata acaaagaaga aataatgaac tgattctctt   6360
cctccttctt gtccttttctt aattctgttg taattacctt cctttgtaat ttttttttgta   6420 attattcttc ttaataatcc aaacaaacac acatattaca atagctgagg atgtatactg   6480
tgggggatta cctgctggat cgcctgcacg aactggggat tgaagaaatt ttcggtgtgc   6540
caggcgatta taacctgcag ttcctggacc agattatctc gcacaaagat atgaagtggg   6600
tcggtaacgc caacgaactg aacgcgagct atatggcaga tggttatgcc cgtaccaaaa   6660
aagctgctgc gtttctgacg acctttggcg ttggcgaact gagcgccgtc aacggactgg   6720
caggaagcta cgccgagaac ctgccagttg tcgaaattgt tgggtcgcct acttctaagg   6780
ttcagaatga aggcaaattt gtgcaccata ctctggctga tggggatttt aaacatttta   6840
tgaaaatgca tgaaccggtt actgcggccc gcacgctgct gacagcagag aatgctacgg   6900
ttgagatcga ccgcgtcctg tctgcgctgc tgaaagagcg caagccggta tatatcaatc   6960
tgcctgtcga tgttgccgca gcgaaagccg aaaagccgtc gctgccactg aaaaaagaaa   7020
acagcacctc caatacatcg gaccaggaaa ttctgaataa aatccaggaa tcactgaaga   7080
atgcgaagaa accgatcgtc atcaccggac atgagatcat ctcttttggc ctggaaaaaa   7140
cggtcacgca gttcatttct aagaccaaac tgcctatcac caccctgaac ttcggcaaat   7200
ctagcgtcga tgaagcgctg ccgagttttc tgggtatcta taatggtacc ctgtccgaac   7260
cgaacctgaa agaattcgtc gaaagcgcgg actttatcct gatgctgggc gtgaaactga   7320
cggatagctc cacaggcgca tttacccacc atctgaacga gaataaaatg atttccctga   7380
atatcgacga aggcaaaatc tttaacgagc gcatccagaa cttcgatttt gaatctctga   7440
ttagttcgct gctggatctg tccgaaattg agtataaagg taaatatatt gataaaaaac   7500
aggaggattt tgtgccgtct aatgcgctgc tgagtcagga tcgtctgtgg caagccgtag   7560
aaaacctgac acagtctaat gaaacgattg ttgcggaaca gggaacttca tttttcggcg   7620
```

```
cctcatccat ttttctgaaa tccaaaagcc atttcattgg ccaaccgctg tggggagta     7680 ttggttatac ctttccggcg gcgctgggtt cacagattgc agataaggaa tcacgccatc    7740
tgctgtttat tggtgacggc agcctgcagc tgactgtcca ggaactgggg ctggcgatcc    7800
gtgaaaaaat caatccgatt tgctttatca tcaataacga cggctacacc gtcgaacgcg    7860
aaattcatgg accgaatcaa agttacaatg acatcccgat gtggaactat agcaaactgc    7920
cggaatcctt tggcgcgaca gaggatcgcg tggtgagtaa aattgtgcgt acggaaaacg    7980
aatttgtgtc ggttatgaaa gaagcgcagg ctgacccgaa tcgcatgtat tggattgaac    8040
tgatcctggc aaaagaaggc gcaccgaaag ttctgaaaaa gatggggaaa ctgtttgcgg    8100
agcaaaataa aagctaatta attaagagta agcgaatttc ttatgattta tgatttttat    8160
tattaaataa gttataaaaa aataagtgt atacaaattt taaagtgact cttaggtttt     8220
aaaacgaaaa ttcttattct tgagtaactc tttcctgtag gtcaggttgc tttctcaggt    8280
atagcatgag gtcgctctta ttgaccacac ctctaccggc atgccgagca atgcctgca     8340 aatcgctccc catttcaccc aattgtagat atgctaactc cagcaatgag ttgatgaatc    8400
tcggtgtgta ttttatgtcc tcagaggaca cacctgtgg tactagttct agagcggcc      8459

<210> SEQ ID NO 100
<211> LENGTH: 64
<212> TYPE: DNA
<213> ORGANISM: artificial sequence
<220> FEATURE:
<223> OTHER INFORMATION: primer

<400> SEQUENCE: 100
gtgatgatac aacgagttag ccaaggtgat tagaagccgc cgagcgggcg acagccctcc    60
gacg                                                                 64

<210> SEQ ID NO 101
<211> LENGTH: 37
<212> TYPE: DNA
<213> ORGANISM: artificial sequence
<220> FEATURE:
<223> OTHER INFORMATION: primer

<400> SEQUENCE: 101
ttttctcctt gacgttaaag tatagaggta tattaac                             37

<210> SEQ ID NO 102
<211> LENGTH: 88
<212> TYPE: DNA
<213> ORGANISM: artificial sequence
<220> FEATURE:
<223> OTHER INFORMATION: primer

<400> SEQUENCE: 102
tgtacacacg taatcgcgcg tgtacatgtc tatatgtgtt acttgaacta tactgttttg    60
gcattgcgga ttacgtattc taatgttc                                       88

<210> SEQ ID NO 103
<211> LENGTH: 97
<212> TYPE: DNA
<213> ORGANISM: artificial sequence
<220> FEATURE:
<223> OTHER INFORMATION: primer

<400> SEQUENCE: 103
aacagctcct aacccgcgga ccaattgtga tggttggcgt ttgaatgaag cagcaagcat    60
```

```
tttctccctt gacgttaaag tatagaggta tattaac                              97
```

<210> SEQ ID NO 104
<211> LENGTH: 30
<212> TYPE: DNA
<213> ORGANISM: artificial sequence
<220> FEATURE:
<223> OTHER INFORMATION: primer

<400> SEQUENCE: 104

```
gattcaggca actcaatttg cactgtgtcc                                      30
```

<210> SEQ ID NO 105
<211> LENGTH: 1449
<212> TYPE: DNA
<213> ORGANISM: Saccharomyces cerevisiae
<220> FEATURE:
<221> NAME/KEY: CDS
<222> LOCATION: (1)..(1449)

<400> SEQUENCE: 105

```
atg tct gcc ttt gtc agg gtg gtt cca aga ata tcc aga agt tca gta      48
Met Ser Ala Phe Val Arg Val Val Pro Arg Ile Ser Arg Ser Ser Val
1               5                   10                  15 ctc acc aga tca ttg aga ctg caa ttg aga tgc tac gca tcg tac cca      96
Leu Thr Arg Ser Leu Arg Leu Gln Leu Arg Cys Tyr Ala Ser Tyr Pro
            20                  25                  30 gag cac acc att att ggt atg ccg gca ctg tct cct acg atg acg caa     144
Glu His Thr Ile Ile Gly Met Pro Ala Leu Ser Pro Thr Met Thr Gln
        35                  40                  45 ggt aat ctt gct gct tgg act aag aag gaa ggt gac caa ttg tct ccc     192
Gly Asn Leu Ala Ala Trp Thr Lys Lys Glu Gly Asp Gln Leu Ser Pro
    50                  55                  60 ggt gaa gtt att gcc gaa ata gaa aca gac aag gct caa atg gac ttt     240
Gly Glu Val Ile Ala Glu Ile Glu Thr Asp Lys Ala Gln Met Asp Phe
65                  70                  75                  80 gag ttc caa gaa gat ggt tac tta gcc aag att cta gtt cct gaa ggt     288
Glu Phe Gln Glu Asp Gly Tyr Leu Ala Lys Ile Leu Val Pro Glu Gly
                85                  90                  95 aca aag gac att cct gtc aac aag cct att gcc gtc tat gtg gag gac     336
Thr Lys Asp Ile Pro Val Asn Lys Pro Ile Ala Val Tyr Val Glu Asp
            100                 105                 110 aaa gct gat gtg cca gct ttt aag gac ttt aag ctg gag gat tca ggt     384
Lys Ala Asp Val Pro Ala Phe Lys Asp Phe Lys Leu Glu Asp Ser Gly
        115                 120                 125 tct gat tca aag acc agt acg aag gct cag cct gcc gaa cca cag gca     432
Ser Asp Ser Lys Thr Ser Thr Lys Ala Gln Pro Ala Glu Pro Gln Ala
    130                 135                 140 gaa aag aaa caa gaa gcg cca gct gaa gag acc aag act tct gca cct     480
Glu Lys Lys Gln Glu Ala Pro Ala Glu Glu Thr Lys Thr Ser Ala Pro
145                 150                 155                 160 gaa gct aag aaa tct gac gtt gct gct cct caa ggt agg att ttt gcc     528
Glu Ala Lys Lys Ser Asp Val Ala Ala Pro Gln Gly Arg Ile Phe Ala
                165                 170                 175 tct cca ctt gcc aag act atc gcc ttg gaa aag ggt att tct ttg aag     576
Ser Pro Leu Ala Lys Thr Ile Ala Leu Glu Lys Gly Ile Ser Leu Lys
            180                 185                 190 gat gtt cac ggc act gga ccc cgc ggt aga att acc aag gct gac att     624
Asp Val His Gly Thr Gly Pro Arg Gly Arg Ile Thr Lys Ala Asp Ile
        195                 200                 205 gag tca tat cta gaa aag tcg tct aag cag tct tct caa acc agt ggt     672
Glu Ser Tyr Leu Glu Lys Ser Ser Lys Gln Ser Ser Gln Thr Ser Gly
    210                 215                 220
```

```
gct gcc gcc gcc act cct gcc gcc gct acc tca agc act act gct ggc    720
Ala Ala Ala Ala Thr Pro Ala Ala Ala Thr Ser Ser Thr Thr Ala Gly
225             230                 235                 240 tct gct cca tcg cct tct tct aca gca tca tat gag gat gtt cca att    768
Ser Ala Pro Ser Pro Ser Ser Thr Ala Ser Tyr Glu Asp Val Pro Ile
                245                 250                 255 tca acc atg aga agc atc att gga gaa cgt tta ttg caa tct act caa    816
Ser Thr Met Arg Ser Ile Ile Gly Glu Arg Leu Leu Gln Ser Thr Gln
            260                 265                 270 ggc att cca tca tac atc gtt tcc tcc aag ata tcc atc tcc aaa ctt    864
Gly Ile Pro Ser Tyr Ile Val Ser Ser Lys Ile Ser Ile Ser Lys Leu
        275                 280                 285 ttg aaa ttg aga cag tcc ttg aac gct aca gca aac gac aag tac aaa    912
Leu Lys Leu Arg Gln Ser Leu Asn Ala Thr Ala Asn Asp Lys Tyr Lys
    290                 295                 300 ctg tcc att aat gac cta tta gta aaa gcc atc act gtt gcg gct aag    960
Leu Ser Ile Asn Asp Leu Leu Val Lys Ala Ile Thr Val Ala Ala Lys
305                 310                 315                 320 agg gtg cca gat gcc aat gcc tac tgg tta cct aat gag aac gtt atc   1008
Arg Val Pro Asp Ala Asn Ala Tyr Trp Leu Pro Asn Glu Asn Val Ile
                325                 330                 335 cgt aaa ttc aag aat gtc gat gtc tca gtc gct gtt gcc aca cca aca   1056
Arg Lys Phe Lys Asn Val Asp Val Ser Val Ala Val Ala Thr Pro Thr
            340                 345                 350 gga tta ttg aca cca att gtc aag aat tgt gag gcc aag ggc ttg tcg   1104
Gly Leu Leu Thr Pro Ile Val Lys Asn Cys Glu Ala Lys Gly Leu Ser
        355                 360                 365 caa atc tct aac gaa atc aag gaa cta gtc aag cgt gcc aga ata aac   1152
Gln Ile Ser Asn Glu Ile Lys Glu Leu Val Lys Arg Ala Arg Ile Asn
    370                 375                 380 aaa ttg gca cca gag gaa ttc caa ggt ggg acc att tgc ata tcc aat   1200
Lys Leu Ala Pro Glu Glu Phe Gln Gly Gly Thr Ile Cys Ile Ser Asn
385                 390                 395                 400 atg ggc atg aat aat gct gtt aac atg ttt act tcg att atc aac cca   1248
Met Gly Met Asn Asn Ala Val Asn Met Phe Thr Ser Ile Ile Asn Pro
                405                 410                 415 cca cag tct aca atc ttg gcc atc gct act gtt gaa agg gtc gct gtg   1296
Pro Gln Ser Thr Ile Leu Ala Ile Ala Thr Val Glu Arg Val Ala Val
            420                 425                 430 gaa gac gcc gct gct gag aac gga ttc tcc ttt gat aac cag gtt acc   1344
Glu Asp Ala Ala Ala Glu Asn Gly Phe Ser Phe Asp Asn Gln Val Thr
        435                 440                 445 ata aca ggg acc ttt gat cat aga acc att gat ggc gcc aaa ggt gca   1392
Ile Thr Gly Thr Phe Asp His Arg Thr Ile Asp Gly Ala Lys Gly Ala
    450                 455                 460 gaa ttc atg aag gaa ttg aaa act gtt att gaa aat cct ttg gaa atg   1440
Glu Phe Met Lys Glu Leu Lys Thr Val Ile Glu Asn Pro Leu Glu Met
465                 470                 475                 480 cta ttg tga                                                        1449
Leu Leu

<210> SEQ ID NO 106
<211> LENGTH: 482
<212> TYPE: PRT
<213> ORGANISM: Saccharomyces cerevisiae

<400> SEQUENCE: 106

Met Ser Ala Phe Val Arg Val Val Pro Arg Ile Ser Arg Ser Ser Val
1               5                   10                  15

Leu Thr Arg Ser Leu Arg Leu Gln Leu Arg Cys Tyr Ala Ser Tyr Pro
```

-continued

```
             20                  25                  30
Glu His Thr Ile Ile Gly Met Pro Ala Leu Ser Pro Thr Met Thr Gln
             35                  40                  45
Gly Asn Leu Ala Ala Trp Thr Lys Lys Glu Gly Asp Gln Leu Ser Pro
 50                  55                  60
Gly Glu Val Ile Ala Glu Ile Glu Thr Asp Lys Ala Gln Met Asp Phe
 65                  70                  75                  80
Glu Phe Gln Glu Asp Gly Tyr Leu Ala Lys Ile Leu Val Pro Glu Gly
                 85                  90                  95
Thr Lys Asp Ile Pro Val Asn Lys Pro Ile Ala Val Tyr Val Glu Asp
                100                 105                 110
Lys Ala Asp Val Pro Ala Phe Lys Asp Phe Lys Leu Glu Asp Ser Gly
                115                 120                 125
Ser Asp Ser Lys Thr Ser Thr Lys Ala Gln Pro Ala Glu Pro Gln Ala
                130                 135                 140
Glu Lys Lys Gln Glu Ala Pro Ala Glu Glu Thr Lys Thr Ser Ala Pro
145                 150                 155                 160
Glu Ala Lys Lys Ser Asp Val Ala Ala Pro Gln Gly Arg Ile Phe Ala
                165                 170                 175
Ser Pro Leu Ala Lys Thr Ile Ala Leu Glu Lys Gly Ile Ser Leu Lys
                180                 185                 190
Asp Val His Gly Thr Gly Pro Arg Gly Arg Ile Thr Lys Ala Asp Ile
                195                 200                 205
Glu Ser Tyr Leu Glu Lys Ser Ser Lys Gln Ser Ser Gln Thr Ser Gly
                210                 215                 220
Ala Ala Ala Ala Thr Pro Ala Ala Ala Thr Ser Ser Thr Thr Ala Gly
225                 230                 235                 240
Ser Ala Pro Ser Pro Ser Ser Thr Ala Ser Tyr Glu Asp Val Pro Ile
                245                 250                 255
Ser Thr Met Arg Ser Ile Ile Gly Glu Arg Leu Leu Gln Ser Thr Gln
                260                 265                 270
Gly Ile Pro Ser Tyr Ile Val Ser Ser Lys Ile Ser Ile Ser Lys Leu
                275                 280                 285
Leu Lys Leu Arg Gln Ser Leu Asn Ala Thr Ala Asn Asp Lys Tyr Lys
                290                 295                 300
Leu Ser Ile Asn Asp Leu Leu Val Lys Ala Ile Thr Val Ala Ala Lys
305                 310                 315                 320
Arg Val Pro Asp Ala Asn Ala Tyr Trp Leu Pro Asn Glu Asn Val Ile
                325                 330                 335
Arg Lys Phe Lys Asn Val Asp Val Ser Val Ala Val Ala Thr Pro Thr
                340                 345                 350
Gly Leu Leu Thr Pro Ile Val Lys Asn Cys Glu Ala Lys Gly Leu Ser
                355                 360                 365
Gln Ile Ser Asn Glu Ile Lys Gly Leu Val Lys Arg Ala Arg Ile Asn
                370                 375                 380
Lys Leu Ala Pro Glu Glu Phe Gln Gly Gly Thr Ile Cys Ile Ser Asn
385                 390                 395                 400
Met Gly Met Asn Asn Ala Val Asn Met Phe Thr Ser Ile Ile Asn Pro
                405                 410                 415
Pro Gln Ser Thr Ile Leu Ala Ile Ala Thr Val Glu Arg Val Ala Val
                420                 425                 430
Glu Asp Ala Ala Ala Glu Asn Gly Phe Ser Phe Asp Asn Gln Val Thr
                435                 440                 445
```

```
Ile Thr Gly Thr Phe Asp His Arg Thr Ile Asp Gly Ala Lys Gly Ala
        450                 455                 460
Glu Phe Met Lys Glu Leu Lys Thr Val Ile Glu Asn Pro Leu Glu Met
465                 470                 475                 480
Leu Leu

<210> SEQ ID NO 107
<211> LENGTH: 1500
<212> TYPE: DNA
<213> ORGANISM: Saccharomyces cerevisiae
<220> FEATURE:
<221> NAME/KEY: CDS
<222> LOCATION: (1)..(1500)

<400> SEQUENCE: 107 atg tta aga atc aga tca ctc cta aat aat aag cgt gcc ttt tcg tcc      48
Met Leu Arg Ile Arg Ser Leu Leu Asn Asn Lys Arg Ala Phe Ser Ser
1               5                   10                  15 aca gtc agg aca ttg acc att aac aag tca cat gat gta gtc atc atc      96
Thr Val Arg Thr Leu Thr Ile Asn Lys Ser His Asp Val Val Ile Ile
            20                  25                  30 ggt ggt ggc cct gct ggt tac gtg gct gct atc aaa gct gct caa ttg     144
Gly Gly Gly Pro Ala Gly Tyr Val Ala Ala Ile Lys Ala Ala Gln Leu
        35                  40                  45 gga ttt aac act gca tgt gta gaa aaa aga ggc aaa tta ggc ggt acc     192
Gly Phe Asn Thr Ala Cys Val Glu Lys Arg Gly Lys Leu Gly Gly Thr
    50                  55                  60 tgt ctt aac gtt gga tgt atc ccc tcc aaa gca ctt cta aat aat tct     240
Cys Leu Asn Val Gly Cys Ile Pro Ser Lys Ala Leu Leu Asn Asn Ser
65                  70                  75                  80 cat tta ttc cac caa atg cat acg gaa gcg caa aag aga ggt att gac     288
His Leu Phe His Gln Met His Thr Glu Ala Gln Lys Arg Gly Ile Asp
                85                  90                  95 gtc aac ggt gat atc aaa att aac gta gca aac ttc caa aag gct aag     336
Val Asn Gly Asp Ile Lys Ile Asn Val Ala Asn Phe Gln Lys Ala Lys
            100                 105                 110 gat gac gct gtt aag caa tta act gga ggt att gag ctt ctg ttc aag     384
Asp Asp Ala Val Lys Gln Leu Thr Gly Gly Ile Glu Leu Leu Phe Lys
        115                 120                 125 aaa aat aag gtc acc tat tat aaa ggt aat ggt tca ttc gaa gac gaa     432
Lys Asn Lys Val Thr Tyr Tyr Lys Gly Asn Gly Ser Phe Glu Asp Glu
    130                 135                 140 acg aag atc aga gta act ccc gtt gat ggg ttg gaa ggc act gtc aag     480
Thr Lys Ile Arg Val Thr Pro Val Asp Gly Leu Glu Gly Thr Val Lys
145                 150                 155                 160 gaa gac cac ata cta gat gtt aag aac atc ata gtc gcc acg ggc tct     528
Glu Asp His Ile Leu Asp Val Lys Asn Ile Ile Val Ala Thr Gly Ser
                165                 170                 175 gaa gtt aca ccc ttc ccc ggt att gaa ata gat gag gaa aaa att gtc     576
Glu Val Thr Pro Phe Pro Gly Ile Glu Ile Asp Glu Glu Lys Ile Val
            180                 185                 190 tct tca aca ggt gct ctt tcg tta aag gaa att ccc aaa aga tta acc     624
Ser Ser Thr Gly Ala Leu Ser Leu Lys Glu Ile Pro Lys Arg Leu Thr
        195                 200                 205 atc att ggt gga gga atc atc gga ttg gaa atg ggt tca gtt tac tct     672
Ile Ile Gly Gly Gly Ile Ile Gly Leu Glu Met Gly Ser Val Tyr Ser
    210                 215                 220 aga tta ggc tcc aag gtt act gta gta gaa ttt caa cct caa att ggt     720
Arg Leu Gly Ser Lys Val Thr Val Val Glu Phe Gln Pro Gln Ile Gly
225                 230                 235                 240 gca tct atg gac ggc gag gtt gcc aaa gcc acc caa aag ttc ttg aaa     768
Ala Ser Met Asp Gly Glu Val Ala Lys Ala Thr Gln Lys Phe Leu Lys
```

```
Ala Ser Met Asp Gly Glu Val Ala Lys Ala Thr Gln Lys Phe Leu Lys
            245                 250                 255 aag caa ggt ttg gac ttc aaa tta agc acc aaa gtt att tct gca aag       816
Lys Gln Gly Leu Asp Phe Lys Leu Ser Thr Lys Val Ile Ser Ala Lys
                260                 265                 270 aga aac gac gac aag aac gtc gtc gaa att gtt gta gaa gat act aaa       864
Arg Asn Asp Asp Lys Asn Val Val Glu Ile Val Val Glu Asp Thr Lys
            275                 280                 285 acg aat aag caa gaa aat ttg gaa gct gaa gtt ttg ctg gtt gct gtt       912
Thr Asn Lys Gln Glu Asn Leu Glu Ala Glu Val Leu Leu Val Ala Val
        290                 295                 300 ggt aga aga cct tac att gct ggc tta ggg gct gaa aag att gga tta       960
Gly Arg Arg Pro Tyr Ile Ala Gly Leu Gly Ala Glu Lys Ile Gly Leu
305                 310                 315                 320 gaa gta gac aaa agg gga cgc cta gtc att gat gac caa ttt aat tcc      1008
Glu Val Asp Lys Arg Gly Arg Leu Val Ile Asp Asp Gln Phe Asn Ser
                325                 330                 335 aag ttc cca cac att aaa gtg gta gga gat gtt aca ttt ggt cca atg      1056
Lys Phe Pro His Ile Lys Val Val Gly Asp Val Thr Phe Gly Pro Met
            340                 345                 350 ctg gct cac aaa gcc gaa gag gaa ggt att gca gct gtc gaa atg ttg      1104
Leu Ala His Lys Ala Glu Glu Glu Gly Ile Ala Ala Val Glu Met Leu
        355                 360                 365 aaa act ggt cac ggt cat gtc aac tat aac aac att cct tcg gtc atg      1152
Lys Thr Gly His Gly His Val Asn Tyr Asn Asn Ile Pro Ser Val Met
370                 375                 380 tat tct cac cca gaa gta gca tgg gtt ggt aaa acc gaa gag caa ttg      1200
Tyr Ser His Pro Glu Val Ala Trp Val Gly Lys Thr Glu Glu Gln Leu
385                 390                 395                 400 aaa gaa gcc ggc att gac tat aaa att ggt aag ttc ccc ttt gcg gcc      1248
Lys Glu Ala Gly Ile Asp Tyr Lys Ile Gly Lys Phe Pro Phe Ala Ala
                405                 410                 415 aat tca aga gcc aag acc aac caa gac act gaa ggt ttc gtg aag att      1296
Asn Ser Arg Ala Lys Thr Asn Gln Asp Thr Glu Gly Phe Val Lys Ile
            420                 425                 430 ttg atc gat tcc aag acc gag cgt att ttg ggg gct cac att atc ggt      1344
Leu Ile Asp Ser Lys Thr Glu Arg Ile Leu Gly Ala His Ile Ile Gly
        435                 440                 445 cca aat gcc ggt gaa atg att gct gaa gct ggc tta gcc tta gaa tat      1392
Pro Asn Ala Gly Glu Met Ile Ala Glu Ala Gly Leu Ala Leu Glu Tyr
450                 455                 460 ggc gct tcc gca gaa gat gtt gct agg gtc tgc cat gct cat cct act      1440
Gly Ala Ser Ala Glu Asp Val Ala Arg Val Cys His Ala His Pro Thr
465                 470                 475                 480 ttg tcc gaa gca ttt aag gaa gct aac atg gct gcc tat gat aaa gct      1488
Leu Ser Glu Ala Phe Lys Glu Ala Asn Met Ala Ala Tyr Asp Lys Ala
                485                 490                 495 att cat tgt tga                                                       1500
Ile His Cys <210> SEQ ID NO 108
<211> LENGTH: 499
<212> TYPE: PRT
<213> ORGANISM: Saccharomyces cerevisiae

<400> SEQUENCE: 108

Met Leu Arg Ile Arg Ser Leu Leu Asn Asn Lys Arg Ala Phe Ser Ser
1               5                   10                  15

Thr Val Arg Thr Leu Thr Ile Asn Lys Ser His Asp Val Val Ile Ile
            20                  25                  30
```

-continued

Gly Gly Gly Pro Ala Gly Tyr Val Ala Ala Ile Lys Ala Ala Gln Leu
        35                  40                  45

Gly Phe Asn Thr Ala Cys Val Glu Lys Arg Gly Lys Leu Gly Gly Thr
 50                  55                  60

Cys Leu Asn Val Gly Cys Ile Pro Ser Lys Ala Leu Leu Asn Asn Ser
 65                  70                  75                  80

His Leu Phe His Gln Met His Thr Glu Ala Gln Lys Arg Gly Ile Asp
                 85                  90                  95

Val Asn Gly Asp Ile Lys Ile Asn Val Ala Asn Phe Gln Lys Ala Lys
                100                 105                 110

Asp Asp Ala Val Lys Gln Leu Thr Gly Gly Ile Glu Leu Leu Phe Lys
            115                 120                 125

Lys Asn Lys Val Thr Tyr Tyr Lys Gly Asn Gly Ser Phe Glu Asp Glu
        130                 135                 140

Thr Lys Ile Arg Val Thr Pro Val Asp Gly Leu Glu Gly Thr Val Lys
145                 150                 155                 160

Glu Asp His Ile Leu Asp Val Lys Asn Ile Ile Val Ala Thr Gly Ser
                165                 170                 175

Glu Val Thr Pro Phe Pro Gly Ile Glu Ile Asp Glu Gly Lys Ile Val
            180                 185                 190

Ser Ser Thr Gly Ala Leu Ser Leu Lys Glu Ile Pro Lys Arg Leu Thr
        195                 200                 205

Ile Ile Gly Gly Gly Ile Ile Gly Leu Glu Met Gly Ser Val Tyr Ser
210                 215                 220

Arg Leu Gly Ser Lys Val Thr Val Val Glu Phe Gln Pro Gln Ile Gly
225                 230                 235                 240

Ala Ser Met Asp Gly Glu Val Ala Lys Ala Thr Gln Lys Phe Leu Lys
                245                 250                 255

Lys Gln Gly Leu Asp Phe Lys Leu Ser Thr Lys Val Ile Ser Ala Lys
            260                 265                 270

Arg Asn Asp Asp Lys Asn Val Val Glu Ile Val Val Glu Asp Thr Lys
        275                 280                 285

Thr Asn Lys Gln Glu Asn Leu Glu Ala Glu Val Leu Leu Val Ala Val
        290                 295                 300

Gly Arg Arg Pro Tyr Ile Ala Gly Leu Gly Ala Glu Lys Ile Gly Leu
305                 310                 315                 320

Glu Val Asp Lys Arg Gly Arg Leu Val Ile Asp Asp Gln Phe Asn Ser
                325                 330                 335

Lys Phe Pro His Ile Lys Val Val Gly Asp Val Thr Phe Gly Pro Met
            340                 345                 350

Leu Ala His Lys Ala Glu Glu Gly Ile Ala Ala Val Glu Met Leu
        355                 360                 365

Lys Thr Gly His Gly His Val Asn Tyr Asn Asn Ile Pro Ser Val Met
        370                 375                 380

Tyr Ser His Pro Glu Val Ala Trp Val Gly Lys Thr Glu Glu Gln Leu
385                 390                 395                 400

Lys Glu Ala Gly Ile Asp Tyr Lys Ile Gly Lys Phe Pro Phe Ala Ala
                405                 410                 415

Asn Ser Arg Ala Lys Thr Asn Gln Asp Thr Glu Gly Phe Val Lys Ile
            420                 425                 430

Leu Ile Asp Ser Lys Thr Glu Arg Ile Leu Gly Ala His Ile Ile Gly
        435                 440                 445

Pro Asn Ala Gly Glu Met Ile Ala Glu Ala Gly Leu Ala Leu Glu Tyr
450                 455                 460

```
Gly Ala Ser Ala Glu Asp Val Ala Arg Val Cys His Ala His Pro Thr
465                 470                 475                 480

Leu Ser Glu Ala Phe Lys Glu Ala Asn Met Ala Ala Tyr Asp Lys Ala
            485                 490                 495

Ile His Cys

<210> SEQ ID NO 109
<211> LENGTH: 1233
<212> TYPE: DNA
<213> ORGANISM: Saccharomyces cerevisiae
<220> FEATURE:
<221> NAME/KEY: CDS
<222> LOCATION: (1)..(1233)

<400> SEQUENCE: 109 atg cta agt gca att tcc aaa gtc tcc act tta aaa tca tgt aca aga     48
Met Leu Ser Ala Ile Ser Lys Val Ser Thr Leu Lys Ser Cys Thr Arg
1               5                   10                  15 tat tta acc aaa tgc aac tat cat gca tca gct aaa tta ctt gct gta    96
Tyr Leu Thr Lys Cys Asn Tyr His Ala Ser Ala Lys Leu Leu Ala Val
                20                  25                  30 aag aca ttt tca atg cct gca atg tct cct act atg gag aaa ggg ggg   144
Lys Thr Phe Ser Met Pro Ala Met Ser Pro Thr Met Glu Lys Gly Gly
            35                  40                  45 att gtg tct tgg aaa tat aaa gtt ggc gaa cca ttc agc gcg ggc gat   192
Ile Val Ser Trp Lys Tyr Lys Val Gly Glu Pro Phe Ser Ala Gly Asp
        50                  55                  60 gtg ata tta gaa gtg gaa aca gat aaa tct caa att gat gtg gaa gca   240
Val Ile Leu Glu Val Glu Thr Asp Lys Ser Gln Ile Asp Val Glu Ala
65                  70                  75                  80 ctg gac gat ggt aaa cta gct aag atc ctg aaa gat gaa ggc tct aaa   288
Leu Asp Asp Gly Lys Leu Ala Lys Ile Leu Lys Asp Glu Gly Ser Lys
                85                  90                  95 gat gtt gat gtt ggt gaa cct att gct tat att gct gat gtt gat gat   336
Asp Val Asp Val Gly Glu Pro Ile Ala Tyr Ile Ala Asp Val Asp Asp
            100                 105                 110 gat tta gct act ata aag tta ccc caa gag gcc aac acc gca aat gcg   384
Asp Leu Ala Thr Ile Lys Leu Pro Gln Glu Ala Asn Thr Ala Asn Ala
        115                 120                 125 aaa tct att gaa att aag aag cca tcc gca gat agt act gaa gca aca   432
Lys Ser Ile Glu Ile Lys Lys Pro Ser Ala Asp Ser Thr Glu Ala Thr
    130                 135                 140 caa caa cat tta aaa aaa gcc aca gtt aca cca ata aaa acc gtt gac   480
Gln Gln His Leu Lys Lys Ala Thr Val Thr Pro Ile Lys Thr Val Asp
145                 150                 155                 160 ggc agc caa gcc aat ctt gaa cag acg cta tta cca tcc gtg tca tta   528
Gly Ser Gln Ala Asn Leu Glu Gln Thr Leu Leu Pro Ser Val Ser Leu
                165                 170                 175 cta ctg gct gag aac aat ata tcc aaa caa aag gct ttg aag gaa att   576
Leu Leu Ala Glu Asn Asn Ile Ser Lys Gln Lys Ala Leu Lys Glu Ile
            180                 185                 190 gcg cca tct ggt tcc aac ggt aga cta tta aag ggt gat gtg cta gca   624
Ala Pro Ser Gly Ser Asn Gly Arg Leu Leu Lys Gly Asp Val Leu Ala
        195                 200                 205 tac cta ggg aaa ata cca caa gat tcg gtt aac aag gta aca gaa ttt   672
Tyr Leu Gly Lys Ile Pro Gln Asp Ser Val Asn Lys Val Thr Glu Phe
    210                 215                 220 atc aag aag aac gaa cgt ctc gat tta tcg aac att aaa cct ata cag   720
Ile Lys Lys Asn Glu Arg Leu Asp Leu Ser Asn Ile Lys Pro Ile Gln
225                 230                 235                 240
```

-continued

```
ctc aaa cca aaa ata gcc gag caa gct caa aca aaa gct gcc gac aag      768
Leu Lys Pro Lys Ile Ala Glu Gln Ala Gln Thr Lys Ala Ala Asp Lys
            245                 250                 255 cca aag att act cct gta gaa ttt gaa gag caa tta gtg ttc cat gct      816
Pro Lys Ile Thr Pro Val Glu Phe Glu Glu Gln Leu Val Phe His Ala
        260                 265                 270 ccc gcc tct att ccg ttt gac aaa ctg agt gaa tca ttg aac tct ttc      864
Pro Ala Ser Ile Pro Phe Asp Lys Leu Ser Glu Ser Leu Asn Ser Phe
    275                 280                 285 atg aaa gaa gct tac cag ttc tca cac gga aca cca cta atg gac aca      912
Met Lys Glu Ala Tyr Gln Phe Ser His Gly Thr Pro Leu Met Asp Thr
290                 295                 300 aat tcg aaa tac ttt gac cct att ttc gag gac ctt gtc acc ttg agc      960
Asn Ser Lys Tyr Phe Asp Pro Ile Phe Glu Asp Leu Val Thr Leu Ser
305                 310                 315                 320 cca aga gag cca aga ttt aaa ttt tcc tat gac ttg atg caa att ccc     1008
Pro Arg Glu Pro Arg Phe Lys Phe Ser Tyr Asp Leu Met Gln Ile Pro
            325                 330                 335 aaa gct aat aac atg caa gac acg tac ggt caa gaa gac ata ttt gac     1056
Lys Ala Asn Asn Met Gln Asp Thr Tyr Gly Gln Glu Asp Ile Phe Asp
        340                 345                 350 ctc tta aca ggt tca gac gcg act gcc tca tca gta aga ccc gtt gaa     1104
Leu Leu Thr Gly Ser Asp Ala Thr Ala Ser Ser Val Arg Pro Val Glu
    355                 360                 365 aag aac tta cct gaa aaa aac gaa tat ata cta gcg ttg aat gtt agc     1152
Lys Asn Leu Pro Glu Lys Asn Glu Tyr Ile Leu Ala Leu Asn Val Ser
370                 375                 380 gtc aac aac aag aag ttt aat gac gcg gag gcc aag gca aaa aga ttc     1200
Val Asn Asn Lys Lys Phe Asn Asp Ala Glu Ala Lys Ala Lys Arg Phe
385                 390                 395                 400 ctt gat tac gta agg gag tta gaa tca ttt tga                         1233
Leu Asp Tyr Val Arg Glu Leu Glu Ser Phe
            405                 410
```

<210> SEQ ID NO 110
<211> LENGTH: 410
<212> TYPE: PRT
<213> ORGANISM: Saccharomyces cerevisiae

<400> SEQUENCE: 110

```
Met Leu Ser Ala Ile Ser Lys Val Ser Thr Leu Lys Ser Cys Thr Arg
1               5                   10                  15

Tyr Leu Thr Lys Cys Asn Tyr His Ala Ser Ala Lys Leu Leu Ala Val
            20                  25                  30

Lys Thr Phe Ser Met Pro Ala Met Ser Pro Thr Met Glu Lys Gly Gly
        35                  40                  45

Ile Val Ser Trp Lys Tyr Lys Val Gly Glu Pro Phe Ser Ala Gly Asp
    50                  55                  60

Val Ile Leu Glu Val Glu Thr Asp Lys Ser Gln Ile Asp Val Glu Ala
65                  70                  75                  80

Leu Asp Asp Gly Lys Leu Ala Lys Ile Leu Lys Asp Glu Gly Ser Lys
                85                  90                  95

Asp Val Asp Val Gly Glu Pro Ile Ala Tyr Ile Ala Asp Val Asp Asp
            100                 105                 110

Asp Leu Ala Thr Ile Lys Leu Pro Gln Glu Ala Asn Thr Ala Asn Ala
        115                 120                 125

Lys Ser Ile Glu Ile Lys Lys Pro Ser Ala Asp Ser Thr Glu Ala Thr
    130                 135                 140

Gln Gln His Leu Lys Lys Ala Thr Val Thr Pro Ile Lys Thr Val Asp
```

```
                145                 150                 155                 160
Gly Ser Gln Ala Asn Leu Glu Gln Thr Leu Pro Ser Val Ser Leu
                165                 170                 175
Leu Leu Ala Glu Asn Asn Ile Ser Lys Gln Lys Ala Leu Lys Glu Ile
                180                 185                 190
Ala Pro Ser Gly Ser Asn Gly Arg Leu Leu Lys Gly Asp Val Leu Ala
                195                 200                 205
Tyr Leu Gly Lys Ile Pro Gln Asp Ser Val Asn Lys Val Thr Glu Phe
                210                 215                 220
Ile Lys Lys Asn Glu Arg Leu Asp Leu Ser Asn Ile Lys Pro Ile Gln
225                 230                 235                 240
Leu Lys Pro Lys Ile Ala Glu Gln Ala Gln Thr Lys Ala Ala Asp Lys
                245                 250                 255
Pro Lys Ile Thr Pro Val Glu Phe Glu Gln Leu Val Phe His Ala
                260                 265                 270
Pro Ala Ser Ile Pro Phe Asp Lys Leu Ser Glu Ser Leu Asn Ser Phe
                275                 280                 285
Met Lys Glu Ala Tyr Gln Phe Ser His Gly Thr Pro Leu Met Asp Thr
                290                 295                 300
Asn Ser Lys Tyr Phe Asp Pro Ile Phe Glu Asp Leu Val Thr Leu Ser
305                 310                 315                 320
Pro Arg Glu Pro Arg Phe Lys Phe Ser Tyr Asp Leu Met Gln Ile Pro
                325                 330                 335
Lys Ala Asn Asn Met Gln Asp Thr Tyr Gly Gln Glu Asp Ile Phe Asp
                340                 345                 350
Leu Leu Thr Gly Ser Asp Ala Thr Ala Ser Ser Val Arg Pro Val Glu
                355                 360                 365
Lys Asn Leu Pro Glu Lys Asn Glu Tyr Ile Leu Ala Leu Asn Val Ser
                370                 375                 380
Val Asn Asn Lys Lys Phe Asn Asp Ala Glu Ala Lys Ala Lys Arg Phe
385                 390                 395                 400
Leu Asp Tyr Val Arg Glu Leu Glu Ser Phe
                405                 410

<210> SEQ ID NO 111
<211> LENGTH: 1692
<212> TYPE: DNA
<213> ORGANISM: Saccharomyces cerevisiae
<220> FEATURE:
<221> NAME/KEY: CDS
<222> LOCATION: (1)..(1692)

<400> SEQUENCE: 111 atg tct gaa att act ttg ggt aaa tat ttg ttc gaa aga tta aag caa      48
Met Ser Glu Ile Thr Leu Gly Lys Tyr Leu Phe Glu Arg Leu Lys Gln
1               5                   10                  15 gtc aac gtt aac acc gtt ttc ggt ttg cca ggt gac ttc aac ttg tcc      96
Val Asn Val Asn Thr Val Phe Gly Leu Pro Gly Asp Phe Asn Leu Ser
            20                  25                  30 ttg ttg gac aag atc tac gaa gtt gaa ggt atg aga tgg gct ggt aac     144
Leu Leu Asp Lys Ile Tyr Glu Val Glu Gly Met Arg Trp Ala Gly Asn
        35                  40                  45 gcc aac gaa ttg aac gct gct tac gcc gct gat ggt tac gct cgt atc     192
Ala Asn Glu Leu Asn Ala Ala Tyr Ala Ala Asp Gly Tyr Ala Arg Ile
    50                  55                  60 aag ggt atg tct tgt atc atc acc acc ttc ggt gtc ggt gaa ttg tct     240
Lys Gly Met Ser Cys Ile Ile Thr Thr Phe Gly Val Gly Glu Leu Ser
65                  70                  75                  80
```

| | | |
|---|---|---|
| gct ttg aac ggt att gcc ggt tct tac gct gaa cac gtc ggt gtt ttg<br>Ala Leu Asn Gly Ile Ala Gly Ser Tyr Ala Glu His Val Gly Val Leu<br>                        85                     90                   95 | 288 |
| cac gtt gtt ggt gtc cca tcc atc tct gct caa gct aag caa ttg ttg<br>His Val Val Gly Val Pro Ser Ile Ser Ala Gln Ala Lys Gln Leu Leu<br>100                        105                     110 | 336 |
| ttg cac cac acc ttg ggt aac ggt gac ttc act gtt ttc cac aga atg<br>Leu His His Thr Leu Gly Asn Gly Asp Phe Thr Val Phe His Arg Met<br>    115                     120                     125 | 384 |
| tct gcc aac att tct gaa acc act gct atg atc act gac att gct acc<br>Ser Ala Asn Ile Ser Glu Thr Thr Ala Met Ile Thr Asp Ile Ala Thr<br>130                        135                     140 | 432 |
| gcc cca gct gaa att gac aga tgt atc aga acc act tac gtc acc caa<br>Ala Pro Ala Glu Ile Asp Arg Cys Ile Arg Thr Thr Tyr Val Thr Gln<br>145                        150                     155                     160 | 480 |
| aga cca gtc tac tta ggt ttg cca gct aac ttg gtc gac ttg aac gtc<br>Arg Pro Val Tyr Leu Gly Leu Pro Ala Asn Leu Val Asp Leu Asn Val<br>                      165                     170                     175 | 528 |
| cca gct aag ttg ttg caa act cca att gac atg tct ttg aag cca aac<br>Pro Ala Lys Leu Leu Gln Thr Pro Ile Asp Met Ser Leu Lys Pro Asn<br>        180                     185                     190 | 576 |
| gat gct gaa tcc gaa aag gaa gtc att gac acc atc ttg gct ttg gtc<br>Asp Ala Glu Ser Glu Lys Glu Val Ile Asp Thr Ile Leu Ala Leu Val<br>195                        200                     205 | 624 |
| aag gat gct aag aac cca gtt atc ttg gct gat gct tgt tgt tcc aga<br>Lys Asp Ala Lys Asn Pro Val Ile Leu Ala Asp Ala Cys Cys Ser Arg<br>210                        215                     220 | 672 |
| cac gac gtc aag gct gaa act aag aag ttg att gac ttg act caa ttc<br>His Asp Val Lys Ala Glu Thr Lys Lys Leu Ile Asp Leu Thr Gln Phe<br>225                        230                     235                     240 | 720 |
| cca gct ttc gtc acc cca atg ggt aag ggt tcc att gac gaa caa cac<br>Pro Ala Phe Val Thr Pro Met Gly Lys Gly Ser Ile Asp Glu Gln His<br>                      245                     250                     255 | 768 |
| cca aga tac ggt ggt gtt tac gtc ggt acc ttg tcc aag cca gaa gtt<br>Pro Arg Tyr Gly Gly Val Tyr Val Gly Thr Leu Ser Lys Pro Glu Val<br>        260                     265                     270 | 816 |
| aag gaa gcc gtt gaa tct gct gac ttg att ttg tct gtc ggt gct ttg<br>Lys Glu Ala Val Glu Ser Ala Asp Leu Ile Leu Ser Val Gly Ala Leu<br>275                        280                     285 | 864 |
| ttg tct gat ttc aac acc ggt tct ttc tct tac tct tac aag acc aag<br>Leu Ser Asp Phe Asn Thr Gly Ser Phe Ser Tyr Ser Tyr Lys Thr Lys<br>290                        295                     300 | 912 |
| aac att gtc gaa ttc cac tcc gac cac atg aag atc aga aac gcc act<br>Asn Ile Val Glu Phe His Ser Asp His Met Lys Ile Arg Asn Ala Thr<br>305                        310                     315                     320 | 960 |
| ttc cca ggt gtc caa atg aaa ttc gtt ttg caa aag ttg ttg acc act<br>Phe Pro Gly Val Gln Met Lys Phe Val Leu Gln Lys Leu Leu Thr Thr<br>                      325                     330                     335 | 1008 |
| att gct gac gcc gct aag ggt tac aag cca gtt gct gtc cca gct aga<br>Ile Ala Asp Ala Ala Lys Gly Tyr Lys Pro Val Ala Val Pro Ala Arg<br>        340                     345                     350 | 1056 |
| act cca gct aac gct gct gtc cca gct tct acc cca ttg aag caa gaa<br>Thr Pro Ala Asn Ala Ala Val Pro Ala Ser Thr Pro Leu Lys Gln Glu<br>           355                     360                     365 | 1104 |
| tgg atg tgg aac caa ttg ggt aac ttc ttg caa gaa ggt gat gtt gtc<br>Trp Met Trp Asn Gln Leu Gly Asn Phe Leu Gln Glu Gly Asp Val Val<br>370                        375                     380 | 1152 |
| att gct gaa acc ggt acc tcc gct ttc ggt atc aac caa acc act ttc<br>Ile Ala Glu Thr Gly Thr Ser Ala Phe Gly Ile Asn Gln Thr Thr Phe<br>385                        390                     395                     400 | 1200 |

```
cca aac aac acc tac ggt atc tct caa gtc tta tgg ggt tcc att ggt   1248
Pro Asn Asn Thr Tyr Gly Ile Ser Gln Val Leu Trp Gly Ser Ile Gly
                405                 410                 415 ttc acc act ggt gct acc ttg ggt gct gct ttc gct gct gaa gaa att   1296
Phe Thr Thr Gly Ala Thr Leu Gly Ala Ala Phe Ala Ala Glu Glu Ile
            420                 425                 430 gat cca aag aag aga gtt atc tta ttc att ggt gac ggt tct ttg caa   1344
Asp Pro Lys Lys Arg Val Ile Leu Phe Ile Gly Asp Gly Ser Leu Gln
        435                 440                 445 ttg act gtt caa gaa atc tcc acc atg atc aga tgg ggc ttg aag cca   1392
Leu Thr Val Gln Glu Ile Ser Thr Met Ile Arg Trp Gly Leu Lys Pro
    450                 455                 460 tac ttg ttc gtc ttg aac aac gat ggt tac acc att gaa aag ttg att   1440
Tyr Leu Phe Val Leu Asn Asn Asp Gly Tyr Thr Ile Glu Lys Leu Ile
465                 470                 475                 480 cac ggt cca aag gct caa tac aac gaa att caa ggt tgg gac cac cta   1488
His Gly Pro Lys Ala Gln Tyr Asn Glu Ile Gln Gly Trp Asp His Leu
                485                 490                 495 tcc ttg ttg cca act ttc ggt gct aag gac tat gaa acc cac aga gtc   1536
Ser Leu Leu Pro Thr Phe Gly Ala Lys Asp Tyr Glu Thr His Arg Val
            500                 505                 510 gct acc acc ggt gaa tgg gac aag ttg acc caa gac aag tct ttc aac   1584
Ala Thr Thr Gly Glu Trp Asp Lys Leu Thr Gln Asp Lys Ser Phe Asn
        515                 520                 525 gac aac tct aag atc aga atg att gaa atc atg ttg cca gtc ttc gat   1632
Asp Asn Ser Lys Ile Arg Met Ile Glu Ile Met Leu Pro Val Phe Asp
    530                 535                 540 gct cca caa aac ttg gtt gaa caa gct aag ttg act gct gct acc aac   1680
Ala Pro Gln Asn Leu Val Glu Gln Ala Lys Leu Thr Ala Ala Thr Asn
545                 550                 555                 560 gct aag caa taa                                                   1692
Ala Lys Gln <210> SEQ ID NO 112
<211> LENGTH: 563
<212> TYPE: PRT
<213> ORGANISM: Saccharomyces cerevisiae

<400> SEQUENCE: 112

Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Phe Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Thr
    130                 135                 140

Ala Pro Ala Glu Ile Asp Arg Cys Ile Arg Thr Thr Tyr Val Thr Gln
```

```
                145                 150                 155                 160
        Arg Pro Val Tyr Leu Gly Leu Pro Ala Asn Leu Val Asp Leu Asn Val
                        165                 170                 175
        Pro Ala Lys Leu Leu Gln Thr Pro Ile Asp Met Ser Leu Lys Pro Asn
                        180                 185                 190
        Asp Ala Glu Ser Glu Lys Glu Val Ile Asp Thr Ile Leu Ala Leu Val
                        195                 200                 205
        Lys Asp Ala Lys Asn Pro Val Ile Leu Ala Asp Ala Cys Cys Ser Arg
        210                 215                 220
        His Asp Val Lys Ala Glu Thr Lys Lys Leu Ile Asp Leu Thr Gln Phe
        225                 230                 235                 240
        Pro Ala Phe Val Thr Pro Met Gly Lys Gly Ser Ile Asp Glu Gln His
                        245                 250                 255
        Pro Arg Tyr Gly Gly Val Tyr Val Gly Thr Leu Ser Lys Pro Glu Val
                        260                 265                 270
        Lys Glu Ala Val Glu Ser Ala Asp Leu Ile Leu Ser Val Gly Ala Leu
                        275                 280                 285
        Leu Ser Asp Phe Asn Thr Gly Ser Phe Ser Tyr Ser Tyr Lys Thr Lys
        290                 295                 300
        Asn Ile Val Glu Phe His Ser Asp His Met Lys Ile Arg Asn Ala Thr
        305                 310                 315                 320
        Phe Pro Gly Val Gln Met Lys Phe Val Leu Gln Lys Leu Leu Thr Thr
                        325                 330                 335
        Ile Ala Asp Ala Ala Lys Gly Tyr Lys Pro Val Ala Val Pro Ala Arg
                        340                 345                 350
        Thr Pro Ala Asn Ala Ala Val Pro Ala Ser Thr Pro Leu Lys Gln Glu
                        355                 360                 365
        Trp Met Trp Asn Gln Leu Gly Asn Phe Leu Gln Glu Gly Asp Val Val
        370                 375                 380
        Ile Ala Glu Thr Gly Thr Ser Ala Phe Gly Ile Asn Gln Thr Thr Phe
        385                 390                 395                 400
        Pro Asn Asn Thr Tyr Gly Ile Ser Gln Val Leu Trp Gly Ser Ile Gly
                        405                 410                 415
        Phe Thr Thr Gly Ala Thr Leu Gly Ala Ala Phe Ala Ala Glu Glu Ile
                        420                 425                 430
        Asp Pro Lys Lys Arg Val Ile Leu Phe Ile Gly Asp Gly Ser Leu Gln
                        435                 440                 445
        Leu Thr Val Gln Glu Ile Ser Thr Met Ile Arg Trp Gly Leu Lys Pro
                        450                 455                 460
        Tyr Leu Phe Val Leu Asn Asn Asp Gly Tyr Thr Ile Glu Lys Leu Ile
        465                 470                 475                 480
        His Gly Pro Lys Ala Gln Tyr Asn Glu Ile Gln Gly Trp Asp His Leu
                        485                 490                 495
        Ser Leu Leu Pro Thr Phe Gly Ala Lys Asp Tyr Glu Thr His Arg Val
                        500                 505                 510
        Ala Thr Thr Gly Glu Trp Asp Lys Leu Thr Gln Asp Lys Ser Phe Asn
                        515                 520                 525
        Asp Asn Ser Lys Ile Arg Met Ile Glu Ile Met Leu Pro Val Phe Asp
                        530                 535                 540
        Ala Pro Gln Asn Leu Val Glu Gln Ala Lys Leu Thr Ala Ala Thr Asn
        545                 550                 555                 560
        Ala Lys Gln
```

<210> SEQ ID NO 113
<211> LENGTH: 1692
<212> TYPE: DNA
<213> ORGANISM: Saccharomyces cerevisiaee
<220> FEATURE:
<221> NAME/KEY: CDS
<222> LOCATION: (1)..(1692)

<400> SEQUENCE: 113

| | | | | | | | | | | | | | | | | |
|---|---|---|---|---|---|---|---|---|---|---|---|---|---|---|---|---|
| atg | tct | gaa | ata | acc | tta | ggt | aaa | tat | tta | ttt | gaa | aga | ttg | agc | caa | 48 |
| Met | Ser | Glu | Ile | Thr | Leu | Gly | Lys | Tyr | Leu | Phe | Glu | Arg | Leu | Ser | Gln | |
| 1 | | | | 5 | | | | | 10 | | | | | 15 | | |
| gtc | aac | tgt | aac | acc | gtc | ttc | ggt | ttg | cca | ggt | gac | ttt | aac | ttg | tct | 96 |
| Val | Asn | Cys | Asn | Thr | Val | Phe | Gly | Leu | Pro | Gly | Asp | Phe | Asn | Leu | Ser | |
| | | | 20 | | | | | 25 | | | | | 30 | | | |
| ctt | ttg | gat | aag | ctt | tat | gaa | gtc | aaa | ggt | atg | aga | tgg | gct | ggt | aac | 144 |
| Leu | Leu | Asp | Lys | Leu | Tyr | Glu | Val | Lys | Gly | Met | Arg | Trp | Ala | Gly | Asn | |
| | | 35 | | | | | 40 | | | | | 45 | | | | |
| gct | aac | gaa | ttg | aac | gct | gcc | tat | gct | gct | gat | ggt | tac | gct | cgt | atc | 192 |
| Ala | Asn | Glu | Leu | Asn | Ala | Ala | Tyr | Ala | Ala | Asp | Gly | Tyr | Ala | Arg | Ile | |
| | 50 | | | | | 55 | | | | | 60 | | | | | |
| aag | ggt | atg | tcc | tgt | att | att | acc | acc | ttc | ggt | gtt | ggt | gaa | ttg | tct | 240 |
| Lys | Gly | Met | Ser | Cys | Ile | Ile | Thr | Thr | Phe | Gly | Val | Gly | Glu | Leu | Ser | |
| 65 | | | | | 70 | | | | | 75 | | | | | 80 | |
| gct | ttg | aat | ggt | att | gcc | ggt | tct | tac | gct | gaa | cat | gtc | ggt | gtt | ttg | 288 |
| Ala | Leu | Asn | Gly | Ile | Ala | Gly | Ser | Tyr | Ala | Glu | His | Val | Gly | Val | Leu | |
| | | | | 85 | | | | | 90 | | | | | 95 | | |
| cac | gtt | gtt | ggt | gtt | cca | tcc | atc | tct | tct | caa | gct | aag | caa | ttg | ttg | 336 |
| His | Val | Val | Gly | Val | Pro | Ser | Ile | Ser | Ser | Gln | Ala | Lys | Gln | Leu | Leu | |
| | | | 100 | | | | | 105 | | | | | 110 | | | |
| ttg | cat | cat | acc | ttg | ggt | aac | ggt | gac | ttc | act | gtt | ttc | cac | aga | atg | 384 |
| Leu | His | His | Thr | Leu | Gly | Asn | Gly | Asp | Phe | Thr | Val | Phe | His | Arg | Met | |
| | | 115 | | | | | 120 | | | | | 125 | | | | |
| tct | gcc | aac | att | tct | gaa | acc | act | gcc | atg | atc | act | gat | att | gct | aac | 432 |
| Ser | Ala | Asn | Ile | Ser | Glu | Thr | Thr | Ala | Met | Ile | Thr | Asp | Ile | Ala | Asn | |
| | 130 | | | | | 135 | | | | | 140 | | | | | |
| gct | cca | gct | gaa | att | gac | aga | tgt | atc | aga | acc | acc | tac | act | acc | caa | 480 |
| Ala | Pro | Ala | Glu | Ile | Asp | Arg | Cys | Ile | Arg | Thr | Thr | Tyr | Thr | Thr | Gln | |
| 145 | | | | | 150 | | | | | 155 | | | | | 160 | |
| aga | cca | gtc | tac | ttg | ggt | ttg | cca | gct | aac | ttg | gtt | gac | ttg | aac | gtc | 528 |
| Arg | Pro | Val | Tyr | Leu | Gly | Leu | Pro | Ala | Asn | Leu | Val | Asp | Leu | Asn | Val | |
| | | | | 165 | | | | | 170 | | | | | 175 | | |
| cca | gcc | aag | tta | ttg | gaa | act | cca | att | gac | ttg | tct | ttg | aag | cca | aac | 576 |
| Pro | Ala | Lys | Leu | Leu | Glu | Thr | Pro | Ile | Asp | Leu | Ser | Leu | Lys | Pro | Asn | |
| | | | 180 | | | | | 185 | | | | | 190 | | | |
| gac | gct | gaa | gct | gaa | gct | gaa | gtt | gtt | aga | act | gtt | gtt | gaa | ttg | atc | 624 |
| Asp | Ala | Glu | Ala | Glu | Ala | Glu | Val | Val | Arg | Thr | Val | Val | Glu | Leu | Ile | |
| | | 195 | | | | | 200 | | | | | 205 | | | | |
| aag | gat | gct | aag | aac | cca | gtt | atc | ttg | gct | gat | gct | tgt | gct | tct | aga | 672 |
| Lys | Asp | Ala | Lys | Asn | Pro | Val | Ile | Leu | Ala | Asp | Ala | Cys | Ala | Ser | Arg | |
| | 210 | | | | | 215 | | | | | 220 | | | | | |
| cat | gat | gtc | aag | gct | gaa | act | aag | aag | ttg | atg | gac | ttg | act | caa | ttc | 720 |
| His | Asp | Val | Lys | Ala | Glu | Thr | Lys | Lys | Leu | Met | Asp | Leu | Thr | Gln | Phe | |
| 225 | | | | | 230 | | | | | 235 | | | | | 240 | |
| cca | gtt | tac | gtc | acc | cca | atg | ggt | aag | ggt | gct | att | gac | gaa | caa | cac | 768 |
| Pro | Val | Tyr | Val | Thr | Pro | Met | Gly | Lys | Gly | Ala | Ile | Asp | Glu | Gln | His | |
| | | | | 245 | | | | | 250 | | | | | 255 | | |
| cca | aga | tac | ggt | ggt | gtt | tac | gtt | ggt | acc | ttg | tct | aga | cca | gaa | gtt | 816 |
| Pro | Arg | Tyr | Gly | Gly | Val | Tyr | Val | Gly | Thr | Leu | Ser | Arg | Pro | Glu | Val | |
| | | | 260 | | | | | 265 | | | | | 270 | | | |
| aag | aag | gct | gta | gaa | tct | gct | gat | ttg | ata | ttg | tct | atc | ggt | gct | ttg | 864 |
| Lys | Lys | Ala | Val | Glu | Ser | Ala | Asp | Leu | Ile | Leu | Ser | Ile | Gly | Ala | Leu | |

```
                 275                 280                 285
ttg tct gat ttc aat acc ggt tct ttc tct tac tcc tac aag acc aaa      912
Leu Ser Asp Phe Asn Thr Gly Ser Phe Ser Tyr Ser Tyr Lys Thr Lys
290                 295                 300 aat atc gtt gaa ttc cac tct gac cac atc aag atc aga aac gcc acc      960
Asn Ile Val Glu Phe His Ser Asp His Ile Lys Ile Arg Asn Ala Thr
305                 310                 315                 320 ttc cca ggt gtt caa atg aaa ttt gcc ttg caa aaa ttg ttg gat gct     1008
Phe Pro Gly Val Gln Met Lys Phe Ala Leu Gln Lys Leu Leu Asp Ala
                325                 330                 335 att cca gaa gtc gtc aag gac tac aaa cct gtt gct gtc cca gct aga     1056
Ile Pro Glu Val Val Lys Asp Tyr Lys Pro Val Ala Val Pro Ala Arg
            340                 345                 350 gtt cca att acc aag tct act cca gct aac act cca atg aag caa gaa     1104
Val Pro Ile Thr Lys Ser Thr Pro Ala Asn Thr Pro Met Lys Gln Glu
        355                 360                 365 tgg atg tgg aac cat ttg ggt aac ttc ttg aga gaa ggt gat att gtt     1152
Trp Met Trp Asn His Leu Gly Asn Phe Leu Arg Glu Gly Asp Ile Val
370                 375                 380 att gct gaa acc ggt act tcc gcc ttc ggt att aac caa act act ttc     1200
Ile Ala Glu Thr Gly Thr Ser Ala Phe Gly Ile Asn Gln Thr Thr Phe
385                 390                 395                 400 cca aca gat gta tac gct atc gtc caa gtc ttg tgg ggt tcc att ggt     1248
Pro Thr Asp Val Tyr Ala Ile Val Gln Val Leu Trp Gly Ser Ile Gly
                405                 410                 415 ttc aca gtc ggc gct cta ttg ggt gct act atg gcc gct gaa gaa ctt     1296
Phe Thr Val Gly Ala Leu Leu Gly Ala Thr Met Ala Ala Glu Glu Leu
            420                 425                 430 gat cca aag aag aga gtt att tta ttc att ggt gac ggt tct cta caa     1344
Asp Pro Lys Lys Arg Val Ile Leu Phe Ile Gly Asp Gly Ser Leu Gln
        435                 440                 445 ttg act gtt caa gaa atc tct acc atg att aga tgg ggt ttg aag cca     1392
Leu Thr Val Gln Glu Ile Ser Thr Met Ile Arg Trp Gly Leu Lys Pro
450                 455                 460 tac att ttt gtc ttg aat aac aac ggt tac acc att gaa aaa ttg att     1440
Tyr Ile Phe Val Leu Asn Asn Asn Gly Tyr Thr Ile Glu Lys Leu Ile
465                 470                 475                 480 cac ggt cct cat gcc gaa tat aat gaa att caa ggt tgg gac cac ttg     1488
His Gly Pro His Ala Glu Tyr Asn Glu Ile Gln Gly Trp Asp His Leu
                485                 490                 495 gcc tta ttg cca act ttt ggt gct aga aac tac gaa acc cac aga gtt     1536
Ala Leu Leu Pro Thr Phe Gly Ala Arg Asn Tyr Glu Thr His Arg Val
            500                 505                 510 gct acc act ggt gaa tgg gaa aag ttg act caa gac aag gac ttc caa     1584
Ala Thr Thr Gly Glu Trp Glu Lys Leu Thr Gln Asp Lys Asp Phe Gln
        515                 520                 525 gac aac tct aag att aga atg att gaa gtt atg ttg cca gtc ttt gat     1632
Asp Asn Ser Lys Ile Arg Met Ile Glu Val Met Leu Pro Val Phe Asp
530                 535                 540 gct cca caa aac ttg gtt aaa caa gct caa ttg act gcc gct act aac     1680
Ala Pro Gln Asn Leu Val Lys Gln Ala Gln Leu Thr Ala Ala Thr Asn
545                 550                 555                 560 gct aaa caa taa                                                     1692
Ala Lys Gln <210> SEQ ID NO 114
<211> LENGTH: 563
<212> TYPE: PRT
<213> ORGANISM: Saccharomyces cerevisiaee

<400> SEQUENCE: 114
```

```
Met Ser Glu Ile Thr Leu Gly Lys Tyr Leu Phe Glu Arg Leu Ser Gln
1               5                   10                  15

Val Asn Cys Asn Thr Val Phe Gly Leu Pro Gly Asp Phe Asn Leu Ser
            20                  25                  30

Leu Leu Asp Lys Leu Tyr Glu Val Lys Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ser Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Asn
    130                 135                 140

Ala Pro Ala Glu Ile Asp Arg Cys Ile Arg Thr Tyr Thr Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Glu Thr Pro Ile Asp Leu Ser Leu Lys Pro Asn
            180                 185                 190

Asp Ala Glu Ala Glu Ala Val Val Arg Thr Val Val Glu Leu Ile
    195                 200                 205

Lys Asp Ala Lys Asn Pro Val Ile Leu Ala Asp Ala Cys Ala Ser Arg
210                 215                 220

His Asp Val Lys Ala Glu Thr Lys Lys Leu Met Asp Leu Thr Gln Phe
225                 230                 235                 240

Pro Val Tyr Val Thr Pro Met Gly Lys Gly Ala Ile Asp Glu Gln His
                245                 250                 255

Pro Arg Tyr Gly Gly Val Tyr Val Gly Thr Leu Ser Arg Pro Glu Val
            260                 265                 270

Lys Lys Ala Val Glu Ser Ala Asp Leu Ile Leu Ser Ile Gly Ala Leu
        275                 280                 285

Leu Ser Asp Phe Asn Thr Gly Ser Phe Ser Tyr Ser Tyr Lys Thr Lys
    290                 295                 300

Asn Ile Val Glu Phe His Ser Asp His Ile Lys Ile Arg Asn Ala Thr
305                 310                 315                 320

Phe Pro Gly Val Gln Met Lys Phe Ala Leu Gln Lys Leu Leu Asp Ala
                325                 330                 335

Ile Pro Glu Val Val Lys Asp Tyr Lys Pro Val Ala Val Pro Ala Arg
            340                 345                 350

Val Pro Ile Thr Lys Ser Thr Pro Ala Asn Thr Pro Met Lys Gln Glu
        355                 360                 365

Trp Met Trp Asn His Leu Gly Asn Phe Leu Arg Glu Gly Asp Ile Val
    370                 375                 380

Ile Ala Glu Thr Gly Thr Ser Ala Phe Gly Ile Asn Gln Thr Thr Phe
385                 390                 395                 400

Pro Thr Asp Val Tyr Ala Ile Val Gln Val Leu Trp Gly Ser Ile Gly
                405                 410                 415

Phe Thr Val Gly Ala Leu Leu Gly Ala Thr Met Ala Ala Glu Glu Leu
```

```
                    420                 425                 430
Asp Pro Lys Lys Arg Val Ile Leu Phe Ile Gly Asp Gly Ser Leu Gln
            435                 440                 445

Leu Thr Val Gln Glu Ile Ser Thr Met Ile Arg Trp Gly Leu Lys Pro
    450                 455                 460

Tyr Ile Phe Val Leu Asn Asn Asn Gly Tyr Thr Ile Glu Lys Leu Ile
465                 470                 475                 480

His Gly Pro His Ala Glu Tyr Asn Glu Ile Gln Gly Trp Asp His Leu
                485                 490                 495

Ala Leu Leu Pro Thr Phe Gly Ala Arg Asn Tyr Glu Thr His Arg Val
            500                 505                 510

Ala Thr Thr Gly Glu Trp Glu Lys Leu Thr Gln Asp Lys Asp Phe Gln
        515                 520                 525

Asp Asn Ser Lys Ile Arg Met Ile Glu Val Met Leu Pro Val Phe Asp
    530                 535                 540

Ala Pro Gln Asn Leu Val Lys Gln Ala Gln Leu Thr Ala Ala Thr Asn
545                 550                 555                 560

Ala Lys Gln

<210> SEQ ID NO 115
<211> LENGTH: 1599
<212> TYPE: DNA
<213> ORGANISM: Saccharomyces cerevisiae
<220> FEATURE:
<221> NAME/KEY: CDS
<222> LOCATION: (1)..(1599)

<400> SEQUENCE: 115 atg tct gaa att act ctt gga aaa tac tta ttt gaa aga ttg aag caa      48
Met Ser Glu Ile Thr Leu Gly Lys Tyr Leu Phe Glu Arg Leu Lys Gln
1               5                   10                  15 gtt aat gtt aac acc att ttt ggg cta cca ggc gac ttc aac ttg tcc     96
Val Asn Val Asn Thr Ile Phe Gly Leu Pro Gly Asp Phe Asn Leu Ser
            20                  25                  30 cta ttg gac aag att tac gag gta gat gga ttg aga tgg gct ggt aat    144
Leu Leu Asp Lys Ile Tyr Glu Val Asp Gly Leu Arg Trp Ala Gly Asn
        35                  40                  45 gca aat gag ctg aac gcc gcc tat gcc gcc gat ggt tac gca cgc atc    192
Ala Asn Glu Leu Asn Ala Ala Tyr Ala Ala Asp Gly Tyr Ala Arg Ile
    50                  55                  60 aag ggt tta tct gtg ctg gta act act ttt ggc gta ggt gaa tta tcc    240
Lys Gly Leu Ser Val Leu Val Thr Thr Phe Gly Val Gly Glu Leu Ser
65                  70                  75                  80 gcc ttg aat ggt att gca gga tcg tat gca gaa cac gtc ggt gta ctg    288
Ala Leu Asn Gly Ile Ala Gly Ser Tyr Ala Glu His Val Gly Val Leu
                85                  90                  95 cat gtt gtt ggt gtc ccc tct atc tcc gct cag gct aag caa ttg ttg    336
His Val Val Gly Val Pro Ser Ile Ser Ala Gln Ala Lys Gln Leu Leu
            100                 105                 110 ttg cat cat acc ttg ggt aac ggt gat ttt acc gtt ttt cac aga atg    384
Leu His His Thr Leu Gly Asn Gly Asp Phe Thr Val Phe His Arg Met
        115                 120                 125 tcc gcc aat atc tca gaa act aca tca atg att aca gac att gct aca    432
Ser Ala Asn Ile Ser Glu Thr Thr Ser Met Ile Thr Asp Ile Ala Thr
    130                 135                 140 gcc cct tca gaa atc gat agg ttg atc agg aca aca ttt ata aca caa    480
Ala Pro Ser Glu Ile Asp Arg Leu Ile Arg Thr Thr Phe Ile Thr Gln
145                 150                 155                 160 agg cct agc tac ttg ggg ttg cca gcg aat ttg gta gat cta aag gtt    528
```

-continued

```
              Arg Pro Ser Tyr Leu Gly Leu Pro Ala Asn Leu Val Asp Leu Lys Val
                              165                 170                 175 cct ggt tct ctt ttg gaa aaa ccg att gat cta tca tta aaa cct aac            576
Pro Gly Ser Leu Leu Glu Lys Pro Ile Asp Leu Ser Leu Lys Pro Asn
                180                 185                 190 gat ccc gaa gct gaa aag gaa gtt att gat acc gta cta gaa ttg atc            624
Asp Pro Glu Ala Glu Lys Glu Val Ile Asp Thr Val Leu Glu Leu Ile
                195                 200                 205 cag aat tcg aaa aac cct gtt ata cta tcg gat gcc tgt gct tct agg            672
Gln Asn Ser Lys Asn Pro Val Ile Leu Ser Asp Ala Cys Ala Ser Arg
            210                 215                 220 cac aac gtt aaa aaa gaa acc cag aag tta att gat ttg acg caa ttc            720
His Asn Val Lys Lys Glu Thr Gln Lys Leu Ile Asp Leu Thr Gln Phe
225                 230                 235                 240 cca gct ttt gtg aca cct cta ggt aaa ggg tca ata gat gaa cag cat            768
Pro Ala Phe Val Thr Pro Leu Gly Lys Gly Ser Ile Asp Glu Gln His
                245                 250                 255 ccc aga tat ggc ggt gtt tat gtg gga acg ctg tcc aaa caa gac gtg            816
Pro Arg Tyr Gly Gly Val Tyr Val Gly Thr Leu Ser Lys Gln Asp Val
                260                 265                 270 aaa cag gcc gtt gag tcg gct gat ttg atc ctt tcg gtc ggt gct ttg            864
Lys Gln Ala Val Glu Ser Ala Asp Leu Ile Leu Ser Val Gly Ala Leu
            275                 280                 285 ctc tct gat ttt aac aca ggt tcg ttt tcc tac tcc tac aag act aaa            912
Leu Ser Asp Phe Asn Thr Gly Ser Phe Ser Tyr Ser Tyr Lys Thr Lys
        290                 295                 300 aat gta gtg gag ttt cat tcc gat tac gta aag gtg aag aac gct acg            960
Asn Val Val Glu Phe His Ser Asp Tyr Val Lys Val Lys Asn Ala Thr
305                 310                 315                 320 ttc ctc ggt gta caa atg aaa ttt gca cta caa aac tta ctg aag gtt           1008
Phe Leu Gly Val Gln Met Lys Phe Ala Leu Gln Asn Leu Leu Lys Val
                325                 330                 335 att ccc gat gtt gtt aag ggc tac aag agc gtt ccc gta cca acc aaa           1056
Ile Pro Asp Val Val Lys Gly Tyr Lys Ser Val Pro Val Pro Thr Lys
                340                 345                 350 act ccc gca aac aaa ggt gta cct gct agc acg ccc ttg aaa caa gag           1104
Thr Pro Ala Asn Lys Gly Val Pro Ala Ser Thr Pro Leu Lys Gln Glu
            355                 360                 365 tgg ttg tgg aac gaa ttg tcc aaa ttc ttg caa gaa ggt gat gtt atc           1152
Trp Leu Trp Asn Glu Leu Ser Lys Phe Leu Gln Glu Gly Asp Val Ile
        370                 375                 380 att tcc gag acc ggc acg tct gcc ttc ggt atc aat caa act atc ttt           1200
Ile Ser Glu Thr Gly Thr Ser Ala Phe Gly Ile Asn Gln Thr Ile Phe
385                 390                 395                 400 cct aag gac gcc tac ggt atc tcg cag gtg ttg tgg ggg tcc atc ggt           1248
Pro Lys Asp Ala Tyr Gly Ile Ser Gln Val Leu Trp Gly Ser Ile Gly
                405                 410                 415 ttt aca aca gga gca act tta ggt gct gcc ttt gcc gct gag gag att           1296
Phe Thr Thr Gly Ala Thr Leu Gly Ala Ala Phe Ala Ala Glu Glu Ile
                420                 425                 430 gac ccc aac aag aga gtc atc tta ttc ata ggt gac ggg tct ttg cag           1344
Asp Pro Asn Lys Arg Val Ile Leu Phe Ile Gly Asp Gly Ser Leu Gln
            435                 440                 445 tta acc gtc caa gaa atc tcc acc atg atc aga tgg ggg tta aag ccg           1392
Leu Thr Val Gln Glu Ile Ser Thr Met Ile Arg Trp Gly Leu Lys Pro
        450                 455                 460 tat ctt ttt gtc ctt aac aac gac ggc tac act atc gaa aag ctg att           1440
Tyr Leu Phe Val Leu Asn Asn Asp Gly Tyr Thr Ile Glu Lys Leu Ile
465                 470                 475                 480 cat ggg cct cac gca gag tac aac gaa atc cag acc tgg gat cac ctc           1488
```

```
His Gly Pro His Ala Glu Tyr Asn Glu Ile Gln Thr Trp Asp His Leu
                485                 490                 495 gcc ctg ttg ccc gca ttt ggt gcg aaa aag tac gaa aat cac aag atc      1536
Ala Leu Leu Pro Ala Phe Gly Ala Lys Lys Tyr Glu Asn His Lys Ile
                500                 505                 510 gcc act acg ggt gag tgg gat gcc tta acc act gat tca gag ttc cag      1584
Ala Thr Thr Gly Glu Trp Asp Ala Leu Thr Thr Asp Ser Glu Phe Gln
                515                 520                 525 aaa aac tcg gtg atc                                                  1599
Lys Asn Ser Val Ile
        530

<210> SEQ ID NO 116
<211> LENGTH: 533
<212> TYPE: PRT
<213> ORGANISM: Saccharomyces cerevisiae

<400> SEQUENCE: 116

Met Ser Glu Ile Thr Leu Gly Lys Tyr Leu Phe Glu Arg Leu Lys Gln
1               5                   10                  15

Val Asn Val Asn Thr Ile Phe Gly Leu Pro Gly Asp Phe Asn Leu Ser
            20                  25                  30

Leu Leu Asp Lys Ile Tyr Glu Val Asp Gly Leu Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Leu Ser Val Leu Val Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ser Met Ile Thr Asp Ile Ala Thr
    130                 135                 140

Ala Pro Ser Glu Ile Asp Arg Leu Ile Arg Thr Thr Phe Ile Thr Gln
145                 150                 155                 160

Arg Pro Ser Tyr Leu Gly Leu Pro Ala Asn Leu Val Asp Leu Lys Val
                165                 170                 175

Pro Gly Ser Leu Leu Glu Lys Pro Ile Asp Leu Ser Leu Lys Pro Asn
            180                 185                 190

Asp Pro Glu Ala Glu Lys Glu Val Ile Asp Thr Val Leu Glu Leu Ile
        195                 200                 205

Gln Asn Ser Lys Asn Pro Val Ile Leu Ser Asp Ala Cys Ala Ser Arg
    210                 215                 220

His Asn Val Lys Lys Glu Thr Gln Lys Leu Ile Asp Leu Thr Gln Phe
225                 230                 235                 240

Pro Ala Phe Val Thr Pro Leu Gly Lys Gly Ser Ile Asp Glu Gln His
                245                 250                 255

Pro Arg Tyr Gly Gly Val Tyr Val Gly Thr Leu Ser Lys Gln Asp Val
            260                 265                 270

Lys Gln Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300
```

```
Asn Val Val Glu Phe His Ser Asp Tyr Val Lys Val Lys Asn Ala Thr
305                 310                 315                 320

Phe Leu Gly Val Gln Met Lys Phe Ala Leu Gln Asn Leu Leu Lys Val
                325                 330                 335

Ile Pro Asp Val Val Lys Gly Tyr Lys Ser Val Pro Val Pro Thr Lys
            340                 345                 350

Thr Pro Ala Asn Lys Gly Val Pro Ala Ser Thr Pro Leu Lys Gln Glu
        355                 360                 365

Trp Leu Trp Asn Glu Leu Ser Lys Phe Leu Gln Glu Gly Asp Val Ile
    370                 375                 380

Ile Ser Glu Thr Gly Thr Ser Ala Phe Gly Ile Asn Gln Thr Ile Phe
385                 390                 395                 400

Pro Lys Asp Ala Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
            420                 425                 430

Asp Pro Asn Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Lys Leu Ile
465                 470                 475                 480

His Gly Pro His Ala Glu Tyr Asn Glu Ile Gln Thr Trp Asp His Leu
                485                 490                 495

Ala Leu Leu Pro Ala Phe Gly Ala Lys Lys Tyr Glu Asn His Lys Ile
            500                 505                 510

Ala Thr Thr Gly Glu Trp Asp Ala Leu Thr Thr Asp Ser Glu Phe Gln
        515                 520                 525

Lys Asn Ser Val Ile
        530

<210> SEQ ID NO 117
<211> LENGTH: 1695
<212> TYPE: DNA
<213> ORGANISM: Candida glabrata
<220> FEATURE:
<221> NAME/KEY: CDS
<222> LOCATION: (1)..(1695)

<400> SEQUENCE: 117 atg tct gag att act ttg ggt aga tac ttg ttc gag aga ttg aac caa        48
Met Ser Glu Ile Thr Leu Gly Arg Tyr Leu Phe Glu Arg Leu Asn Gln
1               5                   10                  15 gtc gac gtt aag acc atc ttc ggt ttg cca ggt gac ttc aac ttg tcc        96
Val Asp Val Lys Thr Ile Phe Gly Leu Pro Gly Asp Phe Asn Leu Ser
            20                  25                  30 cta ttg gac aag atc tac gaa gtt gaa ggt atg aga tgg gct ggt aac       144
Leu Leu Asp Lys Ile Tyr Glu Val Glu Gly Met Arg Trp Ala Gly Asn
        35                  40                  45 gct aac gaa ttg aac gct gct tac gct gct gac ggt tac gct aga atc       192
Ala Asn Glu Leu Asn Ala Ala Tyr Ala Ala Asp Gly Tyr Ala Arg Ile
    50                  55                  60 aag ggt atg tcc tgt atc atc acc acc ttc ggt gtc ggt gaa ttg tct       240
Lys Gly Met Ser Cys Ile Ile Thr Thr Phe Gly Val Gly Glu Leu Ser
65                  70                  75                  80 gcc ttg aac ggt att gcc ggt tct tac gct gaa cac gtc ggt gtc ttg       288
Ala Leu Asn Gly Ile Ala Gly Ser Tyr Ala Glu His Val Gly Val Leu
                85                  90                  95
```

```
cac gtc gtc ggt gtc cca tcc atc tcc tct caa gct aag caa ttg ttg       336
His Val Val Gly Val Pro Ser Ile Ser Ser Gln Ala Lys Gln Leu Leu
            100                 105                 110 ttg cac cac acc ttg ggt aac ggt gac ttc act gtc ttc cac aga atg       384
Leu His His Thr Leu Gly Asn Gly Asp Phe Thr Val Phe His Arg Met
        115                 120                 125 tcc gct aac atc tct gag acc acc gct atg gtc act gac atc gct acc       432
Ser Ala Asn Ile Ser Glu Thr Thr Ala Met Val Thr Asp Ile Ala Thr
    130                 135                 140 gct cca gct gag atc gac aga tgt atc aga acc acc tac atc acc caa       480
Ala Pro Ala Glu Ile Asp Arg Cys Ile Arg Thr Thr Tyr Ile Thr Gln
145                 150                 155                 160 aga cca gtc tac ttg ggt cta cca gct aac ttg gtc gac cta aag gtc       528
Arg Pro Val Tyr Leu Gly Leu Pro Ala Asn Leu Val Asp Leu Lys Val
                165                 170                 175 cca gcc aag ctt ttg gaa acc cca att gac ttg tcc ttg aag cca aac       576
Pro Ala Lys Leu Leu Glu Thr Pro Ile Asp Leu Ser Leu Lys Pro Asn
            180                 185                 190 gac cca gaa gcc gaa act gaa gtc gtt gac acc gtc ttg gaa ttg atc       624
Asp Pro Glu Ala Glu Thr Glu Val Val Asp Thr Val Leu Glu Leu Ile
        195                 200                 205 aag gct gct aag aac cca gtt atc ttg gct gat gct tgt gct tcc aga       672
Lys Ala Ala Lys Asn Pro Val Ile Leu Ala Asp Ala Cys Ala Ser Arg
    210                 215                 220 cac gac gtc aag gct gaa acc aag aag ttg att gac gcc act caa ttc       720
His Asp Val Lys Ala Glu Thr Lys Lys Leu Ile Asp Ala Thr Gln Phe
225                 230                 235                 240 cca tcc ttc gtt acc cca atg ggt aag ggt tcc atc gac gaa caa cac       768
Pro Ser Phe Val Thr Pro Met Gly Lys Gly Ser Ile Asp Glu Gln His
                245                 250                 255 cca aga ttc ggt ggt gtc tac gtc ggt acc ttg tcc aga cca gaa gtt       816
Pro Arg Phe Gly Gly Val Tyr Val Gly Thr Leu Ser Arg Pro Glu Val
            260                 265                 270 aag gaa gct gtt gaa tcc gct gac ttg atc ttg tct gtc ggt gct ttg       864
Lys Glu Ala Val Glu Ser Ala Asp Leu Ile Leu Ser Val Gly Ala Leu
        275                 280                 285 ttg tcc gat ttc aac act ggt tct ttc tct tac tct tac aag acc aag       912
Leu Ser Asp Phe Asn Thr Gly Ser Phe Ser Tyr Ser Tyr Lys Thr Lys
    290                 295                 300 aac atc gtc gaa ttc cac tct gac tac atc aag atc aga aac gct acc       960
Asn Ile Val Glu Phe His Ser Asp Tyr Ile Lys Ile Arg Asn Ala Thr
305                 310                 315                 320 ttc cca ggt gtc caa atg aag ttc gct ttg caa aag ttg ttg aac gcc      1008
Phe Pro Gly Val Gln Met Lys Phe Ala Leu Gln Lys Leu Leu Asn Ala
                325                 330                 335 gtc cca gaa gct atc aag ggt tac aag cca gtc cct gtc cca gct aga      1056
Val Pro Glu Ala Ile Lys Gly Tyr Lys Pro Val Pro Val Pro Ala Arg
            340                 345                 350 gtc cca gaa aac aag tcc tgt gac cca gct acc cca ttg aag caa gaa      1104
Val Pro Glu Asn Lys Ser Cys Asp Pro Ala Thr Pro Leu Lys Gln Glu
        355                 360                 365 tgg atg tgg aac caa gtt tcc aag ttc ttg caa gaa ggt gat gtt gtt      1152
Trp Met Trp Asn Gln Val Ser Lys Phe Leu Gln Glu Gly Asp Val Val
    370                 375                 380 atc act gaa acc ggt acc tcc gct ttt ggt atc aac caa acc cca ttc      1200
Ile Thr Glu Thr Gly Thr Ser Ala Phe Gly Ile Asn Gln Thr Pro Phe
385                 390                 395                 400 cca aac aac gct tac ggt atc tcc caa gtt cta tgg ggt tcc atc ggt      1248
Pro Asn Asn Ala Tyr Gly Ile Ser Gln Val Leu Trp Gly Ser Ile Gly
                405                 410                 415
```

|  |  |
|---|---|
| ttc acc acc ggt gct tgt ttg ggt gcc gct ttc gct gct gaa gaa atc<br>Phe Thr Thr Gly Ala Cys Leu Gly Ala Ala Phe Ala Ala Glu Glu Ile<br>420                           425                      430 | 1296 |
| gac cca aag aag aga gtt atc ttg ttc att ggt gac ggt tct ttg caa<br>Asp Pro Lys Lys Arg Val Ile Leu Phe Ile Gly Asp Gly Ser Leu Gln<br>435                           440                      445 | 1344 |
| ttg act gtc caa gaa atc tcc acc atg atc aga tgg ggc ttg aag cca<br>Leu Thr Val Gln Glu Ile Ser Thr Met Ile Arg Trp Gly Leu Lys Pro<br>450                         455                       460 | 1392 |
| tac ttg ttc gtc ttg aac aac gac ggt tac acc atc gaa aga ttg att<br>Tyr Leu Phe Val Leu Asn Asn Asp Gly Tyr Thr Ile Glu Arg Leu Ile<br>465                      470                       475                  480 | 1440 |
| cac ggt gaa aag gct ggt tac aac gac atc caa aac tgg gac cac ttg<br>His Gly Glu Lys Ala Gly Tyr Asn Asp Ile Gln Asn Trp Asp His Leu<br>485                         490                      495 | 1488 |
| gct cta ttg cca acc ttc ggt gct aag gac tac gaa aac cac aga gtc<br>Ala Leu Leu Pro Thr Phe Gly Ala Lys Asp Tyr Glu Asn His Arg Val<br>500                         505                      510 | 1536 |
| gcc acc acc ggt gaa tgg gac aag ttg acc caa gac aag gaa ttc aac<br>Ala Thr Thr Gly Glu Trp Asp Lys Leu Thr Gln Asp Lys Glu Phe Asn<br>515                         520                      525 | 1584 |
| aag aac tcc aag atc aga atg atc gaa gtt atg ttg cca gtt atg gac<br>Lys Asn Ser Lys Ile Arg Met Ile Glu Val Met Leu Pro Val Met Asp<br>530                         535                      540 | 1632 |
| gct cca act tcc ttg att gaa caa gct aag ttg acc gct tcc atc aac<br>Ala Pro Thr Ser Leu Ile Glu Gln Ala Lys Leu Thr Ala Ser Ile Asn<br>545                         550                       555                  560 | 1680 |
| gct aag caa gaa taa<br>Ala Lys Gln Glu | 1695 |

<210> SEQ ID NO 118
<211> LENGTH: 564
<212> TYPE: PRT
<213> ORGANISM: Candida glabrata

<400> SEQUENCE: 118

Met Ser Glu Ile Thr Leu Gly Arg Tyr Leu Phe Glu Arg Leu Asn Gln
1                 5                    10                  15

Val Asp Val Lys Thr Ile Phe Gly Leu Pro Gly Asp Phe Asn Leu Ser
                20                   25                  30

Leu Leu Asp Lys Ile Tyr Glu Val Gly Met Arg Trp Ala Gly Asn
                35                   40                  45

Ala Asn Glu Leu Asn Ala Ala Tyr Ala Ala Asp Gly Tyr Ala Arg Ile
50                          55                      60

Lys Gly Met Ser Cys Ile Ile Thr Thr Phe Gly Val Gly Glu Leu Ser
65                70                   75                  80

Ala Leu Asn Gly Ile Ala Gly Ser Tyr Ala Glu His Val Gly Val Leu
                85                   90                  95

His Val Val Gly Val Pro Ser Ile Ser Ser Gln Ala Lys Gln Leu Leu
                    100                105                110

Leu His His Thr Leu Gly Asn Gly Asp Phe Thr Val Phe His Arg Met
                115                120                125

Ser Ala Asn Ile Ser Glu Thr Thr Ala Met Val Thr Asp Ile Ala Thr
130                        135                      140

Ala Pro Ala Glu Ile Asp Arg Cys Ile Arg Thr Thr Tyr Ile Thr Gln
145                        150                155                160

Arg Pro Val Tyr Leu Gly Leu Pro Ala Asn Leu Val Asp Leu Lys Val
                165                170                175

```
Pro Ala Lys Leu Leu Glu Thr Pro Ile Asp Leu Ser Leu Lys Pro Asn
        180                 185                 190
Asp Pro Glu Ala Glu Thr Glu Val Val Asp Thr Val Leu Glu Leu Ile
            195                 200                 205
Lys Ala Ala Lys Asn Pro Val Ile Leu Ala Asp Ala Cys Ala Ser Arg
210                 215                 220
His Asp Val Lys Ala Glu Thr Lys Lys Leu Ile Asp Ala Thr Gln Phe
225                 230                 235                 240
Pro Ser Phe Val Thr Pro Met Gly Lys Gly Ser Ile Asp Glu Gln His
                    245                 250                 255
Pro Arg Phe Gly Gly Val Tyr Val Gly Thr Leu Ser Arg Pro Glu Val
                260                 265                 270
Lys Glu Ala Val Glu Ser Ala Asp Leu Ile Leu Ser Val Gly Ala Leu
            275                 280                 285
Leu Ser Asp Phe Asn Thr Gly Ser Phe Ser Tyr Ser Tyr Lys Thr Lys
        290                 295                 300
Asn Ile Val Glu Phe His Ser Asp Tyr Ile Lys Ile Arg Asn Ala Thr
305                 310                 315                 320
Phe Pro Gly Val Gln Met Lys Phe Ala Leu Gln Lys Leu Leu Asn Ala
                    325                 330                 335
Val Pro Glu Ala Ile Lys Gly Tyr Lys Pro Val Pro Val Pro Ala Arg
                340                 345                 350
Val Pro Glu Asn Lys Ser Cys Asp Pro Ala Thr Pro Leu Lys Gln Glu
            355                 360                 365
Trp Met Trp Asn Gln Val Ser Lys Phe Leu Gln Glu Gly Asp Val Val
        370                 375                 380
Ile Thr Glu Thr Gly Thr Ser Ala Phe Gly Ile Asn Gln Thr Pro Phe
385                 390                 395                 400
Pro Asn Asn Ala Tyr Gly Ile Ser Gln Val Leu Trp Gly Ser Ile Gly
                    405                 410                 415
Phe Thr Thr Gly Ala Cys Leu Gly Ala Ala Phe Ala Ala Glu Glu Ile
                420                 425                 430
Asp Pro Lys Lys Arg Val Ile Leu Phe Ile Gly Asp Gly Ser Leu Gln
            435                 440                 445
Leu Thr Val Gln Glu Ile Ser Thr Met Ile Arg Trp Gly Leu Lys Pro
        450                 455                 460
Tyr Leu Phe Val Leu Asn Asn Asp Gly Tyr Thr Ile Glu Arg Leu Ile
465                 470                 475                 480
His Gly Glu Lys Ala Gly Tyr Asn Asp Ile Gln Asn Trp Asp His Leu
                    485                 490                 495
Ala Leu Leu Pro Thr Phe Gly Ala Lys Asp Tyr Glu Asn His Arg Val
                500                 505                 510
Ala Thr Thr Gly Glu Trp Asp Lys Leu Thr Gln Asp Lys Glu Phe Asn
            515                 520                 525
Lys Asn Ser Lys Ile Arg Met Ile Glu Val Met Leu Pro Val Met Asp
        530                 535                 540
Ala Pro Thr Ser Leu Ile Glu Gln Ala Lys Leu Thr Ala Ser Ile Asn
545                 550                 555                 560
Ala Lys Gln Glu

<210> SEQ ID NO 119
<211> LENGTH: 1791
<212> TYPE: DNA
<213> ORGANISM: Pichia stipitis
<220> FEATURE:
```

```
<221> NAME/KEY: CDS
<222> LOCATION: (1)..(1791)

<400> SEQUENCE: 119 atg gct gaa gtc tca tta gga aga tat ctc ttc gag aga ttg tac caa        48
Met Ala Glu Val Ser Leu Gly Arg Tyr Leu Phe Glu Arg Leu Tyr Gln
1               5                  10                  15 ttg caa gtg cag acc atc ttc ggt gtc cct ggt gat ttc aac ttg tcg        96
Leu Gln Val Gln Thr Ile Phe Gly Val Pro Gly Asp Phe Asn Leu Ser
            20                  25                  30 ctt ttg gac aag atc tac gaa gtg gaa gat gcc cat ggc aag aat tcg       144
Leu Leu Asp Lys Ile Tyr Glu Val Glu Asp Ala His Gly Lys Asn Ser
        35                  40                  45 ttt aga tgg gct ggt aat gcc aac gaa ttg aat gca tcg tac gct gct       192
Phe Arg Trp Ala Gly Asn Ala Asn Glu Leu Asn Ala Ser Tyr Ala Ala
    50                  55                  60 gac ggt tac tcg aga gtc aag cgt tta ggg tgt ttg gtc act acc ttt       240
Asp Gly Tyr Ser Arg Val Lys Arg Leu Gly Cys Leu Val Thr Thr Phe
65                  70                  75                  80 ggt gtc ggt gaa ttg tct gct ttg aat ggt att gcc ggt tct tat gcc       288
Gly Val Gly Glu Leu Ser Ala Leu Asn Gly Ile Ala Gly Ser Tyr Ala
                85                  90                  95 gaa cat gtt ggt ttg ctt cat gtc gta ggt gtt cca tcg att tcc tcg       336
Glu His Val Gly Leu Leu His Val Val Gly Val Pro Ser Ile Ser Ser
            100                 105                 110 caa gct aag caa ttg tta ctt cac cac act ttg ggt aat ggt gat ttc       384
Gln Ala Lys Gln Leu Leu Leu His His Thr Leu Gly Asn Gly Asp Phe
        115                 120                 125 act gtt ttc cat aga atg tcc aac aac att tct cag acc aca gcc ttt       432
Thr Val Phe His Arg Met Ser Asn Asn Ile Ser Gln Thr Thr Ala Phe
    130                 135                 140 atc tcc gat atc aac tcg gct cca gct gaa att gat aga tgt atc aga       480
Ile Ser Asp Ile Asn Ser Ala Pro Ala Glu Ile Asp Arg Cys Ile Arg
145                 150                 155                 160 gag gcc tac gtc aaa caa aga cca gtt tat atc ggg tta cca gct aac       528
Glu Ala Tyr Val Lys Gln Arg Pro Val Tyr Ile Gly Leu Pro Ala Asn
                165                 170                 175 tta gtt gat ttg aat gtt ccg gcc tct ttg ctt gag tct cca atc aac       576
Leu Val Asp Leu Asn Val Pro Ala Ser Leu Leu Glu Ser Pro Ile Asn
            180                 185                 190 ttg tcg ttg gaa aag aac gac cca gag gct caa gat gaa gtc att gac       624
Leu Ser Leu Glu Lys Asn Asp Pro Glu Ala Gln Asp Glu Val Ile Asp
        195                 200                 205 tct gtc tta gac ttg atc aaa aag tcg ctg aac cca atc atc ttg gtc       672
Ser Val Leu Asp Leu Ile Lys Lys Ser Leu Asn Pro Ile Ile Leu Val
    210                 215                 220 gat gcc tgt gcc tcg aga cat gac tgt aag gct gaa gtt act cag ttg       720
Asp Ala Cys Ala Ser Arg His Asp Cys Lys Ala Glu Val Thr Gln Leu
225                 230                 235                 240 att gaa caa acc caa ttc cca gta ttt gtc act cca atg ggt aaa ggt       768
Ile Glu Gln Thr Gln Phe Pro Val Phe Val Thr Pro Met Gly Lys Gly
                245                 250                 255 acc gtt gat gag ggt ggt gta gac gga gaa ttg tta gaa gat gat cct       816
Thr Val Asp Glu Gly Gly Val Asp Gly Glu Leu Leu Glu Asp Asp Pro
            260                 265                 270 cat ttg att gcc aag gtc gct gct agg ttg tct gct ggc aag aac gct       864
His Leu Ile Ala Lys Val Ala Ala Arg Leu Ser Ala Gly Lys Asn Ala
        275                 280                 285 gcc tct aga ttc gga ggt gtt tat gtc gga acc ttg tcg aag ccc gaa       912
Ala Ser Arg Phe Gly Gly Val Tyr Val Gly Thr Leu Ser Lys Pro Glu
    290                 295                 300
```

```
gtc aag gac gct gta gag agt gca gat ttg att ttg tct gtc ggt gcc      960
Val Lys Asp Ala Val Glu Ser Ala Asp Leu Ile Leu Ser Val Gly Ala
305                 310                 315                 320 ctt ttg tct gat ttc aac act ggt tca ttt tcc tac tcc tac aga acc     1008
Leu Leu Ser Asp Phe Asn Thr Gly Ser Phe Ser Tyr Ser Tyr Arg Thr
                325                 330                 335 aag aac atc gtc gaa ttc cat tct gat tac act aag att aga caa gcc     1056
Lys Asn Ile Val Glu Phe His Ser Asp Tyr Thr Lys Ile Arg Gln Ala
            340                 345                 350 act ttc cca ggt gtg cag atg aag gaa gcc ttg caa gaa ttg aac aag     1104
Thr Phe Pro Gly Val Gln Met Lys Glu Ala Leu Gln Glu Leu Asn Lys
        355                 360                 365 aaa gtt tca tct gct gct agt cac tat gaa gtc aag cct gtg ccc aag     1152
Lys Val Ser Ser Ala Ala Ser His Tyr Glu Val Lys Pro Val Pro Lys
370                 375                 380 atc aag ttg gcc aat aca cca gcc acc aga gaa gtc aag tta act cag     1200
Ile Lys Leu Ala Asn Thr Pro Ala Thr Arg Glu Val Lys Leu Thr Gln
385                 390                 395                 400 gaa tgg ttg tgg acc aga gtg tct tcg tgg ttc aga gaa ggt gat att     1248
Glu Trp Leu Trp Thr Arg Val Ser Ser Trp Phe Arg Glu Gly Asp Ile
                405                 410                 415 att atc acc gaa acc ggt aca tcc tcc ttc ggt ata gtt caa tcc aga     1296
Ile Ile Thr Glu Thr Gly Thr Ser Ser Phe Gly Ile Val Gln Ser Arg
            420                 425                 430 ttc cca aac aac acc atc ggt atc tcc caa gta ttg tgg ggt tct att     1344
Phe Pro Asn Asn Thr Ile Gly Ile Ser Gln Val Leu Trp Gly Ser Ile
        435                 440                 445 ggt ttc tct gtt ggt gcc act ttg ggt gct gcc atg gct gcc caa gaa     1392
Gly Phe Ser Val Gly Ala Thr Leu Gly Ala Ala Met Ala Ala Gln Glu
450                 455                 460 ctc gac cct aac aag aga acc atc ttg ttt gtt gga gat ggt tct ttg     1440
Leu Asp Pro Asn Lys Arg Thr Ile Leu Phe Val Gly Asp Gly Ser Leu
465                 470                 475                 480 caa ttg acc gtt cag gaa atc tcc acc ata atc aga tgg ggt acc aca     1488
Gln Leu Thr Val Gln Glu Ile Ser Thr Ile Ile Arg Trp Gly Thr Thr
                485                 490                 495 cct tac ctt ttc gtg ttg aac aat gac ggt tac acc atc gag cgt ttg     1536
Pro Tyr Leu Phe Val Leu Asn Asn Asp Gly Tyr Thr Ile Glu Arg Leu
            500                 505                 510 atc cac ggt gta aat gcc tca tat aat gac atc caa cca tgg caa aac     1584
Ile His Gly Val Asn Ala Ser Tyr Asn Asp Ile Gln Pro Trp Gln Asn
        515                 520                 525 ttg gaa atc ttg cct act ttc tcg gcc aag aac tac gac gct gtg aga     1632
Leu Glu Ile Leu Pro Thr Phe Ser Ala Lys Asn Tyr Asp Ala Val Arg
530                 535                 540 atc tcc aac atc gga gaa gca gaa gat atc ttg aaa gac aag gaa ttc     1680
Ile Ser Asn Ile Gly Glu Ala Glu Asp Ile Leu Lys Asp Lys Glu Phe
545                 550                 555                 560 gga aag aac tcc aag att aga ttg ata gaa gtc atg tta cca aga ttg     1728
Gly Lys Asn Ser Lys Ile Arg Leu Ile Glu Val Met Leu Pro Arg Leu
                565                 570                 575 gat gca cca tct aac ctt gcc aaa caa gct gcc att aca gct gcc acc     1776
Asp Ala Pro Ser Asn Leu Ala Lys Gln Ala Ala Ile Thr Ala Ala Thr
            580                 585                 590 aac gcc gaa gct tag                                                 1791
Asn Ala Glu Ala
        595

<210> SEQ ID NO 120
<211> LENGTH: 596
```

```
<212> TYPE: PRT
<213> ORGANISM: Pichia stipitis

<400> SEQUENCE: 120

Met Ala Glu Val Ser Leu Gly Arg Tyr Leu Phe Glu Arg Leu Tyr Gln
1               5                   10                  15

Leu Gln Val Gln Thr Ile Phe Gly Val Pro Gly Asp Phe Asn Leu Ser
            20                  25                  30

Leu Leu Asp Lys Ile Tyr Glu Val Glu Asp Ala His Gly Lys Asn Ser
        35                  40                  45

Phe Arg Trp Ala Gly Asn Ala Asn Glu Leu Asn Ala Ser Tyr Ala Ala
50                  55                  60

Asp Gly Tyr Ser Arg Val Lys Arg Leu Gly Cys Leu Val Thr Thr Phe
65                  70                  75                  80

Gly Val Gly Glu Leu Ser Ala Leu Asn Gly Ile Ala Gly Ser Tyr Ala
            85                  90                  95

Glu His Val Gly Leu Leu His Val Gly Val Pro Ser Ile Ser Ser
            100                 105                 110

Gln Ala Lys Gln Leu Leu Leu His His Thr Leu Gly Asn Gly Asp Phe
        115                 120                 125

Thr Val Phe His Arg Met Ser Asn Asn Ile Ser Gln Thr Thr Ala Phe
130                 135                 140

Ile Ser Asp Ile Asn Ser Ala Pro Ala Glu Ile Asp Arg Cys Ile Arg
145                 150                 155                 160

Glu Ala Tyr Val Lys Gln Arg Pro Val Tyr Ile Gly Leu Pro Ala Asn
                165                 170                 175

Leu Val Asp Leu Asn Val Pro Ala Ser Leu Leu Glu Ser Pro Ile Asn
            180                 185                 190

Leu Ser Leu Glu Lys Asn Asp Pro Glu Ala Gln Asp Glu Val Ile Asp
        195                 200                 205

Ser Val Leu Asp Leu Ile Lys Lys Ser Leu Asn Pro Ile Ile Leu Val
210                 215                 220

Asp Ala Cys Ala Ser Arg His Asp Cys Lys Ala Glu Val Thr Gln Leu
225                 230                 235                 240

Ile Glu Gln Thr Gln Phe Pro Val Phe Val Thr Pro Met Gly Lys Gly
                245                 250                 255

Thr Val Asp Glu Gly Gly Val Asp Gly Glu Leu Leu Glu Asp Asp Pro
            260                 265                 270

His Leu Ile Ala Lys Val Ala Ala Arg Leu Ser Ala Gly Lys Asn Ala
        275                 280                 285

Ala Ser Arg Phe Gly Gly Val Tyr Val Gly Thr Leu Ser Lys Pro Glu
290                 295                 300

Val Lys Asp Ala Val Glu Ser Ala Asp Leu Ile Leu Ser Val Gly Ala
305                 310                 315                 320

Leu Leu Ser Asp Phe Asn Thr Gly Ser Phe Ser Tyr Ser Tyr Arg Thr
                325                 330                 335

Lys Asn Ile Val Glu Phe His Ser Asp Tyr Thr Lys Ile Arg Gln Ala
            340                 345                 350

Thr Phe Pro Gly Val Gln Met Lys Glu Ala Leu Gln Glu Leu Asn Lys
        355                 360                 365

Lys Val Ser Ser Ala Ala Ser His Tyr Glu Val Lys Pro Val Pro Lys
370                 375                 380

Ile Lys Leu Ala Asn Thr Pro Ala Thr Arg Glu Val Lys Leu Thr Gln
385                 390                 395                 400
```

```
Glu Trp Leu Trp Thr Arg Val Ser Ser Trp Phe Arg Glu Gly Asp Ile
            405                 410                 415

Ile Ile Thr Glu Thr Gly Thr Ser Ser Phe Gly Ile Val Gln Ser Arg
        420                 425                 430

Phe Pro Asn Asn Thr Ile Gly Ile Ser Gln Val Leu Trp Gly Ser Ile
            435                 440                 445

Gly Phe Ser Val Gly Ala Thr Leu Gly Ala Ala Met Ala Ala Gln Glu
    450                 455                 460

Leu Asp Pro Asn Lys Arg Thr Ile Leu Phe Val Gly Asp Gly Ser Leu
465                 470                 475                 480

Gln Leu Thr Val Gln Glu Ile Ser Thr Ile Ile Arg Trp Gly Thr Thr
            485                 490                 495

Pro Tyr Leu Phe Val Leu Asn Asn Asp Gly Tyr Thr Ile Glu Arg Leu
        500                 505                 510

Ile His Gly Val Asn Ala Ser Tyr Asn Asp Ile Gln Pro Trp Gln Asn
    515                 520                 525

Leu Glu Ile Leu Pro Thr Phe Ser Ala Lys Asn Tyr Asp Ala Val Arg
        530                 535                 540

Ile Ser Asn Ile Gly Glu Ala Glu Asp Ile Leu Lys Asp Lys Glu Phe
545                 550                 555                 560

Gly Lys Asn Ser Lys Ile Arg Leu Ile Glu Val Met Leu Pro Arg Leu
            565                 570                 575

Asp Ala Pro Ser Asn Leu Ala Lys Gln Ala Ala Ile Thr Ala Ala Thr
        580                 585                 590

Asn Ala Glu Ala
        595

<210> SEQ ID NO 121
<211> LENGTH: 1710
<212> TYPE: DNA
<213> ORGANISM: Pichia stipitis
<220> FEATURE:
<221> NAME/KEY: CDS
<222> LOCATION: (1)..(1710)

<400> SEQUENCE: 121 atg gta tca acc tac cca gaa tca gag gtt act cta gga agg tac ctc      48
Met Val Ser Thr Tyr Pro Glu Ser Glu Val Thr Leu Gly Arg Tyr Leu
1               5                   10                  15 ttt gag cga ctc cac caa ttg aaa gtg gac acc att ttc ggc ttg ccg      96
Phe Glu Arg Leu His Gln Leu Lys Val Asp Thr Ile Phe Gly Leu Pro
            20                  25                  30 ggt gac ttc aac ctt tcc tta ttg gac aaa gtg tat gaa gtt ccg gat     144
Gly Asp Phe Asn Leu Ser Leu Leu Asp Lys Val Tyr Glu Val Pro Asp
        35                  40                  45 atg agg tgg gct gga aat gcc aac gaa ttg aat gct gcc tat gct gcc     192
Met Arg Trp Ala Gly Asn Ala Asn Glu Leu Asn Ala Ala Tyr Ala Ala
    50                  55                  60 gat ggt tac tcc aga ata aag gga ttg tct tgc ttg gtc aca act ttt     240
Asp Gly Tyr Ser Arg Ile Lys Gly Leu Ser Cys Leu Val Thr Thr Phe
65                  70                  75                  80 ggt gtt ggt gaa ttg tct gct tta aac gga gtt ggt ggt gcc tat gct     288
Gly Val Gly Glu Leu Ser Ala Leu Asn Gly Val Gly Gly Ala Tyr Ala
                85                  90                  95 gaa cac gta gga ctt cta cat gtc gtt gga gtt cca tcc ata tcg tca     336
Glu His Val Gly Leu Leu His Val Val Gly Val Pro Ser Ile Ser Ser
            100                 105                 110 cag gct aaa cag ttg ttg ctc cac cat acc ttg ggt aat ggt gac ttc     384
Gln Ala Lys Gln Leu Leu Leu His His Thr Leu Gly Asn Gly Asp Phe
```

```
                    115                 120                     125
act gtt ttt cac aga atg tcc aat agc att tct caa act aca gca ttt       432
Thr Val Phe His Arg Met Ser Asn Ser Ile Ser Gln Thr Thr Ala Phe
        130                 135                 140 ctc tca gat atc tct att gca cca ggt caa ata gat aga tgc atc aga       480
Leu Ser Asp Ile Ser Ile Ala Pro Gly Gln Ile Asp Arg Cys Ile Arg
145                 150                 155                 160 gaa gca tat gtt cat cag aga cca gtt tat gtt ggt tta ccg gca aat       528
Glu Ala Tyr Val His Gln Arg Pro Val Tyr Val Gly Leu Pro Ala Asn
                165                 170                 175 atg gtt gat ctc aag gtt cct tct agt ctc tta gaa act cca att gat       576
Met Val Asp Leu Lys Val Pro Ser Ser Leu Leu Glu Thr Pro Ile Asp
            180                 185                 190 ttg aaa ttg aaa caa aat gat cct gaa gct caa gaa gtt gtt gaa aca       624
Leu Lys Leu Lys Gln Asn Asp Pro Glu Ala Gln Glu Val Val Glu Thr
        195                 200                 205 gtc ctg aag ttg gtg tcc caa gct aca aac ccc att atc ttg gta gac       672
Val Leu Lys Leu Val Ser Gln Ala Thr Asn Pro Ile Ile Leu Val Asp
210                 215                 220 gct tgt gcc ctc aga cac aat tgc aaa gag gaa gtc aaa caa ttg gtt       720
Ala Cys Ala Leu Arg His Asn Cys Lys Glu Glu Val Lys Gln Leu Val
225                 230                 235                 240 gat gcc act aat ttt caa gtc ttt aca act cca atg ggt aaa tct ggt       768
Asp Ala Thr Asn Phe Gln Val Phe Thr Thr Pro Met Gly Lys Ser Gly
                245                 250                 255 atc tcc gaa tct cat cca aga ttg ggc ggt gtc tat gtc ggg aca atg       816
Ile Ser Glu Ser His Pro Arg Leu Gly Gly Val Tyr Val Gly Thr Met
            260                 265                 270 tcg agt cct caa gtc aaa aaa gcc gtt gaa aat gcc gat ctt ata cta       864
Ser Ser Pro Gln Val Lys Lys Ala Val Glu Asn Ala Asp Leu Ile Leu
        275                 280                 285 tct gtt ggt tcg ttg tta tcg gac ttc aat aca ggt tca ttt tca tac       912
Ser Val Gly Ser Leu Leu Ser Asp Phe Asn Thr Gly Ser Phe Ser Tyr
290                 295                 300 tcc tac aag acg aag aat gtt gtt gaa ttc cac tct gac tat atg aaa       960
Ser Tyr Lys Thr Lys Asn Val Val Glu Phe His Ser Asp Tyr Met Lys
305                 310                 315                 320 atc aga cag gcc acc ttc cca gga gtt caa atg aaa gaa gcc ttg caa      1008
Ile Arg Gln Ala Thr Phe Pro Gly Val Gln Met Lys Glu Ala Leu Gln
                325                 330                 335 cag ttg ata aaa agg gtc tct tct tac atc aat cca agc tac att cct      1056
Gln Leu Ile Lys Arg Val Ser Ser Tyr Ile Asn Pro Ser Tyr Ile Pro
            340                 345                 350 act cga gtt cct aaa agg aaa cag cca ttg aaa gct cca tca gaa gct      1104
Thr Arg Val Pro Lys Arg Lys Gln Pro Leu Lys Ala Pro Ser Glu Ala
        355                 360                 365 cct ttg acc caa gaa tat ttg tgg tct aaa gta tcc ggc tgg ttt aga      1152
Pro Leu Thr Gln Glu Tyr Leu Trp Ser Lys Val Ser Gly Trp Phe Arg
370                 375                 380 gag ggt gat att atc gta acc gaa act ggt aca tct gct ttc gga att      1200
Glu Gly Asp Ile Ile Val Thr Glu Thr Gly Thr Ser Ala Phe Gly Ile
385                 390                 395                 400 att caa tcc cat ttt ccc agc aac act atc ggt ata tcc caa gtc ttg      1248
Ile Gln Ser His Phe Pro Ser Asn Thr Ile Gly Ile Ser Gln Val Leu
                405                 410                 415 tgg ggc tca att ggt ttc aca gta ggt gca aca gtt ggt gct gcc atg      1296
Trp Gly Ser Ile Gly Phe Thr Val Gly Ala Thr Val Gly Ala Ala Met
            420                 425                 430 gca gcc cag gaa atc gac cct agc agg aga gta att ttg ttc gtc ggt      1344
Ala Ala Gln Glu Ile Asp Pro Ser Arg Arg Val Ile Leu Phe Val Gly
```

```
                  435                 440                 445
gat ggt tca ttg cag ttg acg gtt cag gaa atc tct acg ttg tgt aaa    1392
Asp Gly Ser Leu Gln Leu Thr Val Gln Glu Ile Ser Thr Leu Cys Lys
450                 455                 460 tgg gat tgt aac aat act tat ctt tac gtg ttg aac aat gat ggt tac    1440
Trp Asp Cys Asn Asn Thr Tyr Leu Tyr Val Leu Asn Asn Asp Gly Tyr
465                 470                 475                 480 act ata gaa agg ttg atc cac ggc aaa agt gcc agc tac aac gat ata    1488
Thr Ile Glu Arg Leu Ile His Gly Lys Ser Ala Ser Tyr Asn Asp Ile
        485                 490                 495 cag cct tgg aac cat tta tcc ttg ctt cgc tta ttc aat gct aag aaa    1536
Gln Pro Trp Asn His Leu Ser Leu Leu Arg Leu Phe Asn Ala Lys Lys
    500                 505                 510 tac caa aat gtc aga gta tcg act gct gga gaa ttg gac tct ttg ttc    1584
Tyr Gln Asn Val Arg Val Ser Thr Ala Gly Glu Leu Asp Ser Leu Phe
515                 520                 525 tct gat aag aaa ttt gct tct cca gat agg ata aga atg att gag gtg    1632
Ser Asp Lys Lys Phe Ala Ser Pro Asp Arg Ile Arg Met Ile Glu Val
530                 535                 540 atg tta tcg aga ttg gat gca cca gca aat ctt gtt gct caa gca aag    1680
Met Leu Ser Arg Leu Asp Ala Pro Ala Asn Leu Val Ala Gln Ala Lys
545                 550                 555                 560 ttg tct gaa cgg gta aac ctt gaa aat tga                            1710
Leu Ser Glu Arg Val Asn Leu Glu Asn
                565

<210> SEQ ID NO 122
<211> LENGTH: 569
<212> TYPE: PRT
<213> ORGANISM: Pichia stipitis

<400> SEQUENCE: 122

Met Val Ser Thr Tyr Pro Glu Ser Glu Val Thr Leu Gly Arg Tyr Leu
1               5                   10                  15

Phe Glu Arg Leu His Gln Leu Lys Val Asp Thr Ile Phe Gly Leu Pro
            20                  25                  30

Gly Asp Phe Asn Leu Ser Leu Leu Asp Lys Val Tyr Glu Val Pro Asp
        35                  40                  45

Met Arg Trp Ala Gly Asn Ala Asn Glu Leu Asn Ala Ala Tyr Ala Ala
50                  55                  60

Asp Gly Tyr Ser Arg Ile Lys Gly Leu Ser Cys Leu Val Thr Thr Phe
65                  70                  75                  80

Gly Val Gly Glu Leu Ser Ala Leu Asn Gly Val Gly Gly Ala Tyr Ala
                85                  90                  95

Glu His Val Gly Leu Leu His Val Gly Val Pro Ser Ile Ser Ser
            100                 105                 110

Gln Ala Lys Gln Leu Leu Leu His His Thr Leu Gly Asn Gly Asp Phe
        115                 120                 125

Thr Val Phe His Arg Met Ser Asn Ser Ile Ser Gln Thr Thr Ala Phe
130                 135                 140

Leu Ser Asp Ile Ser Ile Ala Pro Gly Gln Ile Asp Arg Cys Ile Arg
145                 150                 155                 160

Glu Ala Tyr Val His Gln Arg Pro Val Tyr Val Gly Leu Pro Ala Asn
                165                 170                 175

Met Val Asp Leu Lys Val Pro Ser Ser Leu Leu Glu Thr Pro Ile Asp
            180                 185                 190

Leu Lys Leu Lys Gln Asn Asp Pro Glu Ala Gln Glu Val Val Glu Thr
        195                 200                 205
```

```
Val Leu Lys Leu Val Ser Gln Ala Thr Asn Pro Ile Ile Leu Val Asp
    210                 215                 220

Ala Cys Ala Leu Arg His Asn Cys Lys Glu Glu Val Lys Gln Leu Val
225                 230                 235                 240

Asp Ala Thr Asn Phe Gln Val Phe Thr Thr Pro Met Gly Lys Ser Gly
                245                 250                 255

Ile Ser Glu Ser His Pro Arg Leu Gly Gly Val Tyr Val Gly Thr Met
                260                 265                 270

Ser Ser Pro Gln Val Lys Lys Ala Val Glu Asn Ala Asp Leu Ile Leu
            275                 280                 285

Ser Val Gly Ser Leu Leu Ser Asp Phe Asn Thr Gly Ser Phe Ser Tyr
    290                 295                 300

Ser Tyr Lys Thr Lys Asn Val Val Glu Phe His Ser Asp Tyr Met Lys
305                 310                 315                 320

Ile Arg Gln Ala Thr Phe Pro Gly Val Gln Met Lys Glu Ala Leu Gln
                325                 330                 335

Gln Leu Ile Lys Arg Val Ser Ser Tyr Ile Asn Pro Ser Tyr Ile Pro
                340                 345                 350

Thr Arg Val Pro Lys Arg Lys Gln Pro Leu Lys Ala Pro Ser Glu Ala
            355                 360                 365

Pro Leu Thr Gln Glu Tyr Leu Trp Ser Lys Val Ser Gly Trp Phe Arg
    370                 375                 380

Glu Gly Asp Ile Ile Val Thr Glu Thr Gly Thr Ser Ala Phe Gly Ile
385                 390                 395                 400

Ile Gln Ser His Phe Pro Ser Asn Thr Ile Gly Ile Ser Gln Val Leu
                405                 410                 415

Trp Gly Ser Ile Gly Phe Thr Val Gly Ala Thr Val Gly Ala Ala Met
            420                 425                 430

Ala Ala Gln Glu Ile Asp Pro Ser Arg Arg Val Ile Leu Phe Val Gly
    435                 440                 445

Asp Gly Ser Leu Gln Leu Thr Val Gln Glu Ile Ser Thr Leu Cys Lys
450                 455                 460

Trp Asp Cys Asn Asn Thr Tyr Leu Tyr Val Leu Asn Asn Asp Gly Tyr
465                 470                 475                 480

Thr Ile Glu Arg Leu Ile His Gly Lys Ser Ala Ser Tyr Asn Asp Ile
                485                 490                 495

Gln Pro Trp Asn His Leu Ser Leu Leu Arg Leu Phe Asn Ala Lys Lys
            500                 505                 510

Tyr Gln Asn Val Arg Val Ser Thr Ala Gly Glu Leu Asp Ser Leu Phe
    515                 520                 525

Ser Asp Lys Lys Phe Ala Ser Pro Asp Arg Ile Arg Met Ile Glu Val
530                 535                 540

Met Leu Ser Arg Leu Asp Ala Pro Ala Asn Leu Val Ala Gln Ala Lys
545                 550                 555                 560

Leu Ser Glu Arg Val Asn Leu Glu Asn
                565

<210> SEQ ID NO 123
<211> LENGTH: 1692
<212> TYPE: DNA
<213> ORGANISM: Kluyveromyces lactis
<220> FEATURE:
<221> NAME/KEY: CDS
<222> LOCATION: (1)..(1692)

<400> SEQUENCE: 123
```

```
atg tct gaa att aca tta ggt cgt tac ttg ttc gaa aga tta aag caa       48
Met Ser Glu Ile Thr Leu Gly Arg Tyr Leu Phe Glu Arg Leu Lys Gln
1               5                   10                  15 gtc gaa gtt caa acc atc ttt ggt cta cca ggt gat ttc aac ttg tcc       96
Val Glu Val Gln Thr Ile Phe Gly Leu Pro Gly Asp Phe Asn Leu Ser
            20                  25                  30 cta ttg gac aat atc tac gaa gtc cca ggt atg aga tgg gct ggt aat      144
Leu Leu Asp Asn Ile Tyr Glu Val Pro Gly Met Arg Trp Ala Gly Asn
        35                  40                  45 gcc aac gaa ttg aac gct gct tac gct gct gat ggt tac gcc aga tta      192
Ala Asn Glu Leu Asn Ala Ala Tyr Ala Ala Asp Gly Tyr Ala Arg Leu
50                  55                  60 aag ggt atg tcc tgt atc atc acc acc ttc ggt gtc ggt gaa ttg tct      240
Lys Gly Met Ser Cys Ile Ile Thr Thr Phe Gly Val Gly Glu Leu Ser
65                  70                  75                  80 gct ttg aac ggt att gcc ggt tct tac gct gaa cac gtt ggt gtc ttg      288
Ala Leu Asn Gly Ile Ala Gly Ser Tyr Ala Glu His Val Gly Val Leu
                85                  90                  95 cac gtt gtc ggt gtt cca tcc gtc tct tct caa gct aag caa ttg ttg      336
His Val Val Gly Val Pro Ser Val Ser Ser Gln Ala Lys Gln Leu Leu
            100                 105                 110 ttg cac cac acc ttg ggt aac ggt gac ttc act gtt ttc cac aga atg      384
Leu His His Thr Leu Gly Asn Gly Asp Phe Thr Val Phe His Arg Met
        115                 120                 125 tcc tcc aac att tct gaa acc act gct atg atc acc gat atc aac act      432
Ser Ser Asn Ile Ser Glu Thr Thr Ala Met Ile Thr Asp Ile Asn Thr
130                 135                 140 gcc cca gct gaa atc gac aga tgt atc aga acc act tac gtt tcc caa      480
Ala Pro Ala Glu Ile Asp Arg Cys Ile Arg Thr Thr Tyr Val Ser Gln
145                 150                 155                 160 aga cca gtc tac ttg ggt ttg cca gct aac ttg gtc gac ttg act gtc      528
Arg Pro Val Tyr Leu Gly Leu Pro Ala Asn Leu Val Asp Leu Thr Val
                165                 170                 175 cca gct tct ttg ttg gac act cca att gat ttg agc ttg aag cca aat      576
Pro Ala Ser Leu Leu Asp Thr Pro Ile Asp Leu Ser Leu Lys Pro Asn
            180                 185                 190 gac cca gaa gcc gaa gaa gaa gtc atc gaa aac gtc ttg caa ctg atc      624
Asp Pro Glu Ala Glu Glu Glu Val Ile Glu Asn Val Leu Gln Leu Ile
        195                 200                 205 aag gaa gct aag aac cca gtt atc ttg gct gat gct tgt tgt tcc aga      672
Lys Glu Ala Lys Asn Pro Val Ile Leu Ala Asp Ala Cys Cys Ser Arg
210                 215                 220 cac gat gcc aag gct gag acc aag aag ttg atc gac ttg act caa ttc      720
His Asp Ala Lys Ala Glu Thr Lys Lys Leu Ile Asp Leu Thr Gln Phe
225                 230                 235                 240 cca gcc ttc gtt acc cca atg ggt aag ggt tcc att gac gaa aag cac      768
Pro Ala Phe Val Thr Pro Met Gly Lys Gly Ser Ile Asp Glu Lys His
                245                 250                 255 cca aga ttc ggt ggt gtc tac gtc ggt acc cta tct tct cca gct gtc      816
Pro Arg Phe Gly Gly Val Tyr Val Gly Thr Leu Ser Ser Pro Ala Val
            260                 265                 270 aag gaa gcc gtt gaa tct gct gac ttg gtt cta tcg gtc ggt gct cta      864
Lys Glu Ala Val Glu Ser Ala Asp Leu Val Leu Ser Val Gly Ala Leu
        275                 280                 285 ttg tcc gat ttc aac act ggt tct ttc tct tac tct tac aag acc aag      912
Leu Ser Asp Phe Asn Thr Gly Ser Phe Ser Tyr Ser Tyr Lys Thr Lys
290                 295                 300 aac att gtc gaa ttc cac tct gac tac acc aag atc aga agc gct acc      960
Asn Ile Val Glu Phe His Ser Asp Tyr Thr Lys Ile Arg Ser Ala Thr
305                 310                 315                 320
```

```
ttc cca ggt gtc caa atg aag ttc gct tta caa aaa ttg ttg act aag      1008
Phe Pro Gly Val Gln Met Lys Phe Ala Leu Gln Lys Leu Leu Thr Lys
            325                 330                 335 gtt gcc gat gct gct aag ggt tac aag cca gtt cca gtt cca tct gaa      1056
Val Ala Asp Ala Ala Lys Gly Tyr Lys Pro Val Pro Val Pro Ser Glu
        340                 345                 350 cca gaa cac aac gaa gct gtc gct gac tcc act cca ttg aag caa gaa      1104
Pro Glu His Asn Glu Ala Val Ala Asp Ser Thr Pro Leu Lys Gln Glu
    355                 360                 365 tgg gtc tgg act caa gtc ggt gaa ttc ttg aga gaa ggt gat gtt gtt      1152
Trp Val Trp Thr Gln Val Gly Glu Phe Leu Arg Glu Gly Asp Val Val
370                 375                 380 atc act gaa acc ggt acc tct gcc ttc ggt atc aac caa act cat ttc      1200
Ile Thr Glu Thr Gly Thr Ser Ala Phe Gly Ile Asn Gln Thr His Phe
385                 390                 395                 400 cca aac aac aca tac ggt atc tct caa gtt tta tgg ggt tcc att ggt      1248
Pro Asn Asn Thr Tyr Gly Ile Ser Gln Val Leu Trp Gly Ser Ile Gly
            405                 410                 415 ttc acc act ggt gct acc ttg ggt gct gcc ttc gct gcc gaa gaa att      1296
Phe Thr Thr Gly Ala Thr Leu Gly Ala Ala Phe Ala Ala Glu Glu Ile
        420                 425                 430 gat cca aag aag aga gtt atc tta ttc att ggt gac ggt tct ttg caa      1344
Asp Pro Lys Lys Arg Val Ile Leu Phe Ile Gly Asp Gly Ser Leu Gln
    435                 440                 445 ttg act gtt caa gaa atc tcc acc atg atc aga tgg ggc ttg aag cca      1392
Leu Thr Val Gln Glu Ile Ser Thr Met Ile Arg Trp Gly Leu Lys Pro
450                 455                 460 tac ttg ttc gta ttg aac aac gac ggt tac acc att gaa aga ttg att      1440
Tyr Leu Phe Val Leu Asn Asn Asp Gly Tyr Thr Ile Glu Arg Leu Ile
465                 470                 475                 480 cac ggt gaa acc gct caa tac aac tgt atc caa aac tgg caa cac ttg      1488
His Gly Glu Thr Ala Gln Tyr Asn Cys Ile Gln Asn Trp Gln His Leu
            485                 490                 495 gaa tta ttg cca act ttc ggt gcc aag gac tac gaa gct gtc aga gtt      1536
Glu Leu Leu Pro Thr Phe Gly Ala Lys Asp Tyr Glu Ala Val Arg Val
        500                 505                 510 tcc acc act ggt gaa tgg aac aag ttg acc act gac gaa aag ttc caa      1584
Ser Thr Thr Gly Glu Trp Asn Lys Leu Thr Thr Asp Glu Lys Phe Gln
    515                 520                 525 gac aac acc aga atc aga ttg atc gaa gtt atg ttg cca act atg gat      1632
Asp Asn Thr Arg Ile Arg Leu Ile Glu Val Met Leu Pro Thr Met Asp
530                 535                 540 gct cca tct aac ttg gtt aag caa gct caa ttg act gct gct acc aac      1680
Ala Pro Ser Asn Leu Val Lys Gln Ala Gln Leu Thr Ala Ala Thr Asn
545                 550                 555                 560 gct aag aac taa                                                       1692
Ala Lys Asn <210> SEQ ID NO 124
<211> LENGTH: 563
<212> TYPE: PRT
<213> ORGANISM: Kluyveromyces lactis

<400> SEQUENCE: 124

Met Ser Glu Ile Thr Leu Gly Arg Tyr Leu Phe Glu Arg Leu Lys Gln
1               5                   10                  15

Val Glu Val Gln Thr Ile Phe Gly Leu Pro Gly Asp Phe Asn Leu Ser
            20                  25                  30

Leu Leu Asp Asn Ile Tyr Glu Val Pro Gly Met Arg Trp Ala Gly Asn
        35                  40                  45
```

```
Ala Asn Glu Leu Asn Ala Ala Tyr Ala Ala Asp Gly Tyr Ala Arg Leu
         50                  55                  60
Lys Gly Met Ser Cys Ile Ile Thr Thr Phe Gly Val Gly Glu Leu Ser
 65                  70                  75                  80
Ala Leu Asn Gly Ile Ala Gly Ser Tyr Ala Glu His Val Gly Val Leu
                 85                  90                  95
His Val Val Gly Val Pro Ser Val Ser Ser Gln Ala Lys Gln Leu Leu
            100                 105                 110
Leu His His Thr Leu Gly Asn Gly Asp Phe Thr Val Phe His Arg Met
        115                 120                 125
Ser Ser Asn Ile Ser Glu Thr Thr Ala Met Ile Thr Asp Ile Asn Thr
130                 135                 140
Ala Pro Ala Glu Ile Asp Arg Cys Ile Arg Thr Thr Tyr Val Ser Gln
145                 150                 155                 160
Arg Pro Val Tyr Leu Gly Leu Pro Ala Asn Leu Val Asp Leu Thr Val
                165                 170                 175
Pro Ala Ser Leu Leu Asp Thr Pro Ile Asp Leu Ser Leu Lys Pro Asn
            180                 185                 190
Asp Pro Glu Ala Glu Glu Val Ile Glu Asn Val Leu Gln Leu Ile
        195                 200                 205
Lys Glu Ala Lys Asn Pro Val Ile Leu Ala Asp Ala Cys Cys Ser Arg
210                 215                 220
His Asp Ala Lys Ala Glu Thr Lys Lys Leu Ile Asp Leu Thr Gln Phe
225                 230                 235                 240
Pro Ala Phe Val Thr Pro Met Gly Lys Gly Ser Ile Asp Glu Lys His
                245                 250                 255
Pro Arg Phe Gly Gly Val Tyr Val Gly Thr Leu Ser Ser Pro Ala Val
            260                 265                 270
Lys Glu Ala Val Glu Ser Ala Asp Leu Val Leu Ser Val Gly Ala Leu
        275                 280                 285
Leu Ser Asp Phe Asn Thr Gly Ser Phe Ser Tyr Ser Tyr Lys Thr Lys
290                 295                 300
Asn Ile Val Glu Phe His Ser Asp Tyr Thr Lys Ile Arg Ser Ala Thr
305                 310                 315                 320
Phe Pro Gly Val Gln Met Lys Phe Ala Leu Gln Lys Leu Leu Thr Lys
                325                 330                 335
Val Ala Asp Ala Ala Lys Gly Tyr Lys Pro Val Pro Val Pro Ser Glu
            340                 345                 350
Pro Glu His Asn Glu Ala Val Ala Asp Ser Thr Pro Leu Lys Gln Glu
        355                 360                 365
Trp Val Trp Thr Gln Val Gly Glu Phe Leu Arg Glu Gly Asp Val Val
370                 375                 380
Ile Thr Glu Thr Gly Thr Ser Ala Phe Gly Ile Asn Gln Thr His Phe
385                 390                 395                 400
Pro Asn Asn Thr Tyr Gly Ile Ser Gln Val Leu Trp Gly Ser Ile Gly
                405                 410                 415
Phe Thr Thr Gly Ala Thr Leu Gly Ala Ala Phe Ala Ala Glu Glu Ile
            420                 425                 430
Asp Pro Lys Lys Arg Val Ile Leu Phe Ile Gly Asp Gly Ser Leu Gln
        435                 440                 445
Leu Thr Val Gln Glu Ile Ser Thr Met Ile Arg Trp Gly Leu Lys Pro
450                 455                 460
Tyr Leu Phe Val Leu Asn Asn Asp Gly Tyr Thr Ile Glu Arg Leu Ile
```

```
                465                 470                 475                 480
His Gly Glu Thr Ala Gln Tyr Asn Cys Ile Gln Asn Trp Gln His Leu
                    485                 490                 495

Glu Leu Leu Pro Thr Phe Gly Ala Lys Asp Tyr Glu Ala Val Arg Val
                500                 505                 510

Ser Thr Thr Gly Glu Trp Asn Lys Leu Thr Thr Asp Glu Lys Phe Gln
            515                 520                 525

Asp Asn Thr Arg Ile Arg Leu Ile Glu Val Met Leu Pro Thr Met Asp
        530                 535                 540

Ala Pro Ser Asn Leu Val Lys Gln Ala Gln Leu Thr Ala Ala Thr Asn
545                 550                 555                 560

Ala Lys Asn

<210> SEQ ID NO 125
<211> LENGTH: 1716
<212> TYPE: DNA
<213> ORGANISM: Yarrowia lipolytica
<220> FEATURE:
<221> NAME/KEY: CDS
<222> LOCATION: (1)..(1716)

<400> SEQUENCE: 125 atg agc gac tcc gaa ccc caa atg gtc gac ctg ggc gac tat ctc ttt     48
Met Ser Asp Ser Glu Pro Gln Met Val Asp Leu Gly Asp Tyr Leu Phe
1               5                   10                  15 gcc cga ttc aag cag cta ggc gtg gac tcc gtc ttt gga gtg ccc ggc     96
Ala Arg Phe Lys Gln Leu Gly Val Asp Ser Val Phe Gly Val Pro Gly
                20                  25                  30 gac ttc aac ctc acc ctg ttg gac cac gtg tac aat gtc gac atg cgg    144
Asp Phe Asn Leu Thr Leu Leu Asp His Val Tyr Asn Val Asp Met Arg
            35                  40                  45 tgg gtt ggg aac aca aac gag ctg aat gcc ggc tac tcg gcc gac ggc    192
Trp Val Gly Asn Thr Asn Glu Leu Asn Ala Gly Tyr Ser Ala Asp Gly
        50                  55                  60 tac tcc cgg gtc aag cgg ctg gca tgt ctt gtc acc acc ttt ggc gtg    240
Tyr Ser Arg Val Lys Arg Leu Ala Cys Leu Val Thr Thr Phe Gly Val
65                  70                  75                  80 gga gag ctg tct gcc gtg gct gct gtg gca ggc tcg tac gcc gag cat    288
Gly Glu Leu Ser Ala Val Ala Ala Val Ala Gly Ser Tyr Ala Glu His
                85                  90                  95 gtg ggc gtg gtg cat gtt gtg ggc gtt ccc agc acc tct gct gag aac    336
Val Gly Val Val His Val Val Gly Val Pro Ser Thr Ser Ala Glu Asn
                100                 105                 110 aag cat ctg ctg ctg cac cac aca ctc ggt aac ggc gac ttc cgg gtc    384
Lys His Leu Leu Leu His His Thr Leu Gly Asn Gly Asp Phe Arg Val
            115                 120                 125 ttt gcc cag atg tcc aaa ctc atc tcc gag tac acc cac cat att gag    432
Phe Ala Gln Met Ser Lys Leu Ile Ser Glu Tyr Thr His His Ile Glu
        130                 135                 140 gac ccc agc gag gct gcc gac gta atc gac acc gcc atc cga atc gcc    480
Asp Pro Ser Glu Ala Ala Asp Val Ile Asp Thr Ala Ile Arg Ile Ala
145                 150                 155                 160 tac acc cac cag cgg ccc gtt tac att gct gtg ccc tcc aac ttc tcc    528
Tyr Thr His Gln Arg Pro Val Tyr Ile Ala Val Pro Ser Asn Phe Ser
                165                 170                 175 gag gtc gat att gcc gac cag gct aga ctg gat acc ccc ctg gac ctt    576
Glu Val Asp Ile Ala Asp Gln Ala Arg Leu Asp Thr Pro Leu Asp Leu
                180                 185                 190 tcg ctg cag ccc aac gac ccc gag agc cag tac gag gtg att gag gag    624
Ser Leu Gln Pro Asn Asp Pro Glu Ser Gln Tyr Glu Val Ile Glu Glu
```

-continued

```
            195                 200                 205
att tgc tcg cgt atc aag gcc gcc aag aag ccc gtg att ctc gtc gac       672
Ile Cys Ser Arg Ile Lys Ala Ala Lys Lys Pro Val Ile Leu Val Asp
210                 215                 220 gcc tgc gct tcg cga tac aga tgt gtc gac gag acc aag gag ctg gcc       720
Ala Cys Ala Ser Arg Tyr Arg Cys Val Asp Glu Thr Lys Glu Leu Ala
225                 230                 235                 240 aag atc acc aac ttt gcc tac ttt gtc act ccc atg ggt aag ggt tct       768
Lys Ile Thr Asn Phe Ala Tyr Phe Val Thr Pro Met Gly Lys Gly Ser
                245                 250                 255 gtg gac gag gat act gac cgg tac gga gga aca tac gtc gga tcg ctg       816
Val Asp Glu Asp Thr Asp Arg Tyr Gly Gly Thr Tyr Val Gly Ser Leu
            260                 265                 270 act gct cct gct act gcc gag gtg gtt gag aca gct gat ctc atc atc       864
Thr Ala Pro Ala Thr Ala Glu Val Val Glu Thr Ala Asp Leu Ile Ile
        275                 280                 285 tcc gta gga gct ctt ctg tcg gac ttc aac acc ggt tcc ttc tcg tac       912
Ser Val Gly Ala Leu Leu Ser Asp Phe Asn Thr Gly Ser Phe Ser Tyr
    290                 295                 300 tcc tac tcc acc aaa aac gtg gtg gaa ttg cat tcg gac cac gtc aaa       960
Ser Tyr Ser Thr Lys Asn Val Val Glu Leu His Ser Asp His Val Lys
305                 310                 315                 320 atc aag tcc gcc acc tac aac aac gtc ggc atg aaa atg ctg ttc ccg      1008
Ile Lys Ser Ala Thr Tyr Asn Asn Val Gly Met Lys Met Leu Phe Pro
                325                 330                 335 ccc ctg ctc gaa gcc gtc aag aaa ctg gtt gcc gag acc cct gac ttt      1056
Pro Leu Leu Glu Ala Val Lys Lys Leu Val Ala Glu Thr Pro Asp Phe
            340                 345                 350 gca tcc aag gct ctg gct gtt ccc gac acc act ccc aag atc ccc gag      1104
Ala Ser Lys Ala Leu Ala Val Pro Asp Thr Thr Pro Lys Ile Pro Glu
        355                 360                 365 gta ccc gat gat cac att acg acc cag gca tgg ctg tgg cag cgt ctc      1152
Val Pro Asp Asp His Ile Thr Thr Gln Ala Trp Leu Trp Gln Arg Leu
370                 375                 380 agt tac ttt ctg agg ccc acc gac atc gtg gtc acc gag acc gga acc      1200
Ser Tyr Phe Leu Arg Pro Thr Asp Ile Val Val Thr Glu Thr Gly Thr
385                 390                 395                 400 tcg tcc ttt gga atc atc cag acc aag ttc ccc cac aac gtc cga ggt      1248
Ser Ser Phe Gly Ile Ile Gln Thr Lys Phe Pro His Asn Val Arg Gly
                405                 410                 415 atc tcg cag gtg ctg tgg ggc tct att gga tac tcg gtg gga gca gcc      1296
Ile Ser Gln Val Leu Trp Gly Ser Ile Gly Tyr Ser Val Gly Ala Ala
            420                 425                 430 tgt gga gcc tcc att gct gca cag gag att gac ccc cag cag cga gtg      1344
Cys Gly Ala Ser Ile Ala Ala Gln Glu Ile Asp Pro Gln Gln Arg Val
        435                 440                 445 att ctg ttt gtg ggc gac ggc tct ctt cag ctg acg gtg acc gag atc      1392
Ile Leu Phe Val Gly Asp Gly Ser Leu Gln Leu Thr Val Thr Glu Ile
450                 455                 460 tcg tgc atg atc cgc aac aac gtc aag ccg tac att ttt gtg ctc aac      1440
Ser Cys Met Ile Arg Asn Asn Val Lys Pro Tyr Ile Phe Val Leu Asn
465                 470                 475                 480 aac gac ggc tac acc atc gag agg ctc att cac ggc gaa aac gcc tcg      1488
Asn Asp Gly Tyr Thr Ile Glu Arg Leu Ile His Gly Glu Asn Ala Ser
                485                 490                 495 tac aac gat gtg cac atg tgg aag tac tcc aag att ctc gac acg ttc      1536
Tyr Asn Asp Val His Met Trp Lys Tyr Ser Lys Ile Leu Asp Thr Phe
            500                 505                 510 aac gcc aag gcc cac gag tcg att gtg gtc aac acc aag ggc gag atg      1584
Asn Ala Lys Ala His Glu Ser Ile Val Val Asn Thr Lys Gly Glu Met
```

```
                515                 520                 525
gac gct ctg ttc gac aac gaa gag ttt gcc aag ccc gac aag atc cgg     1632
Asp Ala Leu Phe Asp Asn Glu Glu Phe Ala Lys Pro Asp Lys Ile Arg
530                 535                 540 ctc att gag gtc atg tgc gac aag atg gac gcg cct gcc tcg ttg atc     1680
Leu Ile Glu Val Met Cys Asp Lys Met Asp Ala Pro Ala Ser Leu Ile
545                 550                 555                 560 aag cag gct gag ctc tct gcc aag acc aac gtt tag                     1716
Lys Gln Ala Glu Leu Ser Ala Lys Thr Asn Val
                565                 570

<210> SEQ ID NO 126
<211> LENGTH: 571
<212> TYPE: PRT
<213> ORGANISM: Yarrowia lipolytica

<400> SEQUENCE: 126

Met Ser Asp Ser Glu Pro Gln Met Val Asp Leu Gly Asp Tyr Leu Phe
1               5                   10                  15

Ala Arg Phe Lys Gln Leu Gly Val Asp Ser Val Phe Gly Val Pro Gly
                20                  25                  30

Asp Phe Asn Leu Thr Leu Leu Asp His Val Tyr Asn Val Asp Met Arg
            35                  40                  45

Trp Val Gly Asn Thr Asn Glu Leu Asn Ala Gly Tyr Ser Ala Asp Gly
        50                  55                  60

Tyr Ser Arg Val Lys Arg Leu Ala Cys Leu Val Thr Thr Phe Gly Val
65                  70                  75                  80

Gly Glu Leu Ser Ala Val Ala Ala Val Ala Gly Ser Tyr Ala Glu His
                85                  90                  95

Val Gly Val Val His Val Gly Val Pro Ser Thr Ser Ala Glu Asn
                100                 105                 110

Lys His Leu Leu Leu His His Thr Leu Gly Asn Gly Asp Phe Arg Val
            115                 120                 125

Phe Ala Gln Met Ser Lys Leu Ile Ser Glu Tyr Thr His His Ile Glu
        130                 135                 140

Asp Pro Ser Glu Ala Ala Asp Val Ile Asp Thr Ala Ile Arg Ile Ala
145                 150                 155                 160

Tyr Thr His Gln Arg Pro Val Tyr Ile Ala Val Pro Ser Asn Phe Ser
                165                 170                 175

Glu Val Asp Ile Ala Asp Gln Ala Arg Leu Asp Thr Pro Leu Asp Leu
            180                 185                 190

Ser Leu Gln Pro Asn Asp Pro Glu Ser Gln Tyr Glu Val Ile Glu Glu
        195                 200                 205

Ile Cys Ser Arg Ile Lys Ala Ala Lys Pro Val Ile Leu Val Asp
        210                 215                 220

Ala Cys Ala Ser Arg Tyr Arg Cys Val Asp Glu Thr Lys Glu Leu Ala
225                 230                 235                 240

Lys Ile Thr Asn Phe Ala Tyr Phe Val Thr Pro Met Gly Lys Gly Ser
                245                 250                 255

Val Asp Glu Asp Thr Asp Arg Tyr Gly Gly Thr Tyr Val Gly Ser Leu
            260                 265                 270

Thr Ala Pro Ala Thr Ala Glu Val Val Glu Thr Ala Asp Leu Ile Ile
        275                 280                 285

Ser Val Gly Ala Leu Leu Ser Asp Phe Asn Thr Gly Ser Phe Ser Tyr
290                 295                 300

Ser Tyr Ser Thr Lys Asn Val Val Glu Leu His Ser Asp His Val Lys
```

```
                    305                 310                 315                 320
Ile Lys Ser Ala Thr Tyr Asn Asn Val Gly Met Lys Met Leu Phe Pro
                325                 330                 335

Pro Leu Glu Ala Val Lys Lys Leu Val Ala Glu Thr Pro Asp Phe
            340                 345                 350

Ala Ser Lys Ala Leu Ala Val Pro Asp Thr Thr Pro Lys Ile Pro Glu
            355                 360                 365

Val Pro Asp Asp His Ile Thr Thr Gln Ala Trp Leu Trp Gln Arg Leu
    370                 375                 380

Ser Tyr Phe Leu Arg Pro Thr Asp Ile Val Val Thr Glu Thr Gly Thr
385                 390                 395                 400

Ser Ser Phe Gly Ile Ile Gln Thr Lys Phe Pro His Asn Val Arg Gly
                405                 410                 415

Ile Ser Gln Val Leu Trp Gly Ser Ile Gly Tyr Ser Val Gly Ala Ala
            420                 425                 430

Cys Gly Ala Ser Ile Ala Ala Gln Glu Ile Asp Pro Gln Gln Arg Val
            435                 440                 445

Ile Leu Phe Val Gly Asp Gly Ser Leu Gln Leu Thr Val Thr Glu Ile
    450                 455                 460

Ser Cys Met Ile Arg Asn Asn Val Lys Pro Tyr Ile Phe Val Leu Asn
465                 470                 475                 480

Asn Asp Gly Tyr Thr Ile Glu Arg Leu Ile His Gly Glu Asn Ala Ser
                485                 490                 495

Tyr Asn Asp Val His Met Trp Lys Tyr Ser Lys Ile Leu Asp Thr Phe
            500                 505                 510

Asn Ala Lys Ala His Glu Ser Ile Val Val Asn Thr Lys Gly Glu Met
            515                 520                 525

Asp Ala Leu Phe Asp Asn Glu Glu Phe Ala Lys Pro Asp Lys Ile Arg
    530                 535                 540

Leu Ile Glu Val Met Cys Asp Lys Met Asp Ala Pro Ser Leu Ile
545                 550                 555                 560

Lys Gln Ala Glu Leu Ser Ala Lys Thr Asn Val
                565                 570

<210> SEQ ID NO 127
<211> LENGTH: 1716
<212> TYPE: DNA
<213> ORGANISM: Schizosaccharomyces pombe
<220> FEATURE:
<221> NAME/KEY: CDS
<222> LOCATION: (1)..(1716)

<400> SEQUENCE: 127 atg agt ggg gat att tta gtc ggt gaa tat cta ttc aaa agg ctt gaa      48
Met Ser Gly Asp Ile Leu Val Gly Glu Tyr Leu Phe Lys Arg Leu Glu
1               5                   10                  15 caa tta ggg gtc aag tcc att ctt ggt gtt cca gga gat ttc aat tta      96
Gln Leu Gly Val Lys Ser Ile Leu Gly Val Pro Gly Asp Phe Asn Leu
            20                  25                  30 gct cta ctt gac tta att gag aaa gtt gga gat gag aaa ttt cgt tgg     144
Ala Leu Leu Asp Leu Ile Glu Lys Val Gly Asp Glu Lys Phe Arg Trp
        35                  40                  45 gtt ggc aat acc aat gag ttg aat ggt gct tat gcc gct gat ggt tat     192
Val Gly Asn Thr Asn Glu Leu Asn Gly Ala Tyr Ala Ala Asp Gly Tyr
    50                  55                  60 gct cgt gtt aat ggt ctt tca gcc att gtt aca acg ttc ggc gtg gga     240
Ala Arg Val Asn Gly Leu Ser Ala Ile Val Thr Thr Phe Gly Val Gly
65                  70                  75                  80
```

```
gag ctt tcc gct att aat gga gtg gca ggt tct tat gcg gag cat gtc      288
Glu Leu Ser Ala Ile Asn Gly Val Ala Gly Ser Tyr Ala Glu His Val
                85                  90                  95 cca gta gtt cat att gtt gga atg cct tcc aca aag gtg caa gat act      336
Pro Val Val His Ile Val Gly Met Pro Ser Thr Lys Val Gln Asp Thr
            100                 105                 110 gga gct ttg ctt cat cat act tta gga gat gga gac ttt cgc act ttc      384
Gly Ala Leu Leu His His Thr Leu Gly Asp Gly Asp Phe Arg Thr Phe
        115                 120                 125 atg gat atg ttt aag aaa gtt tct gcc tac agt ata atg atc gat aac      432
Met Asp Met Phe Lys Lys Val Ser Ala Tyr Ser Ile Met Ile Asp Asn
130                 135                 140 gga aac gat gca gct gaa aag atc gat gaa gcc ttg tcg att tgt tat      480
Gly Asn Asp Ala Ala Glu Lys Ile Asp Glu Ala Leu Ser Ile Cys Tyr
145                 150                 155                 160 aaa aag gct agg cct gtt tac att ggt att cct tct gat gct ggc tac      528
Lys Lys Ala Arg Pro Val Tyr Ile Gly Ile Pro Ser Asp Ala Gly Tyr
                165                 170                 175 ttc aaa gca tct tca tca aat ctt ggg aaa aga cta aag ctc gag gag      576
Phe Lys Ala Ser Ser Ser Asn Leu Gly Lys Arg Leu Lys Leu Glu Glu
            180                 185                 190 gat act aac gat cca gca gtt gag caa gaa gtc atc aat cat atc tcg      624
Asp Thr Asn Asp Pro Ala Val Glu Gln Glu Val Ile Asn His Ile Ser
        195                 200                 205 gaa atg gtt gtc aat gca aag aaa cca gtg att tta att gac gct tgt      672
Glu Met Val Val Asn Ala Lys Lys Pro Val Ile Leu Ile Asp Ala Cys
        210                 215                 220 gct gta aga cat cgt gtc gtt cca gaa gta cat gag ctg att aaa ttg      720
Ala Val Arg His Arg Val Val Pro Glu Val His Glu Leu Ile Lys Leu
225                 230                 235                 240 acc cat ttc cct aca tat gta act ccc atg ggt aaa tct gca att gac      768
Thr His Phe Pro Thr Tyr Val Thr Pro Met Gly Lys Ser Ala Ile Asp
                245                 250                 255 gaa act tcg caa ttt ttt gac ggc gtt tat gtt ggt tca att tca gat      816
Glu Thr Ser Gln Phe Phe Asp Gly Val Tyr Val Gly Ser Ile Ser Asp
            260                 265                 270 cct gaa gtt aaa gac aga att gaa tcc act gat ctg ttg cta tcc atc      864
Pro Glu Val Lys Asp Arg Ile Glu Ser Thr Asp Leu Leu Leu Ser Ile
        275                 280                 285 ggt gct ctc aaa tca gac ttt aac acg ggt tcc ttc tct tac cac ctc      912
Gly Ala Leu Lys Ser Asp Phe Asn Thr Gly Ser Phe Ser Tyr His Leu
        290                 295                 300 agc caa aag aat gcc gtt gag ttt cat tca gac cac atg cgc att cga      960
Ser Gln Lys Asn Ala Val Glu Phe His Ser Asp His Met Arg Ile Arg
305                 310                 315                 320 tat gct ctt tat cca aat gta gcc atg aag tat att ctt cgc aaa ctg     1008
Tyr Ala Leu Tyr Pro Asn Val Ala Met Lys Tyr Ile Leu Arg Lys Leu
                325                 330                 335 ttg aaa gta ctt gat gct tct atg tgt cat tcc aag gct gct cct acc     1056
Leu Lys Val Leu Asp Ala Ser Met Cys His Ser Lys Ala Ala Pro Thr
            340                 345                 350 att ggc tac aac atc aag cct aag cat gcg gaa gga tat tct tcc aac     1104
Ile Gly Tyr Asn Ile Lys Pro Lys His Ala Glu Gly Tyr Ser Ser Asn
        355                 360                 365 gag att act cat tgc tgg ttt tgg cct aaa ttt agt gaa ttt ttg aag     1152
Glu Ile Thr His Cys Trp Phe Trp Pro Lys Phe Ser Glu Phe Leu Lys
370                 375                 380 ccc cga gat gtt ttg atc acc gag act gga act gca aac ttt ggt gtc     1200
Pro Arg Asp Val Leu Ile Thr Glu Thr Gly Thr Ala Asn Phe Gly Val
385                 390                 395                 400
```

-continued

```
ctt gat tgc agg ttt cca aag gat gta aca gcc att tcc cag gta tta    1248
Leu Asp Cys Arg Phe Pro Lys Asp Val Thr Ala Ile Ser Gln Val Leu
            405                 410                 415 tgg gga tct att gga tac tcc gtt ggt gca atg ttt ggt gct gtt ttg    1296
Trp Gly Ser Ile Gly Tyr Ser Val Gly Ala Met Phe Gly Ala Val Leu
        420                 425                 430 gcc gtc cac gat tct aaa gag ccc gat cgt cgt acc att ctt gta gta    1344
Ala Val His Asp Ser Lys Glu Pro Asp Arg Arg Thr Ile Leu Val Val
435                 440                 445 ggt gat gga tcc tta caa ctg acg att aca gag att tca acc tgc att    1392
Gly Asp Gly Ser Leu Gln Leu Thr Ile Thr Glu Ile Ser Thr Cys Ile
    450                 455                 460 cgc cat aac ctc aaa cca att att ttc ata att aac aac gac ggt tac    1440
Arg His Asn Leu Lys Pro Ile Ile Phe Ile Ile Asn Asn Asp Gly Tyr
465                 470                 475                 480 acc att gag cgt tta att cat ggt ttg cat gct agc tat aac gaa att    1488
Thr Ile Glu Arg Leu Ile His Gly Leu His Ala Ser Tyr Asn Glu Ile
                485                 490                 495 aac act aaa tgg ggc tac caa cag att ccc aag ttt ttc gga gct gct    1536
Asn Thr Lys Trp Gly Tyr Gln Gln Ile Pro Lys Phe Phe Gly Ala Ala
            500                 505                 510 gaa aac cac ttc cgc act tac tgt gtt aaa act cct act gac gtt gaa    1584
Glu Asn His Phe Arg Thr Tyr Cys Val Lys Thr Pro Thr Asp Val Glu
        515                 520                 525 aag ttg ttt agc gac aag gag ttt gca aat gca gat gtc att caa gta    1632
Lys Leu Phe Ser Asp Lys Glu Phe Ala Asn Ala Asp Val Ile Gln Val
530                 535                 540 gtt gag ctt gta atg cct atg ttg gat gca cct cgt gtc cta gtt gag    1680
Val Glu Leu Val Met Pro Met Leu Asp Ala Pro Arg Val Leu Val Glu
545                 550                 555                 560 caa gcc aag ttg acg tct aag atc aat aag caa tga                    1716
Gln Ala Lys Leu Thr Ser Lys Ile Asn Lys Gln
                565                 570

<210> SEQ ID NO 128
<211> LENGTH: 571
<212> TYPE: PRT
<213> ORGANISM: Schizosaccharomyces pombe

<400> SEQUENCE: 128

Met Ser Gly Asp Ile Leu Val Gly Glu Tyr Leu Phe Lys Arg Leu Glu
1               5                   10                  15

Gln Leu Gly Val Lys Ser Ile Leu Gly Val Pro Gly Asp Phe Asn Leu
            20                  25                  30

Ala Leu Leu Asp Leu Ile Glu Lys Val Gly Asp Glu Lys Phe Arg Trp
        35                  40                  45

Val Gly Asn Thr Asn Glu Leu Asn Gly Ala Tyr Ala Ala Asp Gly Tyr
    50                  55                  60

Ala Arg Val Asn Gly Leu Ser Ala Ile Val Thr Thr Phe Gly Val Gly
65                  70                  75                  80

Glu Leu Ser Ala Ile Asn Gly Val Ala Gly Ser Tyr Ala Glu His Val
                85                  90                  95

Pro Val Val His Ile Val Gly Met Pro Ser Thr Lys Val Gln Asp Thr
            100                 105                 110

Gly Ala Leu Leu His His Thr Leu Gly Asp Gly Asp Phe Arg Thr Phe
        115                 120                 125

Met Asp Met Phe Lys Lys Val Ser Ala Tyr Ser Ile Met Ile Asp Asn
    130                 135                 140
```

```
Gly Asn Asp Ala Ala Glu Lys Ile Asp Glu Ala Leu Ser Ile Cys Tyr
145                 150                 155                 160

Lys Lys Ala Arg Pro Val Tyr Ile Gly Ile Pro Ser Asp Ala Gly Tyr
                165                 170                 175

Phe Lys Ala Ser Ser Ser Asn Leu Gly Lys Arg Leu Lys Leu Glu Glu
                180                 185                 190

Asp Thr Asn Asp Pro Ala Val Glu Gln Glu Val Ile Asn His Ile Ser
            195                 200                 205

Glu Met Val Val Asn Ala Lys Lys Pro Val Ile Leu Ile Asp Ala Cys
    210                 215                 220

Ala Val Arg His Arg Val Pro Glu Val His Glu Leu Ile Lys Leu
225                 230                 235                 240

Thr His Phe Pro Thr Tyr Val Thr Pro Met Gly Lys Ser Ala Ile Asp
                245                 250                 255

Glu Thr Ser Gln Phe Phe Asp Gly Val Tyr Val Gly Ser Ile Ser Asp
            260                 265                 270

Pro Glu Val Lys Asp Arg Ile Glu Ser Thr Asp Leu Leu Leu Ser Ile
            275                 280                 285

Gly Ala Leu Lys Ser Asp Phe Asn Thr Gly Ser Phe Ser Tyr His Leu
290                 295                 300

Ser Gln Lys Asn Ala Val Glu Phe His Ser Asp His Met Arg Ile Arg
305                 310                 315                 320

Tyr Ala Leu Tyr Pro Asn Val Ala Met Lys Tyr Ile Leu Arg Lys Leu
                325                 330                 335

Leu Lys Val Leu Asp Ala Ser Met Cys His Ser Lys Ala Ala Pro Thr
                340                 345                 350

Ile Gly Tyr Asn Ile Lys Pro Lys His Ala Glu Gly Tyr Ser Ser Asn
            355                 360                 365

Glu Ile Thr His Cys Trp Phe Trp Pro Lys Phe Ser Glu Phe Leu Lys
    370                 375                 380

Pro Arg Asp Val Leu Ile Thr Glu Thr Gly Thr Ala Asn Phe Gly Val
385                 390                 395                 400

Leu Asp Cys Arg Phe Pro Lys Asp Val Thr Ala Ile Ser Gln Val Leu
                405                 410                 415

Trp Gly Ser Ile Gly Tyr Ser Val Gly Ala Met Phe Gly Ala Val Leu
                420                 425                 430

Ala Val His Asp Ser Lys Glu Pro Asp Arg Arg Thr Ile Leu Val Val
            435                 440                 445

Gly Asp Gly Ser Leu Gln Leu Thr Ile Thr Glu Ile Ser Thr Cys Ile
450                 455                 460

Arg His Asn Leu Lys Pro Ile Ile Phe Ile Ile Asn Asn Asp Gly Tyr
465                 470                 475                 480

Thr Ile Glu Arg Leu Ile His Gly Leu His Ala Ser Tyr Asn Glu Ile
                485                 490                 495

Asn Thr Lys Trp Gly Tyr Gln Gln Ile Pro Lys Phe Phe Gly Ala Ala
                500                 505                 510

Glu Asn His Phe Arg Thr Tyr Cys Val Lys Thr Pro Thr Asp Val Glu
            515                 520                 525

Lys Leu Phe Ser Asp Lys Glu Phe Ala Asn Ala Asp Val Ile Gln Val
530                 535                 540
```

```
Val Glu Leu Val Met Pro Met Leu Asp Ala Pro Arg Val Leu Val Glu
545                 550                 555                 560

Gln Ala Lys Leu Thr Ser Lys Ile Asn Lys Gln
            565                 570
```

INCREASED PRODUCTION OF ISOBUTANOL IN YEAST WITH REDUCED MITOCHONDRIAL AMINO ACID BIOSYNTHESIS

CROSS-REFERENCE TO RELATED APPLICATIONS

This application is related to and claims the benefit of priority of U.S. Provisional Application No. 61/114,072, filed Nov. 13, 2008, the entirety of which is herein incorporated by reference.

FIELD OF THE INVENTION

The invention relates to the field of microbiology. More specifically, recombinant yeast strains are disclosed that have reduced amino acid biosynthesis and increased isobutanol production.

BACKGROUND OF THE INVENTION

Butanol is an important industrial chemical, useful as a fuel additive, as a feedstock chemical in the plastics industry, and as a foodgrade extractant in the food and flavor industry. Each year 10 to 12 billion pounds of butanol are produced by petrochemical means and the need for this commodity chemical will likely increase.

Isobutanol is produced biologically as a by-product of yeast fermentation. It is a component of "fusel oil" that forms as a result of incomplete metabolism of amino acids by this group of fungi. Isobutanol is specifically produced from catabolism of L-valine in the cytoplasm. After the amine group of L-valine is harvested as a nitrogen source, the resulting α-keto acid is decarboxylated and reduced to isobutanol by enzymes of the so-called Ehrlich pathway (Dickinson et al., *J. Biol. Chem.* 273(40):25752-25756 (1998)). Yields of fusel oil and/or its components achieved during beverage fermentation are typically low. For example, the concentration of isobutanol produced in beer fermentation is reported to be less than 16 parts per million (Garcia et al., *Process Biochemistry* 29:303-309 (1994)). Addition of exogenous L-valine to the fermentation increases the yield of isobutanol, as described by Dickinson et al., supra, wherein it is reported that a yield of isobutanol of 3 g/L is obtained by providing L-valine at a concentration of 20 g/L in the fermentation. However, the use of valine as a feed-stock would be cost prohibitive for industrial scale isobutanol production.

Additionally Van Nedervelde et al (Proceedings of the Congress—European Brewery Convention (2003), 29th, 50/1-50/10) have demonstrated the deletions in the gene encoding the BAT 1 mitochondrial protein in yeast result in strains having increased levels of higher alcohols. Similarly Nako et al (WO 2007032522) note that amyl alcohol and/or isobutanol and/or isoamyl acetate levels in yeast used for the production of alcoholic beverages may be altered via manipulation of the BAT1 and BAT2 genes. The art is silent with respect to the down regulation of other genes encoding proteins that are functional in the mitochondria for the enhanced production of isobutanol in yeast.

There is a need for attaining higher amounts of isobutanol through yeast fermentation without addition of valine or other isobutanol production intermediates.

SUMMARY OF THE INVENTION

Provided herein are recombinant yeast host cells which comprise mitochondria which are substantially devoid of an enzyme activity selected from the group consisting of threonine deaminase and isopropylmalate synthase activity. In some embodiments, the host cells produce isobutanol. In some embodiments, the mitochondria is substantially devoid of branched chain amino acid transaminase activity, and in some embodiments, the mitochondria is substantially devoid of pyruvate dehydrogenase activity. In some embodiments, endogenous pyruvate decarboxylase activity is reduced.

In some embodiments, the threonine deaminase activity is defined by the enzyme classification number EC 4.3.1.19 and the isopropylmalate synthase activity is defined by the enzyme classification number EC 2.3.3.13. In some embodiments, the branched chain amino acid transaminase activity is defined by the enzyme classification number EC 2.6.1.42. In some embodiments, the pyruvate dehydrogenase activity is defined by the enzyme classification number EC 1.2.4.1. In some embodiments, the pyruvate dehydrogenase activity is defined by a multienzyme complex comprising proteins selected from the group consisting of: PDA1, PDA1, PDB1, LAT1, LPD1, and PDX1.

In some embodiments, the yeast is selected from the group consisting of *Saccharomyces, Schizosaccharomyces, Hansenula, Candida, Kluyveromyces, Yarrowia* and *Pichia*.

In some embodiments, yeast cells provided comprise a disruption in a gene selected from the group consisting of ILV1 and LEU4. In some embodiments, yeast cells provided comprise a disruption in the BAT1 gene. In some embodiments, yeast cells provided comprise a disruption in a gene encoding a protein selected from the group consisting of PDA1, PDA1, PDB1, LAT1, LPD1, and PDX1

In some embodiments, yeast cells provided herein are *Saccharomyces* and wherein; a) the ILV1 gene encodes a polypeptide having at least 80% identity to an amino acid sequence as set forth in SEQ ID NO: 2, based on the Clustal W method of alignment using the default parameters of GAP PENALTY=10, GAP LENGTH PENALTY=0.1, and Gonnet 250 series of protein weight matrix; and b) the LEU4 gene encodes a polypeptide having at least 80% identity to the amino acid sequence set forth in SEQ ID NO: 28 based on the Clustal W method of alignment using the default parameters of GAP PENALTY=10, GAP LENGTH PENALTY=0.1, and Gonnet 250 series of protein weight matrix.

In some embodiments, yeast cells provided herein are *Saccharomyces* and wherein the BAT1 gene encodes a protein having at least 80% identity to the amino acid sequence as set forth in SEQ ID NO:16 based on the Clustal W method of alignment using the default parameters of GAP PENALTY=10, GAP LENGTH PENALTY=0.1, and Gonnet 250 series of protein weight matrix.

In some embodiments, yeast cells provided herein are *Saccharomyces* and wherein; a) the PDA1 polypeptide has at least 80% identity to the amino acid sequence as set forth in SEQ ID NO:70; b) the PDB1 polypeptide has at least 80% identity to the amino acid sequence as set forth in SEQ ID NO: 58; c) the LAT1 polypeptide has at least 80% identity to the amino acid sequence as set forth in SEQ ID NO: 106; d) the LPD1 polypeptide has at least 80% identity to the amino acid sequence as set forth in SEQ ID NO: 108; and e) the PDX1 polypeptide has at least 80% identity to the amino acid sequence as set forth in SEQ ID NO: 110; wherein identity of polypeptides recited in parts (a)-(e) is based on the Clustal W method of alignment using the default parameters of GAP PENALTY=10, GAP LENGTH PENALTY=0.1, and Gonnet 250 series of protein weight matrix.

Also provided herein are methods for the production of isobutanol comprising growing provided host cells under conditions wherein isobutanol is produced.

BRIEF DESCRIPTION OF THE FIGURES AND SEQUENCE DESCRIPTIONS

The invention can be more fully understood from the following detailed description, figures, and the accompanying sequence descriptions, which form a part of this application.

FIG. 1 shows biosynthetic pathways for amino acids in yeast mitochondria.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

TABLE 1

SEQ ID NOs of target proteins and encoding sequences for reduction

| Organism and gene name | SEQ ID NO: nucleic acid | SEQ ID NO: amino acid |
|---|---|---|
| *Saccharomyces cerevisiae* YJM789, Ilv1 | 1 | 2 |
| *Schizosaccharomyces pombe*, Ilv1 | 3 | 4 |
| *Candida albicans* SC5314, Ilv1 | 5 | 6 |
| *Candida glabrata*, Ilv1 | 7 | 8 |
| *Kluyveromyces lactis*, Ilv1 | 9 | 10 |
| *Yarrowia lipolytica* strain CLIB122, Ilv1 | 11 | 12 |
| *Pichia stipitis* CBS 6054, Ilv1 | 13 | 14 |
| *Saccharomyces cerevisiae*, BAT1 | 15 | 16 |
| *Schizosaccharomycs pombe*, BAT1 | 17 | 18 |
| *Candida albicans* SC5314, BAT1 | 19 | 20 |
| *Kluyveromyces lactis*, BAT1 | 21 | 22 |
| *Yarrowia lipolytica*, BAT1 | 23 | 24 |
| *Pichia stipitis* CBS 6054, BAT1 | 25 | 26 |
| *Saccharomyces cerevisiae*, Leu4 | 27 | 28 |
| *Schizosaccharomycs pombe*, Leu4 chromosome II | 29 | 30 |
| *Schizosaccharomycs pombe*, Leu4, NP_596103.2 | 31 | 32 |
| *Candida albicans* SC5314, Leu4 | 33 | 34 |
| *Candida albicans* SC5314, Leu4 | 35 | 36 |
| *Candida albicans* SC5314, Leu4 | 37 | 38 |
| *Candida albicans* SC5314, Leu4 | 39 | 40 |
| *Candida glabrata*, Leu4; XP_446653.1 | 41 | 42 |
| *Candida glabrata*, Leu4; XP_446566.1 | 43 | 44 |
| *Kluyveromyces lactis*, Leu4; CAH00792.1 | 45 | 46 |
| *Kluyveromyces lactis*, Leu4; CAG98836.1 | 47 | 48 |
| *Yarrowia lipolytica*, Leu4, CAA88928.1 | 49 | 50 |
| *Yarrowia lipolytica*, Leu4 | 51 | 52 |
| *Pichia stipitis* CBS 6054, Leu4, XP_001387341.1 | 53 | 54 |
| *Pichia stipitis* CBS 6054, Leu4, XP_001384536.2 | 55 | 56 |
| *Saccharomyces cerevisiae*, PDB1 | 57 | 58 |
| *Schizosaccharomycs pombe*, PDB1 | 59 | 60 |
| *Candida albicans* SC5314, PDB1 | 61 | 62 |
| *Kluyveromyces lactis*, PDB1 | 63 | 64 |
| *Yarrowia lipolytica*, PDB1 | 65 | 66 |
| *Pichia stipitis* CBS 6054, PDB1 | 67 | 68 |
| *Saccharomyces cerevisiae*, PDA1 | 69 | 70 |
| *Schizosaccharomycs pombe*, PDA1 | 71 | 72 |
| *Candida albicans*, PDA1 | 73 | 74 |
| *Kluyveromyces lactis*, PDA1 | 75 | 76 |
| *Yarrowia lipolytica*, PDA1 hypothetical protein | 77 | 78 |
| *Pichia stipitis*, PDA1 | 79 | 80 |
| *Saccharomyces cerevisiae* Lat1 pyruvate dehydrogenase complex | 105 | 106 |
| *Saccharomyces cerevisiae* Lpd1 pyruvate dehydrogenase complex | 107 | 108 |
| *Saccharomyces cerevisiae* Pdx1 pyruvate dehydrogenase complex | 109 | 110 |

TABLE 2

SEQ ID NOs for primers and vectors

| Primer or vector name | Description | SEQ ID NO |
|---|---|---|
| 112590-88A | Primer | 81 |
| 112590-88B | Primer | 82 |
| 112590-88C | Primer | 83 |
| 112590-88D | Primer | 84 |
| pUC19-URA3r | Vector | 85 |
| 112590-97A | Primer | 86 |
| 112590-97B | Primer | 87 |
| 112590-49E | Primer | 88 |
| 112590-97C | Primer | 89 |
| 112590-108A | Primer | 90 |
| 112590-108B | Primer | 91 |
| 112590-108C | Primer | 92 |
| 112590-108D | Primer | 93 |
| 112590-108E | Primer | 94 |
| 112590-108F | Primer | 95 |
| BAT1 check | Primer | 96 |
| 112590-118A | Primer | 97 |
| 112590-118B | Primer | 98 |
| pRS426::GAL1p-alsS | Vector | 99 |
| 112590-118C | Primer | 100 |
| 112590-118D | Primer | 101 |
| 112590-118E | Primer | 102 |
| 112590-118F | Primer | 103 |
| 112590-118G | Primer | 104 |

TABLE 3

Yeast pyruvate decarboxylase sequences

| Organism and gene name | SEQ ID NO: nucleic acid | SEQ ID NO: amino acid |
|---|---|---|
| PDC1 pyruvate decarboxylase from *Saccharomyces cerevisiae* | 108 | 109 |
| PDC5 pyruvate decarboxylase from *Saccharomyces cerevisiae* | 110 | 111 |
| PDC6 pyruvate decarboxylase from *Saccharomyces cerevisiae* | 112 | 113 |
| Pyruvate decarboxylase from *Candida glabrata* | 114 | 115 |
| PDC1 pyruvate decarboxylase from *Pichia stipitis* | 116 | 117 |
| PDC2 pyruvate decarboxylase from *Pichia stipitis* | 118 | 119 |
| Pyruvate decarboxylase from *Kluyveromyces lactis* | 120 | 121 |
| Pyruvate decarboxylase from *Yarrowia lipolytica* | 122 | 123 |
| Pyruvate decarboxylase from *Schizosaccharomyces pombe* | 124 | 125 |

DETAILED DESCRIPTION OF THE INVENTION

The present invention relates to recombinant yeast cells engineered to have reduced activity of threonine deaminase and isopropylmalate synthase, and optionally reduced activity of branched chain amino acid transaminase, in the mitochondria. These cells produce increased amounts of isobutanol as compared to cells with normal levels of these enzyme activities. Isobutanol is valuable as a fuel or fuel additive to reduce demand for fossil fuels.

The following abbreviations and definitions will be used for the interpretation of the specification and the claims.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

The term "isobutanol biosynthetic pathway" refers to an enzyme pathway to produce isobutanol from pyruvate.

The term "threonine deaminase refers to an enzyme having the EC number EC 4.3.1.19 (*Enzyme Nomenclature* 1992, Academic Press, San Diego). Threonine deaminase catalyzes the reaction of threonine to 2-oxobutanoate. This is an enzyme involved in branched chain amino acid biosynthesis, specifically of isoleucine. The gene encoding this enzyme is localized in the yeast nucleus however the encoded protein is transported to the mitochondria where it is metabolically active.

The term "isopropylmalate synthase" refers to an enzyme having the EC number EC 2.3.3.13 (*Enzyme Nomenclature* 1992, Academic Press, San Diego). Isopropylmalate synthase catalyzes the reaction of alpha-ketoisovalerate to isopropyl malate. This is an enzyme involved in branched chain amino acid biosynthesis, specifically of leucine. The gene encoding this enzyme is localized in the yeast nucleus however the encoded protein is transported to the mitochondria where it is metabolically active.

The term "branched chain amino acid transaminase" refers to an enzyme having the EC number EC 2.6.1.42 (*Enzyme Nomenclature* 1992, Academic Press, San Diego). Branched chain amino acid transaminase catalyzes the reaction of alpha-ketoisovalerate to valine and catalyzes the reaction of 2-keto-3-methyl-valerate to isoleucine. This is an enzyme involved in branched chain amino acid biosynthesis, specifically of valine and isoleucine. The gene encoding this enzyme is localized in the yeast nucleus however the encoded protein is transported to the mitochondria where it is metabolically active.

The term "pyruvate dehydrogenase" refers to an activity provided by a multienzyme complex that may include proteins PDA1, PDB1, LAT1, LPD1, and PDX1. PDA1 and PDB1 are E1α and E1β subunits of pyruvate dehydrogenase which has EC number EC 1.2.4.1. LAT1 is dihydrolipoyllysine-residue acetyltransferase, also called dihydrolopoyl transacetylase, which has EC number EC 2.3.1.12. LPD1 is dihydrolipoyl dehydrogenase which has EC number EC 1.8.1.4. Pyruvate dehydrogenase activity catalyzes the reaction of pyruvate to acetyl-CoA. The gene encoding this enzyme is localized in the yeast nucleus however the encoded protein is transported to the mitochondria where it is metabolically active.

The term "carbon substrate" or "fermentable carbon substrate" refers to a carbon source capable of being metabolized by host organisms of the present invention and particularly carbon sources selected from the group consisting of monosaccharides, oligosaccharides, polysaccharides, and one-carbon substrates or mixtures thereof.

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign gene" or "heterologous gene" refers to a gene not normally found in the host organism, but that is introduced into the host organism by gene transfer. "Heterologous gene" includes a native coding region, or portion thereof, that is reintroduced into the source organism in a form that is different from the corresponding native gene. For example, a heterologous gene may include a native coding region that is a portion of a chimeric gene including non-native regulatory regions that is reintroduced into the native host. Also foreign genes can comprise native genes inserted into a non-native organism, or chimeric genes. A "transgene" is a gene that has been introduced into the genome by a transformation procedure.

As used herein the term "coding region" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

The term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

The term "substantially devoid" when used in reference to the presence of an enzyme activity in a host cell means that the presences of that enzyme is not detectable using conventional assay methods or is detectable at such low levels that the presence of the enzyme at would not be expected to have any effect on metabolic pathways.

As used herein the term "transformation" refers to the transfer of a nucleic acid fragment into a host organism, resulting in genetically stable inheritance. Host organisms containing the transformed nucleic acid fragments are referred to as "transgenic" or "recombinant" or "transformed" organisms.

The terms "plasmid" and "vector" as used herein, refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

As used herein the term "codon degeneracy" refers to the nature in the genetic code permitting variation of the nucleotide sequence without effecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

As used herein, an "isolated nucleic acid fragment" or "isolated nucleic acid molecule" will be used interchangeably and will mean a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual, 2$^{nd}$ ed.*, Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Altschul, S. F., et al., *J. Mol. Biol.*, 215:403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular fungal proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991).

Preferred methods to determine identity are designed to give the best match between the sequences tested. Methods to determine identity and similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" corresponding to the alignment method labeled Clustal V (described by Higgins and Sharp, *CABIOS.* 5:151-153 (1989); Higgins, D. G. et al., *Comput. Appl. Biosci.*, 8:189-191 (1992)) and found in the MegAlign™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, *CABIOS.* 5:151-153 (1989); Higgins, D. G. et al., *Comput. Appl. Biosci.* 8:189-191 (1992)) and found in the MegAlign™ v6.1 program of the LASERGENE bioinformatics computing suite (DNASTAR Inc.). Default parameters for multiple alignment (GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

It is well understood by one skilled in the art that many levels of sequence identity are useful in identifying polypeptides, from other species, wherein such polypeptides have the same or similar function or activity. Useful examples of percent identities include, but are not limited to: 55%, 60%, 65%, 70%, 75%, 80%, 85%, 90%, or 95%, or any integer percentage from 55% to 100% may be useful in describing the present invention, such as 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.*, 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Press, Cold Spring Harbor, N.Y. (1984); and by Ausubel, F. M. et al., *Current Protocols in Molecular Biology*, published by Greene Publishing Assoc. and Wiley-Interscience (1987). Additional methods used here are in *Methods in Enzymology*, Volume 194, *Guide to Yeast Genetics and Molecular and Cell Biology* (Part A, 2004, Christine Guthrie and Gerald R. Fink (Eds.), Elsevier Academic Press, San Diego, Calif.).

Mitochondrial Enzyme Engineering for Isobutanol Production

Disclosed herein are yeast cells with improved isobutanol production and engineering of endogenous enzyme activities in the mitochondria of yeast cells. This engineering may be performed in any type of yeast cell that is amenable to genetic engineering methods and that naturally produces at least a small amount of isobutanol as a byproduct of incomplete amino acid metabolism. Suitable yeasts include, but are not limited to, *Saccharomyces, Schizosaccharomyces, Hansenula, Candida, Kluyveromyces, Yarrowia* and *Pichia*. Suitable strains include, but are not limited to, *Saccharomyces cerevisiae, Schizosaccharomyces pombe, Kluyveromyces lactis, Kluyveromyces thermotolerans, Candida glabrata, Candida albicans, Pichia stipitis* and *Yarrowia lipolytica*.

Applicants have found that altering branched chain amino acid biosynthesis and pyruvate metabolism in the mitochondria of yeast can affect the amount of isobutanol produced by the yeast cell. Surprisingly, Applicants found that altered cells had increased isobutanol production using endogenous isobutanol biosynthesis. Applicants found that by eliminating threonine deaminase and isopropylmalate synthase activities in the yeast mitochondria, a nine-fold increase in isobutanol production was achieved. With further elimination of branched chain amino acid aminotransferase activity in the mitochondria, over twelve-fold increase in isobutanol production was achieved. Additional reduction of pyruvate dehydrogenase activity in the mitochondria resulted in over thirteen-fold increase in isobutanol production.

Mitochondrial biosynthetic pathways for branched chain amino acid biosynthesis are shown in the diagram in FIG. 1. The following enzymes are encoded by the genes labeled as steps (arrows) in the pathways in FIG. 1:

ILV1: threonine deaminase
ILV2: acetolactate synthase (ALS)
ILV3: dihydroxy-acid dehydratase (DHAD)
ILV5: acetohydroxy acid reductoisomerase (KARI)
BAT1: branched chain amino acid aminotransferase
BAT2: branched chain amino acid transaminase
LEU4: isopropylmalate synthase
PDA1*: refers to the complex including the components:
PDA1: pyruvate dehydrogenase E1α subunit
PDB1: pyruvate dehydrogenase E1β subunit
LAT1: dihydrolipoyllysine-residue acetyltransferase
LPD1: dihydrolipoyl dehydrogenase
PDX1: protein X Threonine deaminase, ALS, KARI, DHAD and branched chain amino acid aminotransferase enzyme activities in the mitochondria form a biosynthetic pathway from threonine to isoleucine. ALS, KARI, DHAD and branched chain amino acid aminotransferase enzyme activities in the mitochondria form a biosynthetic pathway from pyruvate to valine. ALS, KARI, DHAD and isopropylmalate synthase enzyme activities in the mitochondria form a biosynthetic pathway from pyruvate to isopropyl malate, which moves to the cytoplasm and is converted to leucine.

While not intending to suggest a mechanism of the effect of down-regulating or eliminating the activity of various mitochondrial enzymes the presence of the cytosolic valine to isobutanol pathway generally in yeast suggests some possible explanations for the effects seen here. For example, eliminating threonine deaminase activity may affect pathway intermediate flow in the pathway from threonine to isoleucine. Eliminating isopropylmalate synthase activity may reduce metabolism of the α-ketoisovalerate intermediate in the leucine pathway. Eliminating mitochondrial branched chain amino acid aminotransferase activity may reduce metabolism of the alpha-ketoisovalerate intermediate in the valine pathway that is fully within the mitochondrion. Applicants found that the combination of the loss of threonine deaminase and isopropylmalate synthase activities in the mitochondria was very effective in increasing isobutanol production, suggesting that there was substantial increase in transfer of α-ketoisovalerate to the cytoplasm, and it was converted to isobutanol. In the present cells the conversion to isobutanol relies on endogenous enzyme activities of the yeast cell. Applicants found that the combination of the loss of threonine deaminase, isopropylmalate synthase, and branched chain amino acid aminotransferase activities in the mitochondria further increased isobutanol production, suggesting that there was further increase in transfer of α-ketoisovalerate to the cytoplasm, and it was converted to isobutanol.

In the yeast mitochondria pyruvate is also converted to acetyl-CoA through pyruvate dehydrogenase activity (see FIG. 1). Applicants found that eliminating pyruvate dehydrogenase activity in the mitochondria further increased isobutanol production, suggesting that flow of pyruvate to alpha-ketoisovalerate was increased, as well as transfer of alpha-ketoisovalerate to the cytoplasm with conversion to valine and then to isobutanol. The conversion of pyruvate to acetyl-CoA is catalyzed by a multienzyme pyruvate dehydrogenase complex. The pyruvate dehydrogenase enzyme is one enzyme of the multienzyme pyruvate dehydrogenase complex. Pyruvate dehydrogenase (EC 1.2.4.1) itself has alpha and beta subunits: PDA1 and PDB1, respectively, forming the E1α and E1β subunits, respectively, of the E1 component. The complex includes an E2 core which has dihydrolipoamide acetyltransferase activity (EC 2.3.1.12) and E3 which has dihydrolipoamide dehydrogenase activity (EC1.8.1.4). E2 may be encoded by LAT1 and E3 by LPD1. An additional complex protein is encoded by PDX1, which links Lat1p to Lpd1p. Thus the pyruvate dehydrogenase complex may include PDA1, PDB1, Lat1, Lpd1, and Pdx1, or homologous proteins encoded by genes which may have alternative names in various yeasts. The activity of any of these proteins may be reduced to affect the function of the pyruvate dehydrogenase complex, and thereby affect pyruvate dehydrogenase activity, to prepare a strain of one embodiment of the present invention. In the description below when referring to PDA1, it is understood that PDA1 may be substituted by any of PDB1, LAT1, LPD1, or PDX1, any of which may be modified to reduce pyruvate dehydrogenase activity.

In the present invention, any yeast enzymes providing threonine deaminase, isopropylmalate synthase, branched chain amino acid aminotransferase, or pyruvate dehydrogenase activities in the mitochondria may be targets for engineering to reduce these activities. Preferably the activity is reduced such that there is substantially no detectable activity of the target enzyme. Yeast cells are engineered to reduce enzyme activity typically by modification of the gene encoding the target enzyme. The genes encoding these enzymes are ILV1, LEU4, BAT1, and PDA1 (and multienzyme complex genes PDB1, LAT1, LPD1, and PDX1), respectively. Any ILV1, LEU4, BAT1, or PDA1 gene of yeast encoding a mitochondrial targeted protein is a target for engineering for reduced expression of the encoded enzyme activity in the present cells. Examples of target coding region sequences and their encoded proteins from different species of yeast cells are given as SEQ ID NOs: 1-80 and 105-110 in Table 1. Other target proteins, or their encoding sequences, having at least about 70%-75%, 75%-80%, 80-85%, 85%-90%, 90%-95%, or at least about 98% sequence identity to any of the proteins or coding sequences listed in Table 1, and these activities, may be identified in the literature and in bioinformatics databases well known to the skilled person.

There is cytoplasmic isopropylmalate synthase activity encoded by LEU9 and cytoplasmic branched chain amino acid transaminase activity encoded by BAT2, genes which are not targets in the present disclosure.

Because mitochondrial threonine deaminase, isopropylmalate synthase, branched chain amino acid aminotransferase, and pyruvate dehydrogenase complex enzymes are well known, as well as their encoding genes (ILV1, LEU4, BAT1, PDA1, PDB1, LAT1, LPD1, and PDX1, respectively), one skilled in the art can readily identify these proteins and their encoding genes in yeast cells using bioinformatics approaches, to identify additional target genes for engineering as disclosed herein. Typically BLAST (described above) searching of publicly available databases with known target protein sequences, such as those provided herein, is used to identify homologous proteins and their encoding sequences that may be targeted for inactivation in the present strains. For example, endogenous yeast mitochondrial threonine deaminase proteins having amino acid sequence identities of at least about 70%-75%, 75%-80%, 80-85%, 85%-90%, 90%-95% or 98% sequence identity to any of the threonine deaminase proteins of SEQ ID NOs:2, 4, 6, 8, 10, 12, and 14 may have reduced expression in the present strains. Identities are based on the Clustal W method of alignment using the default parameters of GAP PENALTY=10, GAP LENGTH PENALTY=0.1, and Gonnet 250 series of protein weight matrix.

In the following description, ILV1 is used as an example, and the same description applies to any of LEU4, BAT1, PDA1, PDB1, LAT1, LPD1, and PDX1 coding regions. The sequences of, for example, the ILV1 coding regions provided herein may be used to identify other homologs in nature. For example each of the threonine deaminase encoding nucleic acid fragments described herein may be used to isolate genes encoding homologous proteins. Isolation of homologous genes using sequence-dependent protocols is well known in the art. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., Proc. Acad. Sci. USA 82:1074 (1985); or strand displacement amplification (SDA), Walker, et al., Proc. Natl. Acad. Sci. U.S.A., 89:392 (1992)]; and 3.) methods of library construction and screening by complementation.

For example, genes encoding similar proteins or polypeptides to the threonine deaminase encoding genes provided herein could be isolated directly by using all or a portion of the instant nucleic acid fragments as DNA hybridization probes to screen libraries from any desired organism using methodology well known to those skilled in the art. Specific oligonucleotide probes based upon the disclosed nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments by hybridization under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotides as specific hybridization probes in the Diagnosis of Genetic Disorders", in *Human Genetic Diseases: A Practical Approach*, K. E. Davis Ed., (1986) pp 33-50, IRL: Herndon, Va.; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the described sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the described nucleic acid fragments, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (e.g., BRL, Gaithersburg, Md.), specific 3' or 5' cDNA fragments can be isolated (Ohara et al., *PNAS USA* 86:5673 (1989); Loh et al., *Science* 243:217 (1989)).

Alternatively, the provided threonine deaminase encoding sequences may be employed as hybridization reagents for the identification of homologs. The basic components of a nucleic acid hybridization test include a probe, a sample suspected of containing the gene or gene fragment of interest, and a specific hybridization method. Probes are typically single-stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143-5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide and cesium trifluoroacetate, among others. Typically, the chaotropic agent will be present at a final concentration of about 3 M. If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal) and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Threonine deaminase and isopropylmalate synthase, and optionally branched chain amino acid aminotransferase and/or pyruvate dehydrogenase activities may be reduced using genetic manipulations that disrupt expression of active enzyme from the target gene. Many methods for genetic modification of target genes are known to one skilled in the art and may be used to create the present yeast strains. Modifications that may be used to reduce or eliminate expression of a target protein are disruptions that include, but are not limited to, deletion of the entire gene or a portion of the gene, inserting a DNA fragment into the gene (in either the promoter or coding region) so that the protein is not expressed or expressed at lower levels, introducing a mutation into the coding region which adds a stop codon or frame shift such that a functional protein is not expressed, and introducing one or more mutations into the coding region to alter amino acids so that a non-functional or a less enzymatically active protein is expressed. In addition, expression of a gene may be blocked by expression of an antisense RNA or an interfering RNA, and constructs may be introduced that result in cosuppression. In addition, the synthesis or stability of the transcript may be lessened by mutation. Similarly the efficiency by which a protein is translated from mRNA may be modulated by mutation. In addition, since the target proteins are all mitochondrial, disruption of mitochondrial localization may be used such as disrupting the mitochondrial targeting signal sequence. All of these methods may be readily practiced by one skilled in the art making use of the known or identified coding sequences as exemplified in Table 1.

DNA sequences surrounding a target gene coding sequence are also useful in some modification procedures and are available for yeasts such as for *Saccharomyces cerevisiae* in the complete genome sequence coordinated by Genome Project ID9518 of Genome Projects coordinated by NCBI (National Center for Biotechnology Information) with identifying GOPID #13838. Additional examples of yeast genomic sequences include that of *Yarrowia lipolytica*, GOPIC #13837, and of *Candida albicans*, which is included in GPID #10771, #10701 and #16373. Additional genomes have been completely sequenced and annotated and are publicly available for the following yeast strains *Candida glabrata* CBS 138, *Kluyveromyces lactis* NRRL Y-1140, *Pichia stipitis* CBS 6054, and *Schizosaccharomyces pombe* 972h-.

In particular, DNA sequences surrounding a target coding sequence are useful for modification methods using homologous recombination. For example, in this method flanking sequences are placed bounding a selectable marker gene to mediate homologous recombination whereby the marker gene replaces the target gene. Also partial target gene sequences and flanking sequences bounding a selectable marker gene may be used to mediate homologous recombination whereby the marker gene replaces a portion of the target gene. In addition, the selectable marker may be bounded by site-specific recombination sites, so that following expression of the corresponding site-specific recombinase, the resistance gene is excised from the target gene without reactivating the latter. The site-specific recombination leaves behind a recombination site which disrupts expression of the target gene encoded protein. The homologous recombination vector may be constructed to also leave a deletion in the target gene following excision of the selectable marker, as is well known to one skilled in the art.

Deletions may be made using mitotic recombination as described in Wach et al. ((1994) Yeast 10:1793-1808). This method involves preparing a DNA fragment that contains a selectable marker between genomic regions that may be as short as 20 bp, and which bound a target DNA sequence. This DNA fragment can be prepared by PCR amplification of the selectable marker gene using as primers oligonucleotides that hybridize to the ends of the marker gene and that include the genomic regions that can recombine with the yeast genome. The linear DNA fragment can be efficiently transformed into yeast and recombined into the genome resulting in gene replacement including with deletion of the target DNA sequence (as described in Methods in Enzymology, v194, pp 281-301 (1991)).

Moreover, promoter replacement methods may be used to exchange the endogenous transcriptional control elements allowing another means to modulate expression such as described in Mnaimneh et al. ((2004) Cell 118(1):31-44) and in Example 12 herein.

In addition, a target gene in any yeast cell may be disrupted using random mutagenesis, which is followed by screening to identify strains with reduced target gene encided activity. Using this type of method, the DNA sequence of any region of the genome affecting expression of a target protein need not be known. Methods for creating genetic mutations are common and well known in the art and may be applied to the exercise of creating mutants. Commonly used random genetic modification methods (reviewed in *Methods in Yeast Genetics,* 2005, Cold Spring Harbor Laboratory Press, Cold Spring Harbor, N.Y.) include spontaneous mutagenesis, mutagenesis caused by mutator genes, chemical mutagenesis, irradiation with UV or X-rays, or transposon mutagenesis.

Chemical mutagenesis of yeast commonly involves treatment of yeast cells with one of the following DNA mutagens: ethyl methanesulfonate (EMS), nitrous acid, diethyl sulfate, or N-methyl-N'-nitro-N-nitroso-guanidine (MNNG). These methods of mutagenesis have been reviewed in Spencer et al (Mutagenesis in Yeast, 1996, *Yeast Protocols Methods in Cell and Molecular Biology.* Humana Press, Totowa, N.J.). Chemical mutagenesis with EMS may be performed as described in *Methods in Yeast Genetics,* 2005, Cold Spring Harbor Laboratory Press, Cold Spring Harbor, N.Y. Irradiation with ultraviolet (UV) light or X-rays can also be used to produce random mutagenesis in yeast cells. The primary effect of mutagenesis by UV irradiation is the formation of pyrimidine dimers which disrupt the fidelity of DNA replication. Protocols for UV-mutagenesis of yeast can be found in Spencer et al (Mutagenesis in Yeast, 1996, *Yeast Protocols: Methods in Cell and Molecular Biology.* Humana Press, Totowa, N.J.). Introduction of a mutator phenotype can also be used to generate random chromosomal mutations in yeast. Common mutator phenotypes can be obtained through disruption of one or more of the following genes: PMS1, MAG1, RAD18 or RAD51. Restoration of the non-mutator phenotype can be easily obtained by insertion of the wildtype allele. Collections of modified cells produced from any of these or other known random mutagenesis processes may be screened for reduced activity of the target enzyme.

Production of Isobutanol

Strains of yeast disclosed herein may be grown in fermentation media for production of isobutanol. Suitable carbon substrates may include but are not limited to monosaccharides such as fructose, oligosaccharides such as lactose maltose, galactose, or sucrose, polysaccharides such as starch or cellulose or mixtures thereof and unpurified mixtures from renewable feedstocks such as cheese whey permeate, cornsteep liquor, sugar beet molasses, and barley malt. Other carbon substrates may include ethanol, lactate, succinate, or glycerol.

Additionally the carbon substrate may also be one-carbon substrates such as carbon dioxide, or methanol for which metabolic conversion into key biochemical intermediates has been demonstrated. In addition to one and two carbon substrates, methylotrophic organisms are also known to utilize a number of other carbon containing compounds such as methylamine, glucosamine and a variety of amino acids for metabolic activity. For example, methylotrophic yeasts are known to utilize the carbon from methylamine to form trehalose or glycerol (Bellion et al., *Microb. Growth C*1 *Compd.,* [Int. Symp.], 7th (1993), 415-32, Editor(s): Murrell, J. Collin; Kelly, Don P. Publisher: Intercept, Andover, UK). Similarly, various species of *Candida* will metabolize alanine or oleic acid (Sulter et al., *Arch. Microbiol.* 153:485-489 (1990)).

Hence it is contemplated that the source of carbon utilized in the present invention may encompass a wide variety of carbon containing substrates.

Although it is contemplated that all of the above mentioned carbon substrates and mixtures thereof are suitable in the present invention, preferred carbon substrates are glucose, fructose, and sucrose, or mixtures of these with C5 sugars such as xylose and/or arabinose for yeasts cells modified to use C5 sugars. Sucrose may be derived from renewable sugar sources such as sugar cane, sugar beets, cassava, sweet sorghum, and mixtures thereof. Glucose and dextrose may be derived from renewable grain sources through saccharification of starch based feedstocks including grains such as corn, wheat, rye, barley, oats, and mixtures thereof. In addition, fermentable sugars may be derived from renewable cellulosic or lignocellulosic biomass through processes of pretreatment and saccharification, as described, for example, in U.S. Patent Application Publication No. 2007/0031918A1, which is herein incorporated by reference. Biomass refers to any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid. Biomass may be derived from a single source, or biomass can comprise a mixture derived from more than one source; for example, biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, animal manure, and mixtures thereof.

In addition to an appropriate carbon source, fermentation media must contain suitable minerals, salts, cofactors, buffers and other components, known to those skilled in the art, suitable for the growth of the cultures and promotion of the enzymatic pathway necessary for production of the desired product.

Byproduct Formation

It will be appreciated that reduction and preferably elimination of byproducts of carbon metabolism other than carbon dioxide and isobutanol would be advantageous for production of isobutanol. For example microorganisms metabolizing sugar substrates produce a variety of byproducts in a mixed acid fermentation (Moat, A. G. et al., MicrobialPhysiology, 4th edition, John Wiley Publishers, N.Y., 2002). Yeast metabolizing sugar substrates produce a variety of by-products like acids and alcohols such as, but not limited to, formate, lactate, succinate, ethanol, acetate and glycerol. Formation of these byproducts during isobutanol fermentation lower the yield of isobutanol. To prevent yield loss of isobutanol the genes encoding enzyme activities corresponding to byproduct formation can be down-regulated or disrupted using methods described herein and/or known in the art.

Endogenous pyruvate decarboxylase activity in yeast converts pyruvate to acetaldehyde, which is then converted to ethanol or to acetyl-CoA via acetate. Therefore, endogenous pyruvate decarboxylase activity is a target for reduction of byproduct formation. Yeasts may have one or more genes encoding pyruvate decarboylase. For example, there is one gene encoding pyruvate decarboxylase in *Kluyveromyces*

*lactis*, while there are three isozymes of pyruvate decarboxylase encoded by the PDC1, PCD5, and PDC6 genes in *Saccharomyces cerevisiae*, as well as a pyruvate decarboxylase regulatory gene PDC2. Expression of pyruvate decarboxylase from PDC6 is minimal. In yeast strains disclosed herein, the pyruvate decarboxylase activity may be reduced by down-regulating or disrupting at least one gene encoding a pyruvate decarboxylase, or a gene regulating pyruvate decarboxylase gene expression as described in U.S. patent application Ser. No. 12/477,942, which is herein incorporated by reference. For example, in *S. cerevisiae* the PDC1 and PDC5 genes, or all three genes, may be disrupted. Alternatively, pyruvate decarboxylase activity may be reduced by disrupting the PDC2 regulatory gene in *S. cerevisiae*. In other yeasts, genes encoding pyruvate decarboxylase proteins such as those having at least about 80-85%, 85%-90%, 90%-95%, or at least about 98% sequence identity to PDC1 or PDC5 may be down-regulated or disrupted. Examples of yeast pyruvate decarboxylase genes or proteins that may be targeted for down-regulation or disruption are listed in Table 3 (SEQ ID NOs: 108, 110, 112, 114, 116, 118, 120, 122, and 124).

Examples of yeast strains with reduced pyruvate decarboxylase activity due to disruption of pyruvate decarboxylase encoding genes have been reported such as for *Saccharomyces* in Flikweert et al. (Yeast (1996) 12:247-257), for *Kluyveromyces* in Bianchi et al. (Mol. Microbiol. (1996) 19(1):27-36), and disruption of the regulatory gene in Hohmann, (Mol Gen Genet. (1993) 241:657-666). *Saccharomyces* strains having no pyruvate decarboxylase activity are available from the ATCC (Accession #200027 and #200028).

Culture Conditions

Typically cells are grown at a temperature in the range of about 20° C. to about 37° C. in an appropriate medium. Suitable growth media in the present invention are common commercially prepared media such as broth that includes yeast nitrogen base, ammonium sulfate, and dextrose as the carbon/energy source) or YPD Medium, a blend of peptone, yeast extract, and dextrose in optimal proportions for growing most *Saccharomyces cerevisiae* strains. Other defined or synthetic growth media may also be used and the appropriate medium for growth of the particular microorganism will be known by one skilled in the art of microbiology or fermentation science.

Suitable pH ranges for the fermentation are between pH 3.0 to pH 7.5, where pH 4.5.0 to pH 6.5 is preferred as the initial condition.

Fermentations may be performed under aerobic or anaerobic conditions, where anaerobic or microaerobic conditions are preferred.

The amount of isobutanol produced in the fermentation medium can be determined using a number of methods known in the art, for example, high performance liquid chromatography (HPLC) or gas chromatography (GC).

Industrial Batch and Continuous Fermentations

The present process employs a batch method of fermentation. A classical batch fermentation is a closed system where the composition of the medium is set at the beginning of the fermentation and not subject to artificial alterations during the fermentation. Thus, at the beginning of the fermentation the medium is inoculated with the desired organism or organisms, and fermentation is permitted to occur without adding anything to the system. Typically, however, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.*, 36:227, (1992), herein incorporated by reference.

Although the present invention is performed in batch mode it is contemplated that the method would be adaptable to continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using either batch, fed-batch or continuous processes and that any known mode of fermentation would be suitable. Additionally, it is contemplated that cells may be immobilized on a substrate as whole cell catalysts and subjected to fermentation conditions for isobutanol production.

Methods for Isobutanol Isolation from the Fermentation Medium

Bioproduced isobutanol may be isolated from the fermentation medium using methods known in the art. For example, solids may be removed from the fermentation medium by centrifugation, filtration, decantation, or the like. Then, the isobutanol may be isolated from the fermentation medium, which has been treated to remove solids as described above, using methods such as distillation, liquid-liquid extraction, or membrane-based separation. Because isobutanol forms a low boiling point, azeotropic mixture with water, distillation can only be used to separate the mixture up to its azeotropic composition. Distillation may be used in combination with another separation method to obtain separation around the azeotrope. Methods that may be used in combination with distillation to isolate and purify isobutanol include, but are not limited to, decantation, liquid-liquid extraction, adsorption, and membrane-based techniques. Additionally, isobutanol may be isolated using azeotropic distillation using an entrainer (see for example Doherty and Malone, *Conceptual Design of Distillation Systems*, McGraw Hill, New York, 2001).

The isobutanol-water mixture forms a heterogeneous azeotrope so that distillation may be used in combination with decantation to isolate and purify the isobutanol. In this method, the isobutanol containing fermentation broth is distilled to near the azeotropic composition. Then, the azeotropic mixture is condensed, and the isobutanol is separated from the fermentation medium by decantation. The decanted aqueous phase may be returned to the first distillation column as reflux. The isobutanol-rich decanted organic phase may be further purified by distillation in a second distillation column.

The isobutanol may also be isolated from the fermentation medium using liquid-liquid extraction in combination with distillation. In this method, the isobutanol is extracted from the fermentation broth using liquid-liquid extraction with a suitable solvent. The isobutanol-containing organic phase is then distilled to separate the isobutanol from the solvent.

Distillation in combination with adsorption may also be used to isolate isobutanol from the fermentation medium. In this method, the fermentation broth containing the isobutanol is distilled to near the azeotropic composition and then the remaining water is removed by use of an adsorbent, such as molecular sieves (Aden et al. *Lignocellulosic Biomass to Ethanol Process Design and Economics Utilizing Co-Current Dilute Acid Prehydrolysis and Enzymatic Hydrolysis for Corn Stover*, Report NREL/TP-510-32438, National Renewable Energy Laboratory, June 2002).

Additionally, distillation in combination with pervaporation may be used to isolate and purify the isobutanol from the fermentation medium. In this method, the fermentation broth containing the isobutanol is distilled to near the azeotropic composition, and then the remaining water is removed by pervaporation through a hydrophilic membrane (Guo et al., *J. Membr. Sci.* 245, 199-210 (2004)).

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, N.Y. (1989) (Maniatis) and by T. J. Silhavy, M. L. Bennan, and L. W. Enquist, *Experiments with Gene Fusions*, Cold Spring Harbor Laboratory Press, Cold Spring Harbor, N.Y. (1984) and by Ausubel, F. M. et al., *Current Protocols in Molecular Biology*, pub. by Greene Publishing Assoc. and Wiley-Interscience (1987), and by *Methods in Yeast Genetics*, 2005, Cold Spring Harbor Laboratory Press, Cold Spring Harbor, N.Y.

Materials and methods suitable for the maintenance and growth of bacterial cultures are well known in the art. Techniques suitable for use in the following Examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of microbial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.) unless otherwise specified. Microbial strains were obtained from The American Type Culture Collection (ATCC), Manassas, Va., unless otherwise noted. The oligonucleotide primers used in the following Examples are given in Table 2. All the oligonucleotide primers were synthesized by Sigma-Genosys (Woodlands, Tex.) or Integrated DNA Technologies (Coralsville, Iowa).

Synthetic complete medium is described in Amberg, Burke and Strathern, 2005, Methods in Yeast Genetics, Cold Spring Harbor Laboratory Press, Cold Spring Harbor, N.Y.

GC Method

The GC method utilized an HP-InnoWax column (30 m×0.32 mm ID, 0.25 μm film) from Agilent Technologies (Santa Clara, Calif.). The carrier gas was helium at a flow rate of 1 ml/min measured at 150° C. with constant head pressure; injector split was 1:10 at 200° C.; oven temperature was 45° C. for 1 min, 45° C. to 230° C. at 10° C./min, and 230° C. for 30 sec. FID detection was used at 260° C. with 40 ml/min helium makeup gas. Culture broth samples were filtered through 0.2 μM spin filters before injection. Depending on analytical sensitivity desired, either 0.1 μl or 0.5 μl injection volumes were used. Calibrated standard curves were generated for the following compounds: ethanol, isobutanol, acetoin, meso-2,3-butanediol, and (2S,3S)-2,3-butanediol. Analytical standards were also utilized to identify retention times for isobutryaldehyde, isobutyric acid, and isoamyl alcohol.

SEQ ID NOs for primers and vectors in the examples below are listed in Table 2.

The meaning of abbreviations is as follows: "s" means second(s), "min" means minute(s), "h" means hour(s), "psi" means pounds per square inch, "nm" means nanometers, "d" means day(s), "μL" means microliter(s), "mL" means milliliter(s), "L" means liter(s), "mm" means millimeter(s), "nm" means nanometers, "mM" means millimolar, "M" means molar, "mmol" means millimole(s), "μmol" means micromole(s)", "g" means gram(s), "μg" means microgram(s) and "ng" means nanogram(s), "PCR" means polymerase chain reaction, "OD" means optical density, "$OD_{600}$" means the optical density measured at a wavelength of 600 nm, "kDa" means kilodaltons, "g" means the gravitation constant, "bp" means base pair(s), "kbp" means kilobase pair(s), "% w/v" means weight/volume percent, % v/v" means volume/volume percent, "wt %" means percent by weight, "HPLC" means high performance liquid chromatography, "GC" means gas chromatography, "FID" means flame ionization detector.

Example 1

Eliminating Expression of Enzymes in Branched Chain Amino Acid Biosynthesis Pathways in *S. cerevisiae*

Yeast cells were engineered to eliminate activities of specific enzymes of mitochondrial branched chain amino acid biosynthesis. Three chromosomal disruptions were generated in successive fashion in the following genes: ILV1, encoding threonine deaminase; LEU4, encoding 2-isopropylmalate synthase; and BAT1, encoding branched chain amino acid aminotransferase.

An ilv1::LEU2 cassette was constructed by PCR amplification of the LEU2 marker from pRS425 (ATCC No. 77106) using Phusion DNA polymerase (New England Biolabs Inc., Beverly, Mass.; catalog no. F-540S) with primers 112590-88A (SEQ ID NO:81) and 112590-88B (SEQ ID NO:82). The ILV1 portion of each primer was derived from the 5' region upstream of the ILV1 promoter and 3' region downstream of the transcriptional terminator, respectively, such that integration of the LEU2 marker results in replacement of the ILV1 coding region. The ~1.7 kb PCR product was transformed into *Saccharomyces cerevisiae* strain BY4741 (ATCC #201388) with selection on synthetic complete media lacking leucine and supplemented with 2% glucose at 30° C. Transformants were screened by colony PCR using primers 112590-88C (SEQ ID NO:83) and 112590-88D (SEQ ID NO:84). The resulting identified strain had the genotype: BY4741 ilv1::LEU2.

A leu4::URA3r disruption cassette was constructed by PCR amplification of the URA3r marker from pUC19-URA3r (SEQ ID NO:85) using Phusion DNA polymerase (New England Biolabs Inc., Beverly, Mass.; catalog no. F-5405) and primers 112590-97A (SEQ ID NO:86) and 112590-97B (SEQ ID NO:87). pUC19-URA3r contains the URA3 marker from pRS426 (ATCC no. 77107) flanked by 75 by homologous repeat sequences to allow homologous recombination in vivo and removal of the URA3 marker. The LEU4 portion of each primer was derived from the 5' region upstream of the LEU4 promoter and 3' region downstream of the transcriptional terminator, respectively, such that integration of the URA3r marker results in replacement of the LEU4 coding region. The ~1.5 kb PCR product was transformed into BY4741 ilv1::LEU2 cells with selection on synthetic complete media lacking uracil and supplemented with 2% glucose at 30° C. Transformants were screened by PCR using external primers 112590-49E (SEQ ID NO:88) and 112590-97C (SEQ ID NO:89) to verify integration at the correct site. The URA3r marker was recycled by plating on synthetic complete media supplemented with 2% glucose and 5-FOA at 30° C. following standard protocols. Marker removal was confirmed by patching colonies from the 5-FOA plates onto synthetic complete media lacking uracil to verify the absence of growth. The resulting identified strain had the genotype: BY4741 Δilv1 Δleu4.

A bat1:: URA3r disruption cassette was constructed in several steps. A cassette containing the BAT1 5' region was amplified from BY4741 genomic DNA using Phusion DNA polymerase (New England Biolabs Inc., Beverly, Mass.; catalog no. F-5405) and primers 112590-108A (SEQ ID NO:90) and 112590-108B (SEQ ID NO:91). The cassette containing BAT1 3' sequences was amplified from BY4741 genomic DNA using Phusion DNA polymerase and primers 112590-108O (SEQ ID NO:92) and 112590-108D (SEQ ID NO:93). The URA3r marker was PCR-amplified from pUC19-URA3r using Phusion DNA polymerase and primers 112590-108E (SEQ ID NO:94) and 112590-108F (SEQ ID NO:95). The three PCR products were combined in a SOE PCR reaction (Horton et al. (1989) Gene 77:61-68) and amplified using Phusion DNA polymerase and the end primers 112590-108A (SEQ ID NO:90) and 112590-108D (SEQ ID NO:93), generating the full ~2.8 kb BAT1::URA3r disruption cassette. The BAT1 portion of each primer was derived from the 5' region upstream of the BAT1 promoter and 3' region downstream of the transcriptional terminator, respectively, such that integration of the URA3r marker results in replacement of the BAT1 coding region. The cassette was transformed into BY4741 Δilv1 Δleu4 with selection on synthetic complete media lacking uracil and supplemented with 2% glucose at 30° C. Transformants were screened by PCR using external primers 112590-49E (SEQ ID NO:88) and "BAT1 check" (SEQ ID NO:96) to verify integration at the correct site. The URA3r marker was recycled by plating on synthetic complete media supplemented with 2% glucose and 5-FOA at 30° C. following standard protocols. Marker removal was confirmed by patching colonies from the 5-FOA plates onto synthetic complete media lacking uracil supplemented with 2% glucose to verify the absence of growth. The resulting identified strain had the genotype: BY4741 Δilv1 Δleu4 Δbat1.

Example 2

Reduction of Pyruvate Dehydrogenase Activity in *S. cerevisiae*

To reduce levels of mitochondrial pyruvate dehydrogenase activity, the native promoter of the PDA1 gene, encoding the E1α subunit of pyruvate dehydrogenase, was replaced with the inducible GAL1 promoter through homologous recombination. The GAL1 promoter and URA3r marker were joined together by SOE PCR. The URA3r marker was PCR amplified from pUC19-URA3r using Phusion DNA polymerase (New England Biolabs Inc., Beverly, Mass.; catalog no. F-540S) and primers 112590-118A (SEQ ID NO:97) and 112590-118B (SEQ ID NO:98). The GAL1 promoter was PCR-amplified from pRS426::GAL1p-alsS (SEQ ID NO:99) using Phusion DNA polymerase (New England Biolabs Inc., Beverly, Mass.; catalog no. F-540S) and primers 112590-118C (SEQ ID NO:100) and 112590-118D (SEQ ID NO:101). pRS426::GAL1p-alsS contained an F1 origin of replication (nt 4976 to 5432) for maintenance in *E. coli* and a 2 micron origin (nt 2215 to 3560) for replication in yeast. The vector has an GAL1 promoter (nt 7702 to 8144) and CYC1 terminator (nt 5721 to 5970). In addition, it carries the URA3 marker (nt 4042 to 4845) for selection in yeast and ampicillin resistance marker (nt 1225 to 2082) for selection in *E. coli*.

The two products were joined by SOE PCR using Phusion DNA polymerase and primers 112590-118E (SEQ ID NO:102) and 112590-118F (SEQ ID NO:103). The PDA1 portion of each primer was derived from the 5' region upstream of the PDA1 promoter and PDA1 coding sequence, respectively, such that integration of the URA3 marker results in replacement of the native PDA1 promoter with the GAL1 promoter. The PCR product was transformed into BY4741 Δilv1 Δleu4 Δbat1 with selection on synthetic complete media lacking uracil and supplemented with 2% glucose at 30° C. Transformants were screened by PCR using external primers 112590-49E (SEQ ID NO:88) and 112590-118G (SEQ ID NO:104) to verify integration at the PDA1 locus. The URA3r marker was recycled by plating on synthetic complete media supplemented with 2% glucose and 5-FOA at 30° C. following standard protocols. Marker removal was confirmed by patching colonies from the 5FOA plates onto synthetic complete media lacking uracil supplemented with 2% glucose to verify the absence of growth. The resulting identified strain had the genotype: BY4741 Δilv1 Δleu4 Δbat1 GAL1p-PDA1.

Example 3

Isobutanol Production in *S. cerevisiae* Deletion Strains

The purpose of this example is to demonstrate isobutanol production in *S. cerevisiae* in which ILV1 (threonine deaminase) and LEU4 (2-isopropylmalate synthase), and optionally BAT1 (branched-chain amino acid aminotransferase) genes are disrupted. An additional strain has a PDA1 (pyruvate dehydrogenase) disruption.

Strains BY4741, BY4741 Δilv1 Δleu4, BY4741 Δilv1 Δleu4 Δbat1, and BY4741 Δilv1 Δleu4 Δbat1 GAL1p-PDA1, each transformed with control pR423 (ATCC #77104) and pRS426 plasmids, were grown in synthetic complete media lacking histidine and uracil, and supplemented with 2% glucose under aerobic conditions (20 ml media in 125 ml flask) and cultured at 30° C. with shaking at 220 rpm. Cultures were inoculated at 0.1 $OD_{600}$ and assayed for isobutanol titers at 24 hours post-inoculation. Isobutanol was quantitated by GC-FID on a HP-Innowax column using a standard curve of pure isobutanol. A standard curve of isobutanol ranging from 25 mM to 0.6 mM was used to define the linear relationship between raw peak area and isobutanol concentration. Experimental samples were compared against this standard curve to obtain isobutanol titers given in Table 4.

TABLE 4

Isobutanol production in control and different deletion strains of *S. cerevisiae*.

| Strain | Isobutanol (mM) |
| --- | --- |
| BY4741 pRS423/pRS426 | 0.07* |
| BY4741 Δilv1 Δleu4 pRS423/pRS426 | 0.64 |
| BY4741 Δilv1 Δleu4 Δbat1 pRS423/pRS426 | 0.90 |
| BY4741 Δilv1 Δleu4 Δbat1 GAL1p-PDA1 pRS423/pRS426 | 0.95 |

*Sample taken at 48 hours.

What is claimed is:

1. A recombinant yeast host cell which produces isobutanol and comprises mitochondria which is substantially devoid of threonine deaminase activity.

2. The yeast cell of claim 1 wherein the mitochondria is further substantially devoid of branched chain amino acid transaminase activity.

3. The yeast cell of claim 1 wherein the threonine deaminase activity is defined by the enzyme classification number EC 4.3.1.19.

4. The yeast cell of claim 1 wherein endogenous pyruvate decarboxylase activity is reduced.

5. The yeast cell of claim 2 wherein the branched chain amino acid transaminase activity is defined by the enzyme classification number EC 2.6.1.42.

6. The recombinant yeast host cell of claim 1 wherein the yeast is selected from the group consisting of *Saccharomyces, Schizosaccharomyces, Hansenula, Candida, Kluyveromyces, Yarrowia* and *Pichia*.

7. The yeast cell of claim 1 comprising a disruption in ILV1.

8. The yeast cell of claim 2 comprising a disruption in the BAT1 gene.

9. The yeast cell of claim 1 wherein the mitochondria is further substantially devoid of isopropylmalate synthase activity.

10. The yeast cell of claim 9 comprising a disruption in LEU4.

* * * * *